(12) United States Patent
Poslusney et al.

(10) Patent No.: US 12,234,221 B2
(45) Date of Patent: Feb. 25, 2025

(54) PYRIDINE CARBOXAMIDE COMPOUNDS FOR INHIBITING NAV1.8

(71) Applicant: Lieber Institute, Inc., Baltimore, MD (US)

(72) Inventors: Michael Poslusney, Owings Mills, MD (US); Glen Ernst, Bear, DE (US); James Barrow, Arnold, MD (US); Yifang Huang, Baltimore, MD (US)

(73) Assignee: Lieber Institute, Inc., Baltimore, MD (US)

( * ) Notice: Subject to any disclaimer, the term of this patent is extended or adjusted under 35 U.S.C. 154(b) by 549 days.

(21) Appl. No.: 17/256,781

(22) PCT Filed: Jul. 9, 2019

(86) PCT No.: PCT/US2019/041029
§ 371 (c)(1),
(2) Date: Dec. 29, 2020

(87) PCT Pub. No.: WO2020/014246
PCT Pub. Date: Jan. 16, 2020

(65) Prior Publication Data
US 2022/0227732 A1    Jul. 21, 2022

Related U.S. Application Data

(60) Provisional application No. 62/695,571, filed on Jul. 9, 2018.

(51) Int. Cl.
| | | |
|---|---|---|
| *C07D 401/12* | (2006.01) |
| *A61K 31/44* | (2006.01) |
| *A61K 31/4439* | (2006.01) |
| *A61K 31/444* | (2006.01) |
| *A61K 31/51* | (2006.01) |
| *C07D 213/82* | (2006.01) |
| *C07D 413/12* | (2006.01) |
| *C07D 417/12* | (2006.01) |

(52) U.S. Cl.
CPC ............ *C07D 401/12* (2013.01); *A61K 31/44* (2013.01); *A61K 31/4439* (2013.01); *A61K 31/444* (2013.01); *A61K 31/51* (2013.01); *C07D 213/82* (2013.01); *C07D 413/12* (2013.01); *C07D 417/12* (2013.01)

(58) Field of Classification Search
CPC .. C07D 401/12; C07D 213/82; C07D 413/12; C07D 417/12; A61K 31/44; A61K 31/4439; A61K 31/444; A61K 31/51
See application file for complete search history.

(56) References Cited

U.S. PATENT DOCUMENTS

| | | | |
|---|---|---|---|
| 7,504,396 B2 * | 3/2009 | Nunes ................. | C07D 239/48 544/122 |
| 7,705,031 B2 | 4/2010 | Wilson et al. | |
| 7,989,481 B2 | 8/2011 | Neubert et al. | |
| 8,236,829 B2 | 8/2012 | Neubert et al. | |
| 8,236,833 B2 | 8/2012 | Martinborough et al. | |
| 8,309,543 B2 | 11/2012 | Gonzalez, III et al. | |
| 8,314,125 B2 | 11/2012 | Termin et al. | |
| 8,466,188 B2 | 6/2013 | Chafeev et al. | |
| 8,492,403 B2 | 7/2013 | Kawatkar et al. | |
| 8,536,195 B2 | 9/2013 | Termin et al. | |
| 8,883,840 B2 | 11/2014 | Chafeev et al. | |
| 9,783,501 B2 | 10/2017 | Hadida-Ruah et al. | |
| 9,828,397 B2 | 11/2017 | Anderson et al. | |
| 9,969,693 B2 | 5/2018 | Bogdan et al. | |
| 10,000,475 B2 | 6/2018 | Tadesse et al. | |
| 10,005,724 B2 | 6/2018 | Andrez et al. | |
| 10,005,768 B2 | 6/2018 | Yao et al. | |
| 2004/0110725 A1 | 6/2004 | Dolle et al. | |
| 2009/0099233 A1 | 4/2009 | Joshi et al. | |
| 2009/0227587 A1 * | 9/2009 | Connolly ................ | A61P 29/00 544/122 |
| 2014/0228371 A1 | 8/2014 | Hadida-Ruah | |
| 2019/0016671 A1 | 1/2019 | Ahmad et al. | |

FOREIGN PATENT DOCUMENTS

| | | | |
|---|---|---|---|
| CN | 102850321 A | | 1/2013 |
| EP | 0628550 | | 12/1994 |
| JP | 2004-238361 | | 8/2004 |
| JP | 2004/2338361 | * | 8/2004 |
| WO | WO 2001/023356 A1 | | 4/2001 |
| WO | WO 2003/068235 A1 | | 8/2003 |
| WO | WO 2005/042519 A1 | | 5/2005 |
| WO | WO 2009/049180 | | 4/2009 |
| WO | WO 2009/049181 | | 4/2009 |
| WO | WO 2009/049183 | | 4/2009 |
| WO | WO 2010/049302 | | 5/2010 |
| WO | WO 2010/051238 | | 5/2010 |
| WO | WO 2011/026240 | | 3/2011 |

(Continued)

OTHER PUBLICATIONS

O'Hara et al., 135(32) J. Am. Chem. Soc., 12122-12134 (2013) (Year: 2013).*

Cheung et al., A Parallel Synthesis Approach to the Identification of Novel Diheteroarylamide-Based Compounds Blocking HIV Replication: Potential Inhibitors of HIV-1 PremRNA Alternative Splicing, Journal of Medicinal Chemistry, 2016, vol. 59, No. 5, pp. 1869-1879.

Cramp et al., Design and synthesis of N-(2,4-difluorophenyl)-2-(3-trifluoromethylphenoxy)-3-pyridinecarboxamide (diflufenican), a novel pre- and early post-emergence herbicide for use in winter cereals, Pesticide Science, 1987, vol. 18, No. 1, pp. 15-28.

(Continued)

*Primary Examiner* — Timothy R Rozof
(74) *Attorney, Agent, or Firm* — Casimir Jones, SC; Jeffrey W. Childers

(57) ABSTRACT

Pyridine carboxamide compounds for inhibiting NaV1.8 and methods for treating a condition, disease, or disorder associated with an increased NaV1.8 activity or expression are disclosed.

12 Claims, 2 Drawing Sheets

(56) References Cited

FOREIGN PATENT DOCUMENTS

| WO | WO 2011/140425 | 11/2011 |
|---|---|---|
| WO | WO 2012/106499 | 8/2012 |
| WO | WO 2012/112743 | 8/2012 |
| WO | WO 2012/116440 | 9/2012 |
| WO | WO 2012/125613 | 9/2012 |
| WO | WO 2013/109521 | 7/2013 |
| WO | WO 2014/120815 | 8/2014 |
| WO | WO 2014/151393 | 9/2014 |
| WO | WO 2015/010065 | 1/2015 |
| WO | WO 2018/148626 | 8/2018 |
| WO | WO 2019/014352 | 1/2019 |

OTHER PUBLICATIONS

International Search Report and Written Opinion for PCT/US2019/041026. Mailed Oct. 28, 2019. 10 pages.

Extended European Search Report for PCT/US2019041026. Mailed Mar. 18, 2022. 11 pages.

Search Report and Written Opinion from Intellectual Property Office of Singapore for application 11202100137T. May 16, 2022. 10 pages.

International Search Report and Written Opinion for PCT/US2019/041029. Mailed Oct. 28, 2019. 16 pages.

Extended European Search Report for PCT/US2019041029. Mailed Jul. 3, 2022. 11 pages.

International Preliminary Report on Patentability for PCT/US2019/041029. Apr. 23, 2020. 6 pages.

Akopian et al., A tetrodotoxin-resistant voltage-gated sodium channel expressed by sensory neurons. Nature. Jan. 18, 1996;379(6562):257-62.

Akopian et al., The tetrodotoxin-resistant sodium channel SNS has a specialized function in pain pathways. Nat Neurosci. Jun. 1999;2(6):541-8.

Bagal et al., Discovery and Optimization of Selective Nav1.8 Modulator Series That Demonstrate Efficacy in Preclinical Models of Pain. ACS Med Chem Lett. Apr. 29, 2015;6(6):650-4.

Bagal et al., Recent progress in sodium channel modulators for pain. Bioorg Med Chem Lett. Aug. 15, 2014;24(16):3690-9.

Bennett et al., Painful and painless channelopathies. Lancet Neurol. Jun. 2014;13(6):587-99.

Berge et al, Pharmaceutical salts. J Pharm Sci. Jan. 1977;66(1):1-19.

Beyak et al., Inflammation-induced hyperexcitability of nociceptive gastrointestinal DRG neurones: the role of voltage-gated ion channels. Neurogastroenterol Motil. Apr. 2005;17(2):175-186.

Black et al., Sensory neuron-specific sodium channel SNS is abnormally expressed in the brains of mice with experimental allergic encephalomyelitis and humans with multiple sclerosis. Proc Natl Acad Sci U S A. Oct. 10, 2000;97(21):11598-602.

Bucknill et al., Nerve fibers in lumbar spine structures and injured spinal roots express the sensory neuron-specific sodium channels SNS/PN3 and NaN/SNS2. Spine (Phila Pa 1976). Jan. 15, 2002;27(2):135-40.

Catterall. Voltage-gated sodium channels at 60: structure, function and pathophysiology. J Physiol. Jun. 1, 2012;590(11):2577-89.

Cestele et al., Molecular mechanisms of neurotoxin action on voltage-gated sodium channels. Biochimie. Sep.-Oct. 2000;82(9-10):883-92.

Damarjian et al., Upregulation and colocalization of p75 and Nav1.8 in Purkinje neurons in experimental autoimmune encephalomyelitis. Neurosci Lett. Oct. 21, 2004;369(3):186-90.

Deuis et al., The pharmacology of voltage-gated sodium channel activators. Neuropharmacology. Dec. 2017;127:87-108.

Dolle et al., 3-chloro-4-carboxamido-6-arylpyridazines as a non-peptide class of interleukin-1β converting enzyme inhibitor. Bioorganic & Medicinal Chemistry Letters. 1997; vol. 7(8): 1003-1006.

Dong et al., Small interfering RNA-mediated selective knockdown of Na(V)1.8 tetrodotoxin-resistant sodium channel reverses mechanical allodynia in neuropathic rats. Neuroscience. May 11, 2007;146(2):812-21.

Eijkelkamp et al., Neurological perspectives on voltage-gated sodium channels. Brain. Sep. 2012;135(Pt 9):2585-612.

Faber et al., Gain-of-function Nav1.8 mutations in painful neuropathy. Proc Natl Acad Sci U S A. Nov. 20, 2012;109(47):19444-9.

Frings et al., Sulfoximines from a Medicinal Chemist's Perspective: Physicochemical and in vitro Parameters Relevant for Drug Discovery. Eur J Med Chem. Jan. 27, 2017;126:225-245.

Greene's Protective Groups in Organic Synthesis, 4th ed. John Wiley & Sons. 2007. TOC only. 6 pages.

Han et al., Sodium channel Nav1.8: Emerging links to human disease. Neurology. Feb. 2, 2016;86(5):473-83.

Jarvis et al., A-803467, a potent and selective Nav1.8 sodium channel blocker, attenuates neuropathic and inflammatory pain in the rat. Proc Natl Acad Sci U S A. May 15, 2007;104(20):8520-5.

Jukic et al., Isoform selective voltage-gated sodium channel modulators and the therapy of pain. Curr Med Chem. 2014;21(2):164-86.

Kort et al., Discovery and biological evaluation of 5-aryl-2-furfuramides, potent and selective blockers of the Nav1.8 sodium channel with efficacy in models of neuropathic and inflammatory pain. J Med Chem. Feb. 14, 2008;51(3):407-16.

Kort et al., Subtype-selective Na(v)1.8 sodium channel blockers: identification of potent, orally active nicotinamide derivatives. Bioorg Med Chem Lett. Nov. 15, 2010;20(22):6812-5.

Kull et al., Mixtures of quaternary ammonium compounds and long-chain fatty acids as antifungal agents. Appl Microbiol. Nov. 1961;9(6):538-41.

Lu et al., A 3.7 kb fragment of the mouse Scn10a gene promoter directs neural crest but not placodal lineage EGFP expression in a transgenic animal. J Neurosci. May 20, 2015;35(20):8021-34.

McCormack et al., Voltage sensor interaction site for selective small molecule inhibitors of voltage-gated sodium channels. Proc Natl Acad Sci U S A. Jul. 16, 2013;110(29):E2724-32.

McDonnell et al., Efficacy of the Nav1.7 blocker PF-05089771 in a randomised, placebo-controlled, double-blind clinical study in subjects with painful diabetic peripheral neuropathy. Pain. Aug. 2018;159(8):1465-1476.

NCBI accession# NM_001037. Retrieved from the internet Mar. 9, 2023. 2 pages.

NCBI accession# NM_006514. Retrieved from the internet Mar. 9, 2023. 2 pages.

O'Hara et al., Radical-based regioselective C?H functinalization of electron-deficient hetreoarenes: scope, tunability an dpredictabilty. Journal of the American Chemical Society, 2013, vol. 135, pp. 12122-12134.

Payne et al., A novel selective and orally bioavailable Nav 1.8 channel blocker, PF-01247324, attenuates nociception and sensory neuron excitability. Br J Pharmacol. May 2015;172(10):2654-70.

Rannals et al., Psychiatric Risk Gene Transcription Factor 4 Regulates Intrinsic Excitability of Prefrontal Neurons via Repression of SCN10a and KCNQ1. Neuron. Apr. 6, 2016;90(1):43-55.

Remington: The Science and Practice of Pharmacy (21st ed.) Lippincott, Williams & Wilkins. 2005 TOC only. 23 pages.

Renton et al., Sodium channel Nav1.8 immunoreactivity in painful human dental pulp. BMC Oral Health. Jul. 7, 2005;5(1):5. 6 pages.

Ruiz et al., Voltage-Gated Sodium Channels: Structure, Function, Pharmacology, and Clinical Indications. J Med Chem. Sep. 24, 2015;58(18):7093-118.

Scanio et al., Discovery and biological evaluation of potent, selective, orally bioavailable, pyrazine-based blockers of the Na(v) 1.8 sodium channel with efficacy in a model of neuropathic pain. Bioorg Med Chem. Nov. 15, 2010;18(22):7816-25.

Shembalkar et al., Increased sodium channel SNS/PN3 immunoreactivity in a causalgic finger. Eur J Pain. 2001;5(3):319-23.

Shields et al., A channelopathy contributes to cerebellar dysfunction in a model of multiple sclerosis. Ann Neurol. Feb. 2012;71(2):186-94.

Shields et al., Nav1.8 expression is not restricted to nociceptors in mouse peripheral nervous system. Pain. Oct. 2012;153(10):2017-2030.

Shields et al., Oral administration of PF-01247324, a subtype-selective Nav1.8 blocker, reverses cerebellar deficits in a mouse model of multiple sclerosis. PLoS One. Mar. 6, 2015;10(3):e0119067. 8 pages.

(56) References Cited

OTHER PUBLICATIONS

Skolnick. The Opioid Epidemic: Crisis and Solutions. Annu Rev Pharmacol Toxicol. Jan. 6, 2018;58:143-159.

Sweatt. Pitt-Hopkins Syndrome: intellectual disability due to loss of TCF4-regulated gene transcription. Exp Mol Med. May 3, 2013;45(5):e21. 15 pages.

Vetter et al., NaV1.7 as a pain target—From gene to pharmacology. Pharmacol Ther. Apr. 2017;172:73-100.

Yekkirala et al., Breaking barriers to novel analgesic drug development. Nat Rev Drug Discov. Aug. 2017;16(8):545-564.

Yong et al., Pain Medicine: An Essential Review. Springer, Cham, Switzerland. 2017, TOC only. 13 pages.

Yu et al., Overview of the voltage-gated sodium channel family. Genome Biol. 2003;4(3):207.

Zakrzewska et al., Safety and efficacy of a Nav1.7 selective sodium channel blocker in patients with trigeminal neuralgia: a double-blind, placebo-controlled, randomised withdrawal phase 2a trial. Lancet Neurol. Apr. 2017;16(4):291-300.

Zhang et al., A-887826 is a structurally novel, potent and voltage-dependent Na(v)1.8 sodium channel blocker that attenuates neuropathic tactile allodynia in rats. Neuropharmacology. Sep. 2010;59(3):201-7.

\* cited by examiner

PYRIDINE CARBOXAMIDE COMPOUNDS FOR INHIBITING NAV1.8

CROSS-REFERENCE TO RELATED APPLICATIONS

This application claims the benefit of U.S. Provisional Application No. 62/695,571, filed Jul. 9, 2018, which is incorporated herein by reference in its entirety.

BACKGROUND

The modern pharmacopoeia has a variety of treatments for acute and chronic pain, such as steroidal and nonsteroidal anti-inflammatory drugs (NSAIDs), amine reuptake inhibitors, and opioids (Pain Medicine). All have liabilities, and extensive efforts have been undertaken to develop novel approaches for pain management (Yekkirala et al., 2017), especially given the recent epidemic of opioid abuse (Skolnick, 2018). Voltage-gated sodium channels ($Na_v$s), (Catterall, 2012), are logical targets for pain management given their prominent role in neuronal conduction in sensory neurons (Ruiz et al., 2015).

Overall there are nine known subtypes of the main pore-forming a subunit. The $Na_v$ 1.1, $Na_v$ 1.2, and $Na_v$ 1.3 subtypes are primarily expressed in the central nervous system (CNS), while $Na_v$ 1.4 and $Na_v$ 1.5 are abundant in skeletal and cardiac muscle. $Na_v$ 1.6 has been shown to be expressed in both the peripheral nervous system (PNS) and CNS, whereas $Na_v$ 1.7, $Na_v$ 1.8, and $Na_v$ 1.9 are usually thought to be restricted to the PNS (Yu and Catterall, 2003). Non-selective sodium channel inhibitors are available as antiarrhythmic, anticonvulsant, and local anesthetics, but none are appropriate for general treatment of chronic pain (Eijkelkamp et al., 2012). The $Na_v$ family of channels is highly homologous, and obtaining selective drug-like ligands is a significant challenge (Bagal et al., 2014). Identification of selective inhibitors (Jukic et al., 2014), or activators (Deuis et al., 2017), of specific isoforms, however, has potential in numerous disorders.

Both the $Na_v$ 1.7 and $Na_v$ 1.8 isoforms have attracted considerable attention as targets for the treatment of pain due to their presence on nociceptors in the PNS (Jukic et al., 2014). Robust effort has been directed toward $Na_v$ 1.7 (Vetter et al., 2017), given the extensive human genetic validation of this channel (Bennett and Woods, 2014), and the discovery of a selective class of inhibitors (McCormack et al., 2013). Human clinical trials of several selective $Na_v$ 1.7 inhibitors, however, have been disappointing (Donnell et al., 2018; Zakrzewska et al., 2017), suggesting $Na_v$ 1.8 as an alternate target (Han et al., 2016).

The pore-forming a subunit of the $Na_v$ 1.8 sodium channel is encoded by the SCN10A gene and primarily (although not exclusively) expressed in dorsal root ganglion (DRG) neurons and in trigeminal and nodose ganglion neurons (Akopian et al., 1996; Shields et al., 2012). These neurons mediate most of the inward sodium currents during the depolarization phase of neuronal action potentials that are critical for transmission of action potentials and repetitive firing (Akopian et al., 1999).

Rodent SCN10A gene knockout and knockdown studies indicate the involvement of $Na_v$ 1.8 in inflammatory and neuropathic pain (Dong et al., 2007). Heterozygous gain-of-function mutations in SCN10A cause aberrant firing of DRG neurons and have been linked to painful small-fiber neuropathies in humans, which further links $Na_v$ 1.8 to nociceptive neuron function (Faber et al., 2012).

Opportunities also exist for $Na_v$ 1.8 inhibitors beyond treatment of pain. Mounting evidence indicates that $Na_v$ 1.8 is expressed in brain (Lu et al., 2015) and is involved in the pathogenesis of multiple sclerosis (MS). Several reports have shown that $Na_v$ 1.8 is expressed ectopically in mice with experimental autoimmune encephalomyelitis (EAE) (Black et al., 2000) and cerebellar Purkinje neurons of patients with MS (Damarjian et al., 2004). Ectopic expression of $Na_v$ 1.8 causes abnormal firing patterns in the cerebellar Purkinje cells and motor coordination deficits in the absence of obvious signs of ataxia in mice models (Shields et al., 2012).

Importantly, treatment with the $Na_v$ 1.8 blocker N-methyl-6-amino-5-(2,3,5-trichlorophenyl)pyridine-2-carboxamide (PF 01247324) reverses cerebellar deficits in a mouse model of MS, thereby establishing a potential novel approach toward treating MS (Shields et al., 2015). Data from an ex vivo cortical development model of transcription factor 4 (TCF4) disruption on cortical neuronal physiology demonstrates in vivo evidence that TCF4 normally represses expression of the SCN10A gene in the CNS. In an ex vivo cell model and in two independent rodent models of a genetic form of autism called Pitt Hopkins Syndrome (PTHS) that is defined by TCF4 haploinsufficiency (Sweatt, 2013), TCF4 deficiency was shown to produce aberrant electrophysiological phenotypes characterized by a significant reduction in action potential output and these phenotypes were associated with increased expression of SCN10A ($Na_v$ 1.8) (Rannals et al., 2016). Furthermore, it has been shown in these PTHS models that $Na_v$ 1.8 inhibitors, such as N-[6-amino-5-(2-chloro-5-methoxyphenyl)pyridin-2-yl]-1-methyl-1H-pyrazole-5-carboxamide (PF 4531083) and 5-4(-chlorophenyl)-N-(3,5-dimethoxyphenyl)furan-2-carboxamide (A-803467), can rapidly reverse some of the excitability phenotypes. These results suggest that the ectopic expression in the brain of the normally peripherally-restricted sodium channel $Na_v$ 1.8 may drive some of the symptoms of PTHS and that inhibitors of $Na_v$ 1.8 will have therapeutic value for patients with PTHS.

The $Na_v$ 1.8 channel also is expressed in structures relating to the back, (Bucknill et al., 2002), and tooth pulp (Renton et al., 2005), and there is evidence for a role of the $Na_v$ 1.8 channel in causalgia (Shembalkar et al., 2001) and inflammatory bowel conditions (Beyak and Vanner, 2005).

$Na_v$ 1.8 is significantly different from most other members of the family of voltage gated ion channels in that it is "resistant" to inhibition by the classical sodium channel inhibitor tetrodotoxin, which inhibits most other members of the family (Cestele and Catterall, 2000). $Na_v$ 1.8 inhibitors, such as N-methyl-6-amino-5-(2,3,5-trichlorophenyl)pyridine-2-carboxamide (PF 01247324) (Bagal et al., 2015), 5-4(-chlorophenyl)-N-(3,5-dimethoxyphenyl)furan-2-carboxamide (A-803467) (Kort et al., 2008), and 5-(4-butoxy-3-chlorophenyl)-N-[[2-(4-morpholinyl)-3-pyridinyl]methyl-3-pyridine carboxamide (A-887826) (Zhang et al., 2010), are known in the literature (see FIG. 1 (prior art)). Efficacy in a variety of pain models was examined with effects seen in both inflammatory and neuropathic pain rodent models (Jarvis et al., 2007; Payne et al., 2015). These compounds, and ones like them, suffer from a variety of drawbacks, including selectivity versus other ion channels and poor pharmacokinetics.

SUMMARY

In some aspects, the presently disclosed subject matter provides a compound of formula (I):

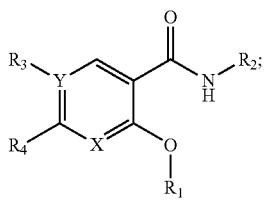

wherein:
X is —CH— or nitrogen;
Y is carbon or nitrogen, provided that at least one of X and Y is nitrogen;
$R_1$ is aryl or heteroaryl, wherein the aryl or heteroaryl is unsubstituted or substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;
$R_2$ is selected from the group consisting of aryl, heteroaryl, and heterocycle, wherein the aryl, heteroaryl, and heterocycle unsubstituted or are substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;
$R_3$, when Y is carbon, is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$, —$N^+$(=O)—$O^-$, and is absent when Y is nitrogen;
$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or
$R_3$ and $R_4$ together form a $C_3$-$C_5$ carbocyclic ring including carbon atoms to which $R_3$ and $R_4$ are attached;
and pharmaceutically acceptable salts thereof.
In certain aspects of the compound of formula (I):
X is —CH— or nitrogen;
Y is carbon or nitrogen, provided that at least one of X and Y is nitrogen;
$R_1$ is selected from the group consisting of phenyl or pyridinyl wherein the phenyl or pyridinyl is unsubstituted or substituted with one or more groups selected from the group consisting of substituted or unsubstituted $C_1$-$C_8$ alkyl, halogen, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, and —S—$CF_3$;
$R_2$ is selected from the group consisting of phenyl, pyridyl, pyrimidinyl, pyridazinyl, pyrazolyl, pyridine-1-oxide, 1,2,3-thiadiazolyl, 1,2,4-triazolyl, and 1,3-benzothiazolyl, wherein the phenyl, pyridyl, pyrimidinyl, pyridazinyl, pyridine-1-oxide, 1,2,3-thiadiazolyl, 1,2,4-triazolyl, and 1,3-benzothiazolyl, are unsubstituted or are substituted with one or more groups selected from the group consisting of unsubstituted or substituted $C_1$-$C_8$ alkyl, halogen, cyano, oxo, —O—$R_5$, wherein $R_5$ is selected from the group consisting of $C_1$-$C_8$ alkyl, —$CF_3$, and —$CHF_2$, —$(CH_2)_q$—OH, wherein q is an integer selected from the group consisting of 1, 2, 3, 4, 5, 6, 7, and 8, —$NR_6R_7$, wherein $R_6$ and $R_7$ are selected from the group consisting of H and $C_1$-$C_4$ alkyl, morpholinyl, oxazolyl, —C(=O)—$R_8$, wherein $R_8$ is selected from the group consisting of —$NR_6R_7$, wherein $R_6$ and $R_7$ are selected from the group consisting of H and $C_1$-$C_4$ alkyl, and $C_1$-$C_4$ alkyl, —S(=O)—$R_9$, —S(=O)$_2$—$R_9$, —S(=O)(=$NR_{10}$)—$R_{11}$, and —N=S(=O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Ru is $C_1$-$C_4$ alkyl, provided that when Y is nitrogen and $R_2$ is phenyl or pyridyl, $R_8$ cannot be —$NR_6R_7$;
$R_3$, when Y is carbon, is selected from the group consisting of hydrogen, cyano, halogen, —$CF_3$, $C_1$-$C_8$ alkoxyl, —O—CH(F)$_2$, substituted or unsubstituted $C_1$-$C_8$ alkyl, $C_3$-$C_8$ cycloalkyl, $NO_2$, and is absent when Y is nitrogen;
$R_4$ is selected from the group consisting of hydrogen, cyano, halogen, $C_1$-$C_8$ alkoxyl, —$CF_3$, substituted or unsubstituted $C_1$-$C_8$ alkyl, and morpholinyl, provided that $R_3$ and $R_4$ are not hydrogen at the same time; or
$R_3$ and $R_4$ together form a $C_3$-$C_5$ carbocyclic ring including carbon atoms to which $R_3$ and $R_4$ are attached;
and pharmaceutically acceptable salts thereof.
In more certain aspects of the compound of formula (I), the compound has the following structure:

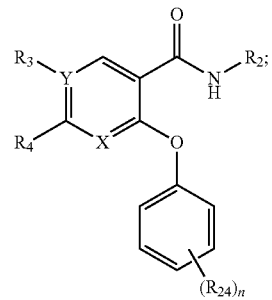

wherein:
X is —CH— or nitrogen;
Y is carbon or nitrogen, provided that at least one of X and Y is nitrogen;
$R_2$ is selected from the group consisting of aryl, heteroaryl, and heterocycle, wherein the aryl, heteroaryl, and heterocycle unsubstituted or are substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;
$R_3$, when Y is carbon, is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$, and is absent when Y is nitrogen;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached;

n is an integer selected from 0, 1, 2, 3, 4, and 5;

each $R_{24}$ is independently selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;

and pharmaceutically acceptable salts thereof.

In particular aspects of the compound of formula (I'), $R_2$ is selected from the group consisting of:

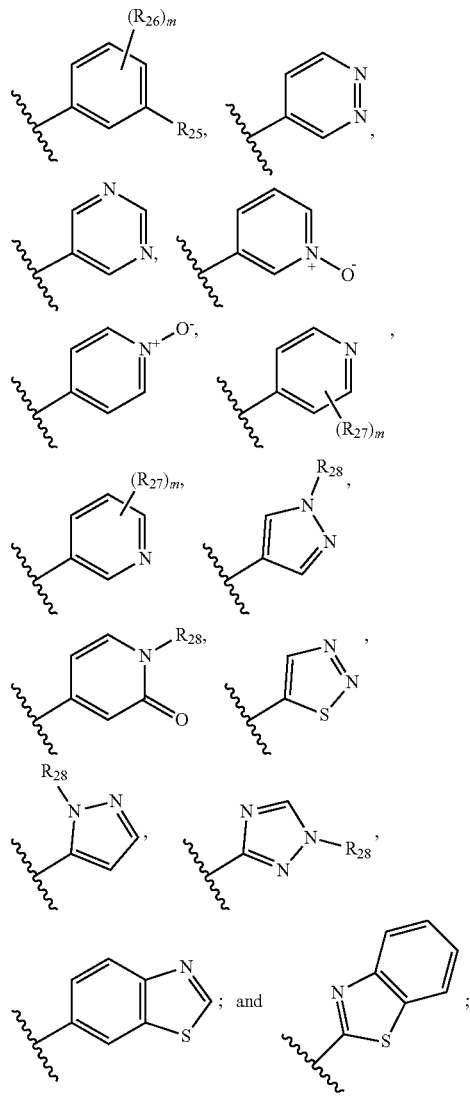

wherein:

m is an integer selected from the group consisting of 0, 1, 2, 3, and 4;

$R_{25}$ is selected from the group consisting of H, morpholinyl, oxazolyl, halogen, cyano, —$(CH_2)_q$—OH, wherein q is an integer selected from the group consisting of 1, 2, 3, 4, 5, 6, 7, and 8, —C(=O)—$R_8$, wherein $R_8$ is selected from the group consisting of —$NR_6R_7$ and $C_1$-$C_4$ alkyl, wherein $R_6$ and $R_7$ are selected from the group consisting of H and $C_1$-$C_4$ alkyl, —S(=O)—$R_9$, —S(=O)$_2$—$R_9$, —S(=O)(=$NR_{10}$)—$R_{11}$, and —N=S(=O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Ru is $C_1$-$C_4$ alkyl, provided that when Y is nitrogen and $R_2$ is phenyl or pyridyl, $R_8$ cannot be —$NR_6R_7$;

$R_{26}$ is halogen or cyano;

each $R_{27}$ is independently selected from the group consisting of H, halogen, $C_1$-$C_8$ alkoxyl, cyano,—and $NR_6R_7$; and each $R_{28}$ is independently H or $C_1$-$C_4$ alkyl;

In other aspects, the presently disclosed subject matter provides a method for modulating a $Na_v$ 1.8 sodium ion channel, the method comprising administering to a subject in need thereof, a modulating-effective amount of a compound of formula (I) to the subject.

In other aspects, the presently disclosed subject matter provides a method for inhibiting $Na_v$ 1.8, the method comprising administering to a subject in need thereof, an inhibiting-effective amount of a compound of formula (I) to the subject.

In yet other aspects, the presently disclosed subject matter provides a method for treating a condition, disease, or disorder associated with an increased $Na_v$ 1.8 activity or expression, the method comprising administering to a subject in need of treatment thereof a therapeutically effective amount of a compound of formula (I) to the subject.

In certain aspects, the condition, disease, or disorder associated with an increased $Na_v$ 1.8 activity or expression is selected from the group consisting of pain, respiratory diseases, neurological disorders, and psychiatric diseases, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

BRIEF DESCRIPTION OF THE FIGURES

Figure 1:
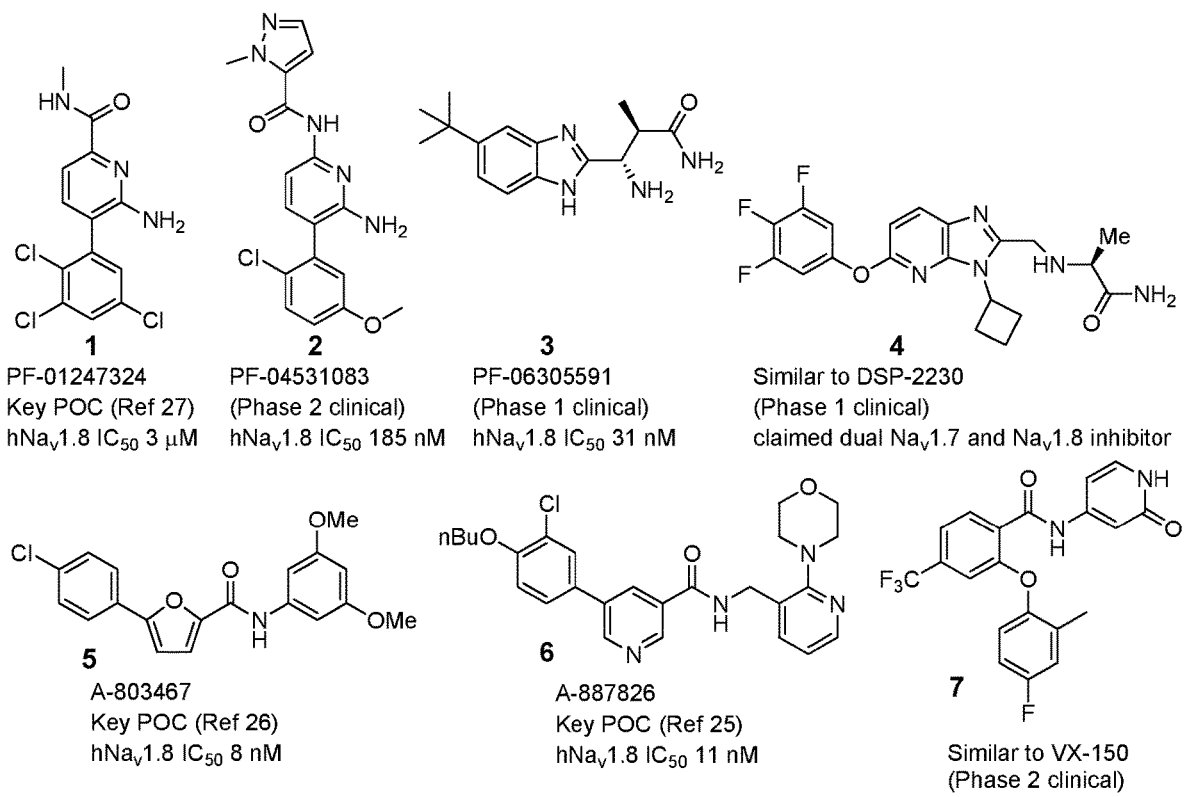

Having thus described the presently disclosed subject matter in general terms, reference will now be made to the accompanying Figure, which are not necessarily drawn to scale, and wherein:

FIG. 1 is representative of preclinical and clinical $Na_v$ 1.8 inhibitors known in the art (prior art).

Figure 2:
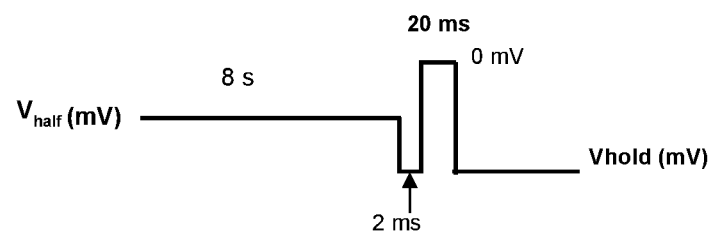

FIG. 2 is representative of Protocol 1 in which cells were initially voltage clamped at a holding potential of –100 mV to maintain $Na_v$ 1.8 in a closed resting state.

DETAILED DESCRIPTION

The presently disclosed subject matter now will be described more fully hereinafter. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

I. Pyridine Carboxamide Compounds for Inhibiting $Na_V 1.8$

The presently disclosed subject matter provides sodium channel inhibitors and their use for treating a condition, disease, or disorder associated with an increased $Na_v$ 1.8 activity or expression.

In some embodiments, the presently disclosed subject matter provides a compound of formula (I):

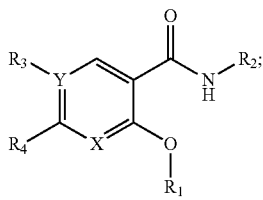

wherein:
X is —CH— or nitrogen;
Y is carbon or nitrogen, provided that at least one of X and Y is nitrogen;
$R_1$ is aryl or heteroaryl, wherein the aryl or heteroaryl is unsubstituted or substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;
$R_2$ is selected from the group consisting of aryl, heteroaryl, and heterocycle, wherein the aryl, heteroaryl, and heterocycle unsubstituted or are substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;
$R_3$, when Y is carbon, is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$, and is absent when Y is nitrogen;
$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or
$R_3$ and $R_4$ together form a $C_3$-$C_5$ carbocyclic ring including carbon atoms to which $R_3$ and $R_4$ are attached;
and pharmaceutically acceptable salts thereof.
In some embodiments of the compound of formula (I):
X is —CH— or nitrogen;
Y is carbon or nitrogen, provided that at least one of X and Y is nitrogen;

$R_1$ is phenyl or pyridinyl wherein the phenyl or pyridinyl is unsubstituted or substituted with one or more groups selected from the group consisting of substituted or unsubstituted $C_1$-$C_8$ alkyl, halogen, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, and —S—$CF_3$;
$R_2$ is selected from the group consisting of phenyl, pyridyl, pyrimidinyl, pyridazinyl, pyrazolyl, pyridine-1-oxide, 1,2,3-thiadiazolyl, 1,2,4-triazolyl, and 1,3-benzothiazolyl, wherein the phenyl, pyridyl, pyrimidinyl, pyridazinyl, pyridine-1-oxide, 1,2,3-thiadiazolyl, 1,2,4-triazolyl, and 1,3-benzothiazolyl, are unsubstituted or are substituted with one or more groups selected from the group consisting of unsubstituted or substituted $C_1$-$C_8$ alkyl, halogen, cyano, oxo, —O—$R_5$, wherein $R_5$ is selected from the group consisting of $C_1$-$C_8$ alkyl, —$CF_3$, and —$CHF_2$, —$(CH_2)_q$—OH, wherein q is an integer selected from the group consisting of 1, 2, 3, 4, 5, 6, 7, and 8, —$NR_6R_7$, wherein $R_6$ and $R_7$ are selected from the group consisting of H and $C_1$-$C_4$ alkyl, morpholinyl, oxazolyl, —C(=O)—$R_8$, wherein $R_8$ is selected from the group consisting of —$NR_6R_7$, wherein $R_6$ and $R_7$ are selected from the group consisting of H and $C_1$-$C_4$ alkyl, and $C_1$-$C_4$ alkyl, —S(=O)—$R_9$, —S(=O)$_2$—$R_9$, —S(=O)(=$NR_{10}$)—Rn, and —N=S(=O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Rn is $C_1$-$C_4$ alkyl, provided that when Y is nitrogen and $R_2$ is phenyl or pyridyl, $R_8$ cannot be —$NR_6R_7$;
$R_3$, when Y is carbon, is selected from the group consisting of hydrogen, cyano, halogen, —$CF_3$, $C_1$-$C_8$ alkoxyl, —O—CH(F)$_2$, substituted or unsubstituted $C_1$-$C_8$ alkyl, $C_3$-$C_8$ cycloalkyl, —$NO_2$, and is absent when Y is nitrogen;
$R_4$ is selected from the group consisting of hydrogen, cyano, halogen, $C_1$-$C_8$ alkoxyl, —$CF_3$, substituted or unsubstituted $C_1$-$C_8$ alkyl, and morpholinyl, provided that $R_3$ and $R_4$ are not hydrogen at the same time; or
$R_3$ and $R_4$ together form a $C_3$-$C_5$ carbocyclic ring including carbon atoms to which $R_3$ and $R_4$ are attached;
and pharmaceutically acceptable salts thereof.
In certain embodiments of the compound of formula (I), the compound has the following structure:

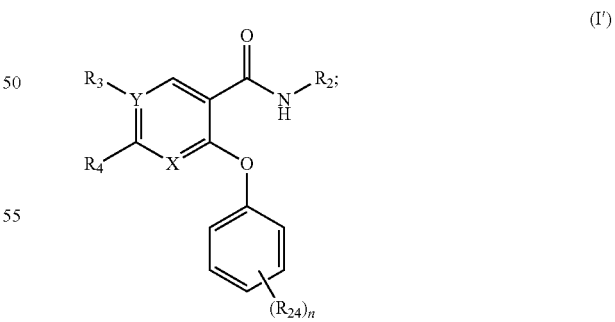

wherein:
X is —CH— or nitrogen;
Y is carbon or nitrogen, provided that at least one of X and Y is nitrogen;
$R_2$ is selected from the group consisting of aryl, heteroaryl, and heterocycle, wherein the aryl, heteroaryl, and heterocycle unsubstituted or are substituted with one or more groups selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, arylalkoxyl, oxo, alkylsulfinyl, alkylsulfonyl, alkyliminosulfanonyl, alkylsulfoxide, sulfonamide, morpholinyl, and oxazolyl;

$R_3$, when Y is carbon, is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$, and is absent when Y is nitrogen;

$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl, provided that $R_3$ and $R_4$ are not hydrogen at the same time; or $R_3$ and $R_4$ together form a $C_3$-$C_5$ carbocyclic ring including carbon atoms to which $R_3$ and $R_4$ are attached;

n is an integer selected from 0, 1, 2, 3, 4, and 5;

each $R_{24}$ is independently selected from the group consisting of mono-, di-, and trihalo-$C_1$-$C_4$ alkyl, substituted or unsubstituted $C_1$-$C_8$ alkyl, $C_3$-$C_{10}$ cycloalkyl, halogen, heteroaryl, cyano, amino, nitro, aryloxyl, aryl, $C_1$-$C_8$ alkoxyl, mono-, di-, or trihaloalkoxyl, sulfanyl, trifluoromethylsulfanyl, and arylalkoxyl;

and pharmaceutically acceptable salts thereof.

In particular embodiments of the compound of formula (I') $R_2$ is selected from the group consisting of:

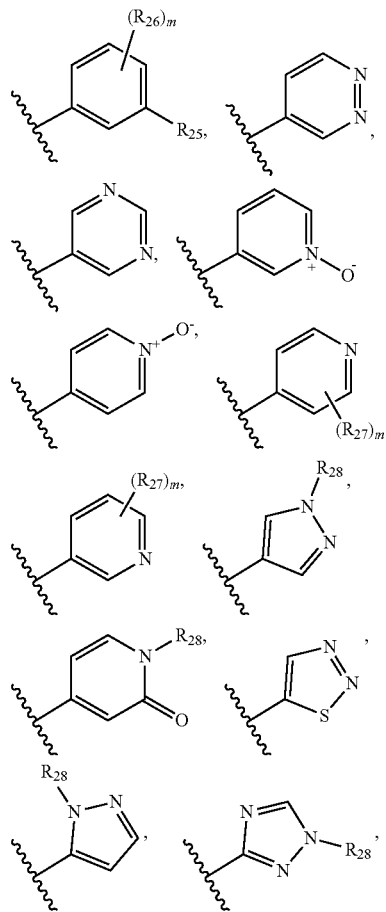

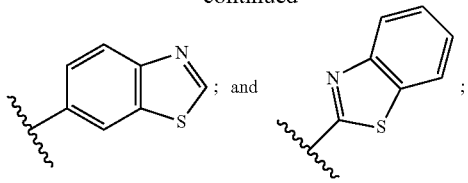

wherein:

m is an integer selected from the group consisting of 0, 1, 2, 3, and 4;

$R_{25}$ is selected from the group consisting of H, morpholinyl, oxazolyl, halogen, cyano, —$(CH_2)_q$—OH, wherein q is an integer selected from the group consisting of 1, 2, 3, 4, 5, 6, 7, and 8, —C(=O)—$R_8$, wherein $R_8$ is selected from the group consisting of —$NR_6R_7$ and $C_1$-$C_4$ alkyl, wherein $R_6$ and $R_7$ are selected from the group consisting of H and $C_1$-$C_4$ alkyl, —S(=O)—$R_9$, —S(=O)$_2$—$R_9$, —S(=O)(=$NR_{10}$)—$R_{11}$, and —N=S(=O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Ru is $C_1$-$C_4$ alkyl, provided that when Y is nitrogen and $R_2$ is phenyl or pyridyl, $R_8$ cannot be —$NR_6R_7$;

$R_{26}$ is halogen or cyano;

each $R_{27}$ is independently selected from the group consisting of H, halogen, $C_1$-$C_8$ alkoxyl, cyano,—and $NR_6R_7$; and each $R_{28}$ is independently H or $C_1$-$C_4$ alkyl;

In some embodiments, the compound of formula (I) is a compound of formula (I-F):

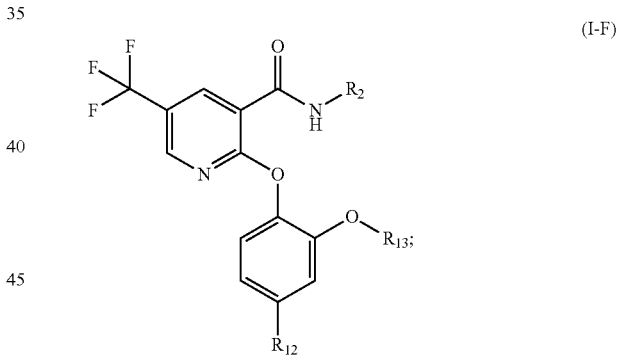

wherein:

$R_2$ is selected from the group consisting of aryl and heteroaryl, wherein the aryl or heteroaryl is optionally substituted with a substituent group selected from the group consisting of cyano, heterocycloalkyl, —S(=O)—$R_9$, —S(=O)$_2$—$R_9$, —S(=O)(=$NR_{10}$)—$R_{11}$, and —N=S(=O)—$(R_{11})_2$, wherein each $R_9$ is independently $C_1$-$C_4$ alkyl, —$CF_3$, or —$NR_6R_7$, wherein $R_6$ and $R_7$ are selected from the group consisting of H and $C_1$-$C_4$ alkyl, $R_{10}$ is H or $C_1$-$C_4$ alkyl, and Ru is $C_1$-$C_4$ alkyl;

$R_{12}$ is halogen; and $R_{13}$ is $C_1$-$C_4$ alkyl.

In some embodiments of the compound of formula (I-F), the aryl and heteroaryl are selected from the group consisting of phenyl, benzothiazolyl, pyridyl, pyridyl N-oxide, and pyrimidinyl, each of which is optionally substituted with a substituent group selected from the group consisting of cyano, heterocycloalkyl, —S(=O)—$R_9$, —S(=O)$_2$—$R_9$, —S(=O)(=NR$_{10}$)—R$_{11}$, and —N=S(=O)—(R$_{11}$)$_2$, wherein each R$_9$ is independently C$_1$-C$_4$ alkyl, —CF$_3$, or —NR$_6$R$_7$, R$_{10}$ is H or C$_1$-C$_4$ alkyl, and Ru is C$_1$-C$_4$ alkyl;

R$_{12}$ is fluorine; and

R$_{13}$ is methyl.

In certain embodiments of the compound of formula (I-F), R$_2$ is selected from the group consisting of 1,3-benzothiazol-6-yl, 3-morpholinophenyl, 3-cyanophenyl, 4-cyanophenyl, 3-pyridyl, 4-pyridyl, 6-cyano-3-pyridyl, 3-methylsulfinylphenyl, 3-oxazol-5-ylphenyl, 3-dimethylsulfamoylphenyl, 1,3-benzothiazol-2-yl, pyrimidin-4-yl, (trifluorosulfonyl)phenyl, 3-(methylsulfonimidoyl)phenyl, 2-methoxy-4-pyridyl, 3-(N,S-dimethylsulfonimidoyl)phenyl, 2-methyl-4-pyridyl, 6-methyl-3-pyridyl, pyridazine-4-yl, and dimethyl(oxo)-λ$^6$-sulfanylidene]amino]phenyl.

In some embodiments of the compound of formula (I), the compound is a compound of formula (I-G):

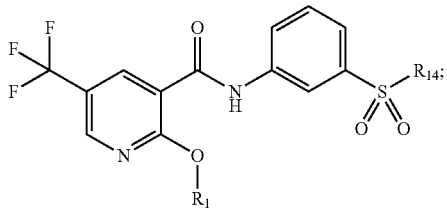

(I-G)

wherein:

R$_1$ is phenyl substituted with one or more of C$_1$-C$_8$ alkyl, halogen, and C$_1$-C$_8$ alkoxyl, and wherein the C$_1$-C$_8$ alkoxyl is optionally substituted with one or more halogen; and R$_{14}$ is C$_1$-C$_4$ alkyl.

In some embodiments of the compound of formula (I-G), R$_1$ is selected from the group consisting of 2,4-dichlorophenyl, 2,4-dimethylphenyl, 2-chloro-4-methoxyphenyl, 2-propylphenyl, 2-methoxy-4-methylphenyl, 2-methoxy-4-chlorophenyl, 2-isopropoxyphenyl, 4-difluoromethoxyphenyl, 2,4-dimethoxyphenyl, 2-chloro-4-methoxyphenyl, 3,4-difluorophenyl, and 2-chloro-4-fluorophenyl.

In some embodiments of the compound of formula (I), the compound is a compound of formula (I-H-i):

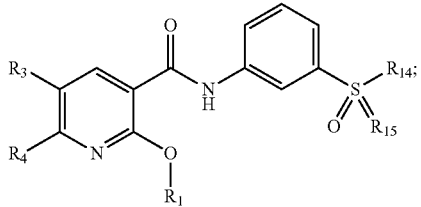

(I-H-i)

wherein:

R$_1$ is selected from the group consisting of phenyl, pyridyl, and 1,3-benzothiazol-4yl, wherein the phenyl and pyridyl can be unsubstituted or substituted with one or more of halogen, C$_1$-C$_8$ alkyl, —O—R$_5$, wherein R$_5$ is selected from the group consisting of C$_1$-C$_8$ alkyl, —CF$_3$, —CHF$_2$, and —(CH$_2$)$_p$—CF$_3$, wherein p is an integer selected from the group consisting of 1, 2, 3, 4, 5, 6, 7, and 8, —S—CF$_3$, —NR$_6$R$_7$, wherein R$_6$ and R$_7$ are selected from the group consisting of H and C$_1$-C$_4$ alkyl;

R$_3$ and R$_4$ are H or —CF$_3$, provided that if R$_3$ is H, then R$_4$ is —CF$_3$ and if R$_4$ is H, then R$_3$ is —CF$_3$;

R$_{14}$ is C$_1$-C$_4$ alkyl; and

R$_{15}$ is O or NR$_{10}$, wherein R$_{10}$ is H or C$_1$-C$_4$ alkyl.

In some embodiments of the compound of formula (I-H-i), R$_1$ is selected from the group consisting of phenyl, 4-fluorophenyl, 4-fluoro-2-methoxyphenyl, 2-chloro-4-fluorophenyl, 2-methyl-4-trifluromethoxyphenyl, 4-trifluoromethoxyphenyl, difluoromethoxyphenyl, 3-fluoro-4-trifluoromethoxyphenyl, 3-fluorophenyl, 2,5-difluorophenyl, 4-methylphenyl, 3-chloro-5-flurophenyl, 2-isopropylphenyl, 3,4-difluorophenyl, 2,4-difluorophenyl, 3,5-difluorophenyl, 4-(2,2,2-trifluoroethoxy)phenyl, 4-(trifluoromethylsulfanyl)phenyl, 2-dimethylaminophenyl, 2-trifluromethylphenyl, 2,4-dimethoxyphenyl, 3,4,5-trifluorophenyl, 3,5-dichlorophenyl, 6-trifluoromethyl-3-pyridyl, 1,3-benzothiazol-4-yl, 4-difluoromethoxyphenyl, 2-chloro-4-fluorophenyl, 2-chloro-4-methoxyphenyl, and 2-chlorophenyl.

In some embodiments of the compound of formula (I), the compound is a compound of formula (I-H-ii):

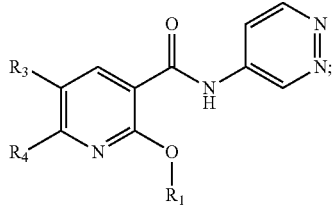

(I-H-ii)

wherein:

R$_1$ is selected from the group consisting of phenyl, pyridyl, and 1,3-benzothiazol-4yl, wherein the phenyl or pyridyl can be unsubstituted or substituted with one or more of halogen, C$_1$-C$_8$ alkyl, —O—R$_5$, wherein R$_5$ is selected from the group consisting of C$_1$-C$_8$ alkyl, —CF$_3$, —CHF$_2$, and —(CH$_2$)$_p$—CF$_3$, wherein p is an integer selected from the group consisting of 1, 2, 3, 4, 5, 6, 7, and 8, —S—CF$_3$, —NR$_6$R$_7$, wherein R$_6$ and R$_7$ are selected from the group consisting of H and C$_1$-C$_4$ alkyl; and R$_3$ and R$_4$ are H or —CF$_3$, provided that if R$_3$ is H, then R$_4$ is —CF$_3$ and if R$_4$ is H, then R$_3$ is —CF$_3$.

In some embodiments of the compound of formula (I-H-ii), R$_1$ is selected from the group consisting of 2,4-dichlorophenyl, 4-difluoromethoxyphenyl, and 2-chloro-4-methoxyphenyl.

In some embodiments of the compound of formula (I0, the compound is a compound of formula (I-I):

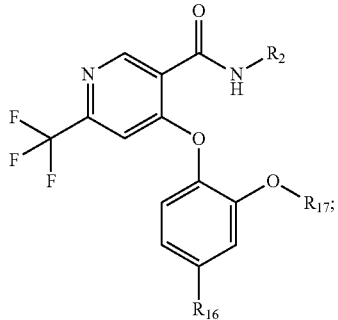

(I-I)

wherein:

$R_2$ is selected from the group consisting of phenyl, pyridazinyl, and pyridyl, wherein the phenyl can be substituted with one or more of halogen, —S(=O)—$R_9$, —S(=O)$_2$—$R_9$, and —S(=O)(=N$R_{10}$)—$R_{11}$, wherein each $R_9$ is independently $C_1$-$C_4$ alkyl, —CF$_3$, or —N$R_6R_7$, wherein $R_6$ and $R_7$ are selected from the group consisting of H and $C_1$-$C_4$ alkyl, $R_{10}$ is H or $C_1$-$C_4$ alkyl, and $R_1$ is $C_1$-$C_4$ alkyl;

$R_{16}$ is halogen; and $R_{17}$ is $C_1$-$C_4$ alkyl.

In some embodiments of the compound of formula (I-I), $R_2$ is selected from the group consisting of 3-methylsulfinylphenyl, 2-fluoro-5-methylsulfonylphenyl, 3-(N,S-dimethylsulfonimidoyl)phenyl, pyridazinyl, and pyridyl.

In some embodiments of the compound of formula (I), the compound is a compound of formula (I-J):

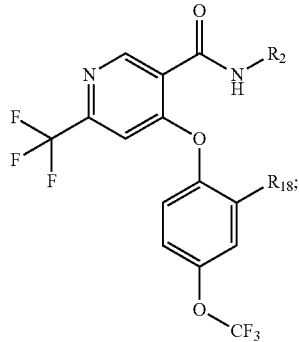

(I-J)

wherein:

$R_2$ is selected from the group consisting of phenyl and pyridyl, wherein the phenyl is substituted with one or more of halogen, —C(=O)—$R_8$, wherein $R_8$ is $C_1$-$C_4$ alkyl, —S(=O)—$R_9$, —S(=O)$_2$—$R_9$, —S(=O)(=N$R_{10}$)—$R_{11}$, and —N=S(=O)—($R_{11}$)$_2$, wherein each $R_9$ is independently $C_1$-$C_4$ alkyl, —CF$_3$, or —N$R_6R_7$, $R_{10}$ is H or $C_1$-$C_4$ alkyl, and Ru is $C_1$-$C_4$ alkyl; and $R_{18}$ is halogen.

In some embodiments of the compound of formula (I-J), $R_2$ is selected from the group consisting of 3-methylsulfonylphenyl, 3-methylsulfinylphenyl, 3-(dimethylsulfamoyl)phenyl, 2-fluoro-5-methylsulfonylphenyl, 3-(methylsulfonimidoyl)phenyl, 3-carbamoylphenyl, 3(N,S-dimethylsulfonimidoyl)phenyl, 3-pyridyl, and 4-pyridyl.

In some embodiments of the compound of formula (I), the compound is a compound of formula (I-K):

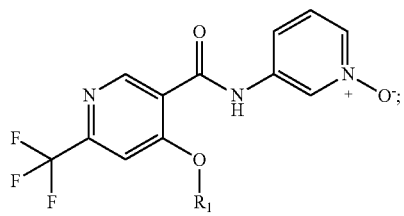

(I-K)

wherein:

$R_1$ is phenyl substituted with one or more of halogen, $C_1$-$C_8$ alkyl, —O—$R_5$, wherein $R_5$ is selected from the group consisting of $C_1$-$C_8$ alkyl, —CF$_3$, —CHF$_2$, and —(CH$_2$)$_p$—CF$_3$, wherein p is an integer selected from the group consisting of 1, 2, 3, 4, 5, 6, 7, and 8.

In some embodiments of the compound of formula (I-K), $R_1$ is selected from the group consisting of 4-fluoro-2-methoxyphenyl, 4-fluoro-2-methylphenyl, 4-difluoromethoxyphenyl, 4-trifluoromethoxyphenyl, 2,4-dimethoxyphenyl, 2,4-difluorophenyl, and 3,4-difluorophenyl.

In some embodiments of the compound of formula (I), the compound is a compound of formula (I-L):

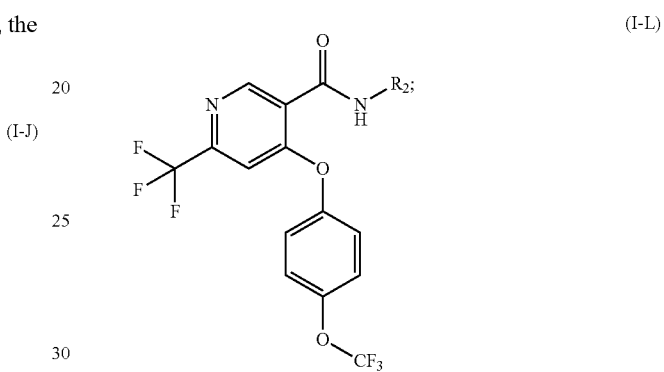

(I-L)

wherein $R_2$ is selected from the group consisting of phenyl, pyridyl, and pyridazin-4-yl, wherein the phenyl is substituted with —S(=O)$_2$—$R_9$, —S(=O)(=N$R_{10}$)—$R_{11}$, and —N=S(=O)—($R_{11}$)$_2$, wherein each $R_9$ is independently $C_1$-$C_4$ alkyl or —N$R_6R_7$, wherein $R_6$ and $R_7$ are each H, $R_{10}$ is H or $C_1$-$C_4$ alkyl, and $R_1$ is $C_1$-$C_4$ alkyl. In particular embodiments, $R_2$ is 3-(N,S-dimethylsulfonimidoyl)phenyl.

In some embodiments of the compound of formula (I), the compound is a compound of formula (I-M-i):

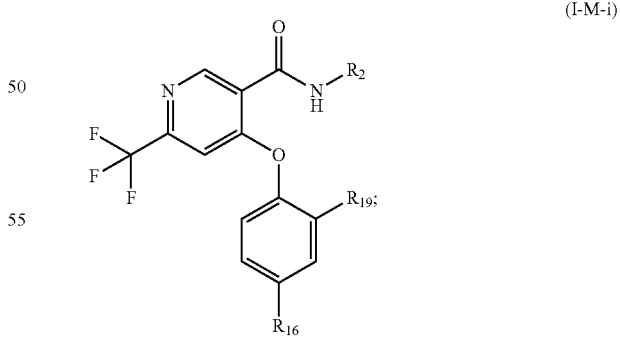

(I-M-i)

wherein:

$R_2$ is 3-(N,S-dimethylsulfonimidoyl)phenyl or pyridizin-4-yl;

$R_{16}$ is halogen; and $R_{19}$ is $C_1$-$C_4$ alkyl.

In some embodiments of the compound of formula (I), the compound is a compound of formula (I-M-ii):

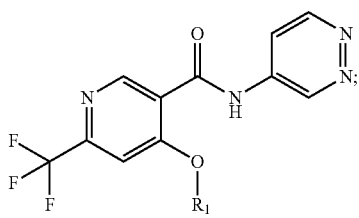
(I-M-ii)

wherein R₁ is selected from the group consisting of 4-trifluoromethoxyphenyl, 4-difluoromethoxyphenyl, 2-chloro-4-trifluoromethoxyphenyl, 2,4-dimethoxyphenyl, and 2,4-difluorophenyl.

In some embodiments of the compound of formula (I), the compound is a compound of formula (I-M-iii):

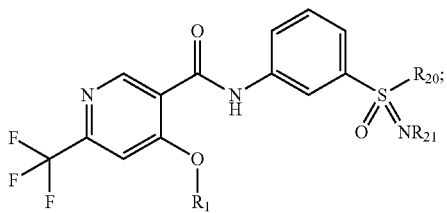
(I-M-iii)

wherein:

R₁ is selected from the group consisting of 4-difluoromethoxyphenyl, 2,4-dimethoxyphenyl, and 2,4-difluorophenyl;

R₂₀ is C₁-C₄ alkyl; and

R₂₁ is H or C₁-C₄ alkyl.

In some embodiments of the compound of formula (I), the compound is a compound of formula (I-M-iv):

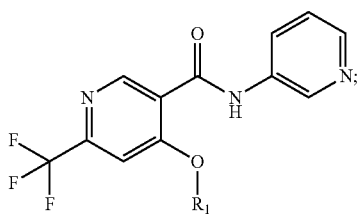
(I-M-iv)

wherein R₁ is selected from the group consisting of 4-difluoromethoxyphenyl, 4-trifluoromethoxyphenyl, 2-chloro-4-trifluoromethoxyphenyl, 2,4-dimethoxyphenyl, and 2,4-difluorophenyl.

In some embodiments of the compound of formula (I), the compound is a compound of formula (I-N):

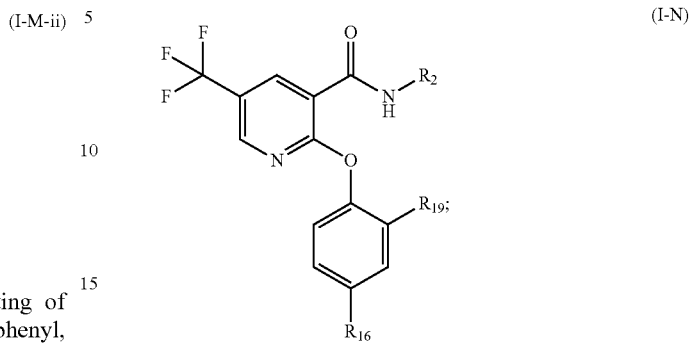
(I-N)

wherein:

R₂ is selected from the group consisting of 3-(N,S-dimethylsulfonimidoyl)phenyl, 3-(methylsulfonimidoyl)phenyl, and pyridazine-4-yl;

R₁₆ is halogen; and

R₁₉ is C₁-C₄ alkyl.

In some embodiments of the compound of formula (I), the compound is a compound of formula (I-O):

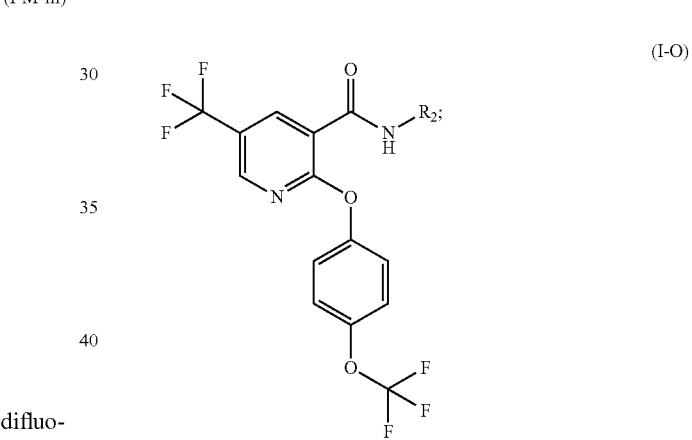
(I-O)

wherein R₂ is selected from the group consisting of phenyl, pyridyl, and pyridazin-4-yl, wherein the phenyl is substituted with —S(=O)₂—R₉, —S(=O)(=NR₁₀)—R₁₁, and —N=S(=O)—(R₁₁)₂, wherein each R₉ is independently C₁-C₄ alkyl or —NR₆R₇, wherein R₆ and R₇ are each H, R₁₀ is H or C₁-C₄ alkyl, and R₁₁ is C₁-C₄ alkyl.

In some embodiments of the compound of formula (I), the compound is a compound of formula (I-P):

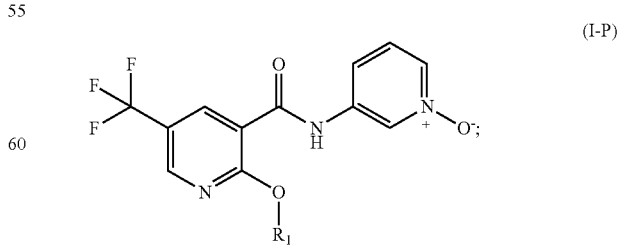
(I-P)

wherein R₁ is selected from the group consisting of 4-fluoro-2-methylphenyl, 4-fluoro-2-methoxyphenyl, 2,4-difluorophenyl, 4-difluoromethoxyphenyl, 2,4-dimethoxyphenyl, 2-chloro-4-methoxyphenyl, 3,4-diflurophenyl, and 2-chloro-4-fluorophenyl.

In some embodiments of the compound of formula (I), the compound is a compound of formula (I-Q):

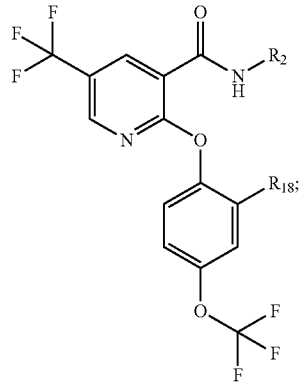

(I-Q)

wherein:
R$_2$ is selected from the group consisting of phenyl, pyridyl, pyrazolyl, pyrimidinyl, pyridazinyl, thiadiazolyl, pyrazolyl, and 1,2,4-triazolyl;
wherein:
phenyl is substituted with one or more groups selected from the group consisting of unsubstituted or substituted C$_1$-C$_8$ alkyl, halogen, cyano, oxo, —O—R$_5$, wherein R$_5$ is selected from the group consisting of C$_1$-C$_8$ alkyl, —CF$_3$, and —CHF$_2$, —(CH$_2$)$_q$—OH, wherein q is an integer selected from the group consisting of 1, 2, 3, 4, 5, 6, 7, and 8, —NR$_6$R$_7$, wherein R$_6$ and R$_7$ are selected from the group consisting of H and C$_1$-C$_4$ alkyl, morpholinyl, oxazolyl, —C(=O)—R$_8$, wherein R$_8$ is selected from the group consisting of —NR$_6$R$_7$, wherein R$_6$ and R$_7$ are selected from the group consisting of H and C$_1$-C$_4$ alkyl, and C$_1$-C$_4$ alkyl, —S(=O)—R$_9$, —S(=O)$_2$—R$_9$, —S(=O)(=NR$_{10}$)—R$_{11}$, and —N=S(=O)—(R$_{11}$)$_2$, wherein each R$_9$ is independently C$_1$-C$_4$ alkyl, —CF$_3$, or —NR$_6$R$_7$, wherein R$_6$ and R$_7$ are selected from the group consisting of H and C$_1$-C$_4$ alkyl, R$_{10}$ is H or C$_1$-C$_4$ alkyl, and R$_1$ is C$_1$-C$_4$ alkyl;
pyridyl is unsubstituted or substituted with C$_1$-C$_8$ alkyl, oxo, C$_1$-C$_8$ alkoxyl, and halogen; and
R$_{18}$ is halogen.

In some embodiments of the compound of formula (I), the compound is a compound of formula (I-R):

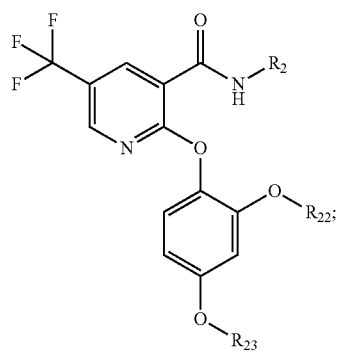

(I-R)

wherein:
R$_2$ is 3-(methylsulfonimidoyl)phenyl or pyridazin-4-yl; and
R$_{22}$ and R$_{23}$ are each C$_1$-C$_4$ alkyl.

In some embodiments of the compound of formula (I), the compound is a compound of formula (I-S):

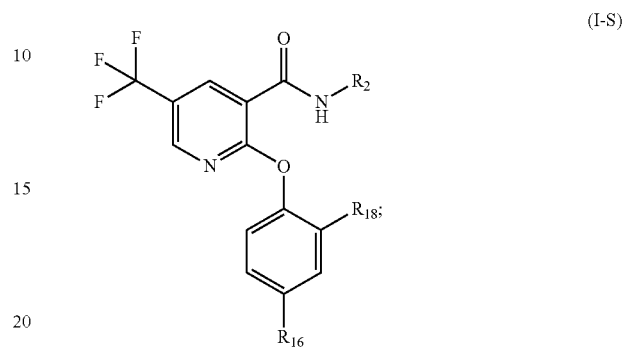

(I-S)

wherein:
R$_2$ is 3-(methylsulfonimidoyl)phenyl or pyridazin-4-yl; and
R$_{16}$ and R$_{18}$ are each halogen.

In some embodiments of the compound of formula (I), the compound of formula (I) is selected from the group consisting of:
6-chloro-2-(4-fluoro-2-methoxy-phenoxy)-N-(3-methyl-sulfonylphenyl)pyridine-3-carboxamide (intermediate 3);
N-(1,3-benzothiazol-6-yl)-2-(4-fluoro-2-methoxy-phenoxy)-5-(trifluoromethyl)pyridine-3-carboxamide (1);
2-(4-fluoro-2-methoxy-phenoxy)-N-(3-morpholinophenyl)-5-(trifluoromethyl)pyridine-3-carboxamide (2);
N-(3-cyanophenyl)-2-(4-fluoro-2-methoxy-phenoxy)-5-(trifluoromethyl)pyridine-3-carboxamide (3);
2-(4-fluoro-2-methoxy-phenoxy)-N-(3-pyridyl)-5-(trifluoromethyl)pyridine-3-carboxamide (4);
N-(4-cyanophenyl)-2-(4-fluoro-2-methoxy-phenoxy)-5-(trifluoromethyl)pyridine-3-carboxamide (5);
2-(4-fluoro-2-methoxy-phenoxy)-N-(4-pyridyl)-5-(trifluoromethyl)pyridine-3-carboxamide (6);
N-(6-cyano-3-pyridyl)-2-(4-fluoro-2-methoxy-phenoxy)-5-(trifluoromethyl)pyridine-3-carboxamide (7);
2-(4-fluoro-2-methoxy-phenoxy)-N-(3-methylsulfinylphenyl)-5-(trifluoromethyl)pyridine-3-carboxamide (8);
2-(4-fluoro-2-methoxy-phenoxy)-N-(3-oxazol-5-ylphenyl)-5-(trifluoromethyl)pyridine-3-carboxamide (9);
N-[3-(dimethylsulfamoyl)phenyl]-2-(4-fluoro-2-methoxy-phenoxy)-5-(trifluoromethyl)pyridine-3-carboxamide (10);
N-(1,3-benzothiazol-2-yl)-2-(4-fluoro-2-methoxy-phenoxy)-5-(trifluoromethyl)pyridine-3-carboxamide (11);
2-(4-fluoro-2-methoxy-phenoxy)-N-pyrimidin-4-yl-5-(trifluoromethyl)pyridine-3-carboxamide (12);
2-(4-fluoro-2-methoxy-phenoxy)-5-(trifluoromethyl)-N-[3-(trifluoromethylsulfonyl)phenyl]pyridine-3-carboxamide (13);
2-(4-fluoro-2-methoxy-phenoxy)-N-[3-(methylsulfonimidoyl)phenyl]-5-(trifluoromethyl)pyridine-3-carboxamide (14);
2-(4-fluoro-2-methoxy-phenoxy)-N-(2-methoxy-4-pyridyl)-5-(trifluoromethyl)pyridine-3-carboxamide (15);
N-[3-(N,S-dimethylsulfonimidoyl)phenyl]-2-(4-fluoro-2-methoxy-phenoxy)-5-(trifluoromethyl)pyridine-3-carboxamide (16);

2-(4-fluoro-2-methoxy-phenoxy)-N-(2-methyl-4-pyridyl)-5-(trifluoromethyl)pyridine-3-carboxamide (17);

2-(4-fluoro-2-methoxy-phenoxy)-N-(6-methyl-3-pyridyl)-5-(trifluoromethyl)pyridine-3-carboxamide (18);

2-(4-fluoro-2-methoxy-phenoxy)-N-pyridazin-4-yl-5-(trifluoromethyl)pyridine-3-carboxamide (19);

N-[3-[[dimethyl(oxo)-$\lambda^6$-sulfanylidene]amino]phenyl]-2-(4-fluoro-2-methoxy-phenoxy)-5-(trifluoromethyl)pyridine-3-carboxamide (20);

2-(2,4-dichlorophenoxy)-N-(3-methylsulfonylphenyl)-5-(trifluoromethyl)pyridine-3-carboxamide (21);

2-(4-fluoro-2-methoxy-phenoxy)-N-(3-morpholinophenyl)-5-(trifluoromethyl)pyridine-3-carboxamide (22);

2-(2-chloro-4-methoxy-phenoxy)-N-(3-methylsulfonylphenyl)-5-(trifluoromethyl)pyridine-3-carboxamide (23);

N-(3-methylsulfonylphenyl)-2-(2-propylphenoxy)-5-(trifluoromethyl)pyridine-3-carboxamide (24);

2-(2-methoxy-4-methyl-phenoxy)-N-(3-methylsulfonylphenyl)-5-(trifluoromethyl)pyridine-3-carboxamide (25);

2-(4-chloro-2-methoxy-phenoxy)-N-(3-methylsulfonylphenyl)-5-(trifluoromethyl)pyridine-3-carboxamide (26);

2-(2-isopropoxyphenoxy)-N-(3-methylsulfonylphenyl)-5-(trifluoromethyl)pyridine-3-carboxamide (27);

2-(4-(difluoromethoxy)phenoxy)-N-(pyridin-3-yl)-5-(trifluoromethyl)nicotinamide (28);

2-(2,4-dimethoxyphenoxy)-N-(pyridin-3-yl)-5-(trifluoromethyl)nicotinamide (29);

2-(2-chloro-4-methoxyphenoxy)-N-(pyridin-3-yl)-5-(trifluoromethyl)nicotinamide (30);

2-(3,4-difluorophenoxy)-N-(pyridin-3-yl)-5-(trifluoromethyl)nicotinamide (31);

2-(2-chloro-4-fluorophenoxy)-N-(pyridin-3-yl)-5-(trifluoromethyl)nicotinamide (32);

2-(2,6-dimethylphenoxy)-N-(3-methylsulfonylphenyl)-5-(trifluoromethyl)pyridine-3-carboxamide (33);

2-(4-fluorophenoxy)-N-(3-methylsulfonylphenyl)-5-(trifluoromethyl)pyridine-3-carboxamide (34);

2-(4-fluoro-2-methoxy-phenoxy)-N-(3-methylsulfonylphenyl)-5-(trifluoromethyl)pyridine-3-carboxamide (35);

2-(2-chloro-4-fluoro-phenoxy)-N-(3-methylsulfonylphenyl)-5-(trifluoromethyl)pyridine-3-carboxamide (36);

N-(3-methylsulfonylphenyl)-2-[2-methyl-4-(trifluoromethoxy)phenoxy]-5-(trifluoromethyl)pyridine-3-carboxamide (37);

N-(3-methylsulfonylphenyl)-2-[4-(trifluoromethoxy)phenoxy]-5-(trifluoromethyl)pyridine-3-carboxamide (38);

2-[4-(difluoromethoxy)phenoxy]-N-(3-methylsulfonylphenyl)-5-(trifluoromethyl)pyridine-3-carboxamide (39);

2-[3-fluoro-4-(trifluoromethoxy)phenoxy]-N-(3-methylsulfonylphenyl)-5-(trifluoromethyl)pyridine-3-carboxamide (40);

N-(3-methylsulfonylphenyl)-2-phenoxy-5-(trifluoromethyl)pyridine-3-carboxamide (41);

2-(3-fluorophenoxy)-N-(3-methylsulfonylphenyl)-5-(trifluoromethyl)pyridine-3-carboxamide (42);

2-(2,5-difluorophenoxy)-N-(3-methylsulfonylphenyl)-5-(trifluoromethyl)pyridine-3-carboxamide (43);

2-(4-methylphenoxy)-N-(3-methylsulfonylphenyl)-5-(trifluoromethyl)pyridine-3-carboxamide (44);

2-(3-chloro-5-fluoro-phenoxy)-N-(3-methylsulfonylphenyl)-5-(trifluoromethyl)pyridine-3-carboxamide (45);

2-(2-isopropylphenoxy)-N-(3-methylsulfonylphenyl)-5-(trifluoromethyl)pyridine-3-carboxamide (46);

2-(3,4-difluorophenoxy)-N-(3-methylsulfonylphenyl)-5-(trifluoromethyl)pyridine-3-carboxamide (47);

2-(2,4-difluorophenoxy)-N-(3-methylsulfonylphenyl)-5-(trifluoromethyl)pyridine-3-carboxamide (48);

2-(3,5-difluorophenoxy)-N-(3-methylsulfonylphenyl)-5-(trifluoromethyl)pyridine-3-carboxamide (49);

N-(3-methylsulfonylphenyl)-2-[4-(2,2,2-trifluoroethoxy)phenoxy]-5-(trifluoromethyl)pyridine-3-carboxamide (50);

N-(3-methylsulfonylphenyl)-5-(trifluoromethyl)-2-[4-(trifluoromethylsulfanyl)phenoxy]pyridine-3-carboxamide (51);

2-[2-(dimethylamino)phenoxy]-N-(3-methylsulfonylphenyl)-5-(trifluoromethyl)pyridine-3-carboxamide (52);

N-(3-methylsulfonylphenyl)-5-(trifluoromethyl)-2-[2-(trifluoromethyl)phenoxy]pyridine-3-carboxamide (53);

2-(2,4-dimethoxyphenoxy)-N-(3-methylsulfonylphenyl)-5-(trifluoromethyl)pyridine-3-carboxamide (54);

N-(3-methylsulfonylphenyl)-5-(trifluoromethyl)-2-(3,4,5-trifluorophenoxy)pyridine-3-carboxamide (55);

2-(3,5-dichlorophenoxy)-N-(3-methylsulfonylphenyl)-5-(trifluoromethyl)pyridine-3-carboxamide (56);

N-(3-methylsulfonylphenyl)-5-(trifluoromethyl)-2-[[6-(trifluoromethyl)-3-pyridyl]oxy]pyridine-3-carboxamide (57);

2-(1,3-benzothiazol-4-yloxy)-N-(3-methylsulfonylphenyl)-5-(trifluoromethyl)pyridine-3-carboxamide (58);

2-[4-(difluoromethoxy)phenoxy]-N-[3-(methylsulfonimidoyl)phenyl]-5-(trifluoromethyl)pyridine-3-carboxamide (59);

2-(2-chloro-4-fluoro-phenoxy)-N-[3-(methylsulfonimidoyl)phenyl]-5-(trifluoromethyl)pyridine-3-carboxamide (60);

2-(2-chloro-4-methoxy-phenoxy)-N-[3-(methylsulfonimidoyl)phenyl]-5-(trifluoromethyl)pyridine-3-carboxamide (61);

2-(2-chlorophenoxy)-N-[3-(methylsulfonimidoyl)phenyl]-5-(trifluoromethyl)pyridine-3-carboxamide (62);

2-(2,4-dichlorophenoxy)-N-pyridazin-4-yl-5-(trifluoromethyl)pyridine-3-carboxamide (63);

2-[4-(difluoromethoxy)phenoxy]-N-pyridazin-4-yl-5-(trifluoromethyl)pyridine-3-carboxamide (64);

2-(2-chloro-4-methoxy-phenoxy)-N-pyridazin-4-yl-5-(trifluoromethyl)pyridine-3-carboxamide (65);

2-(4-fluoro-2-methoxy-phenoxy)-N-(3-methylsulfonylphenyl)-6-(trifluoromethyl)pyridine-3-carboxamide (66);

4-(4-fluoro-2-methoxy-phenoxy)-N-(3-methylsulfonylphenyl)-6-(trifluoromethyl)pyridine-3-carboxamide (67);

4-(4-fluoro-2-methoxy-phenoxy)-N-(3-methylsulfinylphenyl)-6-(trifluoromethyl)pyridine-3-carboxamide (68);

4-(4-fluoro-2-methoxy-phenoxy)-N-(2-fluoro-5-methylsulfonyl-phenyl)-6-(trifluoromethyl)pyridine-3-carboxamide (69);

N-[3-(N,S-dimethylsulfonimidoyl)phenyl]-4-(4-fluoro-2-methoxy-phenoxy)-6-(trifluoromethyl)pyridine-3-carboxamide (70);

4-(4-fluoro-2-methoxy-phenoxy)-N-pyridazin-4-yl-6-(trifluoromethyl)pyridine-3-carboxamide (71);

4-(4-fluoro-2-methoxy-phenoxy)-N-(4-pyridyl)-6-(trifluoromethyl)pyridine-3-carboxamide (72);

4-[2-chloro-4-(trifluoromethoxy)phenoxy]-N-[2-(dimethylamino)-4-pyridyl]-6-(trifluoromethyl)pyridine-3-carboxamide (73);

4-[2-chloro-4-(trifluoromethoxy)phenoxy]-N-(3-methylsulfonylphenyl)-6-(trifluoromethyl)pyridine-3-carboxamide (74);

4-[2-chloro-4-(trifluoromethoxy)phenoxy]-N-(3-methylsulfinylphenyl)-6-(trifluoromethyl)pyridine-3-carboxamide (75);

4-[2-chloro-4-(trifluoromethoxy)phenoxy]-N-[3-(dimethylsulfamoyl)phenyl]-6-(trifluoromethyl)pyridine-3-carboxamide (76);

4-[2-chloro-4-(trifluoromethoxy)phenoxy]-N-(2-fluoro-5-methylsulfonyl-phenyl)-6-(trifluoromethyl)pyridine-3-carboxamide (77);
4-[2-chloro-4-(trifluoromethoxy)phenoxy]-N-(3-pyridyl)-6-(trifluoromethyl)pyridine-3-carboxamide (78);
4-[2-chloro-4-(trifluoromethoxy)phenoxy]-N-(4-pyridyl)-6-(trifluoromethyl)pyridine-3-carboxamide (79);
4-[2-chloro-4-(trifluoromethoxy)phenoxy]-N-[3-(methylsulfonimidoyl)phenyl]-6-(trifluoromethyl)pyridine-3-carboxamide (80);
4-[2-chloro-4-(trifluoromethoxy)phenoxy]-N-[3-(N,S-dimethylsulfonimidoyl)phenyl]-6-(trifluoromethyl)pyridine-3-carboxamide (82);
4-[2-chloro-4-(trifluoromethoxy)phenoxy]-N-(1-oxidopyridin-1-ium-3-yl)-6-(trifluoromethyl)pyridine-3-carboxamide (83);
4-(4-fluoro-2-methoxy-phenoxy)-N-(1-oxidopyridin-1-ium-3-yl)-6-(trifluoromethyl)pyridine-3-carboxamide (84);
4-(4-fluoro-2-methyl-phenoxy)-N-(1-oxidopyridin-1-ium-3-yl)-6-(trifluoromethyl)pyridine-3-carboxamide (85);
4-[4-(difluoromethoxy)phenoxy]-N-(1-oxidopyridin-1-ium-3-yl)-6-(trifluoromethyl)pyridine-3-carboxamide (86);
N-(1-oxidopyridin-1-ium-3-yl)-4-[4-(trifluoromethoxy)phenoxy]-6-(trifluoromethyl)pyridine-3-carboxamide (87);
4-(2,4-dimethoxyphenoxy)-N-(1-oxidopyridin-1-ium-3-yl)-6-(trifluoromethyl)pyridine-3-carboxamide (88);
4-(2,4-difluorophenoxy)-N-(1-oxidopyridin-1-ium-3-yl)-6-(trifluoromethyl)pyridine-3-carboxamide (89);
3-(4-(3,4-difluorophenoxy)-6-(trifluoromethyl)nicotinamido)pyridine 1-oxide (90);
N-[3-(methylsulfonimidoyl)phenyl]-4-[4-(trifluoromethoxy)phenoxy]-6-(trifluoromethyl)pyridine-3-carboxamide (91);
N-[3-(N,S-dimethylsulfonimidoyl)phenyl]-4-[4-(trifluoromethoxy)phenoxy]-6-(trifluoromethyl)pyridine-3-carboxamide (92);
4-(4-fluoro-2-methyl-phenoxy)-N-[3-(methylsulfonimidoyl)phenyl]-6-(trifluoromethyl)pyridine-3-carboxamide (93);
N-[3-(N,S-dimethylsulfonimidoyl)phenyl]-4-(4-fluoro-2-methyl-phenoxy)-6-(trifluoromethyl)pyridine-3-carboxamide (94);
4-(4-fluoro-2-methyl-phenoxy)-N-pyridazin-4-yl-6-(trifluoromethyl)pyridine-3-carboxamide (95);
N-pyridazin-4-yl-4-[4-(trifluoromethoxy)phenoxy]-6-(trifluoromethyl)pyridine-3-carboxamide (96);
4-[4-(difluoromethoxy)phenoxy]-N-pyridazin-4-yl-6-(trifluoromethyl)pyridine-3-carboxamide (97);
4-[2-chloro-4-(trifluoromethoxy)phenoxy]-N-pyridazin-4-yl-6-(trifluoromethyl)pyridine-3-carboxamide (98);
4-(2,4-dimethoxyphenoxy)-N-pyridazin-4-yl-6-(trifluoromethyl)pyridine-3-carboxamide (99);
4-(2,4-difluorophenoxy)-N-pyridazin-4-yl-6-(trifluoromethyl)pyridine-3-carboxamide (100);
4-[4-(difluoromethoxy)phenoxy]-N-[3-(methylsulfonimidoyl)phenyl]-6-(trifluoromethyl)pyridine-3-carboxamide (101);
4-(2,4-dimethoxyphenoxy)-N-[3-(methylsulfonimidoyl)phenyl]-6-(trifluoromethyl)pyridine-3-carboxamide (102);
4-(2,4-difluorophenoxy)-N-[3-(methylsulfonimidoyl)phenyl]-6-(trifluoromethyl)pyridine-3-carboxamide (103);
4-(4-(difluoromethoxy)phenoxy)-N-(pyridin-3-yl)-6-(trifluoromethyl)nicotinamide_(104);
N-(pyridin-3-yl)-4-(4-(trifluoromethoxy)phenoxy)-6-(trifluoromethyl)nicotinamide (105)

4-(2-chloro-4-(trifluoromethoxy)phenoxy)-N-(pyridin-3-yl)-6-(trifluoromethyl)nicotinamide (106);
4-(2,4-dimethoxyphenoxy)-N-(pyridin-3-yl)-6-(trifluoromethyl)nicotinamide (107);
4-(2,4-difluorophenoxy)-N-(pyridin-3-yl)-6-(trifluoromethyl)nicotinamide (108);
2-(4-fluoro-2-methyl-phenoxy)-N-(2-methoxy-4-pyridyl)-5-(trifluoromethyl)pyridine-3-carboxamide (109);
2-(4-fluoro-2-methyl-phenoxy)-N-(2-oxo-1H-pyridin-4-yl)-5-(trifluoromethyl)pyridine-3-carboxamide (110);
5-bromo-2-(4-fluoro-2-methoxy-phenoxy)-N-(3-methylsulfonylphenyl)pyridine-3-carboxamide (111);
5-cyclopropyl-2-(4-fluoro-2-methoxy-phenoxy)-N-(3-methylsulfonylphenyl)pyridine-3-carboxamide (112);
2-(4-fluoro-2-methyl-phenoxy)-N-(3-methylsulfonylphenyl)-5-(trifluoromethyl)pyridine-3-carboxamide (113);
N-[3-(N,S-dimethylsulfonimidoyl)phenyl]-2-(4-fluoro-2-methyl-phenoxy)-5-(trifluoromethyl)pyridine-3-carboxamide (114);
2-(4-fluoro-2-methyl-phenoxy)-N-[3-(methylsulfonimidoyl)phenyl]-5-(trifluoromethyl)pyridine-3-carboxamide (115);
2-(4-fluoro-2-methyl-phenoxy)-N-pyridazin-4-yl-5-(trifluoromethyl)pyridine-3-carboxamide (116);
2-(4-fluoro-2-methoxy-phenoxy)-6-methyl-N-(3-methylsulfonylphenyl)pyridine-3-carboxamide (117);
2-(4-fluoro-2-methoxy-phenoxy)-5,6-dimethyl-N-(3-methylsulfonylphenyl)pyridine-3-carboxamide (118);
5-chloro-2-(4-fluoro-2-methoxy-phenoxy)-N-(3-methylsulfonylphenyl)pyridine-3-carboxamide (119);
2-(4-fluoro-2-methoxy-phenoxy)-N-(3-methylsulfonylphenyl)-6,7-dihydro-5H-cyclopenta[b]pyridine-3-carboxamide (120);
N-(3-methylsulfinylphenyl)-2-[4-(trifluoromethoxy)phenoxy]-5-(trifluoromethyl)pyridine-3-carboxamide (121);
N-(3-sulfamoylphenyl)-2-[4-(trifluoromethoxy)phenoxy]-5-(trifluoromethyl)pyridine-3-carboxamide (122);
N-[3-(methylsulfonimidoyl)phenyl]-2-[4-(trifluoromethoxy)phenoxy]-5-(trifluoromethyl)pyridine-3-carboxamide (123);
N-[3-(N,S-dimethylsulfonimidoyl)phenyl]-2-[4-(trifluoromethoxy)phenoxy]-5-(trifluoromethyl)pyridine-3-carboxamide (124);
N-(3-ethylsulfonylphenyl)-2-[4-(trifluoromethoxy)phenoxy]-5-(trifluoromethyl)pyridine-3-carboxamide (125);
N-(3-pyridyl)-2-[4-(trifluoromethoxy)phenoxy]-5-(trifluoromethyl)pyridine-3-carboxamide (126);
N-(4-pyridyl)-2-[4-(trifluoromethoxy)phenoxy]-5-(trifluoromethyl)pyridine-3-carboxamide (127);
N-pyridazin-4-yl-2-[4-(trifluoromethoxy)phenoxy]-5-(trifluoromethyl)pyridine-3-carboxamide (128);
N-[3-[[dimethyl(oxo)-$\lambda^6$-sulfanylidene]amino]phenyl]-2-[4-(trifluoromethoxy)phenoxy]-5-(trifluoromethyl)pyridine-3-carboxamide (129);
N-[3-(methylsulfonimidoyl)phenyl]-2-[4-(trifluoromethoxy)phenoxy]-5-(trifluoromethyl)pyridine-3-carboxamide enantiomer A (130);
N-[3-(methylsulfonimidoyl)phenyl]-2-[4-(trifluoromethoxy)phenoxy]-5-(trifluoromethyl)pyridine-3-carboxamide, enantiomer B (131);
N-(1-oxidopyridin-1-ium-3-yl)-2-[4-(trifluoromethoxy)phenoxy]-5-(trifluoromethyl)pyridine-3-carboxamide (132);
2-(4-fluoro-2-methyl-phenoxy)-N-(1-oxidopyridin-1-ium-3-yl)-5-(trifluoromethyl)pyridine-3-carboxamide (133);
2-(4-fluoro-2-methoxy-phenoxy)-N-(1-oxidopyridin-1-ium-3-yl)-5-(trifluoromethyl)pyridine-3-carboxamide (134);

2-(2,4-difluorophenoxy)-N-(1-oxidopyridin-1-ium-3-yl)-5-(trifluoromethyl)pyridine-3-carboxamide (135);
3-(2-(4-(difluoromethoxy)phenoxy)-5-(trifluoromethyl) nicotinamido)pyridine 1-oxide (136);
3-(2-(2,4-dimethoxyphenoxy)-5-(trifluoromethyl)nicotinamido)pyridine 1-oxide (137);
3-(2-(2-chloro-4-methoxyphenoxy)-5-(trifluoromethyl) nicotinamido)pyridine 1-oxide (138);
3-(2-(3,4-difluorophenoxy)-5-(trifluoromethyl)nicotinamido)pyridine 1-oxide (139);
2-(2-chloro-4-fluoro-phenoxy)-N-(1-oxidopyridin-1-ium-3-yl)-5-(trifluoromethyl)pyridine-3-carboxamide (140);
N-(1-oxidopyridin-1-ium-4-yl)-2-[4-(trifluoromethoxy)phenoxy]-5-(trifluoromethyl)pyridine-3-carboxamide (141);
2-[2-chloro-4-(trifluoromethoxy)phenoxy]-N-(3-methylsulfonylphenyl)-5-(trifluoromethyl)pyridine-3-carboxamide (142);
2-[2-chloro-4-(trifluoromethoxy)phenoxy]-N-(3-ethylsulfonylphenyl)-5-(trifluoromethyl)pyridine-3-carboxamide (143);
2-[2-chloro-4-(trifluoromethoxy)phenoxy]-N-[3-(N,S-dimethylsulfonimidoyl)phenyl]-5-(trifluoromethyl)pyridine-3-carboxamide (144);
4-pyridyl 2-[2-chloro-4-(trifluoromethoxy)phenoxy]-5-(trifluoromethyl)pyridine-3-carboxylate (145);
2-[2-chloro-4-(trifluoromethoxy)phenoxy]-N-(3-cyanophenyl)-5-(trifluoromethyl)pyridine-3-carboxamide (146);
2-[2-chloro-4-(trifluoromethoxy)phenoxy]-N-(1-methylpyrazol-4-yl)-5-(trifluoromethyl)pyridine-3-carboxamide (147);
N-(3-carbamoylphenyl)-2-[2-chloro-4-(trifluoromethoxy)phenoxy]-5-(trifluoromethyl)pyridine-3-carboxamide (148);
N-(3-acetylphenyl)-2-[2-chloro-4-(trifluoromethoxy)phenoxy]-5-(trifluoromethyl)pyridine-3-carboxamide (149);
2-[2-chloro-4-(trifluoromethoxy)phenoxy]-N-(1-methyl-2-oxo-4-pyridyl)-5-(trifluoromethyl)pyridine-3-carboxamide (150);
2-[2-chloro-4-(trifluoromethoxy)phenoxy]-N-[3-(dimethylcarbamoyl)phenyl]-5-(trifluoromethyl)pyridine-3-carboxamide (151);
2-[2-chloro-4-(trifluoromethoxy)phenoxy]-N-(4-methylsulfonylphenyl)-5-(trifluoromethyl)pyridine-3-carboxamide (152);
2-[2-chloro-4-(trifluoromethoxy)phenoxy]-N-(4-methylsulfonylphenyl)-5-(trifluoromethyl)pyridine-3-carboxamide (153);
2-[2-chloro-4-(trifluoromethoxy)phenoxy]-N-[3-(dimethylsulfamoyl)phenyl]-5-(trifluoromethyl)pyridine-3-carboxamide (154);
2-[2-chloro-4-(trifluoromethoxy)phenoxy]-N-(3,4-difluorophenyl)-5-(trifluoromethyl)pyridine-3-carboxamide (155);
2-[2-chloro-4-(trifluoromethoxy)phenoxy]-N-(6-methoxy-3-pyridyl)-5-(trifluoromethyl)pyridine-3-carboxamide (156);
2-[2-chloro-4-(trifluoromethoxy)phenoxy]-N-pyrimidin-5-yl-5-(trifluoromethyl)pyridine-3-carboxamide (157);
N-(2-chloro-4-pyridyl)-2-[2-chloro-4-(trifluoromethoxy) phenoxy]-5-(trifluoromethyl)pyridine-3-carboxamide (158);
2-[2-chloro-4-(trifluoromethoxy)phenoxy]-N-(6-fluoro-3-pyridyl)-5-(trifluoromethyl)pyridine-3-carboxamide (159);
2-[2-chloro-4-(trifluoromethoxy)phenoxy]-N-[3-(hydroxymethyl)phenyl]-5-(trifluoromethyl)pyridine-3-carboxamide (160);
2-[2-chloro-4-(trifluoromethoxy)phenoxy]-N-pyridazin-4-yl-5-(trifluoromethyl)pyridine-3-carboxamide (161);
2-[2-chloro-4-(trifluoromethoxy)phenoxy]-N-(2-fluoro-5-methylsulfonyl-phenyl)-5-(trifluoromethyl)pyridine-3-carboxamide (162);
2-[2-chloro-4-(trifluoromethoxy)phenoxy]-N-(3-fluorophenyl)-5-(trifluoromethyl)pyridine-3-carboxamide (163);
2-[2-chloro-4-(trifluoromethoxy)phenoxy]-N-(2-methyl-4-pyridyl)-5-(trifluoromethyl)pyridine-3-carboxamide (164);
2-[2-chloro-4-(trifluoromethoxy)phenoxy]-N-(2-fluoro-4-pyridyl)-5-(trifluoromethyl)pyridine-3-carboxamide (165);
2-[2-chloro-4-(trifluoromethoxy)phenoxy]-N-(thiadiazol-5-yl)-5-(trifluoromethyl)pyridine-3-carboxamide (166);
2-[2-chloro-4-(trifluoromethoxy)phenoxy]-N-(2-methylpyrazol-3-yl)-5-(trifluoromethyl)pyridine-3-carboxamide (167);
2-[2-chloro-4-(trifluoromethoxy)phenoxy]-N-(2-methyl-5-methylsulfonyl-phenyl)-5-(trifluoromethyl)pyridine-3-carboxamide (168);
2-[2-chloro-4-(trifluoromethoxy)phenoxy]-N-(2-methyl-1,2,4-triazol-3-yl)-5-(trifluoromethyl)pyridine-3-carboxamide (169);
2-[2-chloro-4-(trifluoromethoxy)phenoxy]-N-(1-methyl-1,2,4-triazol-3-yl)-5-(trifluoromethyl)pyridine-3-carboxamide (170);
2-(2,4-dimethoxyphenoxy)-N-[3-(N,S-dimethylsulfonimidoyl)phenyl]-5-(trifluoromethyl)pyridine-3-carboxamide (171);
2-(2,4-dimethoxyphenoxy)-N-[3(methylsulfonimidoyl)phenyl]-5-(trifluoromethyl)pyridine-3-carboxamide (172);
2-(2,4-dimethoxyphenoxy)-N-pyridazin-4-yl-5-(trifluoromethyl)pyridine-3-carboxamide (173);
2-(2,4-difluorophenoxy)-N-[3-(methylsulfonimidoyl)phenyl]-5-(trifluoromethyl)pyridine-3-carboxamide (174);
2-(2,4-difluorophenoxy)-N-[3-(N,S-dimethylsulfonimidoyl) phenyl]-5(trifluoromethyl)pyridine-3-carboxamide (175);
2-(2,4-difluorophenoxy)-N-pyridazin-4-yl-5-(trifluoromethyl)pyridine-3-carboxamide (176);
5-cyano-2-(4-fluoro-2-methoxy-phenoxy)-6-methyl-N-(3-methylsulfonylphenyl)pyridine-3-carboxamide (177);
5-fluoro-2-(4-fluoro-2-methoxy-phenoxy)-6-methoxy-N-(3-methylsulfonylphenyl)pyridine-3-carboxamide (178);
5-(difluoromethoxy)-2-(4-fluoro-2-methoxy-phenoxy)-N-(3-methylsulfonylphenyl)pyridine-3-carboxamide (179);
N-(3-methylsulfonylphenyl)-5-nitro-2-[4-(trifluoromethoxy)phenoxy]pyridine-3-carboxamide (180); and
5-chloro-N-(3-methylsulfonylphenyl)-2-[4-(trifluoromethoxy)phenoxy]pyridine-3-carboxamide (181).

B. Methods for Treating a Condition, Disease, or Disorder Associated with an Increased NAV1.8 Activity or Expression In some embodiments, the presently disclosed subject matter provides a method for modulating a $Na_v$ 1.8 sodium ion channel, the method comprising administering to a subject in need thereof, a modulating-effective amount of a compound of formula (I) to the subject.

In other embodiments, the presently disclosed subject matter provides a method for inhibiting $Na_v$ 1.8, the method comprising administering to a subject in need thereof, an inhibiting-effective amount of a compound of formula (I) to the subject.

As used herein, the term "inhibit," and grammatical derivations thereof, refers to the ability of a presently disclosed compound, e.g., a presently disclosed compound of formula (I), to block, partially block, interfere, decrease, or reduce the activity or expression of $Na_v$ 1.8 in a subject. Thus, one of ordinary skill in the art would appreciate that the term "inhibit" encompasses a complete and/or partial decrease in the function of the channel, e.g., a decrease by at least 10%, in some embodiments, a decrease by at least 20%, 30%, 50%, 75%, 95%, 98%, and up to and including 100%.

In particular embodiments, the presently disclosed subject matter provides a method for treating a condition, disease, or disorder associated with an increased $Na_v$ 1.8 activity or expression. In more particular embodiments, the condition, disease, or disorder associated with an increased $Na_v$ 1.8 activity or expression is selected from the group consisting of pain, especially inflammatory, visceral, and neuropathic pain, neurological disorders, especially multiple sclerosis, autism, especially Pitt Hopkins Syndrome, and psychiatric diseases, and combinations thereof, wherein the method comprises administering to the subject in need thereof a therapeutically effective amount of a compound of formula I, or a pharmaceutically acceptable salt thereof.

In particular embodiments, the disease or condition is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury or a combination thereof.

In other embodiments, the disease or condition is selected from the group consisting of pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions caused by stroke or neural trauma, tach-arrhythmias, atrial fibrillation and ventricular fibrillation.

In some embodiments, the disease or condition is Pitt Hopkins Syndrome (PTHS).

The presently disclosed subject matter also includes use of a compound of formula (I) in the manufacture of a medicament for treating a condition, disease, or disorder associated with an increased $Na_v$ 1.8 activity or expression in a subject afflicted with such a disorder.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The term "combination" is used in its broadest sense and means that a subject is administered at least two agents, more particularly a compound of formula (I) and at least one analgesic; and, optionally, one or more analgesic agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more analgesic agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index(SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

More particularly, in some embodiments, the presently disclosed methods include co-administering to the subject a compound of formula (I) and/or a pharmaceutically acceptable salt thereof with one or more compounds selected from the group consisting of one or more:

nonsteroidal anti-inflammatory drugs (NSAIDs), including, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, and zomepirac;

opioid analgesics, including, but not limited to, morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, and pentazocine;

barbiturates, including, but not limited to, amobarbital, aprobarbital, butabarbital, butabital, mephobarbital, metharbital, methohexital, pentobarbital, phenobartital, secobarbital, talbutal, thiamylal, and thiopental;

benzodiazapines, including, but not limited to, chlordiazepoxide, clorazepate, diazepam, flurazepam, lorazepam, oxazepam, temazepam, and triazolam;

histamine $H_1$ antagonists, including, but not limited to, diphenhydramine, pyrilamine, promethazine, chlorpheniramine, and chlorcyclizine;

sedatives, including, but not limited to, glutethimide, meprobamate, methaqualone, and dichloralphenazone;

a skeletal muscle relaxant, including, but not limited to, baclofen, carisoprodol, chlorzoxazone, cyclobenzaprine, methocarbamol, and orphrenadine;

an NMDA receptor antagonist, including, but not limited to, dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil, and (−)—(R)-6-{2-[4-(3-fluorophenyl)-4-hydroxy-1-piperidinyl]-1-hydroxyethyl-3,4-dihydro-2(1H)-quinolinone;

transient receptor potential ion channel antagonists;

α-adrenergics, including, but not limited to, doxazosin, tamsulosin, clonidine, guanfacine, dexmetatomidine, modafinil, and 4-amino-6,7-dimethoxy-2-(5-methane-sulfonamido-1,2,3,4-tetrahydroisoquinol-2-yl)-5-(2-pyridyl) quinazoline;

tricyclic antidepressants, including, but not limited to, desipramine, imipramine, amitriptyline, and nortriptyline;

anticonvulsants, including, but not limited to, carbamazepine (Tegretol®), lamotrigine, topiramate, lacosamide (Vimpat®), and valproate;

tachykinin antagonists, particularly an NK-3, NK-2 or NK-1 antagonist, including, but not limited to, (alphaR,9R)-7-[3,5-bis(trifluoromethyl)benzyl]-8,9,10,11-tetrahydro-9-met-hyl-5-(4-methylphenyl)-7H-[1,4]diazocino[2,1-g][1,7]-naphthyridine-6-13-di-one (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant, and 3-[[2-methoxy-5-(trifluoromethoxy)phenyl]-methylamino]-2-phenylpiperidine (2S,3S);

muscarinic antagonists, including, but not limited to, oxybutynin, tolterodine, propiverine, tropsium chloride, darifenacin, solifenacin, temiverine, and ipratropium;

cyclooxygenase-2 selective (COX-2) inhibitors, including, but not limited to, celecoxib, rofecoxib, parecoxib, valdecoxib, deracoxib, etoricoxib, and lumiracoxib;

a coal-tar analgesic, including, but not limited to, paracetamol;

neuroleptics, including, but not limited to, droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion®, and sarizotan;

vanilloid receptor agonists, including, but not limited to, resinferatoxin or civamide);

vanilloid receptor antagonists, including, but not limited to, capsazepine or GRC-15300);

β-adrenergics, including, but not limited to, propranolol;

local anaesthetics, including, but not limited to, mexiletine;

corticosteroids, including, but not limited to, dexamethasone and prednisone;

5-HT receptor agonists or antagonists, in particular a 5-HT$_{1B/1D}$ agonist, including, but not limited to, eletriptan, sumatriptan, naratriptan, zolmitriptan or rizatriptan;

5-HT$_{2A}$ receptor antagonists, including, but not limited to, R(+)-alpha-(2,3-dimethoxy-phenyl)-1-[2-(4-fluorophenylethyl)]-4-piperidinemethanol (MDL-100907), eplivanserin, ketanserin, and pimavanserin;

cholinergic (nicotinic) analgesics, including, but not limited to, ispronicline (TC-1734), (E)-N-methyl-4-(3-pyridinyl)-3-buten-1-amine (RJR-2403), (R)-5-(2-azetidinylmethoxy)-2-chloropyridine (ABT-594), and nicotine;

α$_2$δ ligands, including, but not limited to, gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo [3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo [3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S, 5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

cannabinoid receptor ligands, including, but not limited to, cannabidiol, KHK-6188;

metabotropic glutamate subtype 1 receptor antagonists;

serotonin reuptake inhibitors, including, but not limited to, sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, and trazodone;

noradrenaline (norepinephrine) reuptake inhibitors, including, but not limited to, maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor, such as reboxetine, in particular (S,S)-reboxetine;

dual serotonin-noradrenaline reuptake inhibitors, including, but not limited to, venlafaxine, venlafaxine metabolite O-desmethylvenlafaxine, clomipramine, clomipramine metabolite desmethylclomipramine, duloxetine (Cymbalta®), milnacipran and imipramine;

Rho kinase inhibitors;

inducible nitric oxide synthase (iNOS) inhibitors, including, but not limited to, S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonit-rile, N-[4-[2-(3-chlorobenzylamino)ethyl]phenyl]thiophene-2-carboxamidine, NXN-462, and guanidinoethyldisulfide;

acetylcholinesterase inhibitors, including, but not limited to, donepezil;

prostaglandin E2 subtype 4 antagonists, including, but not limited to, N-[({2-[4-(2-ethyl-4,6-dimethyl-1H-imidazo[4,5-c]pyridin-1-yl)phenyl]ethyl}amino)-carbonyl]-4-methylbenzenesulfonamide, and 4-[(15)-1-({[5-chloro-2-(3-fluorophenoxy)pyridin-3-yl]carbonyl}amino)ethyl]benzoic acid;

leukotriene B4 antagonists, including, but not limited to, 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057), and DPC-11870;

5-lipoxygenase inhibitors, including, but not limited to, zileuton, 6-[(3-fluoro-5-[4-methoxy-3,4,5,6-tetrahydro-2H-pyran-4-yl])phenoxy-methyl]-1-methyl-2-quinolone (ZD-2138), and 2,3,5-trimethyl-6-(3-pyridylmethyl)-1,4-benzoquinone (CV-6504);

sodium channel blockers, including, but not limited to, lidocaine, lidocaine plus tetracaine cream (ZRS-201), and eslicarbazepine acetate;

5-HT$_3$ antagonists, including, but not limited to, ondansetron;

N-methyl-D-aspartic acid receptor antagonists;

voltage-gated calcium channel blockers (e.g., N-type and T-type), including, but not limited to ziconctide, Z-160, (R)-2-(4-cyclopropylphenyl)-N-(1-(5-(2,2,2-trifluoroethoxy)pyridin-2-yl)ethyl) acetamide;

KCNQ openers (e.g., KCNQ2/3 (K$_v$ 7.2/3));

TPRV 1 receptor agonists, including, but not limited to, capsaicin (Neuroges®, Qutenza®); and the pharmaceutically acceptable salts and solvates thereof;

nicotinic receptor antagonists, including, but not limited to, varenicline;

nerve growth factor antagonists, including, but not limited to, tanezumab;

endopeptidase stimulants, including, but not limited to, senrebotase;

angiotensin II antagonists, including, but not limited to, EMA-401;

Tramadol®, Tramadol ER (Ultram ER®), Tapentadol ER (Nucynta®);

PDE5 inhibitors, including, but not limited to, 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6, 1]-pyrido[3,4-b]indole-1,4-dione (IC-351 or tadalafil), 2-[2- ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-di-hydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulfonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

$Na_v1.7$ blockers, including, but not limited to, XEN-402, XEN403, TV-45070, PF-05089771, CNV1014802, GDC-0276, RG7893 and such as those disclosed in WO2011/140425; WO2012/106499; WO2012/112743; WO2012/125613, WO2012/116440, WO2011026240, U.S. Pat. Nos. 8,883,840, or 8,466,188, or PCT/US2013/21535 the entire contents of each application hereby incorporated by reference; and $Na_v1.7$ blockers, including, but not limited to, (2-benzyl-spiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2-,4-dimethyl-spiro[3,4-dihydropyrrolo[1,2-a]pyrazine-1,4'-piperidine]-6-yl]-ethanone, [8-fluoro-2-methyl-6-(trifluoromethyl)spiro[3,4-dihydropyrrolo[1-,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl] methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl) spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo-[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro [3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl] ethanone, 2,2,2-trifluoro-1-[1'-(5-isopropoxy-6-methyl-pyridine-2-carbonyl)-3,-3-dimethyl-spiro[2,4-dihydropyrrolo[1,2-a]pyrazine-1,4'-piperidine]-6-yl] ethanone, 2,2,2-trifluoro-1-[1'-(5-isopentyloxypyridine-2-carbonyl)-2-methy-1-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-di-hydropyrrolo[1,2-a]pyrazine-1,4'-piperidine]-1'-yl] methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl] spiro[3,-4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy] phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl] ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl] methanone, [2-methyl-6-(1-methylcyclopropanecarbonyl) spiro[3,4-dihydropyrrolo[1,2-a]-pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[34-dihydropyrrolo[1,2-a]pyrazine-1,4'-piperidine]-1'-yl] methanone.

In some embodiments, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In some embodiments, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such as aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

C. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of ordinary skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of ordinary skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_1$-20 inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-$C_8$ straight-chain alkyls. In other embodiments, "alkyl" refers, in particular, to $C_1$-$C_8$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "heteroalkyl," by itself or in combination with another term, means, unless otherwise stated, a stable straight or branched chain having from 1 to 20 carbon atoms or heteroatoms or a cyclic hydrocarbon group having from 3 to 10 carbon atoms or heteroatoms, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic monoor multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkylene moiety, also as defined above, e.g., a $C_{1-20}$ alkylene moiety. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidinyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated hydrocarbon has one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{2-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{2-20}$ hydrocarbon of a designed number of carbon atoms containing at least one carbon-carbon triple bond. Examples of "alkynyl"

include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$CH_2CH_2CH_2CH_2$—, —$CH_2$CH=CH$CH_2$—, —$CH_2$CsCC$H_2$—, —$CH_2CH_2$CH($CH_2CH_2CH_3$)$CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

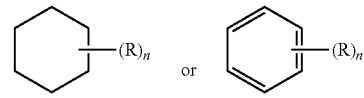

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

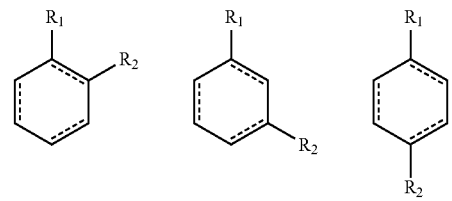

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⋺⋺⋺⋺ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R")=NR"', —S(O)R', —S(O)$_2$R', —S(O)$_2$NR'R", —NRSO$_2$R', —CN, CF$_3$, fluorinated C$_{1-4}$ alkyl, and —NO$_2$ in a number ranging from zero to (2m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of ordinary skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"'—S(O)R', —S(O)$_2$R', —S(O)$_2$NR'R", —NRSO$_2$R', —CN and —NO$_2$, —R', —N$_3$, —CH(Ph)$_2$, fluoro(C$_{1-4}$)alkoxo, and fluoro(C$_1$-4)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_1$-20 inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(═O)— group. An exemplary aralkoxycarbonyl group is benzyloxycarbonyl.

"Carbamoyl" refers to an amide group of the formula —C(═O)NH$_2$.

"Alkylcarbamoyl" refers to a R'RN—C(═O)— group wherein one of R and R' is hydrogen and the other of R and R' is alkyl and/or substituted alkyl as previously described. "Dialkylcarbamoyl" refers to a R'RN—C(═O)— group wherein each of R and R' is independently alkyl and/or substituted alkyl as previously described.

The term carbonyldioxyl, as used herein, refers to a carbonate group of the formula —O—C(═O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic groups. For example, the terms "acylamino" and "alkylamino" refer to specific N-substituted organic groups with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom.

The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(═O)— group, and can include an aldehyde group represented by the general formula R—C(═O)H.

The term "carboxyl" refers to the —COOH group. Such groups also are referred to herein as a "carboxylic acid" moiety.

The term "cyano" refers to the —C═N group.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_{1-4}$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element, including to the nitrogen of a pyridine ring to make a pyridine N-oxide.

The term "nitro" refers to the —NO$_2$ group, which also can be represented as —N$^+$(═O)—O$^-$.

The term "thio" refers to a compound described previously herein wherein a carbon or oxygen atom is replaced by a sulfur atom.

The term "sulfate" refers to the —S04 group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

The "—S(═O)(═NR$_{10}$)—R$_{11}$" group is described, for example, in Frings et al., Sulfoximines from a Medicinal Chemist's Perspective: Physicochemical and in vitro Parameters Relevant for Drug Discovery, European Journal of Medicinal Chemistry 126 (2017) 225e245, which is incorporated herein by reference in its entirety.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon or sulfur atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example deuterium ($^2H$), tritium (H), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

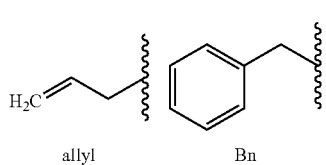

allyl       Bn

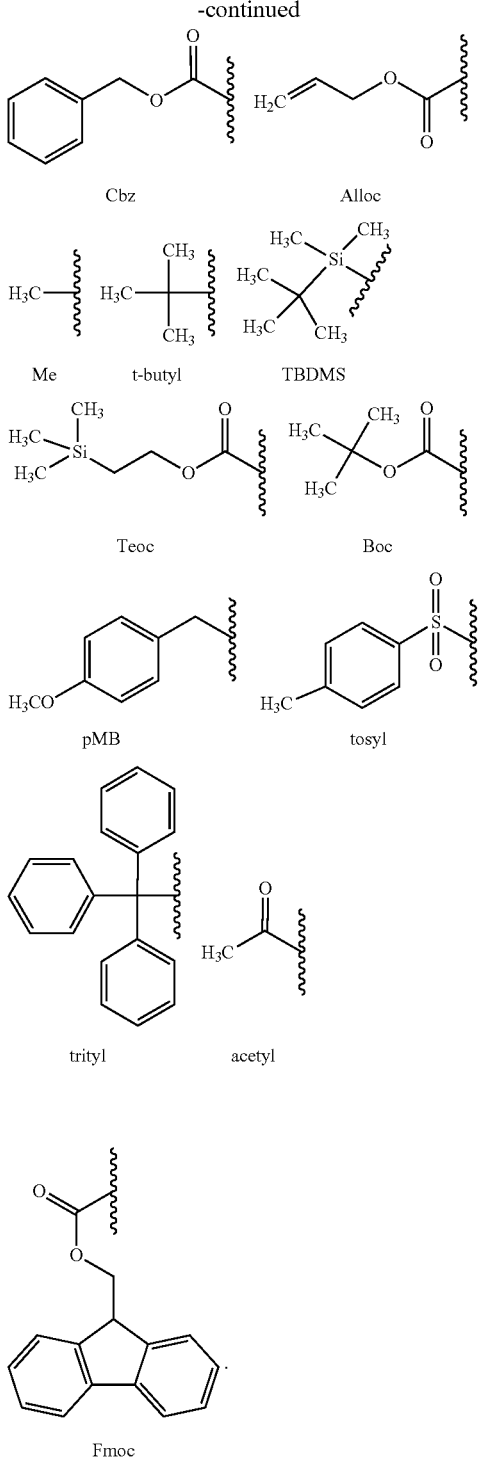

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of ordinary skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Synthetic Procedures

Exemplary compounds were prepared via several general synthetic routes set forth in the Examples below. Any of the disclosed compounds of the present invention can be prepared according to one or more of these synthetic routes or specific examples, or via modifications thereof accessible to the person of ordinary skill in the art.

Intermediate 1: 2-(4-fluoro-2-methoxy-phenoxy)-5-(trifluoromethyl)pyridine-3-carboxylic acid

Method A

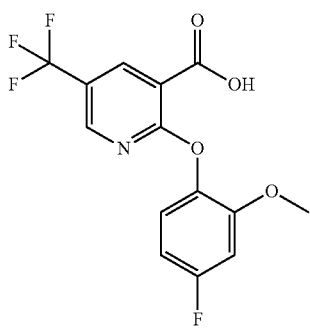 [SMILES: COc1cc(F)ccc1Oc1ncc(C(F)(F)F)cc1C(=O)O]

A mixture of 2-chloro-5-(trifluoromethyl)pyridine-3-carboxylic acid (500 mg, 2.22 mmol), 4-fluoro-2-methoxyphenol (278 µL, 2.44 mmol) and cesium carbonate (1806 mg, 5.54 mmol) in MeCN (5 mL) was stirred at 80° C. for 18 h. After cooling, the contents were diluted with 20 mL water and acidified to pH 5 via careful addition of 2 N HCl, then stirred for 2 h. The precipitate was collected by filtration, washed with water and dried under vacuum to give 2-(4-fluoro-2-methoxy-phenoxy)-5-(trifluoromethyl)pyridine-3-carboxylic acid (695 mg, 2.10 mmol, 94.6% yield) as a beige solid. MS, ES$^+$ m/z 332.0 [M+H]$^+$.
$^1$H-NMR (400 MHz, DMSO-d$_6$) δ 13.74 (br. s., 1H), 8.67 (br. s., 1H), 8.50 (s, 1H), 7.22 (dd, J=8.97, 5.68 Hz, 1H), 7.10 (dd, J=11.12, 2.78 Hz, 1H), 6.79-6.86 (m, 1H), 3.70 (s, 3H).

Intermediate 2: 2-(benzotriazol-1-yloxy)-N-(3-methylsulfonylphenyl)-5-(trifluoromethyl)pyridine-3-carboxamide

Method B

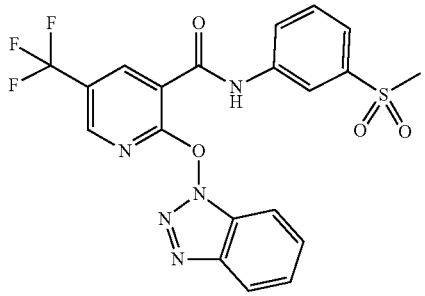 [SMILES: CS(=O)(=O)c1cccc(NC(=O)c2cc(C(F)(F)F)cnc2On2nnc3ccccc32)c1]

A mixture of 2-chloro-5-(trifluoromethyl)pyridine-3-carboxylic acid (508 mg, 2.25 mmol), 3-methylsulfonylaniline (424 mg, 2.48 mmol), HBTU (854 mg, 2.25 mmol) and DIPEA (981 µL, 5.63 mmol) in chloroform (10 mL) was stirred at room temperature for 40 h. The solvent was removed under a stream of N$_2$, and the residue treated with water/MeOH (5:1). This mixture was briefly sonicated then stirred at room temperature for 24 h. The resulting precipitate was collected by filtration, washed with water and dried under vacuum to give 2-(benzotriazol-1-yloxy)-N-(3-methylsulfonylphenyl)-5-(trifluoromethyl)pyridine-3-carboxamide (665 mg, 1.39 mmol, 61.9% yield) as a beige solid. MS, ES$^+$ m/z 448.0 [M+H]$^+$. 1H-NMR (400 MHz, DMSO-d$_6$) δ 11.37 (s, 1H), 8.88 (d, J=2.27 Hz, 1H), 8.72 (d, J=1.01 Hz, 1H), 8.43 (s, 1H), 8.20 (d, J=8.59 Hz, 1H), 8.03-8.07 (m, 1H), 7.83 (d, J=8.59 Hz, 1H), 7.67-7.77 (m, 3H), 7.54-7.58 (m, 1H), 3.25 (s, 3H).

Intermediate 3: 6-chloro-2-(4-fluoro-2-methoxy-phenoxy)-N-(3-methylsulfonylphenyl)pyridine-3-carboxamide

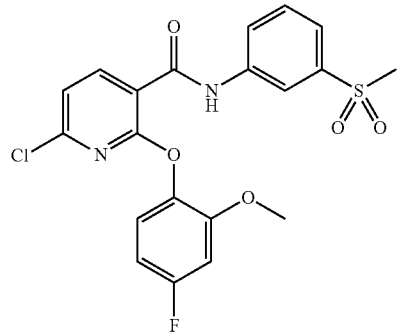 [SMILES: COc1cc(F)ccc1Oc1nc(Cl)ccc1C(=O)Nc1cccc(S(C)(=O)=O)c1]

Step 1: Synthesis of 2,6-dichloro-N-(3-methylsulfonylphenyl)pyridine-3-carboxamide

Method C

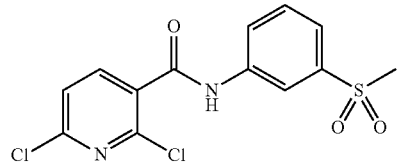

A mixture of 2,6-dichloropyridine-3-carbonyl chloride (200 mg, 0.950 mmol), 3-methylsulfonylaniline (179 mg, 1.05 mmol) and DIPEA (414 µL, 2.38 mmol) in chloroform (5 mL) was stirred at room temperature for 24 h. The contents were treated with 10% Na$_2$CO$_3$, extracted with CHCl$_3$ (3×) and the solvent removed in vacuo to give 2,6-dichloro-N-(3-methylsulfonylphenyl)pyridine-3-carboxamide (378 mg, 1.10 mmol, 115% yield) as a yellow foam, which was used without further purification. MS, ES$^+$ m/z 344.9 [M+H]$^+$.

Step 2: Synthesis of 6-chloro-2-(4-fluoro-2-methoxy-phenoxy)-N-(3-methylsulfonylphenyl)pyridine-3-carboxamide Method D

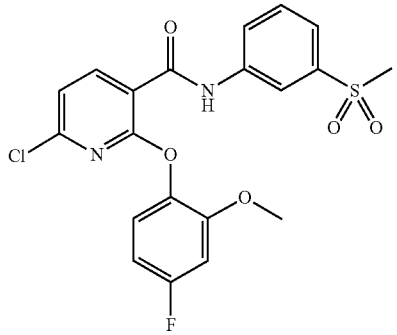

A mixture of crude 2,6-dichloro-N-(3-methylsulfonylphenyl)pyridine-3-carboxamide (276 mg, 0.800 mmol), 4-fluoro-2-methoxyphenol (91.1 μL, 0.800 mmol) and cesium carbonate (273 mg, 0.840 mmol) in MeCN (2 mL) was stirred at room temperature for 23 h. The contents were diluted with 20 mL water and stirred at room temperature for 2 h. The resulting precipitate was collected by filtration, washed with water and dried under vacuum to give 6-chloro-2-(4-fluoro-2-methoxy-phenoxy)-N-(3-methylsulfonylphenyl)pyridine-3-carboxamide (242 mg, 0.536 mmol, 67.0% yield) as a white solid. MS, ES+ m/z 451.1 [M+H]+.

$^1$H-NMR (400 MHz, DMSO-$d_6$) δ 10.82 (s, 1H), 8.41 (s, 1H), 8.19 (d, J=7.83 Hz, 1H), 7.96 (d, J=7.58 Hz, 1H), 7.63-7.71 (m, 2H), 7.32-7.39 (m, 2H), 7.12 (dd, J=10.74, 2.91 Hz, 1H), 6.86 (td, J=8.46, 2.78 Hz, 1H), 3.73 (s, 3H), 3.22 (s, 3H)

Intermediate 4: 2-chloro-N-(3-methylsulfonylphenyl)-5-(trifluoromethyl)pyridine-3-carboxamide Method E

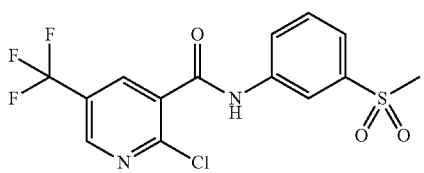 [SMILES: CS(=O)(=O)c1cccc(NC(=O)c2cc(C(F)(F)F)cnc2Cl)c1]

A mixture of 2-chloro-5-(trifluoromethyl)pyridine-3-carbonyl chloride (250 mg, 1.02 mmol), 3-methylsulfonylaniline (193 mg, 1.13 mmol) and DIPEA (446 μL, 2.56 mmol) in chloroform (5 mL) was stirred at room temperature for 24 h. The contents were treated with 10% Na$_2$CO$_3$, extracted with CHCl$_3$ (3×) and the solvent removed in vacuo to give a yellow foam, which was triturated with MeOH/2% Na$_2$CO$_3$ (1:10). The solid was collected by filtration, washed with water and dried under vacuum to give 2-chloro-N-(3-methylsulfonylphenyl)-5-(trifluoromethyl)pyridine-3-carboxamide (175 mg, 0.462 mmol, 45.1% yield) as a beige solid. MS, ES+ m/z 379.0 [M+H]+. $^1$H-NMR (400 MHz, DMSO-$d_6$) δ 11.17 (s, 1H), 9.04 (s, 1H), 8.72 (d, J=2.27 Hz, 1H), 8.35 (s, 1H), 7.94 (d, J=7.83 Hz, 1H), 7.67-7.76 (m, 2H), 3.25 (s, 3H).

Example 1: N-(1,3-benzothiazol-6-yl)-2-(4-fluoro-2-methoxy-phenoxy)-5-(trifluoromethyl)pyridine-3-carboxamide Method F

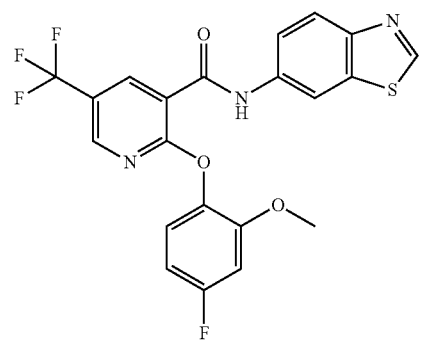 [SMILES: COc1cc(F)ccc1Oc1ncc(C(F)(F)F)cc1C(=O)Nc1ccc2ncsc2c1]

A mixture of 2-(4-fluoro-2-methoxy-phenoxy)-5-(trifluoromethyl)pyridine-3-carboxylic acid (Intermediate 1) (30.0 mg, 0.090 mmol), 1,3-Benzothiazol-6-amine (15.0 mg, 0.100 mmol), HBTU (37.8 mg, 0.100 mmol) and DIPEA (29.3 mg, 39.4 μL, 0.230 mmol) in Chloroform (2 mL) was stirred at room temperature for 20 h. The solvent was removed under a stream of N$_2$, and the residue treated with water/MeOH (3:1). This mixture was briefly sonicated then stirred at room temperature for 3 h. The resulting precipitate was collected by filtration, washed with water and dried under vacuum to give N-(1,3-benzothiazol-6-yl)-2-(4-fluoro-2-methoxy-phenoxy)-5-(trifluoromethyl)pyridine-3-carboxamide (35.4 mg, 0.0764 mmol, 84.3% yield) as a beige solid. MS, ES+ m/z 464.0 [M+H]+. $^1$H-NMR (400 MHz, DMSO-$d_6$) δ 10.88 (s, 1H), 9.32 (s, 1H), 8.70 (d, J=2.02 Hz, 1H), 8.66-8.68 (m, 1H), 8.53 (d, J=2.53 Hz, 1H), 8.09 (d, J=8.84 Hz, 1H), 7.75 (dd, J=8.84, 2.02 Hz, 1H), 7.35 (dd, J=8.84, 5.81 Hz, 1H), 7.11 (dd, J=10.74, 2.91 Hz, 1H), 6.85 (td, J=8.53, 2.91 Hz, 1H), 3.72 (s, 3H).

The following compounds have been synthesized according to Method F

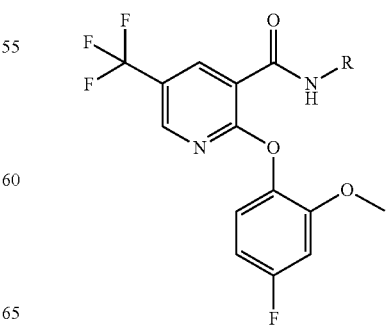

| Example | Name | R | Analytical data | Preparation details |
|---|---|---|---|---|
| 2 | 2-(4-fluoro-2-methoxy-phenoxy)-N-(3-morpholinophenyl)-5-(trifluoromethyl)pyridine-3-carboxamide | (phenyl-morpholine) | MS, ES+ m/z, 492.1 (M + H)+. $^1$H NMR (400 MHz, DMSO-d6) δ ppm 10.45 (s, 1H), 8.64 (d, J = 1.01 Hz, 1H), 8.45 (d, J = 2.53 Hz, 1H), 7.40 (s, 1H), 7.33 (dd, J = 8.72, 5.94 Hz, 1H), 7.19-7.24 (m, 1H), 7.14-7.18 (m, 1H), 7.11 (dd, J = 10.74, 2.91 Hz, 1H), 6.85 (td, J = 8.40, 2.65 Hz, 1H), 6.75 (d, J = 7.33 Hz, 1H), 3.73-3.77 (m, 4H), 3.71 (s, 3H), 3.07-3.11 (m, 4H). | Method F using 3-morpholin-4-ylaniline (95.1% yield) |
| 3 | N-(3-cyanophenyl)-2-(4-fluoro-2-methoxy-phenoxy)-5-(trifluoromethyl)pyridine-3-carboxamide | (3-cyanophenyl) | MS, ES+ m/z, 432.0 (M + H)+. $^1$H NMR (400 MHz, DMSO-d6) δ ppm 10.95 (s, 1H), 8.68 (s, 1H), 8.53 (d, J = 2.53 Hz, 1H), 8.22 (s, 1H) 7.94-7.99 (m, 1H), 7.58-7.65 (m, 2H), 7.32 (dd, J = 8.84, 5.81 Hz, 1H), 7.11 (dd, J = 10.86, 2.78 Hz, 1H), 6.85 (td, J = 8.46, 3.03 Hz, 1H), 3.71 (s, 3H). | Method F using 3-aminobenzonitrile. (64.5% yield) |
| 4 | 2-(4-fluoro-2-methoxy-phenoxy)-N-(3-pyridyl)-5-(trifluoromethyl)pyridine-3-carboxamide | (3-pyridyl) | MS, ES+ m/z, 408.0 (M + H)+. $^1$H NMR (400 MHz, DMSO-d6) δ ppm 10.82 (s, 1H), 8.87 (s, 1H), 8.67 (s, 1H), 8.53 (s, 1H), 8.36 (d, J = 4.80 Hz, 1H), 8.18 (d, J = 8.08 Hz, 1H), 7.41-7.47 (m, 1H), 7.30-7.36 (m, 1H), 7.11 (d, J = 10.86 Hz, 1H), 6.85 (t, J = 9.09 Hz, 1H), 3.71 (s, 3H). | Method F using 3-aminopyridine. (73.7% yield) |
| 5 | N-(4-cyanophenyl)-2-(4-fluoro-2-methoxy-phenoxy)-5-(trifluoromethyl)pyridine-3-carboxamide | (4-cyanophenyl) | MS, ES+ m/z, 432.0 (M + H)+. $^1$H NMR (400 MHz, DMSO-d6) δ ppm 11.04 (s, 1H) 8.67 (s, 1H) 8.54 (s, 1H) 7.89-7.94 (m, 2H) 7.84-7.88 (m, 2H) 7.30-7.36 (m, 1H) 7.10 (d, J = 8.08 Hz, 1H) 6.81-6.88 (m, 1H) 3.71 (s, 3H) | Method F using 4-aminobenzonitrile. (57.6% yield) |
| 6 | 2-(4-fluoro-2-methoxy-phenoxy)-N-(4-pyridyl)-5-(trifluoromethyl)pyridine-3-carboxamide | (4-pyridyl) | MS, ES+ m/z, 408.0 (M + H)+. $^1$H NMR (400 MHz, DMSO-d6) δ ppm 10.99 (s, 1H), 8.67 (d, J = 1.26 Hz, 1H), 8.53 (d, J = 2.27 Hz, 1H), 8.50-8.53 (m, 2H), 7.69 (d, J = 6.32 Hz, 2H), 7.33 (dd, J = 8.72, 5.94 Hz, 1H), 7.11 (dd, J = 10.74, 2.91 Hz, 1H), 6.84 (td, J = 8.53, 2.91 Hz, 1H), 3.71 (s, 3H). | Method F using 4-aminopyridine. (70.5% yield) |
| 7 | N-(6-cyano-3-pyridyl)-2-(4-fluoro-2-methoxy-phenoxy)-5-(trifluoromethyl)pyridine-3-carboxamide | (6-cyano-3-pyridyl) | MS, ES+ m/z, 433.0 (M + H)+. $^1$H NMR (400 MHz, DMSO-d6) δ ppm 11.30 (s, 1H), 8.99 (d, J = 2.27 Hz, 1H), 8.68-8.71 (m, 1H), 8.57 (d, J = 2.53 Hz, 1H), 8.41 (dd, J = 8.59, 2.53 Hz, 1H), 8.08 (d, J = 8.59 Hz, 1H), 7.32 (dd, J = 8.72, 5.94 Hz, 1H), 7.11 (dd, J = 10.61, 2.78 Hz, 1H), 6.84 (td, J = 8.46, 2.78 Hz, 1H), 3.71 (s, 3H). | Method F using 5-amino-2-cyanopyridine. (41.4% yield) |
| 8 | 2-(4-fluoro-2-methoxy-phenoxy)-N-(3-methylsulfinylphenyl)-5-(trifluoromethyl)pyridine-3-carboxamide | (3-methylsulfinylphenyl) | MS, ES+ m/z, 469.0 (M + H)+. $^1$H NMR (400 MHz, DMSO-d6) δ ppm 10.89 (s, 1H), 8.66 (d, J = 1.52 Hz, 1H), 8.51 (d, J = 2.53 Hz, 1H), 8.15 (s, 1H), 7.82 (d, J = 9.35 Hz, 1H), 7.58 (t, J = 7.96 Hz, 1H), 7.41 (d, J = 7.83 Hz, 1H), 7.33 (dd, J = 8.72, 5.94 Hz, 1H), 7.11 (dd, J = 10.86, 2.78 Hz, 1H), 6.85 (td, J = 8.53, 2.91 Hz, 1H), 3.71 (s, 3H), 2.75 (s, 3H). | Method F using 3-methylsulfinylaniline. (77.8% yield) |
| 9 | 2-(4-fluoro-2-methoxy-phenoxy)-N-(3-oxazol-5-ylphenyl)-5-(trifluoromethyl)pyridine-3-carboxamide | (3-oxazol-5-ylphenyl) | MS, ES+ m/z, 474.0 (M + H)+. $^1$H NMR (400 MHz, DMSO-d6) δ ppm 10.76 (s, 1H), 8.65-8.67 (m, 1H), 8.52 (d, J = 2.53 Hz, 1H), 8.49 (s, 1H), 8.18 (s, 1H), 7.66-7.70 (m, 2H), 7.47-7.56 (m, 2H), 7.34 (dd, J = 8.84, 5.81 Hz, 1H), 7.11 (dd, J = 10.74, 2.91 Hz, 1H), 6.85 (td, J = 8.53, 2.91 Hz, 1H), 3.72 (s, 3H). | Method F using 3-oxazol-5-ylaniline. (94.5% yield) |
| 10 | N-[3-(dimethylsulfamoyl)phenyl]-2-(4-fluoro-2-methoxy-phenoxy)-5-(trifluoromethyl)pyridine-3-carboxamide | (3-dimethylsulfamoylphenyl) | MS, ES+ m/z, 514.0 (M + H)+. $^1$H NMR (400 MHz, DMSO-d6) δ ppm 10.98 (s, 1H), 8.67 (d, J = 1.52 Hz, 1H), 8.55 (d, J = 2.53 Hz, 1H), 8.26 (s, 1H), 7.97 (d, J = 8.08 Hz, 1H), 7.67 (t, J = 7.96 Hz, 1H), 7.51 (dd, J = 7.83, 1.01 Hz, 1H), 7.33 (dd, J = 8.84, 6.06 Hz, 1H), 7.11 (dd, J = 10.74, 2.91 Hz, 1H), 6.85 (td, J = 8.59, 3.03 Hz, 1H), 3.71 (s, 3H), 2.65 (s, 6H). | Method F using 3-amino-N,N-dimethyl-benzenesulfonamide. (83.2% yield) |

-continued

| Example | Name | R | Analytical data | Preparation details |
|---|---|---|---|---|
| 11 | N-(1,3-benzothiazol-2-yl)-2-(4-fluoro-2-methoxy-phenoxy)-5-(trifluoromethyl)pyridine-3-carboxamide | | MS, ES+ m/z, 464.0 (M + H)+.<br>$^1$H NMR (400 MHz, DMSO-d6) δ ppm 12.93 (br. s., 1H), 8.71 (d, J = 1.52 Hz, 1H), 8.64 (d, J = 2.27 Hz, 1H), 8.06 (d, J = 7.58 Hz, 1H), 7.81 (d, J = 8.08 Hz, 1H), 7.46-7.51 (m, 1H), 7.38 (td, J = 8.84, 6.57 Hz, 2H), 7.12 (dd, J = 10.61, 2.78 Hz, 1H), 6.87 (td, J = 8.46, 2.78 Hz, 1H), 3.72 (s, 3H). | Method F using 2-aminobenzothiazole. (89.7% yield) |
| 12 | 2-(4-fluoro-2-methoxy-phenoxy)-N-pyrimidin-4-yl-5-(trifluoromethyl)pyridine-3-carboxamide | | MS, ES+ m/z, 409.0 (M + H)+.<br>$^1$H NMR (400 MHz, DMSO-d6) δ ppm 11.38 (s, 1H), 8.96 (d, J = 1.26 Hz, 1H), 8.78 (d, J = 5.56 Hz, 1H), 8.68 (d, J = 2.53, 1.01 Hz, 1H), 8.55 (d, J = 2.53 Hz, 1H), 8.20-8.23 (m, 1H), 7.36 (dd, J = 8.84, 6.06 Hz, 1H), 7.12 (dd, J = 10.74, 2.91 Hz, 1H), 6.86 (td, J = 8.53, 2.91 Hz, 1H), 3.72 (s, 3H) | Method F using 4-aminopyrimidine. (78.9% yield) |
| 13 | 2-(4-fluoro-2-methoxy-phenoxy)-5-(trifluoromethyl)-N-[3-(trifluoromethylsulfonyl)phenyl]pyridine-3-carboxamide | | MS, ES+ m/z, 539.0 (M + H)+.<br>$^1$H NMR (400 MHz, DMSO-d6) δ ppm 11.24 (s, 1H), 8.68-8.70 (m, 2H), 8.59 (d, J = 2.53 Hz, 1H), 8.19 (d, J = 7.83 Hz, 1H), 7.86-7.94 (m, 2H), 7.32 (dd, J = 8.97, 5.94 Hz, 1H), 7.11 (dd, J = 10.74, 2.91 Hz, 1H), 6.85 (td, J = 8.46, 2.78 Hz, 1H), 3.71 (s, 3H). | Method F using 3-(trifluoromethyl-sulfonyl)aniline. (86.1% yield) |
| 14 | 2-(4-fluoro-2-methoxy-phenoxy)-N-[3-(methylsulfonimidoyl)phenyl]-5-(trifluoromethyl)pyridine-3-carboxamide | | MS, ES+ m/z, 484 (M + H)+<br>$^1$H NMR (400 MHz, DMSO-d6) d ppm 3.07 (s, 3H) 3.72 (s, 3H) 4.25 (s, 1H) 6.79-6.98 (m, 1H) 7.11 (dd, J = 10.74, 2.91 Hz, 1H) 7.33 (dd, J = 8.84, 5.81 Hz, 1H) 7.57-7.81 (m, 2H) 7.96 (d, J = 7.83 Hz, 1H) 8.40 (d, J = 1.77 Hz, 1H) 8.47-8.60 (m, 1H) 8.67 (br. s., 1H) 10.93 (s, 1H) | Method F using (3-aminophenyl)(imino)(methyl)-λ$^6$-sulfanone |
| 15 | 2-(4-fluoro-2-methoxy-phenoxy)-N-(2-methoxy-4-pyridyl)-5-(trifluoromethyl)pyridine-3-carboxamide | | MS, ES+ m/z, 438 (M + H)+<br>$^1$H NMR (400 MHz, DMSO-d6) d ppm 3.71 (s, 3H) 3.85 (s, 3H) 6.85 (td, J = 8.53, 2.91 Hz, 1H) 7.11 (dd, J = 10.86, 3.03 Hz, 1H) 7.18-7.27 (m, 2H) 7.33 (dd, J = 8.84, 5.81 Hz, 1H) 8.11 (d, J = 5.56 Hz, 1H) 8.52 (dd, J = 2.53, 0.51 Hz, 1H) 8.67 (dd, J = 2.53, 1.01 Hz, 1H) 10.94 (s, 1H) | Method F using 2-methoxypyridin-4-amine |
| 16 | N-[3-(N,S-dimethylsulfonimidoyl)phenyl]-2-(4-fluoro-2-methoxy-phenoxy)-5-(trifluoromethyl)pyridine-3-carboxamide | | MS, ES+ m/z, 498 (M + H)+<br>$^1$H NMR (400 MHz, DMSO-d6) d ppm 2.49 (s, 3H) 3.12 (s, 3H) 3.72 (s, 3H) 6.85 (td, J = 8.46, 2.78 Hz, 1H) 7.11 (dd, J = 10.74, 2.91 Hz, 1H) 7.33 (dd, J = 8.84, 6.06 Hz, 1H) 7.59 (dt, J = 7.77, 1.42 Hz, 1H) 7.65 (t, J = 7.83 Hz, 1H) 7.92-7.99 (m, 1H) 8.29-8.34 (m, 1H) 8.50-8.56 (m, 1H) 8.67 (dd, J = 2.40, 0.88 Hz, 1H) 10.95 (s, 1H) | Method F using (3-aminophenyl)(methyl)(methylimino)-λ$^6$-sulfanone |
| 17 | 2-(4-fluoro-2-methoxy-phenoxy)-N-(2-methyl-4-pyridyl)-5-(trifluoromethyl)pyridine-3-carboxamide | | MS, ES+ m/z, 422 (M + H)+<br>$^1$H NMR (400 MHz, DMSO-d6) d ppm 2.46 (s, 3H) 3.71 (s, 3H) 6.85 (td, J = 8.53, 2.91 Hz, 1H) 7.11 (dd, J = 10.74, 2.91 Hz, 1H) 7.33 (dd, J = 8.84, 6.06 Hz, 1H) 7.50 (dd, J = 5.56, 1.77 Hz, 1H) 7.54-7.60 (m, 1H) 8.38 (d, J = 5.56 Hz, 1H) 8.49-8.54 (m, 1H) 8.67 (dd, J = 2.53, 1.01 Hz, 1H) 10.90 (s, 1H) | Method F using 2-methylpyridin-4-amine |
| 18 | 2-(4-fluoro-2-methoxy-phenoxy)-N-(6-methyl-3-pyridyl)-5-(trifluoromethyl)pyridine-3-carboxamide | | MS, ES+ m/z, 422 (M + H)+<br>$^1$H NMR (400 MHz, DMSO-d6) d ppm 2.45 (s, 3H) 3.71 (s, 3H) 7.11 (d, J = 10.86 Hz, 1H) 7.26-7.38 (m, 2H) 8.05 (d, J = 8.34 Hz, 1H) 8.52 (d, J = 2.53 Hz, 1H) 8.64-8.70 (m, 1H) 8.75 (d, J = 2.53 Hz, 1H) 10.71 (s, 1H) | Method F using 6-methylpyridin-3-amine |
| 19 | 2-(4-fluoro-2-methoxy-phenoxy)-N-pyridazin-4-yl-5-(trifluoromethyl)pyridine-3-carboxamide | | MS, ES+ m/z, 409 (M + H)+<br>$^1$H NMR (400 MHz, DMSO-d6) d ppm 3.71 (s, 3H) 6.85 (td, J = 8.46, 2.78 Hz, 1H) 7.11 (dd, J = 10.86, 2.78 Hz, 1H) 7.33 (dd, J = 8.84, 6.06 Hz, 1H) 8.08 (dd, J = 5.81, 2.78 Hz, 1H) 8.55-8.63 (m, 1H) 8.70 (dd, J = 2.40, 0.88 Hz, 1H) 9.14 (dd, J = 5.81, 1.01 Hz, 1H) 9.41 (dd, J = 2.78, 1.01 Hz, 1H) 11.28 (s, 1H) | Method F using pyridazin-4-amine |

| Example | Name | R | Analytical data | Preparation details |
|---|---|---|---|---|
| 20 | N-[3-[[dimethyl(oxo)-$\lambda^6$-sulfanylidene]amino]phenyl]-2-(4-fluoro-2-methoxy-phenoxy)-5-(trifluoromethyl)pyridine-3-carboxamide | | MS, ES+ m/z, 498 (M + H)+ $^1$H NMR (400 MHz, DMSO-d6) d ppm 3.23 (s, 6H) 3.72 (s, 3H) 6.70 (d, J = 7.83 Hz, 1H) 6.85 (t, J = 8.46 Hz, 1H) 7.03-7.21 (m, 2H) 7.28 (d, J = 8.08 Hz, 1H) 7.31-7.41 (m, 2H) 8.46 (s, 1H) 8.64 (s, 1H) 10.44 (s, 1H) | Method F, using ((3-aminophenyl)imino)dimethyl-$\lambda^6$-sulfanone |

Example 21: 2-(2,4-dichlorophenoxy)-N-(3-methylsulfonylphenyl)-5-(trifluoromethyl)pyridine-3-carboxamide Method G

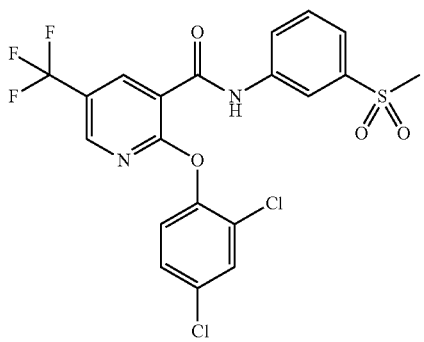 [SMILES: CS(=O)(=O)c1cccc(NC(=O)c2cc(C(F)(F)F)cnc2Oc2ccc(Cl)cc2Cl)c1]

A mixture of 2-(benzotriazol-1-yloxy)-N-(3-methylsulfonylphenyl)-5-(trifluoromethyl)pyridine-3-carboxamide (Intermediate 2) (50.0 mg, 0.100 mmol), 2,4-dichlorophenol (20.5 mg, 0.130 mmol) and cesium carbonate (102 mg, 0.310 mmol) in MeCN (3 mL) was stirred at 50° C. for 1 h.

The solvent was removed under a stream of N$_2$, and the residue treated with water/MeOH (4:1). This mixture was briefly sonicated then stirred at room temperature for 24 h. The resulting precipitate was collected by filtration, washed with water and dried under vacuum to give 2-(2,4-dichlorophenoxy)-N-(3-methylsulfonylphenyl)-5-(trifluoromethyl)pyridine-3-carboxamide (43.6 mg, 0.0863 mmol, 82.4 0 yield) as an off-white solid. MS, ES$^+$ m/z 505.0 [M+H]$^+$.

$^1$H-NMR (400 MHz, DMSO-d$_6$) δ 11.07 (s, 1H), 8.71-8.73 (m, 1H), 8.63 (d, J=2.53 Hz, 1H), 8.39-8.42 (m, 1H), 7.97-8.01 (m, 1H), 7.82-7.84 (m, 1H), 7.66-7.74 (m, 2H), 7.53-7.60 (m, 2H), 3.24 (s, 3H).

The following compounds have been synthesized according to Method G

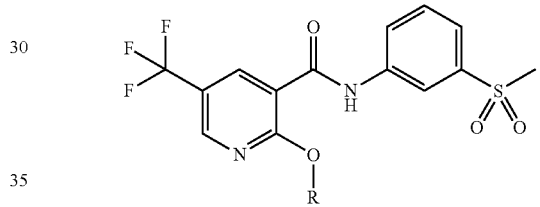

| Example | Name | R | Analytical data | Preparation details |
|---|---|---|---|---|
| 22 | 2-(2,4-dimethylphenoxy)-N-(3-methylsulfonylphenyl)-5-(trifluoromethyl)pyridine-3-carboxamide | | MS, ES$^+$ m/z, 465.1 (M + H)$^+$. $^1$H NMR (400 MHz, DMSO-d6) δ ppm 11.04 (s, 1H), 8.65 (d, J = 1.52 Hz, 1H), 8.55 (d, J = 2.27 Hz, 1H), 8.41 (s, 1H), 7.96-8.00 (m, 1H), 7.65-7.73 (m, 2H), 7.07-7.14 (m, 3H), 3.23 (s, 3H), 2.30 (s, 3H), 2.05 (s, 3H). | Method G using 2,4-dimethylphenol. (92.1% yield) |
| 23 | 2-(2-chloro-4-methoxy-phenoxy)-N-(3-methylsulfonylphenyl)-5-(trifluoromethyl)pyridine-3-carboxamide | | MS, ES$^+$ m/z, 500.9 (M + H)$^+$. $^1$H NMR (400 MHz, DMSO-d6) δ ppm 11.04 (s, 1H), 8.70 (dd, J = 2.27, 1.01 Hz, 1H), 8.58 (d, J = 2.53 Hz, 1H), 8.40-8.43 (m, 1H), 7.98 (dt, J = 7.58, 1.89 Hz, 1H), 7.65-7.73 (m, 2H), 7.40 (d, J = 8.84 Hz, 1H), 7.19 (d, J = 2.78 Hz, 1H), 7.03 (dd, J = 8.97, 2.91 Hz, 1H), 3.81 (s, 3H), 3.23 (s, 3H). | Method G using 2-chloro-4-methoxyphenol. (24.8% yield) |
| 24 | N-(3-methylsulfonylphenyl)-2-(2-propylphenoxy)-5-(trifluoromethyl)pyridine-3-carboxamide | | MS, ES$^+$ m/z, 479.0 (M + H)$^+$. $^1$H NMR (400 MHz, DMSO-d6) δ ppm 11.06 (s, 1H), 8.66-8.68 (m, 1H), 8.57 (d, J = 2.53 Hz, 1H), 8.38-8.40 (m, 1H), 7.98 (dt, J = 7.14, 1.99 Hz, 1H), 7.66-7.73 (m, 2H), 7.27-7.34 (m, 2H), 7.19-7.24 (m, 2H), 3.23 (s, 3H), 2.42-2.47 (m, 2H), 1.46 (dq, J = 15.00, 7.46 Hz, 2H), 0.76 (t, J = 7.33 Hz, 3H). | Method G using 2-propylphenol. (89.6% yield) |

| Example | Name | R | Analytical data | Preparation details |
|---|---|---|---|---|
| 25 | 2-(2-methoxy-4-methyl-phenoxy)-N-(3-methylsulfonylphenyl)-5-(trifluoromethyl)pyridine-3-carboxamide | (structure: 2-methoxy-4-methylphenyl) | MS, ES+ m/z, 481.0 (M + H)+. <br> 1H NMR (400 MHz, DMSO-d6) δ ppm 10.99 (s, 1H), 8.65 (d, J = 1.52 Hz, 1H), 8.51 (d, J = 2.53 Hz, 1H), 8.41 (s, 1H), 7.96-8.00 (m, 1H), 7.65-7.73 (m, 2H), 7.15 (d, J = 8.08 Hz, 1H), 6.99 (d, J = 1.77 Hz, 1H), 6.82 (d, J = 7.58 Hz, 1H), 3.68 (s, 3H), 3.23 (s, 3H), 2.34 (s, 3H). | Method G using 2-methoxy-4-methylphenol. (76.3% yield) |
| 26 | 2-(4-chloro-2-methoxy-phenoxy)-N-(3-methylsulfonylphenyl)-5-(trifluoromethyl)pyridine-3-carboxamide | (structure: 4-chloro-2-methoxyphenyl) | MS, ES+ m/z, 501.0 (M + H)+. <br> 1H NMR (400 MHz, DMSO-d6) δ ppm 11.01 (s, 1H), 8.67 (d, J = 1.52 Hz, 1H), 8.55 (d, J = 2.53 Hz, 1H), 8.40-8.42 (m, 1H), 7.96-8.01 (m, 1H), 7.66-7.73 (m, 2H), 7.33 (d, J = 8.34 Hz, 1H), 7.27 (d, J = 2.53 Hz, 1H), 7.09 (dd, J = 8.46, 2.40 Hz, 1H), 3.73 (s, 3H), 3.23 (s, 3H). | Method G using 4-chloro-2-methoxyphenol. (90.6% yield) |
| 27 | 2-(2-isopropoxyphenoxy)-N-(3-methylsulfonylphenyl)-5-(trifluoromethyl)pyridine-3-carboxamide | (structure: 2-isopropoxyphenyl) | MS, ES +m/z, 495.0 (M + H)+. <br> 1H NMR (400 MHz, DMSO-d6) δ ppm 10.95 (s, 1H), 8.67 (d, J = 1.52 Hz, 1H), 8.53 (d, J = 2.27 Hz, 1H), 8.41 (s, 1H), 7.98-8.02 (m, 1H), 7.66-7.73 (m, 2H), 7.31 (dd, J = 7.83, 1.52 Hz, 1H), 7.20-7.25 (m, 1H), 7.13-7.16 (m, 1H), 7.01 (td, J = 7.64, 1.39 Hz, 1H), 4.49 (quin, J = 6.00 Hz, 1H), 3.23 (s, 3H), 1.02 (d, J = 6.06 Hz, 6H). | Method G using 2-isopropoxyphenol. (79.2% yield) |

The following compounds have been synthesized according to Method G

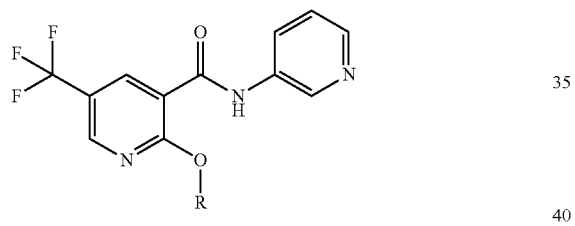

| Example | Name | R | Analytical data | Prep details |
|---|---|---|---|---|
| 28 | 2-(4-(difluoromethoxy)phenoxy)-N-(pyridin-3-yl)-5-(trifluoromethyl)nicotinamide | (structure: 4-(difluoromethoxy)phenyl) | MS (ES+) m/z 426.0 [M + H]+. <br> 1H NMR (400 MHz, DMSO-d6) δ ppm 7.21-7.33 (m, 2H) 7.33-7.39 (m, 2H) 7.64 (dd, J = 8.46, 4.93 Hz, 1H) 8.28-8.36 (m, 1H) 8.47 (dd, J = 4.93, 1.39 Hz, 1H) 8.57 (d, J = 2.27 Hz, 1H) 8.68-8.75 (m, 1H) 9.03 (d, J = 2.27 Hz, 1H) 11.12 (s, 1H) | Method G, using 4-(difluoromethyl)phenol |
| 29 | 2-(2,4-dimethoxyphenoxy)-N-(pyridin-3-yl)-5-(trifluoromethyl)nicotinamide | (structure: 2,4-dimethoxyphenyl) | MS (ES+) m/z 420.0 [M + H]+. <br> 1H NMR (400 MHz, DMSO-d6) d ppm 3.63-3.71 (m, 3H) 3.72-3.85 (m, 3H) 6.51-6.62 (m, 1H) 6.67-6.77 (m, 1H) 7.19 (d, J = 8.84 Hz, 1H) 7.66 (dd, J = 8.34, 5.05 Hz, 1H) 8.28-8.36 (m, 1H) 8.43-8.54 (m, 2H) 8.63-8.75 (m, 1H) 9.05 (d, J = 2.27 Hz, 1H) 11.07 (s, 1H) | Method G, using 2,4-dimethoxyphenol |

| Example | Name | R | Analytical data | Prep details |
|---|---|---|---|---|
| 30 | 2-(2-chloro-4-methoxyphenoxy)-N-(pyridin-3-yl)-5-(trifluoromethyl)nicotinamide | | MS (ES+) m/z 424.0 [M + H]⁺.<br>$^1$H NMR (400 MHz, DMSO-d6) δ ppm 3.76-3.85 (m, 3H) 6.98-7.08 (m, 1H) 7.14-7.22 (m, 1H) 7.41 (d, J = 9.09 Hz, 1H) 7.65-7.75 (m, 1H) 8.38 (dd, J = 8.46, 1.14 Hz, 1H) 8.51 (dd, J = 5.05, 1.52 Hz, 1H) 8.61 (d, J = 2.27 Hz, 1H) 8.72 (d, J = 1.52 Hz, 1H) 9.09 (d, J = 2.27 Hz, 1H) 11.21 | Method G, using 2-chloro-4-methoxyphenol |
| 31 | 2-(3,4-difluorophenoxy)-N-(pyridin-3-yl)-5-(trifluoromethyl)nicotinamide | | MS (ES+) m/z 396.0 [M + H]⁺.<br>$^1$H NMR (400 Hz, DMSO-d6) δ ppm 7.15-7.25 (m, 1H) 7.50-7.59 (m, 2H) 7.60-7.69 (m, 1H) 8.27-8.36 (m, 1H) 8.47 (dd, J = 4.93, 1.39 Hz, 1H) 8.59 (d, J = 2.53 Hz, 1H) 8.71-8.79 (m, 1H) 9.02 (d, J = 2.27 Hz, 1H) 11.10 (s, 1H) | Method G, using 3,4-difluorophenol |
| 32 | 2-(2-chloro-4-fluorophenoxy)-N-(pyridin-3-yl)-5-(trifluoromethyl)nicotinamide | | MS (ES+) m/z 412.0 [M + H]⁺.<br>$^1$H NMR (400 MHz, DMSO-d6) δ ppm 7.31-7.40 (m, 1H) 7.57 (dd, J = 9.09, 5.31 Hz, 1H) 7.62-7.70 (m, 2H) 8.28-8.41 (m, 1H) 8.48 (dd, J = 4.93, 1.39 Hz, 1H) 8.64 (d, J = 2.53 Hz, 1H) 8.74 (dd, J = 2.40, 0.88 Hz, 1H) 9.05 (d, J = 2.27 Hz, 1H) 11.16 (s, 1H) | Method G, using 2-chloro-4-fluorophenol |

Example 33: 2-(2,6-dimethylphenoxy)-N-(3-methylsulfonylphenyl)-5-(trifluoromethyl)pyridine-3-carboxamide Method H

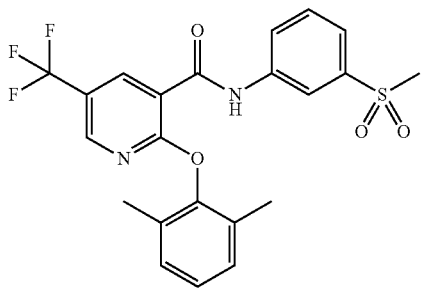 [SMILES: Cc1cccc(C)c1Oc1ncc(C(F)(F)F)cc1C(=O)Nc1cccc(S(C)(=O)=O)c1]

A mixture of 2-chloro-N-(3-methylsulfonylphenyl)-5-(trifluoromethyl)pyridine-3-carboxamide (Intermediate 4) (59 mg, 0.160 mmol), 2,6-dimethylphenol (20.9 mg, 0.170 mmol) and cesium carbonate (152 mg, 0.470 mmol) in MeCN (2 mL) was stirred at room temperature for 18 h. The contents were diluted with EtOAc, washed with water (3×), brine (1×), dried over MgSO4, filtered and the solvent removed in vacuo to give a residue which was purified by automated normal-phase chromatography (0-100% EtOAc/heptane, 4 g silica gel cartridge) to give 2-(2,6-dimethylphenoxy)-N-(3-methylsulfonylphenyl)-5-(trifluoromethyl)pyridine-3-carboxamide (32.6 mg, 0.0702 mmol, 45.1% yield) as a white foam. MS, ES⁺ m/z 465.0 [M+H]⁺.

$^1$H-NMR (400 MHz, DMSO-d$_6$) δ 11.08 (s, 1H), 8.64 (dd, J=2.53, 1.01 Hz, 1H), 8.59 (d, J=2.53 Hz, 1H), 8.42-8.44 (m, 1H), 7.98 (dt, J=7.58, 1.89 Hz, 1H), 7.66-7.73 (m, 2H), 7.08-7.16 (m, 3H), 3.23 (s, 3H), 2.07 (s, 6H).

The following compounds have been synthesized according to Method H

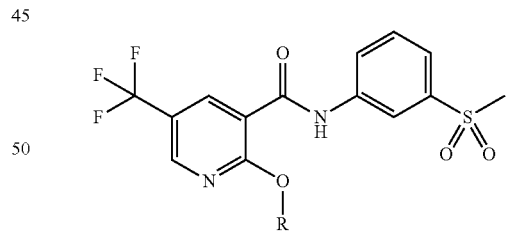

| Example | Name | R | Analytical data | Preparation details |
|---|---|---|---|---|
| 34 | 2-(4-fluorophenoxy)-N-(3-methylsulfonylphenyl)-5-(trifluoromethyl)pyridine-3-carboxamide | | MS, ES⁺ m/z, 455.1 (M + H)⁺.<br>$^1$H NMR (400 MHz, DMSO-d6) δ ppm 11.05 (br. s., 1 H), 8.66 (s, 1 H), 8.50 (s, 1 H), 8.37 (s, 1 H), 7.94 (d, J = 3.03 Hz, 1 H), 7.61-7.66 (m, 2 H), 7.28-7.33 (m, 4 H), 3.21 (s, 3 H). | Method H using 4-fluorophenol. (14.5% yield) |

| Example | Name | R | Analytical data | Preparation details |
|---------|------|---|-----------------|---------------------|
| 35 | 2-(4-fluoro-2-methoxy-phenoxy)-N-(3-methylsulfonyl-phenyl)-5-(trifluoromethyl)pyridine-3-carboxamide | 4-fluoro-2-methoxyphenyl | MS, ES+ m/z, 485.0 (M + H)+. $^1$H NMR (400 MHz, DMSO-d6) δ ppm 11.00 (s, 1 H), 8.67 (d, J = 1.52 Hz, 1H), 8.53 (d, J = 2.53 Hz, 1H), 8.41 (s, 1 H), 7.98 (d, J = 7.58 Hz, 1 H), 7.65-7.73 (m, 2 H), 7.33 (dd, J = 8.84, 6.06 Hz, 1H), 7.11 (dd, J = 10.74, 2.91 Hz, 1 H), 6.85 (td, J = 8.46, 2.78 Hz, 1 H), 3.71 (s, 3 H), 3.23 (s, 3 H). | Method H using 4-fluoro-2-methoxyphenol. (50.6% yield) |
| 36 | 2-(2-chloro-4-fluoro-phenoxy)-N-(3-methylsulfonyl-phenyl)-5-(trifluoromethyl)pyridine-3-carboxamide | 2-chloro-4-fluorophenyl | MS, ES+ m/z, 488.9 (M + H)+. $^1$H NMR (400 MHz, DMSO-d6) δ ppm 11.06 (s, 1 H), 8.72 (d, J = 1.52 Hz, 1H), 8.62 (d, J = 2.53 Hz, 1H), 8.41 (s, 1 H), 7.97-8.01 (m, 1 H), 7.63-7.73 (m, 3 H), 7.57 (dd, J = 9.09, 5.31 Hz, 1H), 7.37 (td, J = 8.46, 3.03 Hz, 1 H), 3.23 (s, 3 H). | Method H using 2-chloro-4-fluorophenol. (33.6% yield) |
| 37 | N-(3-methylsulfonyl-phenyl)-2-[2-methyl-4-(trifluoromethoxy)phenoxy]-5-(trifluoromethyl)pyridine-3-carboxamide | 2-methyl-4-(trifluoromethoxy)phenyl | MS, ES+ m/z, 535.0 (M + H)+. $^1$H NMR (400 MHz, DMSO-d6) δ ppm 11.06 (s, 1 H), 8.70 (s, 1 H), 8.60 (d, J = 2.78 Hz, 1 H), 8.40 (s, 1 H), 7.98 (d, J = 7.58 Hz, 1 H), 7.66-7.73 (m, 2 H), 7.38 (d, J = 8.59 Hz, 2 H), 7.28-7.33 (m, 1H), 3.23 (s, 3 H), 2.14 (s, 3 H). | Method H using 2-methyl-4-(trifluoromethoxy)phenol. (82.7% yield) |
| 38 | N-(3-methylsulfonyl-phenyl)-2-[4-(trifluoromethoxy)phenoxy]-5-(trifluoromethyl)pyridine-3-carboxamide | 4-(trifluoromethoxy)phenyl | MS, ES+ m/z, 521.0 (M + H)+. $^1$H NMR (400 MHz, DMSO-d6) δ ppm 11.05 (s, 1 H), 8.72-8.74 (m, 1 H), 8.57-8.59 (m, 1 H), 8.38-8.40 (m, 1 H), 7.98 (dt, J = 7.52, 1.93 Hz, 1 H), 7.65-7.73 (m, 2 H), 7.47-7.51 (m, 2 H), 7.41-7.46 (m, 2 H), 3.23 (s, 3 H). | Method H using 4-(trifluoromethoxy)phenol. (18.7% yield) |
| 39 | 2-[4-(difluoromethoxy)phenoxy]-N-(3-methylsulfonyl-phenyl)-5-(trifluoromethyl)pyridine-3-carboxamide | 4-(difluoromethoxy)phenyl | MS, ES+ m/z, 503.0 (M + H)+. $^1$H NMR (400 MHz, DMSO-d6) δ ppm 11.04 (s, 1 H), 8.70 (s, 1 H), 8.56 (d, J = 2.02 Hz, 1 H), 8.39 (s, 1 H), 7.98 (d, J = 7.58 Hz, 1 H), 7.65-7.74 (m, 1 H), 7.33-7.38 (m, 2 H), 7.25-7.31 (m, 3 H), 7.26 (d, J = 148.00 Hz, 1 H), 3.23 (s, 3 H). | Method H using 4-(difluoromethoxy)phenol. (72.9% yield) |
| 40 | 2-[3-fluoro-4-(trifluoromethoxy)phenoxy]-N-(3-methylsulfonyl-phenyl)-5-(trifluoromethyl)pyridine-3-carboxamide | 3-fluoro-4-(trifluoromethoxy)phenyl | MS, ES+ m/z, 538.9 (M + H)+. $^1$H NMR (400 MHz, DMSO-d6) δ ppm 11.03 (s, 1 H), 8.76 (s, 1 H), 8.60 (d, J = 2.53 Hz, 1 H), 8.39 (s, 1 H), 7.98 (d, J = 7.58 Hz, 1 H), 7.66-7.74 (m, 3 H), 7.63 (dd, J = 11.12, 2.78 Hz, 1 H), 7.31 (d, J = 9.09 Hz, 1H), 3.23 (s, 3 H). | Method H using 3-fluoro-4-(trifluoromethoxy)phenol. (29.5% yield) |

-continued

| Example | Name | R | Analytical data | Preparation details |
|---|---|---|---|---|
| 41 | N-(3-methylsulfonyl-phenyl)-2-phenoxy-5-(trifluoromethyl)pyridine-3-carboxamide | 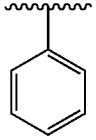 | MS, ES+ m/z, 437.8 (M + H)+ <br> 1H NMR (400 MHz, DMSO-d6) δ ppm 3.23 (s, 3 H) 7.24-7.32 (m, 3 H) 7.44-7.51 (m, 2 H) 7.65-7.74 (m, 2 H) 7.99 (dt, J = 7.52, 1.93 Hz, 1 H) 8.40 (t, J = 1.64 Hz, 1 H) 8.56 (dd, J = 2.53, 0.51 Hz, 1 H) 8.70 (dd, J = 2.40, 0.88 Hz, 1 H) 11.05 (s, 1H) | Method H, using phenol |
| 42 | 2-(3-fluorophenoxy)-N-(3-methylsulfonyl-phenyl)-5-(trifluoromethyl)pyridine-3-carboxamide | 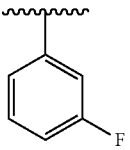 | MS, ES+ m/z, 455.8 (M + H)+ <br> 1H NMR (400 MHz, DMSO-d6) δ ppm 3.24 (s, 3 H) 7.12-7.20 (m, 2 H) 7.25 (dt, J = 10.11, 2.27 Hz, 1H) 7.52 (td, J = 8.34, 6.82 Hz, 1 H) 7.65-7.74 (m, 2 H) 7.98 (dt, J = 7.52, 1.80 Hz, 1 H) 8.37-8.42 (m, 1H) 8.58 (d, J = 2.53 Hz, 1 H) 8.71-8.76 (m, 1 H) 11.03 (s, 1 H) | Method H, using 3-fluorophenol |
| 43 | 2-(2,5-difluorophenoxy)-N-(3-methylsulfonyl-phenyl)-5-(trifluoromethyl)pyridine-3-carboxamide | 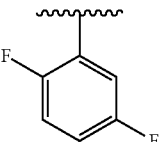 | MS, ES+ m/z, 473.9 (M + H)+ <br> 1H NMR (400 MHz, DMSO-d6) δ ppm 3.24 (s, 3 H) 7.20-7.29 (m, 1 H) 7.45-7.54 (m, 2 H) 7.66-7.75 (m, 2 H) 7.99 (dt, J = 7.58, 1.89 Hz, 1 H) 8.38-8.43 (m, 1 H) 8.64 (d, J = 2.53 Hz, 1 H) 8.75 (dd, J = 2.40, 0.88 Hz, 1 H) 11.08 (s, 1H) | Method H, using 2,5-difluorophenol |
| 44 | 2-(4-methylphenoxy)-N-(3-methylsulfonyl-phenyl)-5-(trifluoromethyl)pyridine-3-carboxamide | 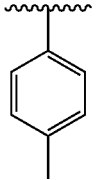 | MS, ES+ m/z, 451.8 (M + H)+ <br> 1H NMR (400 MHz, DMSO-d6) δ ppm 2.33 (s, 3 H) 3.23 (s, 3 H) 7.10-7.19 (m, 2 H) 7.26 (m, J = 8.08 Hz, 2 H) 7.61-7.75 (m, 2 H) 7.98 (dt, J = 7.33, 1.89 Hz, 1H) 8.36-8.44 (m, 1H) 8.53 (d, J = 2.53 Hz, 1 H) 8.68 (dd, J = 2.40, 0.88 Hz, 1H) 11.03 (s, 1 H) | Method H, using 4-methylphenol |
| 45 | 2-(3-chloro-5-fluoro-phenoxy)-N-(3-methylsulfonyl-phenyl)-5-(trifluoromethyl)pyridine-3-carboxamide | 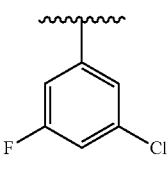 [SMILES: *c1cc(F)cc(Cl)c1] | MS, ES+ m/z, 489.0 (M + H)+ <br> 1H NMR (400 MHz, DMSO-d6) δ ppm 3.24 (s, 3 H) 7.24-7.51 (m, 3 H) 7.62-7.77 (m, 2 H) 7.97 (dt, J = 7.58, 1.77 Hz, 1 H) 8.34-8.44 (m, 1 H) 8.60 (d, J = 2.53 Hz, 1 H) 8.70-8.83 (m, 1H) 11.01 (s, 1 H) | Method H, using 3-chloro-5-fluorophenol |
| 46 | 2-(2-isopropylphenoxy)-N-(3-methylsulfonyl-phenyl)-5-(trifluoromethyl)pyridine-3-carboxamide | 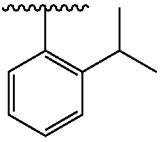 | MS, ES+ m/z, 479.2 (M + H)+ <br> 1H NMR (400 MHz, DMSO-d6) δ ppm 1.10 (d, J = 7.07 Hz, 6 H) 2.96-3.09 (m, 1 H) 3.23 (s, 3 H) 7.14-7.22 (m, 1 H) 7.23-7.32 (m, 2 H) 7.37-7.45 (m, 1 H) 7.62-7.75 (m, 2 H) 7.98 (dt, J = 7.39, 1.99 Hz, 1 H) 8.36-8.43 (m, 1 H) 8.57 (d, J = 2.53 Hz, 1 H) 8.65-8.72 (m, 1 H) 11.08 (s, 1 H) | Method H, using 2-isopropylphenol |
| 47 | 2-(3,4-difluorophenoxy)-N-(3-methylsulfonyl-phenyl)-5-(trifluoromethyl)pyridine-3-carboxamide | 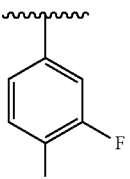 | MS, ES+ m/z, 473.0 (M + H)+ <br> 1H NMR (400 MHz, DMSO-d6) δ ppm 3.24 (s, 3 H) 7.15-7.26 (m, 1 H) 7.48-7.62 (m, 2 H) 7.63-7.77 (m, 2 H) 7.99 (dt, J = 7.58, 1.89 Hz, 1 H) 8.41 (t, J = 1.64 Hz, 1 H) 8.58 (d, J = 2.53 Hz, 1H) 8.74 (dd, J = 2.40, 0.88 Hz, 1 H) 11.04 (s, 1H) | Method H, using 3,4-difluorophenol |

| Example | Name | R | Analytical data | Preparation details |
| --- | --- | --- | --- | --- |
| 48 | 2-(2,4-difluorophenoxy)-N-(3-methylsulfonyl-phenyl)-5-(trifluoromethyl)pyridine-3-carboxamide | 2,4-difluorophenyl | MS, ES+ m/z, 473.1 (M + H)+ <br> 1H NMR (400 MHz, DMSO-d6) δ ppm 3.24 (s, 3 H) 7.14-7.27 (m, 1 H) 7.45-7.60 (m, 2 H) 7.63-7.76 (m, 2H) 7.99 (dt, J = 7.52, 1.80 Hz, 1 H) 8.36-8.44 (m, 1 H) 8.63 (d, J = 2.27 Hz, 1 H) 8.68-8.77 (m, 1 H) 11.10 (s, 1 H) | Method H, using 2,4-difluorophenol |
| 49 | 2-(3,5-difluorophenoxy)-N-(3-methylsulfonyl-phenyl)-5-(trifluoromethyl)pyridine-3-carboxamide | 3,5-difluorophenyl | MS, ES+ m/z, 473.0 (M + H)+ <br> 1H NMR (400 MHz, DMSO-d6) δ ppm 3.24 (s, 3 H) 7.13-7.29 (m, 3 H) 7.62-7.77 (m, 2 H) 7.92-8.04 (m, 1 H) 8.34-8.44 (m, 1 H) 8.61 (d, J = 2.53 Hz, 1 H) 8.77 (d, J = 1.52 Hz, 1 H) 11.02 (s, 1 H) | Method H, using 3,5-difluorophenol |
| 50 | N-(3-methylsulfonyl-phenyl)-2-[4-(2,2,2-trifluoroethoxy)phenoxy]-5-(trifluoromethyl)pyridine-3-carboxamide | 4-(2,2,2-trifluoroethoxy)phenyl | MS, ES+ m/z, 535.1 (M + H)+ <br> 1H NMR (400 MHz, DMSO-d6) δ ppm 3.24 (s, 3 H) 4.80 (q, J = 8.76 Hz, 2 H) 7.10-7.18 (m, 2 H) 7.22-7.29 (m, 2 H) 7.64-7.74 (m, 2 H) 7.98 (dt, J = 7.52, 1.93 Hz, 1 H) 8.36-8.44 (m, 1H) 8.54 (d, J = 2.53 Hz, 1 H) 8.65-8.72 (m, 1 H) 11.04 (s, 1H) | Method H, using 4-(2,2,2-trifluoroethoxy)phenol |
| 51 | N-(3-methylsulfonyl-phenyl)-5-(trifluoromethyl)-2-[4-(trifluoromethyl-sulfanyl)phenoxy]pyridine-3-carboxamide | 4-(trifluoromethylsulfanyl)phenyl | MS, ES+ m/z, 537.0 (M + H)+ <br> 1H NMR (400 MHz, DMSO-d6) δ ppm 3.23 (s, 3 H) 7.42-7.52 (m, 2 H) 7.62-7.75 (m, 2 H) 7.83 (m, J = 8.59 Hz, 2H) 7.98 (dt, J = 7.64, 1.86 Hz, 1 H) 8.34-8.43 (m, 1 H) 8.61 (d, J = 2.53 Hz, 1H) 8.71-8.80 (m, 1H) 11.08 (s, 1H) | Method H, using 4-((trifluoromethyl)thio)phenol |
| 52 | 2-[2-(dimethylamino)phenoxy]-N-(3-methylsulfonyl-phenyl)-5-(trifluoromethyl)pyridine-3-carboxamide | 2-(dimethylamino)phenyl | MS, ES+ m/z, 480.1 (M + H)+ | Method H, using 2-(dimethylamino)phenol |
| 53 | N-(3-methylsulfonyl-phenyl)-5-(trifluoromethyl)-2-[2-(trifluoromethyl)phenoxy]pyridine-3-carboxamide | 2-(trifluoromethyl)phenyl | MS, ES+ m/z, 505.0 (M + H)+ <br> 1H NMR (400 MHz, DMSO-d6) δ ppm 3.24 (s, 3 H) 7.45-7.61 (m, 2 H) 7.63-7.75 (m, 2 H) 7.76-7.87 (m, 2 H) 7.97 (dt, J = 7.58, 1.77 Hz, 1 H) 8.32-8.41 (m, 1 H) 8.64 (d, J = 2.53 Hz, 1 H) 8.73 (d, J = 1.52 Hz, 1H) 11.05 (s, 1H) | Method H, using 2-(trifluoromethyl)phenol |
| 54 | 2-(2,4-dimethoxyphenoxy)-N-(3-methylsulfonyl-phenyl)-5-(trifluoromethyl)pyridine-3-carboxamide | 2,4-dimethoxyphenyl | MS, ES+ m/z, 497.1 (M + H)+ <br> 1H NMR (400 MHz, DMSO-d6) δ ppm 3.23 (s, 3 H) 3.69 (s, 3 H) 3.79 (s, 3 H) 6.57 (dd, J = 8.84, 2.78 Hz, 1 H) 6.72 (d, J = 2.78 Hz, 1 H) 7.20 (d, J = 8.59 Hz, 1 H) 7.63-7.75 (m, 2 H) 7.98 (dt, J = 7.39, 1.99 Hz, 1 H) 8.38-8.45 (m, 1 H) 8.51 (d, J = 2.53 Hz, 1 H) 8.61-8.70 (m, 1 H) 10.99 (s, 1 H) | Method H, using 2,4-dimethoxyphenol |

| Example | Name | R | Analytical data | Preparation details |
|---|---|---|---|---|
| 55 | N-(3-methylsulfonyl-phenyl)-5-(trifluoromethyl)-2-(3,4,5-trifluorophenoxy)pyridine-3-carboxamide | 3,4,5-trifluorophenyl | MS, ES+ m/z, 491.0 (M + H)+ <br> 1H NMR (400 MHz, DMSO-d6) δ ppm 3.24 (s, 3 H) 7.39-7.55 (m, 2 H) 7.62-7.77 (m, 2 H) 7.97 (dt, J = 7.52, 1.80 Hz, 1 H) 8.33-8.44 (m, 1 H) 8.61 (d, J = 2.53 Hz, 1 H) 8.71-8.82 (m, 1H) 11.02 (s, 1 H) | Method H, using 3,4,5-trifluorophenol |
| 56 | 2-(3,5-dichlorophenoxy)-N-(3-methylsulfonyl-phenyl)-5-(trifluoromethyl)pyridine-3-carboxamide | 3,5-dichlorophenyl | MS, ES+ m/z, 505.0/503.0 (M + H)+ <br> 1H NMR (400 MHz, DMSO-d6) δ ppm 3.24 (s, 3 H) 7.53 (d, J = 1.71 Hz, 2 H) 7.59 (t, J = 1.89 Hz, 1 H) 7.65-7.77 (m, 2 H) 7.89-8.04 (m, 1 H) 8.34-8.45 (m, 1H) 8.60 (d, J = 2.53 Hz, 1 H) 8.72-8.84 (m, 1 H) 10.99 (s, 1 H) | Method H, using 3,5-dichlorophenol |
| 57 | N-(3-methylsulfonyl-phenyl)-5-(trifluoromethyl)-2-[[6-(trifluoromethyl)-3-pyridyl]oxy]pyridine-3-carboxamide | 6-(trifluoromethyl)pyridin-3-yl | MS, ES+ m/z, 506.1 (M + H)+ <br> 1H NMR (400 MHz, DMSO-d6) δ ppm 3.24 (s, 3 H) 7.65-7.75 (m, 2 H) 8.00 (dt, J = 7.58, 1.89 Hz, 1H) 8.06-8.14 (m, 2 H) 8.40 (t, J = 1.64 Hz, 1 H) 8.66 (d, J = 2.53 Hz, 1 H) 8.73-8.79 (m, 1 H) 8.82 (s, 1 H) 11.12 (s, 1H) | Method H, using 6-(trifluoromethyl)pyridin-3-ol |
| 58 | 2-(1,3-benzothiazol-4-yloxy)-N-(3-methylsulfonyl-phenyl)-5-(trifluoromethyl)pyridine-3-carboxamide | 1,3-benzothiazol-4-yl | MS, ES+ m/z, 494.0 (M + H)+ <br> 1H NMR (400 MHz, DMSO-d6) δ ppm 3.23 (s, 3 H) 7.53 (dd, J = 7.83, 1.01 Hz, 1 H) 7.60 (t, J = 7.96 Hz, 1H) 7.65-7.74 (m, 2 H) 8.03 (dt, J = 7.33, 2.02 Hz, 1 H) 8.12 (dd, J = 7.96, 0.88 Hz, 1 H) 8.42-8.47 (m, 1 H) 8.57-8.66 (m, 2 H) 9.32 (s, 1 H) 11.17 (s, 1 H) | Method H, using benzo[d]thiazol-4-ol |

The following compounds have been synthesized according to Method H

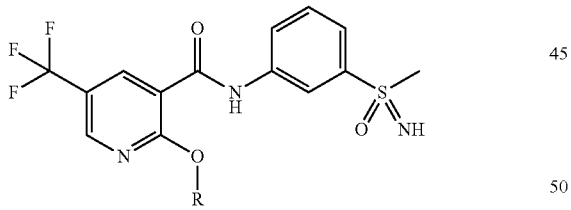

| Example | Name | R | Analytical data | Preparation details |
|---|---|---|---|---|
| 59 | 2-[4-(difluoromethoxy)phenoxy]-N-[3-(methylsulfonimidoyl)phenyl]-5-(trifluoromethyl)pyridine-3-carboxamide | 4-(difluoromethoxy)phenyl | MS, ES+ m/z, 502.0 (M + H)+ <br> 1H NMR (400 MHz, DMSO-d6) δ ppm 3.07 (s, 3 H) 4.27 (s, 1 H) 7.17-7.41 (m, 5 H) 7.62 (t, J = 7.83 Hz, 1 H) 7.70 (d, J = 7.83 Hz, 1 H) 7.96 (d, J = 8.34 Hz, 1 H) 8.38 (t, J = 1.77 Hz, 1H) 8.55 (d, J = 2.53 Hz, 1 H) 8.70 (d, J = 1.26 Hz, 1H) 10.99 (s, 1 H) | Method H, using 4-(difluoromethoxy)phenol |

-continued

| Example | Name | R | Analytical data | Preparation details |
|---|---|---|---|---|
| 60 | 2-(2-chloro-4-fluoro-phenoxy)-N-[3-(methylsulfonimidoyl)phenyl]-5-(trifluoromethyl)pyridine-3-carboxamide | 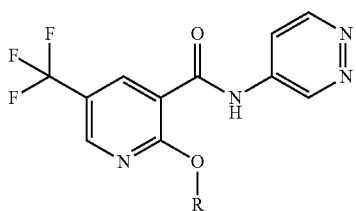 | MS, ES⁺ m/z, 488.0 (M + H)⁺ ¹H NMR (400 MHz, DMSO-d6) δ ppm 3.07 (s, 3 H) 4.27 (s, 1 H) 7.33-7.41 (m, 1 H) 7.54-7.73 (m, 4 H) 7.92-7.99 (m, 1H) 8.39 (t, J = 1.89 Hz, 1 H) 8.61 (d, J = 2.27 Hz, 1 H) 8.72 (dd, J = 2.15, 0.88 Hz, 1 H) 11.01 (s, 1 H) | Method H, using 2-chloro-4-fluorophenol |
| 61 | 2-(2-chloro-4-methoxy-phenoxy)-N-[3-(methylsulfonimidoyl)phenyl]-5-(trifluoromethyl)pyridine-3-carboxamide |  | MS, ES⁺ m/z, 500.0 (M + H)⁺ ¹H NMR (400 MHz, DMSO-d6) δ ppm 3.00-3.12 (m, 3 H) 3.81 (s, 3 H) 4.27 (s, 1 H) 7.03 (dd, J = 9.10, 3.03 Hz. 1 H) 7.19 (d, J = 3.03 Hz, 1H) 7.41 (d, J = 8.84 Hz, 1 H) 7.62 (t, J = 7.96 Hz, 1 H) 7.70 (dt, J = 7.96, 1.33 Hz, 1 H) 7.91-8.00 (m, 1H) 8.40 (t, J = 1.77 Hz, 1H) 8.57 (d, J = 2.53 Hz, 1 H) 8.69 (dd, J = 2.40, 0.88 Hz, 1 H) 10.99 (s, 1 H) | Method H, using 2-chloro-4-methoxyphenol |
| 62 | 2-(2-chlorophenoxy)-N-[3-(methylsulfonimidoyl)phenyl]-5-(trifluoromethyl)pyridine-3-carboxamide |  | MS, ES⁺ m/z, 470.0 (M + H)⁺ | Method H, using 2-chlorophenol |

The following compounds have been synthesized according to Method H

| Example | Name | R | Analytical data | Preparation details |
|---|---|---|---|---|
| 63 | 2-(2,4-dichlorophenoxy)-N-pyridazin-4-yl-5-(trifluoromethyl)pyridine-3-carboxamide |  | MS, ES⁺ m/z, 428.6/430.6 (M + H)⁺ ¹H NMR (400 MHz, DMSO-d6) δ ppm 7.52-7.59 (m, 2 H) 7.83 (d, J = 1.77 Hz, 1 H) 8.09 (dd, J = 5.81, 2.78 Hz, 1 H) 8.69 (d, J = 2.53 Hz, 1 H) 8.76 (dd, J = 2.40, 0.88 Hz, 1 H) 9.14 (dd, J = 5.94, 0.88 Hz, 1 H) 9.40 (dd, J = 2.65, 0.88 Hz, 1H) 11.36 (s, 1H) | Method H, using 2,4-dichlorophenol |

-continued

| Example | Name | R | Analytical data | Preparation details |
|---|---|---|---|---|
| 64 | 2-[4-(difluoromethoxy)phenoxy]-N-pyridazin-4-yl-5-(trifluoromethyl)pyridine-3-carboxamide | | MS, ES+ m/z, 427.0 (M + H)+ $^1$H NMR (400 MHz, DMSO-d6) δ ppm 7.17-7.41 (m, 5 H) 8.07 (dd, J = 5.81, 2.78 Hz, 1 H) 8.61 (d, J = 2.53 Hz, 1 H) 8.74 (dd, J = 2.53, 1.01 Hz, 1 H) 9.14 (dd, J = 5.94, 0.88 Hz, 1 H) 9.40 (dd, J = 2.65, 0.88 Hz, 1H) 11.33 (s, 1H) | Method H, using 4-(difluoromethyl)phenol |
| 65 | 2-(2-chloro-4-methoxy-phenoxy)-N-pyridazin-4-yl-5-(trifluoromethyl)pyridine-3-carboxamide | | MS, ES+ m/z, 425.0 (M + H)+ $^1$H NMR (400 MHz, DMSO-d6) δ ppm 3.81 (s, 3 H) 7.03 (dd, J = 9.09, 3.03 Hz, 1 H) 7.19 (d, J = 3.03 Hz, 1 H) 7.41 (d, J = 8.84 Hz, 1 H) 8.09 (dd, J = 5.94, 2.65 Hz, 1 H) 8.65 (d, J = 2.53 Hz, 1 H) 8.74 (dd, J = 2.27, 1.01 Hz, 1 H) 9.14 (dd, J = 5.81, 1.01 Hz, 1 H) 9.40 (dd, J = 2.78, 1.01 Hz, 1 H) 11.34 (s, 1 H) | Method H, using 2-chloro-4-methoxyphenol |

Example 66: 2-(4-fluoro-2-methoxy-phenoxy)-N-(3-methylsulfonylphenyl)-6-(trifluoromethyl)pyridine-3-carboxamide

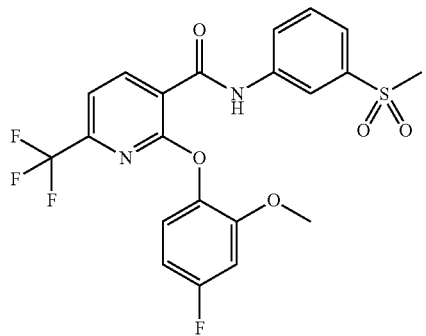 [SMILES: COc1cc(F)ccc1Oc1nc(C(F)(F)F)ccc1C(=O)Nc1cccc(S(C)(=O)=O)c1]

Step 1: Synthesis of 2-chloro-N-(3-methylsulfonylphenyl)-6-(trifluoromethyl)pyridine-3-carboxamide

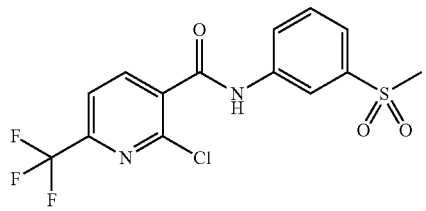 [SMILES: CS(=O)(=O)c1cccc(NC(=O)c2ccc(C(F)(F)F)nc2Cl)c1]

A mixture of HBTU (185 mg, 0.490 mmol), DIPEA (170 µL, 0.980 mmol), 2-chloro-6-(trifluoromethyl)pyridine-3-carboxylic acid (100 mg, 0.440 mmol) and 3-methylsulfonylaniline (79.7 mg, 0.470 mmol) in chloroform (5 mL) was stirred at room temperature for 4 days (for convenience). The contents were treated with 5% Na$_2$CO$_3$ and extracted with CHCl$_3$ (3×). The organic extracts were combined and the solvent removed in vacuo to give a residue which was purified by automated normal-phase chromatography (0-100% EtOAc/heptane, 12 g silica gel cartridge) to give 2-chloro-N-(3-methylsulfonylphenyl)-6-(trifluoromethyl)pyridine-3-carboxamide (86.2 mg, 0.229 mmol, 51.3% yield) as a yellow solid. MS, ES+ m/z 379.0 [M+H]+.

$^1$H-NMR (400 MHz, DMSO-d$_6$) δ 11.19 (s, 1H), 8.48 (d, J=7.83 Hz, 1H), 8.37 (t, J=1.77 Hz, 1H), 8.17 (d, J=7.58 Hz, 1H), 7.92 (dt, J=7.71, 1.83 Hz, 1H), 7.72-7.76 (m, 1H), 7.67-7.72 (m, 1H), 3.25 (s, 3H).

Step 2: Synthesis of 2-(4-fluoro-2-methoxy-phenoxy)-N-(3-methylsulfonylphenyl)-6-(trifluoromethyl)pyridine-3-carboxamide

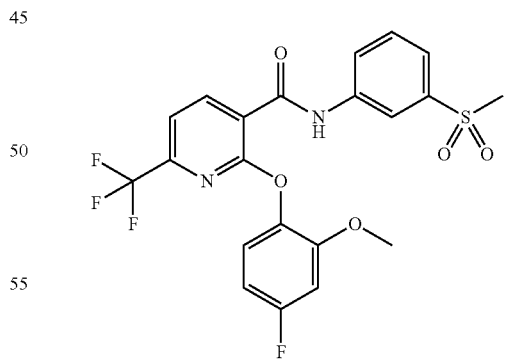

A mixture of 2-chloro-N-(3-methylsulfonylphenyl)-6-(trifluoromethyl)pyridine-3-carboxamide (40.0 mg, 0.110 mmol), 4-fluoro-2-methoxyphenol (15.1 µL, 0.130 mmol) and cesium carbonate (103 mg, 0.320 mmol) in MeCN (2 mL) was stirred at 80° C. for 1 h, then overnight at room temperature. The contents were diluted with EtOAc, washed with water (3×), brine (1×), dried over MgSO4, filtered and the solvent removed in vacuo to give a residue which was purified by automated normal-phase chromatography (0-100% EtOAc/heptane, 4 g silica gel cartridge) to give 2-(4-fluoro-2-methoxy-phenoxy)-N-(3-methylsulfonylphenyl)-6-(trifluoromethyl)pyridine-3-carboxamide (46.5 mg, 0.0960 mmol, 90.9% yield) as a yellow solid. MS, ES⁺ m/z 485.0 [M+H]⁺.

¹H-NMR (400 MHz, DMSO-d₆) δ 11.02 (s, 1H), 8.42 (s, 1H), 8.37 (d, J=7.33 Hz, 1H), 7.96 (d, J=7.58 Hz, 1H), 7.75 (d, J=7.58 Hz, 1H), 7.65-7.73 (m, 2H), 7.33 (dd, J=8.72, 5.94 Hz, 1H), 7.12 (dd, J=10.61, 2.78 Hz, 1H), 6.85 (td, J=8.46, 2.78 Hz, 1H), 3.69 (s, 3H), 3.23 (s, 3H).

Example 67: 4-(4-fluoro-2-methoxy-phenoxy)-N-(3-methylsulfonylphenyl)-6-(trifluoromethyl)pyridine-3-carboxamide Method I

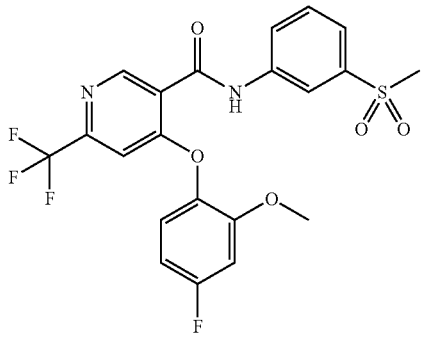 [SMILES: COc1cc(F)ccc1Oc1cc(C(F)(F)F)ncc1C(=O)Nc1cccc(S(C)(=O)=O)c1]

Step 1: Synthesis of ethyl 4-(4-fluoro-2-methoxy-phenoxy)-6-(trifluoromethyl)pyridine-3-carboxylate

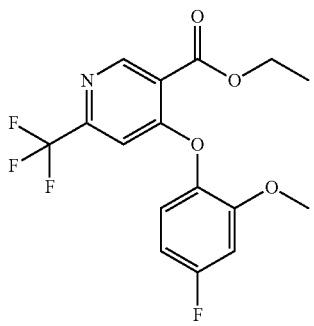 [SMILES: CCOC(=O)c1cnc(C(F)(F)F)cc1Oc1ccc(F)cc1OC]

A mixture of ethyl 4-chloro-6-(trifluoromethyl)pyridine-3-carboxylate (150 mg, 0.668 mmol), 4-fluoro-2-methoxy-phenol (95.1 μL, 0.834 mmol) and cesium carbonate (653 mg, 2.00 mmol) in MeCN (3 mL) was stirred at room temperature for 1 h. The contents were treated with water and stirred 3 days at room temperature (for convenience). A precipitate was collected by filtration, washed with water and dried under vacuum to give ethyl 4-(4-fluoro-2-methoxy-phenoxy)-6-(trifluoromethyl)pyridine-3-carboxylate (186 mg, 0.518 mmol, 77.5% yield) as an off-white solid. MS, ES⁺ m/z 360.0 [M+H]⁺. ¹H-NMR (400 MHz, DMSO-d₆) δ 9.03 (s, 1H), 7.35 (dd, J=8.84, 5.81 Hz, 1H), 7.23 (dd, J=10.61, 3.03 Hz, 1H), 6.88-6.95 (m, 2H), 4.37 (q, J=7.07 Hz, 2H), 3.76 (s, 3H), 1.33 (t, J=7.07 Hz, 3H).

Step 2: Synthesis of 4-(4-fluoro-2-methoxy-phenoxy)-6-(trifluoromethyl)pyridine-3-carboxylic acid

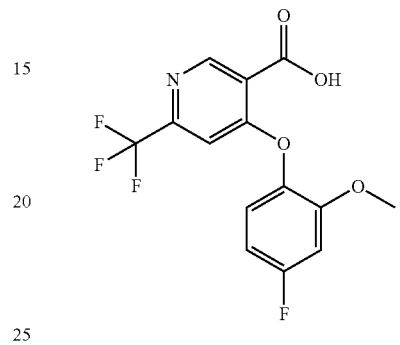

A mixture of ethyl 4-(4-fluoro-2-methoxy-phenoxy)-6-(trifluoromethyl)pyridine-3-carboxylate (182 mg, 0.507 mmol) and Lithium hydroxide monohydrate (23.4 mg, 0.558 mmol) in THF (2 mL) and water (0.1 mL) was stirred at room temperature for 7 days (for convenience). The solvent was removed with a stream of N₂ and the contents diluted with water (15 mL). The pH was lowered to pH 5 by careful addition of 6N HCl. After stirring for 3 h, the precipitate was collected by filtration, washed with water and dried under vacuum to give 4-(4-fluoro-2-methoxy-phenoxy)-6-(trifluoromethyl)pyridine-3-carboxylic acid (102.6 mg, 0.3098 mmol, 61.1% yield) as a white solid. MS, ES⁺ m/z 332.0 [M+H]⁺. ¹H-NMR (400 MHz, DMSO-d₆) δ 13.83 (br. s., 1H), 9.00 (s, 1H), 7.35 (dd, J=8.72, 5.68 Hz, 1H), 7.23 (dd, J=10.74, 2.65 Hz, 1H), 6.92 (td, J=8.46, 3.03 Hz, 1H), 6.86 (s, 1H), 3.76 (s, 3H).

Step 3: Synthesis of 4-(4-fluoro-2-methoxy-phenoxy)-N-(3-methylsulfonylphenyl)-6-(trifluoromethyl)pyridine-3-carboxamide

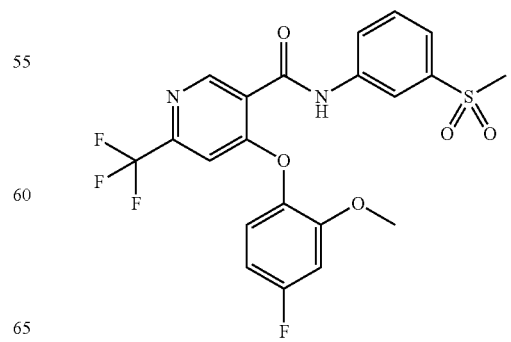

A mixture of 4-(4-fluoro-2-methoxy-phenoxy)-6-(trifluoromethyl)pyridine-3-carboxylic acid (46.0 mg, 0.139 mmol), 3-methylsulfonylaniline (26.2 mg, 0.153 mmol), HBTU (57.9 mg, 0.153 mmol) and DIPEA (60.5 μL, 0.347 mmol) in chloroform (2 mL) was stirred at room temperature for 18 h. The solvent was removed under a stream of $N_2$, and the residue treated with water/MeOH (5:1). This mixture was briefly sonicated then stirred at room temperature for 24 h. The resulting precipitate was collected by filtration, washed with water and dried under vacuum to give 4-(4-fluoro-2-methoxy-phenoxy)-N-(3-methylsulfonylphenyl)-6-(trifluoromethyl)pyridine-3-carboxamide (55.0 mg, 0.114 mmol, 81.7% yield) as a white solid. MS, ES$^+$ m/z 485.0 [M+H]$^+$. $^1$H-NMR (400 MHz, DMSO-d$_6$) δ 11.08 (s, 1H), 8.93 (s, 1H), 8.41 (s, 1H), 7.95 (d, J=7.33 Hz, 1H), 7.65-7.73 (m, 2H), 7.42 (dd, J=8.84, 5.81 Hz, 1H), 7.22 (dd, J=10.61, 2.78 Hz, 1H), 6.96 (s, 1H), 6.92 (td, J=8.46, 2.78 Hz, 1H), 3.77 (s, 3H), 3.23 (s, 3H).

The following compounds have been synthesized according to Method I

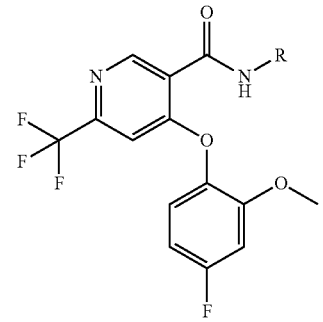

| Example | Name | R | Analytical data | Preparation details |
|---|---|---|---|---|
| 68 | 4-(4-fluoro-2-methoxy-phenoxy)-N-(3-methylsulfinylphenyl)-6-(trifluoromethyl)pyridine-3-carboxamide | 3-methylsulfinylphenyl | MS, ES$^+$ m/z, 469.0 (M + H)$^+$ $^1$H NMR (400 MHz, DMSO-d6) δ ppm 2.75 (s, 3 H) 3.77 (s, 3 H) 6.87-6.99 (m, 2 H) 7.22 (dd, J = 10.74, 2.91 Hz, 1 H) 7.37-7.47 (m, 2 H) 7.58 (t, J = 7.96 Hz, 1 H) 7.80 (dd, J = 7.71, 1.64 Hz, 1H) 8.16 (t, J = 1.77 Hz, 1H) 8.92 (s, 1 H) 10.97 (s, 1 H) | Method I, using 3-(methylsulfinyl)aniline |
| 69 | 4-(4-fluoro-2-methoxy-phenoxy)-N-(2-fluoro-5-methylsulfonyl-phenyl)-6-(trifluoromethyl)pyridine-3-caroxamide | 2-fluoro-5-methylsulfonylphenyl | MS, ES$^+$ m/z, 503.0 (M + H)$^+$ $^1$H NMR (400 MHz, CHLOROFORM-d) δ ppm 3.09-3.24 (m, 3 H) 3.78-3.87 (m, 3 H) 6.81-6.94 (m, 2 H) 6.96-7.03 (m, 1 H) 7.24-7.38 (m, 2 H) 7.77 (ddd, J = 8.59, 4.80, 2.27 Hz, 1 H) 9.23 (dd, J = 7.07, 2.27 Hz, 1 H) 9.43 (s, 1 H) 9.85 (br. s., 1 H) | Method I, using 2-fluoro-5-(methylsulfonyl)aniline |
| 70 | N-[3-(N,S-dimethylsulfonimidoyl)phenyl]-4-(4-fluoro-2-methoxy-phenoxy)-6-(trifluoromethyl)pyridine-3-carboxamide | 3-(N,S-dimethylsulfonimidoyl)phenyl | MS, ES$^+$ m/z, 498.0 (M + H)$^+$ $^1$H NMR (400 MHz, DMSO-d6) δ ppm 2.49 (s, 3H) 3.12 (s, 3 H) 3.73-3.80 (m, 3 H) 6.88-6.98 (m. 2 H) 7.22 (dd, 10.74, 2.91 Hz, 1H) 7.43 (dd, J = 8.84, 5.81 Hz, 1 H) 7.59 (dd, J = 7.83, 1.01 Hz, 1 H) 7.65 (t, J = 7.96 Hz, 1 H) 7.89-7.95 (m, 1H) 8.32 (t, J = 1.77 Hz, 1 H) 8.93 (s, 1 H) 11.03 | Method I, using (3-aminophenyl)(methyl)(methylimino)-λ$^6$-sulfanone |
| 71 | 4-(4-fluoro-2-methoxy-phenoxy)-N-pyridazin-4-yl-6-(trifluoromethyl)pyridine-3-carboxamide | pyridazin-4-yl | MS, ES$^+$ m/z, 409.0 (M + H)$^+$ $^1$H NMR (400 MHz, DMSO-d6) δ ppm 3.76 (s, 3 H) 6.87-6.96 (m, 1 H) 7.00 (s, 1H) 7.21 (dd, J = 10.74, 2.91 Hz, 1 H) 7.42 (dd, J = 8.84, 5.81 Hz, 1H) 8.05 (dd, J = 5.81, 2.78 Hz, 1 H) 8.97 (s, 1H) 9.14 (dd, J = 5.81, 1.01 Hz, 1 H) 9.39 (dd, J = 2.65, 1.14 Hz, 1H) 11.34 (s, 1H) | Method I, using pyridazin-4-amine |
| 72 | 4-(4-fluoro-2-methoxy-phenoxy)-N-(4-pyridyl)-6-(trifluoromethyl)pyridine-3-carboxamide | pyridin-4-yl | MS, ES$^+$ m/z, 408.0 (M + H)$^+$ $^1$H NMR (400 MHz, DMSO-d6) δ ppm 3.72-3.80 (m, 3 H) 6.87-7.00 (m, 2 H) 7.21 (dd, J = 10.61, 2.78 Hz, 1 H) 7.42 (dd, J = 8.97, 5.94 Hz, 1 H) 7.62-7.73 (m, 2 H) 8.48-8.55 (m, 2 H) 8.93 (s, 1H) 11.05 (s, 1 H) | Method I, using pyridin-4-amine |

Example 73: 4-[2-chloro-4-(trifluoromethoxy)phenoxy]-N-[2-(dimethylamino)-4-pyridyl]-6-(trifluoromethyl)pyridine-3-carb oxamide

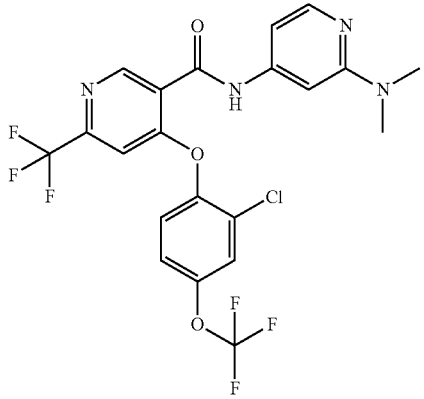 [SMILES: CN(C)c1cc(NC(=O)c2cnc(C(F)(F)F)cc2Oc2ccc(OC(F)(F)F)cc2Cl)ccn1]

Step 1: Synthesis of 4-chloro-6-(trifluoromethyl)pyridine-3-carbaldehyde

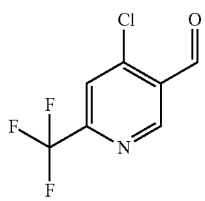

To a stirring solution of 4-chloro-2-(trifluoromethyl)pyridine (24.7 g, 136.06 mmol) in THF (2 mL) at −78° C., LiHMDS (149.66 mL, 149.66 mmol) was added slowly into the solution. The solution was stirred at −78° C. for two hours, then 0° C. for ten minutes. The solution was cooled back to −78° C., and then N,N-dimethylformamide (12.64 mL, 163.27 mmol) was added. The solution was allowed to return to room temperature overnight. Diluted hydrochloric acid (0.5 N, 200 mL) was added. The solution was extracted with ethyl acetate (3×200 mL). The combined ethyl acetate solution was washed with brine (100 mL), and dried over sodium sulfate. The solution was filtered and concentrated. The residue was purified by silica gel chromatography, eluted with ethyl acetate/hexane (0-40%) to give 4-chloro-6-(trifluoromethyl)pyridine-3-carbaldehyde (5.7 g, 27.22 mmol, 20% yield).

Step 2: Synthesis of 4-[2-chloro-4-(trifluoromethoxy)phenoxy]-6-(trifluoromethyl)pyridine-3-carbaldehyde

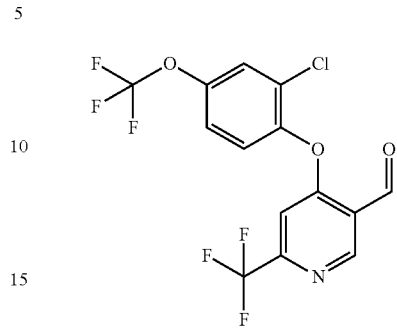

To a stirring solution of 2-chloro-4-(trifluoromethoxy)phenol (2.79 g, 13.12 mmol), 4-chloro-6-(trifluoromethyl)pyridine-3-carbaldehyde (2.5 g, 11.93 mmol) in acetonitrile (50 mL), potassium carbonate (3.3 g, 23.86 mmol) was added. The solution was heated at 80° C. for three hours. The solution was cooled to room temperature. Ethyl acetate (50 mL) was added. The solution was filtered and concentrated. The residue was purified by silica gel chromatography, eluting with ethyl acetate/heptane (0-30%) to give 4-[2-chloro-4-(trifluoromethoxy)phenoxy]-6-(trifluoromethyl)pyridine-3-carbaldehyde (4.6 g, 11.928 mmol, 99.98% yield) as colorless oil.
$^1$H NMR (400 MHz, CHLOROFORM-d) δ ppm 6.89 (s, 1H) 7.33-7.42 (m, 2H) 7.49-7.55 (m, 1H) 9.15 (s, 1H) 10.68-10.75 (m, 9H)

Step 3: Synthesis of 4-[2-chloro-4-(trifluoromethoxy)phenoxy]-6-(trifluoromethyl)pyridine-3-carboxylic acid

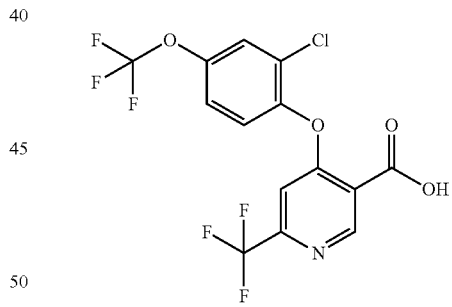

To a stirring solution of sodium phosphate monobasic monohydrate (7.53 g, 54.58 mmol) and sodium chlorite (3.7 g, 32.75 mmol) in water (50 mL), acetonitrile (50 mL) was added. 4-[2-chloro-4-(trifluoromethoxy)phenoxy]-6-(trifluoromethyl)pyridine-3-carbaldehyde (4.21 g, 10.92 mmol) was added afterward. The solution was stirred at room temperature for three hours. Sodium sulfite (aqueous, 10%, 0.5 mL) was added.
The solution was stirred at room temperature for 30 min. The solution was concentrated. Hydrochloric acid (1 N, 2 mL) was added. The white precipitate was collected by filtration. It was washed with water and dried to give 4-[2-chloro-4-(trifluoromethoxy)phenoxy]-6-(trifluoromethyl)pyridine-3-carboxylic acid (4.2 g, 10.4 mmol, 95.4% yield), white solid.

¹H NMR (400 MHz, CHLOROFORM-d) δ ppm 6.88 (s, 1H) 7.31 (d, J=1.52 Hz, 2H) 7.48-7.57 (m, 1H) 9.31 (s, 1H)

Step 4: Synthesis of 4-[2-chloro-4-(trifluoromethoxy)phenoxy]-N-[2-(dimethylamino)-4-pyridyl]-6-(trifluoromethyl)pyridine-3-carboxamide

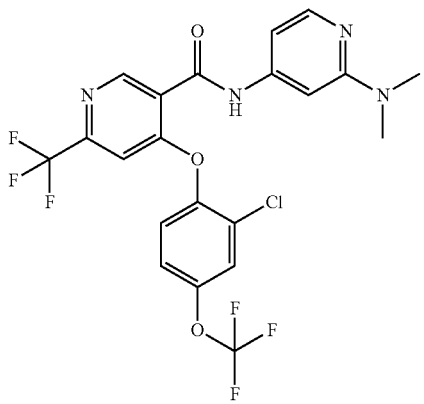 [SMILES: CN(C)c1cc(NC(=O)c2cnc(C(F)(F)F)cc2Oc2ccc(OC(F)(F)F)cc2Cl)ccn1]

To a stirring solution of 4-[2-chloro-4-(trifluoromethoxy)phenoxy]-6-(trifluoromethyl)pyridine-3-carboxylic acid (50 mg, 0.1200 mmol) in DCM (2 mL) at room temperature, oxalyl chloride (23.7 mg, 0.19 mmol) was added. DMF (one drop) was added. The solution was stirred at room temperature for one hour. The solution was concentrated. The residue was dissolved in DCM (2 mL). triethylamine (0.03 mL, 0.25 mmol) and N2,N2-dimethylpyridine-2,4-diamine (20.5 mg, 0.15 mmol) were added. The solution was stirred at room temperature for one hour. The solution was extracted with hydrochloric acid (1N, 2 mL) once, and concentrated. The residue was purified by preparative reversed-phase HPLC to give 4-[2-chloro-4-(trifluoromethoxy)phenoxy]-N-[2-(dimethylamino)-4-pyridyl]-6-(trifluoromethyl)pyridine-3-carboxamide (21 mg, 0.04 mmol, 32.4% yield) as white solid.

¹H NMR (400 MHz, CHLOROFORM-d) δ ppm 3.33 (s, 6H) 6.91 (s, 1H) 7.37 (d, J=9.85 Hz, 1H) 7.48-7.60 (m, 3H) 8.03 (s, 1H) 9.18 (s, 1H) 10.48 (br. s., 1H)

The following compounds have been synthesized according to Method J

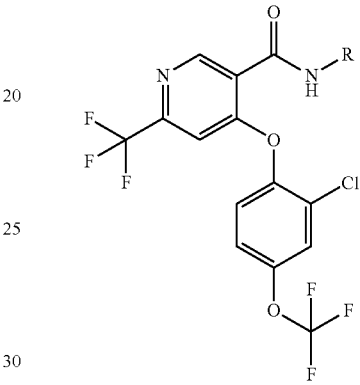

| Example | Name | R | Analytical data | Preparation details |
|---|---|---|---|---|
| 74 | 4-[2-chloro-4-(trifluoromethoxy)phenoxy]-N-(3-methylsulfonylphenyl)-6-(trifluoromethyl)pyridine-3-carboxamide | 3-(methylsulfonyl)phenyl | MS, ES⁺ m/z, 555.8 (M + H)⁺ ¹H NMR (400 MHz, DMSO-d6) δ ppm 3.23 (s, 3 H) 7.35 (s, 1 H) 7.51-7.58 (m, 1 H) 7.61-7.75 (m, 3 H) 7.85 (d, J = 2.53 Hz, 1 H) 7.93 (dt, J = 7.96, 1.58 Hz, 1 H) 8.37 (t, J = 1.89 Hz, 1H) 9.03 (s, 1H) 11.14 (s, 1H) | Method J, using 3-(methylsulfonyl) aniline |
| 75 | 4-[2-chloro-4-(trifluoromethoxy)phenoxy]-N-(3-methylsulfinylphenyl)-6-(trifluoromethyl)pyridine-3-carboxamide | 3-(methylsulfinyl)phenyl | MS, ES⁺ m/z, 539.8 (M + H)⁺ ¹H NMR (400 MHz, DMSO-d6) δ ppm 2.75 (s, 3 H) 7.34 (s, 1 H) 7.42 (dd, J = 7.58, 1.01 Hz, 1H) 7.50-7.60 (m, 2H) 7.61-7.67 (m, 1 H) 7.77 (dt, J = 8.08, 1.01 Hz, 1 H) 7.81-7.87 (m, 1H) 8.07-8.15 (m, 1 H) 9.02 (s, 1H) 11.03 (s, 1 H) | Method J, using 3-(methylsulfinyl) aniline |
| 76 | 4-[2-chloro-4-(trifluoromethoxy)phenoxy]-N-[3-(dimethylsulfamoyl)phenyl]-6-(trifluoromethyl)pyridine-3-carboxamide | 3-(dimethylsulfamoyl)phenyl | MS, ES⁺ m/z, 584.8 (M + H)⁺ ¹H NMR (400 MHz, DMSO-d6) δ ppm 2.64 (s, 6 H) 7.37 (s, 1 H) 7.48-7.57 (m, 2 H) 7.59-7.69 (m, 2 H) 7.84 (s, 1 H) 7.88-7.95 (m, 1 H) 8.20 (s, 1H) 9.04 (s, 1H) 11.10 (s, 1H) | Method J, using 3-amino-N,N-dimethylbenzenesulfonamide |

| Example | Name | R | Analytical data | Preparation details |
| --- | --- | --- | --- | --- |
| 77 | 4-[2-chloro-4-(trifluoromethoxy)phenoxy]-N-(2-fluoro-5-methylsulfonyl-phenyl)-6-(trifluoromethyl)pyridine-3-carboxamide | 4-fluoro-3-(methylsulfonyl)phenyl | MS, ES+ m/z, 573.0 (M + H)+ $^1$H NMR (400 MHz, CHLOROFORM-d) δ ppm 3.10-3.19 (m, 3 H) 6.92 (s, 1 H) 7.30-7.48 (m, 4 H) 7.57 (d, J = 2.53 Hz, 1 H) 7.80 (ddd, J = 8.59, 4.80, 2.27 Hz, 1 H) 9.21 (dd, J = 6.95, 2.15 Hz, 1H) 9.52 (s, 1 H) 9.63 (br. s, 1 H) | Method J, using 2-fluoro-5-(methylsulfonyl)aniline |
| 78 | 4-[2-chloro-4-(trifluoromethoxy)phenoxy]-N-(3-pyridyl)-6-(trifluoromethyl)pyridine-3-carboxamide | pyridin-3-yl | MS, ES+ m/z, 478.0 (M + H)+ $^1$H NMR (400 MHz, DMSO-d6) δ ppm 7.38 (s, 1 H) 7.39-7.45 (m, 1 H) 7.53 (ddt, J = 9.09, 1.83, 0.98, 0.98 Hz, 1 H) 7.62 (d, J = 9.09 Hz, 1 H) 7.83 (d, J = 2.78 Hz, 1 H) 8.11 (ddd, J = 8.34, 2.53, 1.52 Hz, 1H) 8.35 (dd, J = 4.67, 1.39 Hz, 1 H) 8.78-8.84 (m, 1 H) 9.03 (s, 1 H) 10.95 (s, 1 H) | Method J, using pyridin-3-amine |
| 79 | 4-[2-chloro-4-(trifluoromethoxy)phenoxy]-N-(4-pyridyl)-6-(trifluoromethyl)pyridine-3-carboxamide | pyridin-4-yl | MS, ES+ m/z, 478.0 (M + H)+ $^1$H NMR (400 MHz, DMSO-d6) δ ppm 7.37 (s, 1 H) 7.50-7.56 (m, 1 H) 7.59-7.69 (m, 3 H) 7.83 (d, J = 2.78 Hz, 1 H) 8.47-8.54 (m, 2 H) 9.02 (s, 1H) 11.12 (s, 1 H) | Method J, using pyridin-4-amine |
| 80 | 4-[2-chloro-4-(trifluoromethoxy)phenoxy]-N-[3-(methylsulfonimidoyl)phenyl]-6-(trifluoromethyl)pyridine-3-carboxamide | 3-(methylsulfonimidoyl)phenyl | MS, ES+ m/z, 554.0 (M + H)+ $^1$H NMR (400 MHz, DMSO-d6) δ ppm 2.99-3.16 (m, 3H) 4.25 (s, 1 H) 7.33 (s, 1H) 7.51-7.80 (m, 4 H) 7.81-8.03 (m, 2 H) 8.30-8.51 (m, 1H) 9.02 (s, 1 H) 11.07 (s, 1H) | Method J, using (3-aminophenyl)(imino)(methyl)-λ$^6$-sulfanone |
| 81 | N-(3-carbamoylphenyl)-4-[2-chloro-4-(trifluoromethoxy)phenoxy]-6-(trifluoromethyl)pyridine-3-carboxamide | 3-carbamoylphenyl | MS, ES+ m/z, 520.0 (M + H)+ $^1$H NMR (400 MHz, DMSO-d6) δ ppm 7.33 (s, 1 H) 7.37-7.49 (m, 2 H) 7.51-7.59 (m, 1 H) 7.60-7.69 (m, 2 H) 7.77-7.89 (m, 2 H) 8.00 (s, 1 H) 8.16 (t, J = 1.77 Hz, 1 H) 9.00 (s, 1 H) 10.84 (s, 1 H) | Method J, using 3-aminobenzamide |
| 82 | 4-[2-chloro-4-(trifluoromethoxy)phenoxy]-N-[3-(N,S-dimethylsulfonimidoyl)phenyl]-6-(trifluoromethyl)pyridine-3-carboxamide | 3-(N,S-dimethylsulfonimidoyl)phenyl | MS, ES+ m/z, 568.0 (M + H)+ $^1$H NMR (400 MHz, DMSO-d6) δ ppm 2.48 (s, 3 H) 3.12 (s, 3 H) 7.35 (s, 1 H) 7.50-7.69 (m, 4 H) 7.85 (d, J = 2.78 Hz, 1 H) 7.89 (dt, J = 8.46, 1.45 Hz, 1H) 8.27 (t, J = 1.77 Hz, 1H) 9.03 (s, 1H) 11.08 (s, 1H) | Method J, using (3-aminophenyl)(methyl)(methylimino)-λ$^6$-sulfanone |

Example 83: 4-[2-chloro-4-(trifluoromethoxy)phenoxy]-N-(1-oxidopyridin-1-ium-3-yl)-6-(trifluoromethyl)pyridine-3-carboxamide Method K

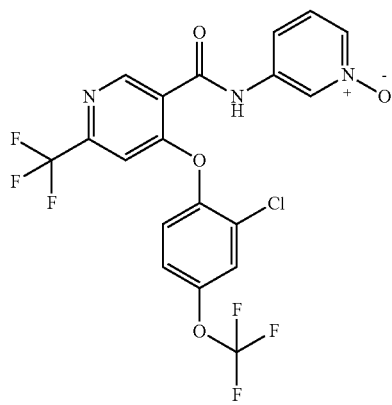

4-[2-chloro-4-(trifluoromethoxy)phenoxy]-N-(3-pyridyl)-6-(trifluoromethyl)pyridine-3-carboxamide (Example LI-1971, 100 mg, 0.21 mmol) was added to a screw-cap vial and dissolved in DCM (5 mL). m-CPBA (56 mg, 0.25 mmol) was added, and the mixture was allowed to stir at room temperature for 15 minutes. Volatiles were evaporated under reduced pressure, and the residue was purified by preparative reversed-phase HPLC (high pH method) to afford the title compound as a colorless glass (81 mg, 0.16 mmol, 78% yield). MS, ES$^+$ m/z 494 [M+H]$^+$.

The following compounds have been synthesized according to Method K

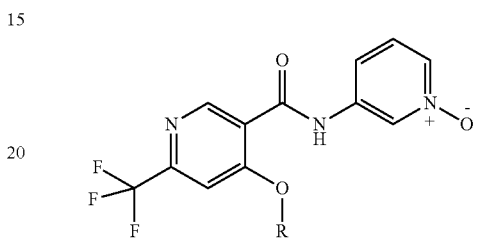

| Example | Name | R | Analytical data | Prep details |
|---|---|---|---|---|
| 84 | 4-(4-fluoro-2-methoxy-phenoxy)-N-(1-oxidopyridin-1-ium-3-yl)-6-(trifluoromethyl)pyridine-3-carboxamide | (4-fluoro-2-methoxyphenyl) | MS, ES$^+$ m/z 482.0 [M + H]$^+$ $^1$H NMR (400 MHz, DMSO-d6) δ ppm 3.77 (s, 3 H) 6.92 (t, J = 8.46 Hz, 1 H) 6.98 (s, 1 H) 7.22 (d, J = 10.86 Hz, 1 H) 7.35-7.47 (m, 2 H) 8.05 (d, J = 6.32 Hz, 1 H) 8.74 (s, 1 H) 8.94 (s, 1H) 11.07 (s, 1H) | Method K, using 4-fluoro-2-methoxyphenol |
| 85 | 4-(4-fluoro-2-methyl-phenoxy)-N-(1-oxidopyridin-1-ium-3-yl)-6-(trifluoromethyl)pyridine-3-carboxamide | (4-fluoro-2-methylphenyl) | MS, ES$^+$ m/z 408.0 [M + H]$^+$ $^1$H NMR (400 MHz, DMSO-d6) δ ppm 2.15 (s, 3 H) 7.02 (s, 1H) 7.19 (td, J = 8.53, 3.16 Hz, 1 H) 7.27-7.36 (m, 2 H) 7.43 (dd, J = 8.46, 6.44 Hz, 1 H) 7.49-7.57 (m, 1 H) 8.06 (ddd, J = 6.44, 1.77, 0.88 Hz, 1 H) 8.73 (t, J = 1.64 Hz, 1 H) 8.97 (s, 1H) 11.11 (s, 1H) | Method K, using 4-fluoro-2-methylphenol |
| 86 | 4-[4-(difluoromethoxy)phenoxy]-N-(1-oxidopyridin-1-ium-3-yl)-6-(trifluoromethyl)pyridine-3-carboxamide | (4-difluoromethoxyphenyl) | MS (ES+) m/z 441.6 [M + H]$^+$ $^1$H NMR (400 MHz, DMSO-d6) δ ppm 7.16 (s, 1 H) 7.31-7.37 (m, 2 H) 7.37-7.48 (m, 3 H) 7.51-7.58 (m, 1 H) 8.07 (ddd, J = 6.38, 1.71, 1.01 Hz, 1 H) 8.75 (t, J = 1.64 Hz, 1 H) 8.97 (s, 1H) 11.12 (s, 1H) | Method K, using 4-(difluoromethoxy)phenol |

-continued

| Example | Name | R | Analytical data | Prep details |
|---------|------|---|-----------------|--------------|
| 87 | N-(1-oxidopyridin-1-ium-3-yl)-4-[4-(trifluoromethoxy)phenoxy]-6-(trifluoromethyl)pyridine-3-carboxamide | 4-(trifluoromethoxy)phenyl | MS (ES+) m/z 459.6 [M + H]$^+$ $^1$H NMR (400 MHz, DMSO-d6) δ ppm 7.30 (s, 1 H) 7.39-7.49 (m, 3 H) 7.49-7.59 (m, 3 H) 8.03-8.10 (m, 1 H) 8.73 (t, J = 1.64 Hz, 1 H) 8.95-9.01 (m, 1H) 11.12 (s, 1H) | Method K, using 4-(trifluoromethoxy)phenol |
| 88 | 4-(2,4-dimethoxyphenoxy)-N-(1-oxidopyridin-1-ium-3-yl)-6-(trifluoromethyl)pyridine-3-carboxamide | 2,4-dimethoxyphenyl | MS (ES+) m/z 435.7 [M + H]$^+$ $^1$H NMR (400 MHz, DMSO-d6) δ ppm 3.74 (s, 3H) 3.77-3.84 (m, 3 H) 6.59-6.69 (m, 1 H) 6.77-6.83 (m, 1 H) 6.87-6.93 (m, 1 H) 7.29 (d, J = 8.84 Hz, 1 H) 7.45 (dd, J = 8.46, 6.44 Hz, 1 H) 7.54-7.65 (m, 1 H) 8.03-8.12 (m, 1 H) 8.78 (t, J = 1.52 Hz, 1H) 8.89-8.97 (m, 1H) 11.09 (s, 1H) | Method K, using 4-(trifluoromethoxy)phenol |
| 89 | 4-(2,4-difluorophenoxy)-N-(1-oxidopyridin-1-ium-3-yl)-6-(trifluoromethyl)pyridine-3-carboxamide | 2,4-difluorophenyl | MS (ES+) m/z 411.7 [M + H]$^+$ $^1$H NMR (400 MHz, DMSO-d6) δ ppm 7.21-7.29 (m, 1 H) 7.28-7.35 (m, 1 H) 7.45 (dd, J = 8.46, 6.44 Hz, 1 H) 7.51-7.64 (m, 3 H) 8.04-8.11 (m, 1 H) 8.74 (s, 1 H) 9.00 (s, 1 H) 11.16 (s, 1H) | Method K, using 2,4-difluorophenol |
| 90 | 3-(2-(3,4-difluorophenoxy)-5-(trifluoromethyl)nicotinamido)pyridine-1-oxide | 3,4-difluorophenyl | | |

Example 91: N-[3-(methylsulfonimidoyl)phenyl]-4-[4-(trifluoromethoxy)phenoxy]-6-(trifluoromethyl)pyridine-3-carboxamide Method L

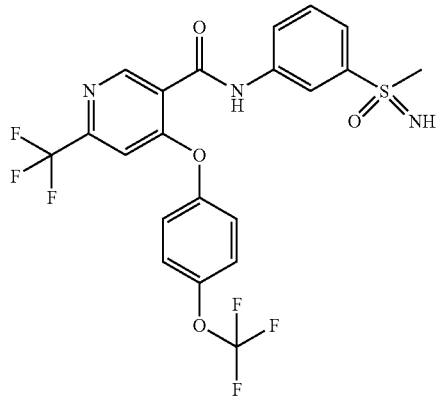 [SMILES: CS(=N)(=O)c1cccc(NC(=O)c2cnc(C(F)(F)F)cc2Oc2ccc(OC(F)(F)F)cc2)c1]

Step 1: Synthesis of methyl 4-[4-(trifluoromethoxy)phenoxy]-6-(trifluoromethyl)pyridine-3-carboxylate

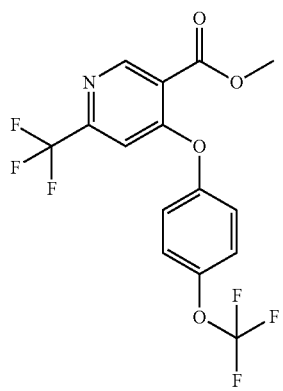

Methyl 4-chloro-6-(trifluoromethyl)pyridine-3-carboxylate (1 g, 4.2 mmol) was added to a 20 mL scintillation vial equipped with a magnetic stir bar and dissolved in acetonitrile (10 mL). 4-(trifluoromethoxy)phenol (892 mg, 5 mmol) and cesium carbonate (2.72 g, 8.34 mmol) were added, and the mixture was heated to 50° C. for 1 hour. After cooling to room temperature, the mixture was diluted with water (100 mL) and extracted with dichloromethane. The combined dichloromethane solution was dried over magnesium sulfate and concentrated to give an oil (1.2 g, 3.15 mmol, 75% yield) containing the desired product.

Step 2: Synthesis of 4-[4-(trifluoromethoxy)phenoxy]-6-(trifluoromethyl)pyridine-3-carboxylic acid

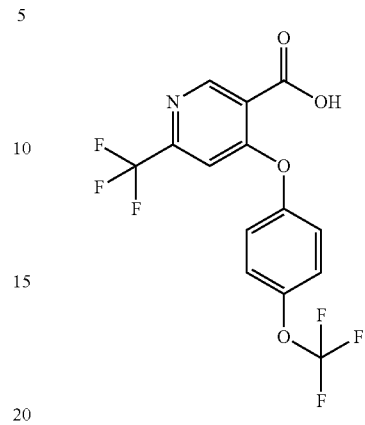

4-[4-(trifluoromethoxy)phenoxy]-6-(trifluoromethyl)pyridine-3-carboxylate (1.2 g, 3.15 mmol) was added to a round-bottom flask equipped with magnetic stir bar and dissolved in THF (9 mL) and water (1 mL). Excess sodium hydroxide was added, and the mixture was allowed to stir at room temperature for 1 hour. The resulting mixture was diluted with water (200 mL) and made strongly acidic by careful addition of 6N HCl. The resulting solution was extracted with dichloromethane, and the combined organic extracts were dried over magnesium sulfate. Concentration under reduced pressure afforded a clear oil (1.1 g, 3.0 mmol) which solidified on standing, and was used without further purification. MS, ES+ m/z 368 [M+H]+.

Step three: Synthesis of N-[3-(methylsulfonimidoyl)phenyl]-4-[4-(trifluoromethoxy)phenoxy]-6-(trifluoromethyl)pyridine-3-carboxamide

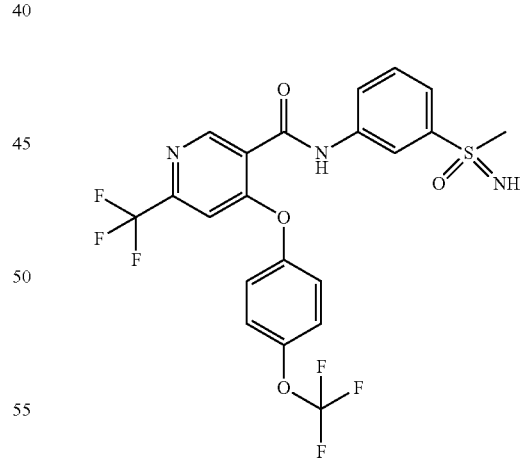

A screw-cap vial was charged with 4-[4-(trifluoromethoxy)phenoxy]-6-(trifluoromethyl)pyridine-3-carboxylic acid (150 mg, 0.41 mmol), and DMF (3 mL) was added. Triethylamine (115 µL, 0.82 mmol) and HBTU (186 mg, 0.49 mmol) were added, and the mixture was stirred at room temperature for 10 minutes. 3-(methylsulfonimidoyl)aniline (70 mg, 0.41 mol) was added, and stirring was continued for an additional 12 hours. Purification of the crude mixture by preparative reversed-phase HPLC (high pH method)

afforded the desired product (97 mg, 0.19 mmol, 46% yield) as a beige solid. MS, ES+ m/z 520.0 [M+H]+. ¹H NMR (400 MHz, DMSO-d₆) δ ppm 3.06 (s, 3H) 4.25 (s, 1H) 7.26 (s, 1H) 7.44-7.50 (m, 2H) 7.51-7.57 (m, 2H) 7.60 (t, J=7.96 Hz, 1H) 7.69 (d, J=7.83 Hz, 1H) 7.90 (d, J=8.08 Hz, 1H) 8.35 (t, J=1.89 Hz, 1H) 8.98 (s, 1H)

The following compounds have been synthesized according to Method L

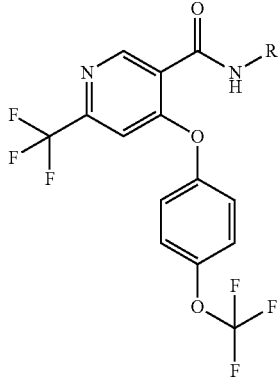

Step 1: Synthesis of methyl 4-(4-fluoro-2-methyl-phenoxy)-6-(trifluoromethyl)pyridine-3-carboxylate

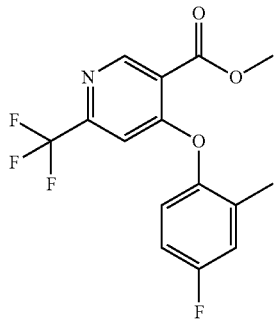

Methyl 4-chloro-6-(trifluoromethyl)pyridine-3-carboxylate (1 g, 4.2 mmol) was charged to a round-bottom flask and dissolved in acetonitrile (10 mL). Cesium carbonate (2.7 g, 8.3 mmol) and 4-fluoro-2-methyl-phenol (632 mg, 5.0 mmol) were added, and the mixture was heated to 50° C. with stirring for 1 hour. After cooling to room temperature, the mixture was diluted with water (150 mL) and extracted with dichloromethane. The combined dichloromethane

| Example | Name | R | Analytical data | Prep details |
|---|---|---|---|---|
| 92 | N-[3-(N,S-dimethylsulfonimidoyl)phenyl]-4-[4-(trifluoromethoxy)phenoxy]-6-(trifluoromethyl)pyridine-3-carboxamide | ![R group structure] | MS, ES+ m/z 534.0 [M + H]+ ¹H NMR (400 MHz, DMSO-d6) δ ppm 2.48 (s, 3 H) 3.12 (s, 3 H) 7.27 (s, 1 H) 7.43-7.50 (m, 2 H) 7.50-7.56 (m, 2 H) 7.58 (dd, J = 7.71, 1.14 Hz, 1 H) 7.64 (t, J = 7.83 Hz, 1 H) 7.83-7.97 (m, 1 H) 8.27 (t, J = 1.77 Hz, 1 H) 8.99 (s, 1 H) 11.06 (s, 1 H) | Method L, using (3-aminophenyl)(methyl)(methylimino)-λ⁶-sulfanone |

Example 93: 4-(4-fluoro-2-methyl-phenoxy)-N-[3-(methylsulfonimidoyl)phenyl]-6-(trifluoromethyl)pyridine-3-carboxamide Method M

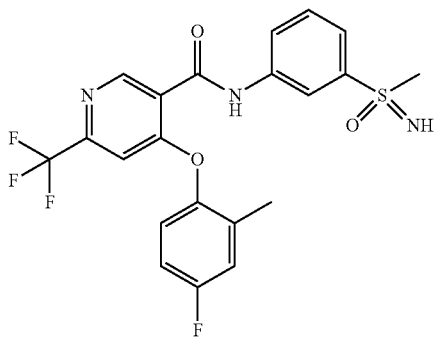 [SMILES: Cc1cc(F)ccc1Oc1cc(C(F)(F)F)ncc1C(=O)Nc1cccc(S(C)(=N)=O)c1]

extracts were dried over magnesium sulfate and concentrated under reduced pressure to give a clear oil (1.13 g, 3.42 mmol, 82% yield), which was used without further purification.

Step 2: Synthesis of 4-(4-fluoro-2-methyl-phenoxy)-6-(trifluoromethyl)pyridine-3-carboxylic acid

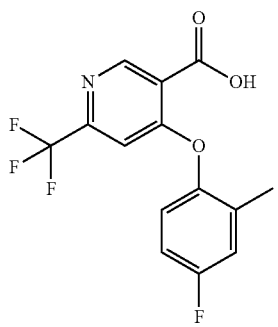 [SMILES: Cc1cc(F)ccc1Oc1cc(C(F)(F)F)ncc1C(=O)O]

Methyl 4-(4-fluoro-2-methyl-phenoxy)-6-(trifluoromethyl)pyridine-3-carboxylate (1.4 g, 4.2 mmol) was charged to a round-bottom flask and dissolved in THF (12 mL) and water (2 mL). Sodium hydroxide (960 mg, 21 mmol) was added, and the mixture was allowed to stir at room temperature for 1 hour. The crude mixture was diluted with water (200 mL) and made strongly acidic by adding 6N HCl. The resulting cloudy solution was extracted with dichloromethane, and the combined dichloromethane extracts were dried over magnesium sulfate and concentrated under reduced pressure to give a colorless solid (980 mg, 3.1 mmol, 74% yield) which was used without further purification.

Step 3: Synthesis of 4-(4-fluoro-2-methyl-phenoxy)-N-[3-(methylsulfonimidoyl)phenyl]-6-(trifluoromethyl)pyridine-3-carboxamide 4-(4-fluoro-2-methyl-phenoxy)-6-(trifluoromethyl)pyridine-3-carboxylic acid (150 mg, 0.48 mmol) was charged to a screw-top vial equipped with a magnetic stir bar and dissolved in DMF (3 mL). Triethylamine (133 μL, 0.95 mmol) and HBTU (217 mg, 0.57 mmol) were added, and the mixture was stirred at room temperature for 10 minutes. 3-(methylsulfonimidoyl)aniline (81 mg, 0.48 mmol) was added, and stirring was continued for an additional 12 hours. Purification by preparative reversed phase HPLC (high pH method) afforded the title compound (129 mg, 0.28 mmol, 58% yield) as a beige solid. MS, ES+ m/z 468.0 [M+H]+. 1H NMR (400 MHz, DMSO-d 6) δ ppm 2.13 (s, 3H) 3.53 (s, 3H) 5.66-5.88 (m, 2H) 6.81-6.95 (m, 2H) 7.06-7.35 (m, 6H) 9.05 (s, 1H).

The following compounds have been synthesized according to Method M:

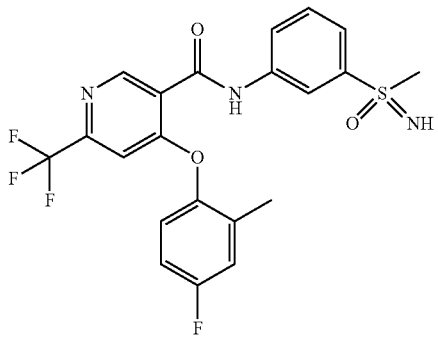 [SMILES: Cc1cc(F)ccc1Oc1cc(C(F)(F)F)ncc1C(=O)Nc1cccc(S(C)(=N)=O)c1]
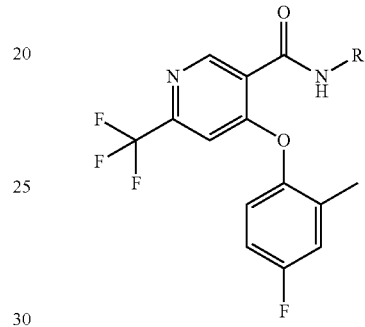

| Example | Name | R | Analytical data | Prep details |
|---|---|---|---|---|
| 94 | N-[3-(N,S-dimethylsulfonimidoyl)phenyl]-4-(4-fluoro-2-methyl-phenoxy)-6-(trifluoromethyl)pyridine-3-carboxamide | | MS, ES+ m/z 482.0 [M + H]+. 1H NMR (400 MHz, DMSO-d6) δ ppm 2.16 (s, 3 H) 2.49 (s, 3 H) 3.12 (s, 3 H) 7.00 (s, 1 H) 7.19 (td, J = 8.53, 3.16 Hz, 1 H) 7.26-7.37 (m, 2 H) 7.59 (dt, J = 7.83, 1.39 Hz, 1 H) 7.65 (t, J = 7.96 Hz, 1 H) 7.87-7.94 (m, 1 H) 8.30 (t, J = 1.77 Hz, 1 H) 8.97 (s, 1 H) 11.06 (s, 1H) | Method M, using (3-aminophenyl)(methyl)(methylimino)-λ6-sulfanone |
| 95 | 4-(4-fluoro-2-methyl-phenoxy)-N-pyridazin-4-yl-6-(trifluoromethyl)pyridine-3-carboxamide | | MS, ES+ m/z 393.0 [M+H]+. 1H NMR (400 MHz, DMSO-d6) δ ppm 2.14 (s, 3 H) 7.03 (s, 1 H) 7.26-7.37 (m, 2 H) 8.13 (dd, J = 5.81, 2.78 Hz, 1H) 9.01 (s, 1 H) 9.19 (dd, J = 6.06, 0.76 Hz, 1 H) 9.38 (dd, J = 2.65, 0.88 Hz, 1H) 11.53 (s, 1H) | Method M, using pyridazin-4-amine |

The following compounds have been synthesized according to Method M:

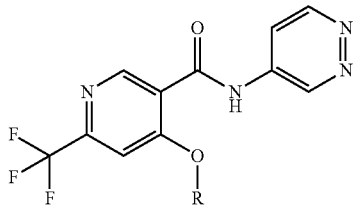

| Example | Name | R | Analytical data | Prep details |
|---|---|---|---|---|
| 96 | N-pyridazin-4-yl-4-[4-(trifluoromethoxy)phenoxy]-6-(trifluoromethyl)pyridine-3-carboxamide | 4-(trifluoromethoxy)phenyl | MS (ES+) m/z 445.0<br>$^1$H NMR (400 MHz, DMSO-d6) δ ppm 7.31 (s, 1 H) 7.41-7.57 (m, 4 H) 8.07 (dd, J = 5.94, 2.65 Hz, 1H) 9.02 (s, 1 H) 9.16 (dd, J = 5.94, 0.88 Hz, 1H) 9.37 (dd, J = 2.78, 1.01 Hz, 1 H) 11.48 (s, 1 H) | Method M, using 4-(trifluoromethoxy)phenol |
| 97 | 4-[4-(difluoromethoxy)phenoxy]-N-pyridazin-4-yl-6-(trifluoromethyl)pyridine-3-carboxamide | 4-(difluoromethoxy)phenyl | MS (ES+) m/z 501.6 [M + H]$^+$<br>$^1$H NMR (400 MHz, CHLOROFORM-d) δ ppm 7.06 (s, 1 H) 7.28-7.36 (m, 3 H) 7.38-7.47 (m, 2 H) 8.25-8.35 (m, 1H) 9.13-9.24 (m, 2 H) 9.49 (s, 2 H) | Method M, using 4-(difluoromethoxy)phenol |
| 98 | 4-[2-chloro-4-(trifluoromethoxy)phenoxy]-N-pyridazin-4-yl-6-(trifluoromethyl)pyridine-3-carboxamide | 2-chloro-4-(trifluoromethoxy)phenyl | MS (ES+) m/z 478.6 [M + H]$^+$<br>$^1$H NMR (400 MHz, DMSO-d6) δ ppm 5.72-5.80 (m, 1 H) 7.41 (s, 1H) 7.50-7.57 (m, 1 H) 7.60-7.68 (m, 1 H) 7.85 (d, J = 2.78 Hz, 1 H) 8.09 (dd, J = 5.94, 2.65 Hz, 1 H) 9.06 (s, 1 H) 9.17 (dd, J = 5.94, 0.88 Hz, 1 H) 9.36 (dd, J = 2.65, 0.88 Hz, 1 H) 11.53 (s, 1H) | Method M, using 2-chloro-4-(trifluoromethoxy)phenol |
| 99 | 4-(2,4-dimethoxyphenoxy)-N-pyridazin-4-yl-6-(trifluoromethyl)pyridine-3-carboxamide | 2,4-dimethoxyphenyl | MS (ES+) m/z 420.8 [M + H]$^+$.<br>$^1$H NMR (400 MHz, DMSO-d6) δ ppm 3.17 (s, 1H) 3.74 (s, 3 H) 3.77-3.87 (m, 3 H) 6.63 (dd, J = 8.84, 2.78 Hz, 1 H) 6.80 (d, J = 2.78 Hz, 1 H) 6.92 (s, 1 H) 7.30 (d, J = 8.59 Hz, 1 H) 8.16 (dd, J = 6.06, 2.78 Hz, 1 H) 8.95 (s, 1H) 9.20 (d, J = 5.81 Hz, 1 H) 9.40 (dd, J = 2.78, 0.76 Hz, 1H) 11.51 (s, 1H) | Method M, using 2,4-dimethoxyphenol |

-continued

| Example | Name | R | Analytical data | Prep details |
|---|---|---|---|---|
| 100 | 4-(2,4-difluorophenoxy)-N-pyridazin-4-yl-6-(trifluoromethyl)pyridine-3-carboxamide | 2,4-difluorophenyl | MS (ES+) m/z 396.6 [M + H]⁺ ¹H NMR (400 MHz, DMSO-d6) δ ppm 7.16-7.30 (m, 1 H) 7.35 (s, 1 H) 7.50-7.70 (m, 2 H) 8.15 (dd, J = 5.94, 2.65 Hz, 1 H) 9.04 (s, 1H) 9.14-9.27 (m, 1H) 9.34-9.45 (m, 1 H) 11.60 (s, 1 H) | Method M, using 2,4-difluorophenol |

The following compounds have been synthesized according to Method M:

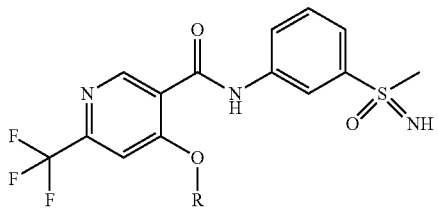

| Example | Name | R | Analytical data | Prep details |
|---|---|---|---|---|
| 101 | 4-[4-(difluoromethoxy)phenoxy]-N-[3-(methylsulfonimidoyl)phenyl]-6-(trifluoromethyl)-pyridine-3-carboxamide | 4-(difluoromethoxy)phenyl | MS (ES+) m/z 426.6 [M + H]⁺ ¹H NMR (400 MHz, DMSO-d6) δ ppm 3.50 (s, 3 H) 6.87 (dd, J = 8.08, 2.27 Hz, 1 H) 7.07-7.12 (m, 1 H) 7.13-7.18 (m, 1 H) 7.21 (t, J = 2.02 Hz, 1H) 7.24-7.31 (m, 5 H) 9.09 (s, 1 H) | Method M, using 4-(difluoromethoxy)phenol |
| 102 | 4-(2,4-dimethoxyphenoxy)-N-[3-(methylsulfonimidoyl)phenyl]-6-(trifluoromethyl)-pyridine-3-carboxamide | 2,4-dimethoxyphenyl | MS (ES+) m/z 495.6 [M + H]⁺ ¹H NMR (400 MHz, DMSO-d6) δ ppm 3.17 (s, 3 H) 3.69-3.78 (m, 3 H) 3.79-3.83 (m, 3 H) 6.58-6.68 (m, 1 H) 6.77 (s, 1 H) 6.81 (d, J = 2.78 Hz, 1 H) 6.89 (dd, J = 8.08, 2.27 Hz, 1H) 7.13-7.20 (m, 2 H) 7.24 (t, J = 2.02 Hz, 1 H) 7.27-7.34 (m, 1 H) 9.03-9.07 (m, 1 H) | Method M, using 2,4-dimethoxyphenol |
| 103 | 4-(2,4-difluorophenoxy)-N-[3-(methylsulfonimidoyl)phenyl]-6-(trifluoromethyl)-pyridine-3-carboxamide | 2,4-difluorophenyl | MS (ES+) m/z 472.0 [M + H]⁺ ¹H NMR (400 MHz, DMSO-d6) δ ppm 3.47-3.57 (m, 3 H) 6.83-6.92 (m, 1 H) 7.08-7.15 (m, 1 H) 7.17-7.23 (m, 3 H) 7.25-7.32 (m, 1 H) 7.42-7.53 (m, 1 H) 7.55-7.65 (m, 1 H) 9.11 (s, 1 H) | Method M, using 2,4-difluorophenol |

The following compounds have been synthesized according to Method M:

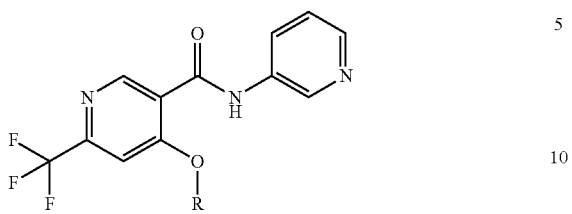

| Example | Name | R | Analytical data | Prep details |
|---|---|---|---|---|
| 104 | 2-(4-difluoromethoxy)-phenoxy)-N-(pyridin-3-yl)-5-(trifluoromethyl)-nicotinamide | 4-(OCHF₂)-C₆H₄- | MS (ES+) m/z 425.8 [M + H]⁺. ¹H NMR (400 MHz, CHLOROFORM-d) δ ppm 7.02 (s, 1 H) 7.22-7.41 (m, 5 H) 7.76 (dd, J = 8.34, 5.56 Hz, 1 H) 8.43 (br. s., 1 H) 8.98 (d, J = 8.59 Hz, 1 H) 9.10 (br. s., 1 H) 9.30 (s, 1 H) 10.37 (br. s., 1 H) | Method M, using 4-(difluoromethoxy)phenol |
| 105 | N-(pyridin-3-yl)-4-(4-(trifluoromethoxy)-phenoxy)-6-(trifluoromethyl)nicotinamide | 4-(OCF₃)-C₆H₄- | MS (ES+) m/z 443.6 [M + H]⁺. ¹H NMR (400 MHz, DMSO-d6) δ ppm 7.30 (s, 1 H) 7.42-7.49 (m, 2 H) 7.50-7.56 (m, 2 H) 7.64 (dd, J = 8.34, 5.05 Hz, 1 H) 8.23-8.32 (m, 1 H) 8.47 (dd, J = 5.05, 1.52 Hz, 1H) 8.97-9.03 (m, 2 H) 11.21 (s, 1 H) | Method M, using 4-(trifluoromethoxy)phenol |
| 106 | 4-(2-chloro-4-(trifluoromethoxy)phenoxy)-N-(pyridin-3-yl)-6-(trifluoromethyl)-nicotinamide | 2-Cl-4-(OCF₃)-C₆H₃- | MS (ES+) m/z 477.6 [M + H]⁺. ¹H NMR (400 MHz, DMSO-d6) δ ppm 7.39 (s, 1 H) 7.51-7.57 (m, 1 H) 7.57-7.67 (m, 2 H) 7.85 (d, J = 2.78 Hz, 1 H) 8.21-8.28 (m, 1 H) 8.46 (dd, J = 4.93, 1.14 Hz, 1 H) 8.96 (d, J = 2.27 Hz, 1 H) 9.04 (s, 1 H) 11.17 (s, 1 H) | Method M, using 2-chloro-4-(trifluoromethoxy)-phenol |
| 107 | 4-(2,4-dimethoxyphenoxy)-N-(pyridin-3-yl)-6-(trifluoromethyl)-nicotinamide | 2,4-(OMe)₂-C₆H₃- | MS (ES+) m/z 419.8 [M + H]+. ¹H NMR (400 MHz, DMSO-d6) δ ppm 2.09-2.21 (m, 3 H) 6.98-7.05 (m, 1 H) 7.19 (td, J = 8.53, 3.16 Hz, 1 H) 7.26-7.37 (m, 2 H) 7.60 (dd, J = 8.46, 4.93 Hz, 1 H) 8.26 (dt, J = 8.46, 1.83 Hz, 1 H) 8.45 (dd, J = 5.05, 1.26 Hz, 1 H) 8.95-9.03 (m, 2 H) 11.14 (s, 1 H) | Method M, using 2,4-dimethoxyphenol |

| Example | Name | R | Analytical data | Prep details |
|---|---|---|---|---|
| 108 | 4-(2,4-difluorophen-oxy)-N-(pyridin-3-yl)-6-(trifluoromethyl)-nicotinamide | 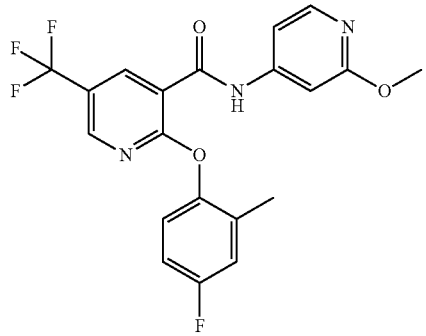 | MS (ES+) m/z 395.6 [M + H]+. ¹H NMR (400 MHz, DMSO-d6) δ ppm 7.20-7.29 (m, 1 H) 7.33 (s, 1 H) 7.54-7.65 (m, 3 H) 8.26 (dt, J = 8.72, 1.71 Hz, 1 H) 8.45 (dd, J = 4.80, 1.26 Hz, 1 H) 8.97 (d, J = 2.27 Hz, 1 H) 9.01 (s, 1 H) 11.17 (s, 1 H) | Method M, using, 2,4-difluorophenol |

Example 109: 2-(4-fluoro-2-methyl-phenoxy)-N-(2-methoxy-4-pyridyl)-5-(trifluoromethyl)pyridine-3-carboxamide

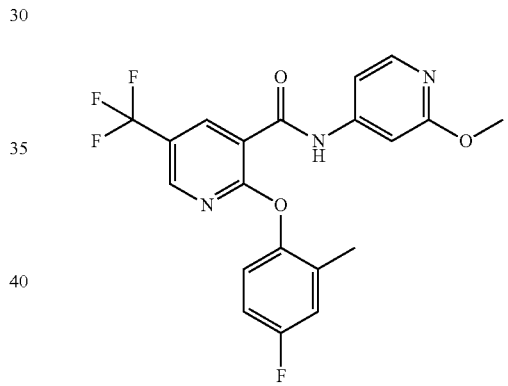

Step 1: Synthesis of 2-chloro-N-(2-methoxy-4-pyridyl)-5-(trifluoromethyl)pyridine-3-carboxamide

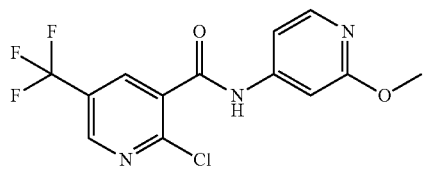 [SMILES: COc1cc(NC(=O)c2cc(C(F)(F)F)cnc2Cl)ccn1]

A mixture of 2-chloro-5-(trifluoromethyl)pyridine-3-carbonyl chloride (250 mg, 1.02 mmol), 2-Methoxypyridin-4-amine (127 mg, 1.02 mmol) and DIPEA (446 μL, 2.56 mmol) in chloroform (5 mL) was stirred at room temperature for 24 h. The contents were treated with 10% Na₂CO₃, extracted with CHCl₃ (3×) and the solvent removed in vacuo to give 2-chloro-N-(2-methoxy-4-pyridyl)-5-(trifluoromethyl)pyridine-3-carboxamide (290 mg, 0.874 mmol, 85.3% yield) as a pink solid. This material was used without further purification. MS, ES⁺ m/z 379.0 [M+H]⁺.

Step 2: Synthesis of 2-(4-fluoro-2-methyl-phenoxy)-N-(2-methoxy-4-pyridyl)-5-(trifluoromethyl)pyridine-3-carboxamide A mixture of 2-chloro-N-(2-methoxy-4-pyridyl)-5-(trifluoromethyl)pyridine-3-carboxamide (84.0 mg, 0.253 mmol), 4-fluoro-2-methyl-phenol (47.9 mg, 0.380 mmol) and cesium carbonate (248 mg, 0.760 mmol) in MeCN (3 mL) was stirred at 80° C. for 2 h. After cooling, the contents were diluted with EtOAc, washed with water (3×), brine (1×), dried over MgSO4, filtered and the solvent removed in vacuo to give a residue which was triturated with 10% MeCN/water to give a precipitate which was collected by filtration, washed with water and dried under vacuum to give 2-(4-fluoro-2-methyl-phenoxy)-N-(2-methoxy-4-pyridyl)-5-(trifluoromethyl)pyridine-3-carboxamide (50.0 mg, 0.119 mmol, 46.9% yield) as a beige solid. MS, ES⁺ m/z 422.2 [M+H]⁺.

¹H-NMR (400 MHz, DMSO-d₆) δ 10.99 (s, 1H), 8.68 (s, 1H), 8.57 (s, 1H), 8.11 (d, J=5.81 Hz, 1H), 7.18-7.30 (m, 4H), 7.08-7.15 (m, 1H), 3.85 (s, 3H), 2.08 (s, 3H).

Example 110: 2-(4-fluoro-2-methyl-phenoxy)-N-(2-oxo-1H-pyridin-4-yl)-5-(trifluoromethyl)pyridine-3-carboxamide

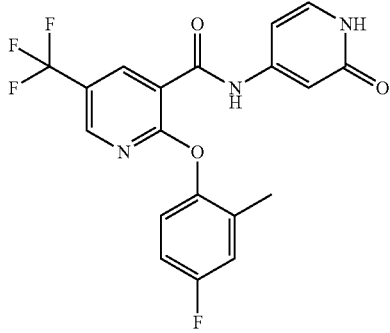 [SMILES: Cc1cc(F)ccc1Oc1ncc(C(F)(F)F)cc1C(=O)Nc1cc[nH]c(=O)c1]

A solution of 2-(4-fluoro-2-methyl-phenoxy)-N-(2-methoxy-4-pyridyl)-5-(trifluoromethyl)pyridine-3-carboxamide (50.0 mg, 0.119 mmol) in HBr (33% in HOAc) (538 µL, 2.97 mmol) was stirred at 80° C. for 18 h. After cooling, the contents were quenched by slow addition to 5% Na₂CO₃. The aqueous layer was extracted with EtOAc, washed with 5% Na₂CO₃ (3×), brine (1×), dried over MgSO4, filtered and the solvent removed in vacuo to give 2-(4-fluoro-2-methyl-phenoxy)-N-(2-oxo-1H-pyridin-4-yl)-5-(trifluoromethyl)pyridine-3-carboxamide (26.0 mg, 0.0638 mmol, 53.8% yield) as a tan solid. MS, ES⁺ m/z 408.0 [M+H]⁺.

¹H-NMR (400 MHz, DMSO-d₆) δ 11.08 (s, 1H), 8.64 (dd, J=2.53, 1.01 Hz, 1H), 8.59 (d, J=2.53 Hz, 1H), 8.42-8.44 (m, 1H), 7.98 (dt, J=7.58, 1.89 Hz, 1H), 7.66-7.73 (m, 2H), 7.08-7.16 (m, 3H), 3.23 (s, 3H), 2.07 (s, 6H).

Example 111: 5-bromo-2-(4-fluoro-2-methoxy-phenoxy)-N-(3-methylsulfonylphenyl)pyridine-3-carboxamide

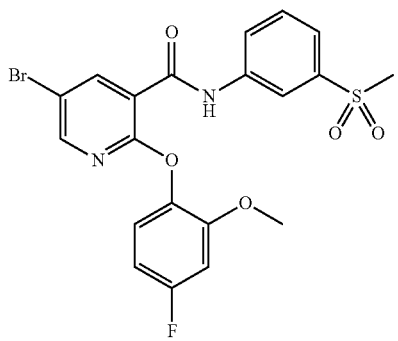 [SMILES: COc1cc(F)ccc1Oc1ncc(Br)cc1C(=O)Nc1cccc(S(C)(=O)=O)c1]

Step 1: Synthesis of methyl 5-bromo-2-(4-fluoro-2-methoxy-phenoxy)pyridine-3-carboxylate

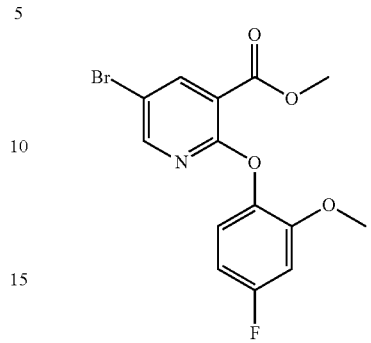

A mixture of methyl 5-bromo-2-chloronicotinate (100 mg, 0.399 mmol), 4-fluoro-2-methoxyphenol (47.8 µL, 0.419 mmol) and cesium carbonate (325 mg, 0.998 mmol) in MeCN (3 mL) was stirred at 50° C. for 20 h. The contents were diluted with EtOAc, washed with 2% Na₂CO₃ (3×), brine (1×), dried over MgSO4, filtered and the solvent removed in vacuo to give methyl 5-bromo-2-(4-fluoro-2-methoxy-phenoxy)pyridine-3-carboxylate (90.7 mg, 0.255 mmol, 63.8% yield) as a tan solid. This material was carried forward without further purification. MS, ES⁺ m/z 355.9/357.9 [M+H]⁺.

¹H-NMR (400 MHz, DMSO-d₆) δ 8.40 (s, 2H), 7.18 (dd, J=8.84, 5.81 Hz, 1H), 7.08 (dd, J=10.74, 2.91 Hz, 1H), 6.80 (td, J=8.46, 2.78 Hz, 1H), 3.87 (s, 3H), 3.69 (s, 3H).

Step 2: Synthesis of 5-bromo-2-(4-fluoro-2-methoxy-phenoxy)pyridine-3-carboxylic

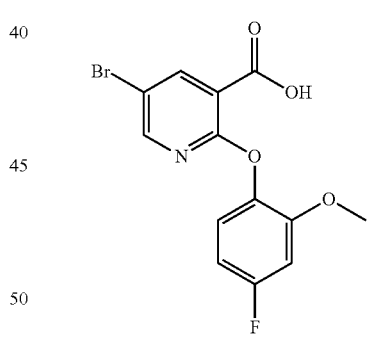

A mixture of methyl 5-bromo-2-(4-fluoro-2-methoxy-phenoxy)pyridine-3-carboxylate (65 mg, 0.183 mmol) and lithium hydroxide monohydrate (38.3 mg, 0.913 mmol) in THF (1 mL) and Water (1 mL) was stirred at 50° C. for 2 h. After cooling, the pH was lowered to pH 5 by careful addition of 6N HCl. After cooling to 0° C., a precipitate was collected by filtration, washed with cold water and dried under vacuum to give 5-bromo-2-(4-fluoro-2-methoxy-phenoxy)pyridine-3-carboxylic acid (39.3 mg, 0.115 mmol, 62.9% yield) as a white solid. MS, ES⁺ m/z 341.9/343.9 [M+H]⁺. ¹H-NMR (400 MHz, DMSO-d₆) δ 13.56 (br. s., 1H), 8.33-8.37 (m, 2H), 7.17 (dd, J=8.72, 5.94 Hz, 1H), 7.07 (dd, J=10.86, 2.78 Hz, 1H), 6.79 (td, J=8.46, 2.78 Hz, 1H), 3.69 (s, 3H).

Step 3: Synthesis of 5-bromo-2-(4-fluoro-2-methoxy-phenoxy)-N-(3-methylsulfonylphenyl)pyridine-3-carboxamide

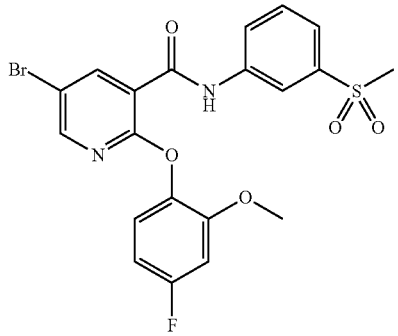 [SMILES: COc1cc(F)ccc1Oc1ncc(Br)cc1C(=O)Nc1cccc(S(C)(=O)=O)c1]

A mixture of HBTU (42.7 mg, 0.113 mmol), DIPEA (39.2 μL, 0.225 mmol), 5-bromo-2-(4-fluoro-2-methoxy-phenoxy)pyridine-3-carboxylic acid (35 mg, 0.102 mmol) and 3-methylsulfonylaniline (18.4 mg, 0.107 mmol) in chloroform (3 mL) was stirred at room temperature for 18 h. The contents were treated with 5% $Na_2CO_3$ and extracted with $CHCl_3$ (3×). The solvent was removed in vacuo to give a residue which was purified by automated normal-phase chromatography (0-100% EtOAc/heptane, 4 g silica gel cartridge) to give 5-bromo-2-(4-fluoro-2-methoxy-phenoxy)-N-(3-methylsulfonylphenyl)pyridine-3-carboxamide (13.0 mg, 0.0262 mmol, 25.6% yield) as a white solid. MS, $ES^+$ m/z 494.9/496.9 $[M+H]^+$.

$^1$H-NMR (400 MHz, DMSO-$d_6$) δ 10.91 (s, 1H), 8.40-8.42 (m, 1H), 8.34-8.36 (m, 2H), 7.95-7.98 (m, 1H), 7.64-7.71 (m, 2H), 7.29 (dd, J=8.84, 6.06 Hz, 1H), 7.08 (dd, J=10.74, 2.91 Hz, 1H), 6.82 (td, J=8.59, 3.03 Hz, 1H), 3.70 (s, 3H), 3.22 (s, 3H).

Example 112: 5-cyclopropyl-2-(4-fluoro-2-methoxy-phenoxy)-N-(3-methylsulfonylphenyl)pyridine-3-carboxamide

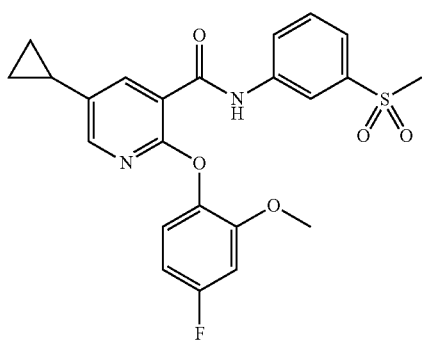 [SMILES: COc1cc(F)ccc1Oc1ncc(C2CC2)cc1C(=O)Nc1cccc(S(C)(=O)=O)c1]

Step 1: Synthesis of methyl 2-chloro-5-cyclopropyl-pyridine-3-carboxylate

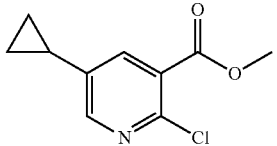

To a solution of methyl 5-bromo-2-chloronicotinate (200 mg, 0.799 mmol) in 1,4-Dioxane (5 mL) was added cyclopropylboronic acid (206 mg, 2.40 mmol), tribasic potassium phosphate (508 mg, 2.40 mmol) and tetrakis(triphenylphosphine)palladium(O) (46.1 mg, 0.0399 mmol). The mixture was heated in a microwave reactor at 100° C. for 30 min. Reaction complete by LCMS. The reaction mixture was diluted with EtOAc, washed with water (1×), 5% NH4Cl (1×), water (1×), brine (1×), dried over MgSO4, filtered and the solvent removed in vacuo to give a yellow residue which was purified by automated normal-phase chromatography (0-100% EtOAc/heptanes, 12 g silica gel cartridge) to give methyl 2-chloro-5-cyclopropyl-pyridine-3-carboxylate (73.0 mg, 0.345 mmol, 43.2% yield) as a colorless oil. MS, $ES^+$ m/z 212.0 $[M+H]^+$. $^1$H-NMR (400 MHz, DMSO-$d_6$) δ 8.41 (d, J=2.53 Hz, 1H), 7.86 (d, J=2.53 Hz, 1H), 3.87 (s, 3H), 2.05 (tt, J=8.46, 5.05 Hz, 1H), 1.02-1.09 (m, 2H), 0.79-0.85 (m, 2H).

Step 2: Synthesis of methyl 5-cyclopropyl-2-(4-fluoro-2-methoxy-phenoxy)pyridine-3-carboxylate

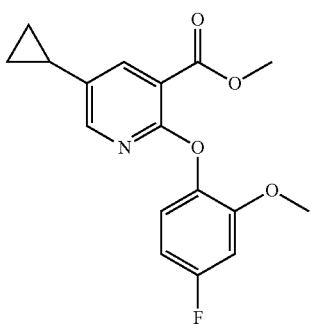 [SMILES: COC(=O)c1cc(C2CC2)cnc1Oc1ccc(F)cc1OC]

A mixture of methyl 2-chloro-5-cyclopropyl-pyridine-3-carboxylate (71 mg, 0.336 mmol), 4-fluoro-2-methoxyphenol (47.8 μL, 0.419 mmol) and cesium carbonate (327.91 mg, 1.01 mmol) in MeCN (2 mL) was stirred at 80° C. for 24 h. After cooling, the solvent was removed under a stream of $N_2$. The residue was treated with water and stirred vigorously for 2 h. The precipitate was collected by filtration, washed with water and dried under vacuum to give methyl 5-cyclopropyl-2-(4-fluoro-2-methoxy-phenoxy)pyridine-3-carboxylate (20.0 mg, 0.0630 mmol, 18.8% yield) as a tan solid. This material was used without further purification. MS, $ES^+$ m/z 318.0 $[M+H]^+$.

Step 3: Synthesis of 5-cyclopropyl-2-(4-fluoro-2-methoxy-phenoxy)pyridine-3-carboxylic acid

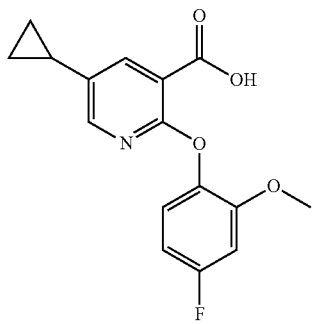 [SMILES: COc1cc(F)ccc1Oc1ncc(C2CC2)cc1C(=O)O]

A mixture of methyl 5-cyclopropyl-2-(4-fluoro-2-methoxy-phenoxy)pyridine-3-carboxylate (20.1 mg, 0.0633 mmol) and lithium hydroxide monohydrate (10.0 mg, 0.238 mmol) in THF (2 mL) and Methanol (0.2 mL) was stirred at room temperature for 5 days (for convenience). The solvent was removed with a stream of N₂ and the contents diluted with water (3 mL). The pH was lowered to pH 5 by careful addition of 6 N HCl. After stirring for 3 h, the precipitate was collected by filtration, washed with water and dried under vacuum to give 5-cyclopropyl-2-(4-fluoro-2-methoxy-phenoxy)pyridine-3-carboxylic acid (9.5 mg, 0.031 mmol, 49.4% yield) as an off-white solid. This material was used without further purification. MS, ES⁺ m/z 304.0 [M+H]⁺.

Step 4: Synthesis of 5-cyclopropyl-2-(4-fluoro-2-methoxy-phenoxy)-N-(3-methylsulfonylphenyl)pyridine-3-carboxamide

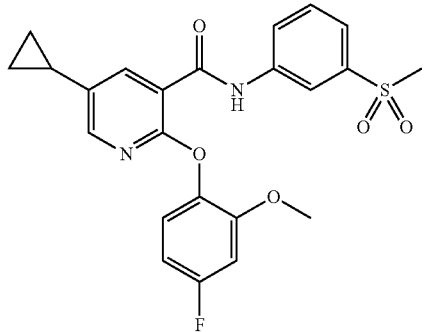 [SMILES: COc1cc(F)ccc1Oc1ncc(C2CC2)cc1C(=O)Nc1cccc(S(C)(=O)=O)c1]

A mixture of 5-cyclopropyl-2-(4-fluoro-2-methoxy-phenoxy)pyridine-3-carboxylic acid (9.5 mg, 0.0313 mmol), HBTU (14.3 mg, 0.0376 mmol), 3-methylsulfonylaniline (5.9 mg, 0.0345 mmol) and DIPEA (16.4 µL, 0.0940 mmol) in chloroform (0.5 mL) was stirred at room temperature for 3 days (for convenience). The contents were diluted with EtOAc, washed with water (3x), brine (1x), dried over MgSO4, filtered and the solvent removed in vacuo to give a residue which was purified by automated normal-phase chromatography (0-100% EtOAc/heptane, 4 g silica gel cartridge) to give 5-cyclopropyl-2-(4-fluoro-2-methoxy-phenoxy)-N-(3-methylsulfonylphenyl)pyridine-3-carboxamide (2.6 mg, 0.0057 mmol, 18.2% yield) a white solid. MS, ES⁺ m/z 457.0 [M+H]⁺. ¹H-NMR (400 MHz, DMSO-d₆) δ 10.73 (s, 1H), 8.40-8.43 (m, 1H), 8.02 (d, J=2.53 Hz, 1H), 7.97 (dt, J=7.07, 2.02 Hz, 1H), 7.75 (d, J=2.53 Hz, 1H), 7.63-7.70 (m, 2H), 7.27 (dd, J=8.72, 5.94 Hz, 1H), 7.05 (dd, J=10.74, 2.91 Hz, 1H), 6.81 (td, J=8.46, 3.03 Hz, 1H), 3.70 (s, 3H), 3.22 (s, 3H), 1.93-2.01 (m, 1H), 0.95-1.00 (m, 2H), 0.72-0.77 (m, 2H).

Example 113: 2-(4-fluoro-2-methyl-phenoxy)-N-(3-methylsulfonylphenyl)-5-(trifluoromethyl)pyridine-3-carboxamide Method N

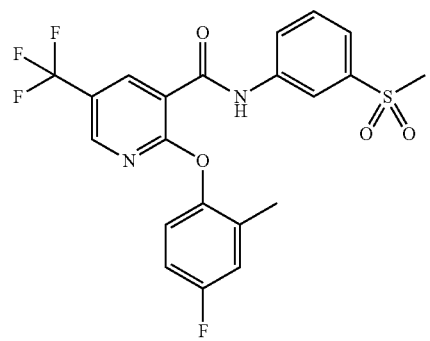 [SMILES: Cc1cc(F)ccc1Oc1ncc(C(F)(F)F)cc1C(=O)Nc1cccc(S(C)(=O)=O)c1]

Step 1: Synthesis of 2-(4-fluoro-2-methyl-phenoxy)-5-(trifluoromethyl)pyridine-3-carboxylic acid

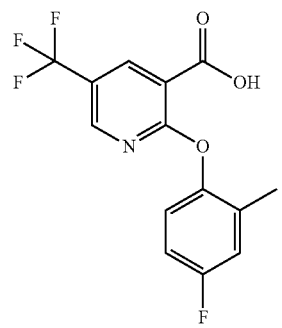 [SMILES: Cc1cc(F)ccc1Oc1ncc(C(F)(F)F)cc1C(=O)O]

A mixture of 2-chloro-5-(trifluoromethyl)pyridine-3-carboxylic acid (497 mg, 2.20 mmol), 4-fluoro-2-methyl-phenol (306 mg, 2.42 mmol) and cesium carbonate (1.79 g, 5.51 mmol) in MeCN (5 mL) was stirred at 80° C. for 5 h, then 4 days at room temperature (for convenience). The solvent was removed under a stream of N₂, and the residue dissolved in water (10 mL). The pH was lowered to pH 5 by careful addition of 6 N HCl. After stirring for 3 h, the precipitate was collected by filtration, washed with water and dried under vacuum to give 2-(4-fluoro-2-methyl-phenoxy)-5-(trifluoromethyl)pyridine-3-carboxylic acid (407.5 mg, 1.293 mmol, 58.7% yield) as a beige solid. MS, ES⁺ m/z 316.0 [M+H]⁺.

Step 2: Synthesis of 2-(4-fluoro-2-methyl-phenoxy)-N-(3-methylsulfonylphenyl)-5-(trifluoromethyl)pyridine-3-carboxamide

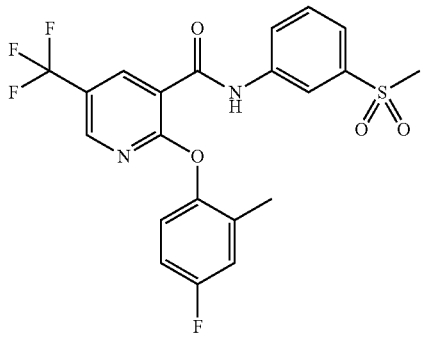 [SMILES: Cc1cc(F)ccc1Oc1ncc(C(F)(F)F)cc1C(=O)Nc1cccc(S(C)(=O)=O)c1]

A mixture of 2-(4-fluoro-2-methyl-phenoxy)-5-(trifluoromethyl)pyridine-3-carboxylic acid (100 mg, 0.317 mmol), 3-methylsulfonylaniline (59.8 mg, 0.349 mmol), HBTU (132 mg, 0.349 mmol) and DIPEA (138 μL, 0.793 mmol) in chloroform (2 mL) was stirred at room temperature for 18 h. The solvent was removed under a stream of $N_2$, and the residue treated with water/MeOH (5:1). This mixture was briefly sonicated then stirred at room temperature for 4 h. The resulting precipitate was collected by filtration, washed with water and dried under vacuum to give 2-(4-fluoro-2-methyl-phenoxy)-N-(3-methylsulfonylphenyl)-5-(trifluoromethyl)pyridine-3-carboxamide (121.7 mg, 0.260 mmol, 81.9% yield) as a tan solid. MS, ES+ m/z 469.0 [M+H]+. $^1$H-NMR (400 MHz, DMSO-d$_6$) δ 11.05 (s, 1H), 8.67-8.69 (m, 1H), 8.57 (d, J=2.53 Hz, 1H), 8.40-8.42 (m, 1H), 7.97 (dt, J=7.58, 1.89 Hz, 1H), 7.65-7.73 (m, 2H), 7.27 (dd, J=8.84, 5.05 Hz, 1H), 7.21 (dd, J=9.35, 3.03 Hz, 1H), 7.12 (td, J=8.78, 3.16 Hz, 1H), 3.23 (s, 3H), 2.09 (s, 3H).

The following compounds have been synthesized according to Method N

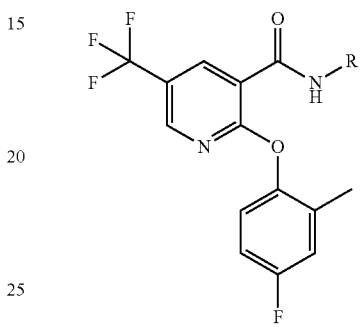

| Example | Name | R | Analytical data | Preparation details |
|---|---|---|---|---|
| 114 | N-[3-(N,S-dimethylsulfonimidoyl)-phenyl]-2-(4-fluoro-2-methylphenoxy)-5-(trifluoromethyl)-pyridine-3-carboxamide | 3-(N,S-dimethylsulfonimidoyl)phenyl | MS, ES+ m/z 482.4 [M + H]+ $^1$H NMR (400 MHz, DMSO-d6) δ ppm 2.00-2.14 (m, 3 H) 2.49 (s, 3 H) 3.13 (s, 3 H) 7.12 (d, J = 3.03 Hz, 1 H) 7.18-7.31 (m, 2 H) 7.55-7.62 (m, 1 H) 7.62-7.69 (m, 1 H) 7.91-8.01 (m, 1 H) 8.31 (s, 1 H) 8.55-8.59 (m, 1 H) 8.67 (s, 1 H) 11.00 (s, 1 H) | Method N, using (3-aminophenyl)-(methylimino)-λ$^6$-sulfanone |
| 115 | 2-(4-fluoro-2-methylphenoxy)-N-[3-(methylsulfonimidoyl)phenyl]-5-(trifluoromethy)-pyridine-3-carboxamide | 3-(methylsulfonimidoyl)phenyl | MS, ES+ m/z 468.4 [M + H]+ $^1$H NMR (400 MHz, DMSO-d6) δ ppm 2.07-2.12 (m, 3 H) 3.07 (s. 3 H) 7.12 (td, J = 8.53, 3.16 Hz, 1 H) 7.21 (dd, J = 9.35, 3.28 Hz, 1 H) 7.28 (dd, J = 8.84, 5.05 Hz, 1 H) 7.62 (t, J = 7.96 Hz, 1 H) 7.70 (d, J = 7.83 Hz, 1 H) 7.95 (d, J = 8.08 Hz, 1 H) 8.39 (s, 1 H) 8.56 (d, J = 2.53 Hz, 1 H) 8.67 (d, J = 1.52 Hz, 1 H) 10.99 (s, 1 H) | Method N, using (3-aminophenyl)-(imino)(methyl)-λ$^6$-sulfanone |
| 116 | 2-(4-fluoro-2-methylphenoxy)-N-pyridazin-4-yl-5-(trifluoromethyl)-pyridine-3-carboxamide | pyridazin-4-yl | MS, ES+ m/z 393.2 [M + H]+ $^1$H NMR (400 MHz, DMSO-d6) δ ppm 2.09 (s, 3 H) 7.12 (td, J = 8.59, 3.28 Hz, 1 H) 7.22 (dd, J = 9.47, 2.91 Hz, 1 H) 7.27 (dd, J = 8.97, 5.18 Hz, 1 H) 8.08 (dd, J = 5.81, 2.78 Hz, 1 H) 8.63 (d, J = 2.53 Hz, 1 H) 8.71 (dd, J = 1.77, 0.76 Hz, 1 H) 9.14 (dd, J = 6.06, 0.51 Hz, 1 H) 9.38 - 9.45 (m, 1 H) 11.33 (s, 1 H) | Method N, using 4-aminopyridazine |

Example 117: 2-(4-fluoro-2-methoxy-phenoxy)-6-methyl-N-(3-methylsulfonylphenyl)pyridine-3-carboxamide

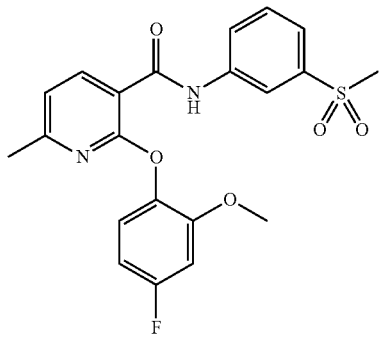

Step 1: Synthesis of 2-chloro-6-methyl-N-(3-methylsulfonylphenyl)pyridine-3-carboxamide

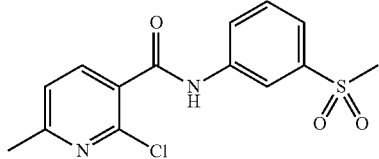

A mixture of HBTU (243 mg, 0.641 mmol), DIPEA (223 µL, 1.28 mmol), 2-chloro-6-methylnicotinic acid (100 mg, 0.583 mmol) and 3-methylsulfonylaniline (105 mg, 0.613 mmol) in chloroform (5 mL) was stirred at room temperature for 48 h. The contents were treated with 5% Na$_2$CO$_3$ and extracted with CHCl3 (3×). The solvent was removed in vacuo to give 2-chloro-6-methyl-N-(3-methylsulfonylphenyl)pyridine-3-carboxamide (175 mg, 0.539 mmol, 92.5% yield) as a residue which was used without further purification. MS, ES$^+$ m/z 325.0 [M+H]$^+$.

Step 2: Synthesis of 2-(4-fluoro-2-methoxy-phenoxy)-6-methyl-N-(3-methylsulfonylphenyl)pyridine-3-carboxamide

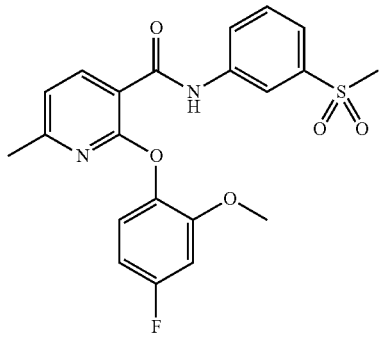

A mixture of crude 2-chloro-6-methyl-N-(3-methylsulfonylphenyl)pyridine-3-carboxamide (70.0 mg, 0.216 mmol), 4-fluoro-2-methoxyphenol (30.7 µL, 0.269 mmol) and cesium carbonate (211 mg, 0.647 mmol) in MeCN (2 mL) was stirred at 60° C. for 24 h. After cooling, the contents were treated with water and stirred overnight at room temperature. A precipitate was collected by filtration, washed with water and dried under vacuum to give 2-(4-fluoro-2-methoxy-phenoxy)-6-methyl-N-(3-methylsulfonylphenyl)pyridine-3-carboxamide (29.0 mg, 0.0674 mmol, 31.3% yield) as a beige solid. MS, ES$^+$ m/z 431.0 [M+H]$^+$. $^1$H-NMR (400 MHz, DMSO-d$_6$) δ 10.63 (s, 1H), 8.41 (s, 1H), 8.04 (d, J=7.58 Hz, 1H), 7.96 (d, J=7.07 Hz, 1H), 7.62-7.69 (m, 2H), 7.33 (dd, J=8.72, 5.94 Hz, 1H), 7.05-7.13 (m, 2H), 6.83 (td, J=8.46, 3.03 Hz, 1H), 3.71 (s, 3H), 3.22 (s, 3H), 2.30 (s, 3H).

Example 118: 2-(4-fluoro-2-methoxy-phenoxy)-5,6-dimethyl-N-(3-methylsulfonylphenyl)pyridine-3-carboxamide

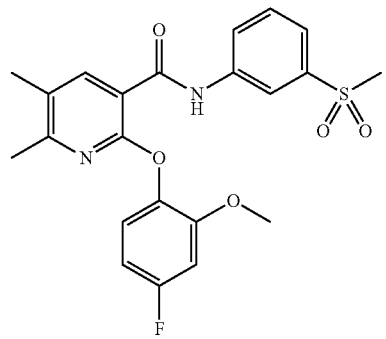

Step 1: Synthesis of 2-chloro-5,6-dimethyl-N-(3-methylsulfonylphenyl)pyridine-3-carboxamide

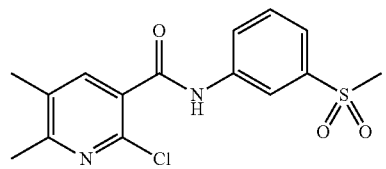

To a mixture of 2-chloro-5,6-dimethyl-pyridine-3-carboxylic acid (100 mg, 0.539 mmol), 3-methylsulfonylaniline (96.9 mg, 0.566 mmol) and HBTU (225 mg, 0.593 mmol) in chloroform (4 mL) was added DIPEA (206.5 µL, 1.19 mmol). The resulting mixture was stirred at room temperature for 6 days (for convenience). The solvent was removed under a stream of N$_2$, and the residue treated with water/MeOH (4:1). This mixture was briefly sonicated then stirred at room temperature for 18 h. The resulting precipitate was collected by filtration, washed with water and dried under vacuum to give 2-chloro-5,6-dimethyl-N-(3-methylsulfonylphenyl)pyridine-3-carboxamide (137 mg, 0.404 mmol, 75.1% yield) as a beige solid. MS, ES$^+$ m/z 339.0 [M+H]$^+$. $^1$H-NMR (400 MHz, DMSO-d$_6$) δ 10.96 (s, 1H), 8.37 (s, 1H), 7.94 (d, J=7.33 Hz, 1H), 7.88 (s, 1H), 7.64-7.72 (m, 2H), 3.23 (s, 3H), 2.48 (s, 3H), 2.31 (s, 3H).

Step 2: Synthesis of 2-(4-fluoro-2-methoxy-phenoxy)-5,6-dimethyl-N-(3-methylsulfonylphenyl)pyridine-3-carboxamide

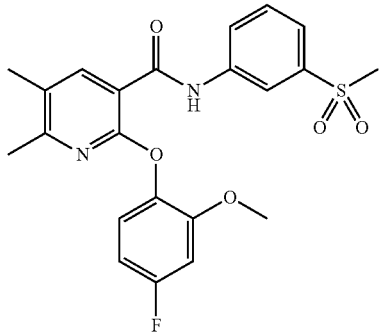

A mixture of 2-chloro-5,6-dimethyl-N-(3-methylsulfonylphenyl)pyridine-3-carboxamide (50.0 mg, 0.148 mmol), 4-fluoro-2-methoxyphenol (17.7 μL, 0.155 mmol) and cesium carbonate (106 mg, 0.327 mmol) in MeCN (4 mL) was stirred at 80° C. for 10 h. The solvent was removed under a stream of $N_2$, and the residue treated with water/MeOH (2:1). This mixture was briefly sonicated then stirred at room temperature for 18 h. The resulting precipitate was collected by filtration, washed with water and dried under vacuum to give 2-(4-fluoro-2-methoxy-phenoxy)-5,6-dimethyl-N-(3-methylsulfonylphenyl)pyridine-3-carboxamide (21.0 mg, 0.0472 mmol, 32.0% yield) as a reddish-brown solid. MS, $ES^+$ m/z 445.0 $[M+H]^+$.

$^1$H-NMR (400 MHz, DMSO-$d_6$) δ 10.58 (s, 1H), 8.40 (s, 1H), 7.97 (d, J=7.07 Hz, 1H), 7.92 (s, 1H), 7.62-7.70 (m, 2H), 7.30 (dd, J=8.84, 6.06 Hz, 1H), 7.07 (dd, J=10.74, 2.91 Hz, 1H), 6.82 (td, J=8.59, 3.03 Hz, 1H), 3.71 (s, 3H), 3.22 (s, 3H), 2.25 (br. s., 3H), 2.24 (br. s., 3H).

Example 119: 5-chloro-2-(4-fluoro-2-methoxy-phenoxy)-N-(3-methylsulfonylphenyl)pyridine-3-carboxamide

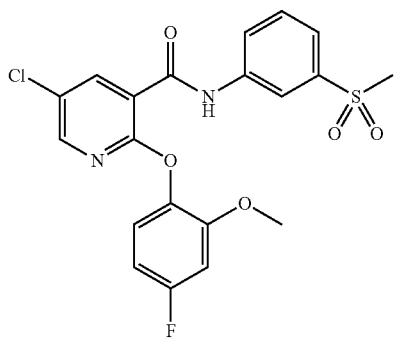 [SMILES: COc1cc(F)ccc1Oc1ncc(Cl)cc1C(=O)Nc1cccc(S(C)(=O)=O)c1]

Step 1: Synthesis of 2,5-dichloro-N-(3-methylsulfonylphenyl)pyridine-3-carboxamide

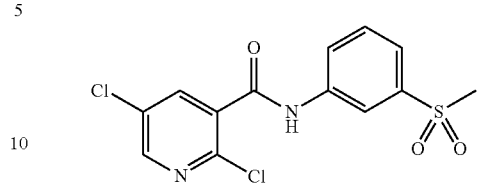

A mixture of HBTU (217 mg, 0.571 mmol), DIPEA (200 μL, 1.15 mmol), 2,5-dichloropyridine-3-carboxylic acid (100 mg, 0.521 mmol) and 3-methylsulfonylaniline (93.6 mg, 0.547 mmol) in chloroform (5 mL) was stirred at room temperature for 22 h. The contents were treated with 5% $Na_2CO_3$ and extracted with CHCl3 (3×). The solvent was removed in vacuo to give 2,5-dichloro-N-(3-methylsulfonylphenyl)pyridine-3-carboxamide (150 mg, 0.435 mmol, 83.4% yield) as a semi-solid which was used without further purification. MS, $ES^+$ m/z 344.8 $[M+H]^+$.

Step 2: Synthesis of 5-chloro-2-(4-fluoro-2-methoxy-phenoxy)-N-(3-methylsulfonylphenyl)pyridine-3-carboxamide

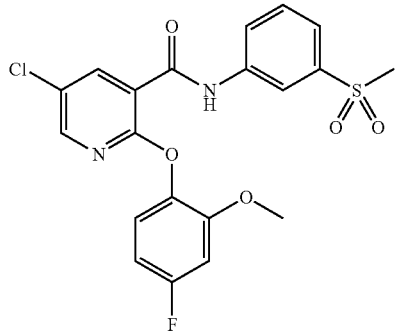 [SMILES: COc1cc(F)ccc1Oc1ncc(Cl)cc1C(=O)Nc1cccc(S(C)(=O)=O)c1]

A mixture of crude 2,5-dichloro-N-(3-methylsulfonylphenyl)pyridine-3-carboxamide (59.3 mg, 0.172 mmol), 4-fluoro-2-methoxyphenol (27.4 μL, 0.241 mmol) and Cesium carbonate (168 mg, 0.517 mmol) in MeCN (3 mL) was stirred at 80° C. for 3 h. After cooling, water was added and a precipitate began to form. After stirring for 1 h, this material was collected by filtration, washed with water and dried under vacuum to give 5-chloro-2-(4-fluoro-2-methoxy-phenoxy)-N-(3-methylsulfonylphenyl)pyridine-3-carboxamide (21 mg, 0.047 mmol, 27.1% yield) as a beige solid. MS, $ES^+$ m/z 451.0 $[M+H]^+$.

$^1$H-NMR (400 MHz, DMSO-$d_6$) δ 10.91 (s, 1H), 8.41 (s, 1H), 8.25-8.31 (m, 2H), 7.97 (d, J=7.58 Hz, 1H), 7.64-7.72 (m, 2H), 7.26-7.32 (m, 1H), 7.08 (d, J=10.86 Hz, 1H), 6.83 (t, J=8.08 Hz, 1H), 3.70 (s, 3H), 3.22 (s, 3H).

Example 120: 2-(4-fluoro-2-methoxy-phenoxy)-N-(3-methylsulfonylphenyl)-6,7-dihydro-5H-cyclopenta[b]pyridine-3-carboxamide

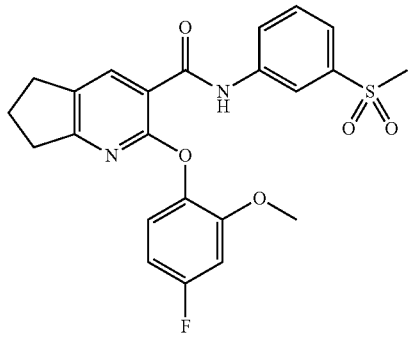 [SMILES: COc1cc(F)ccc1Oc1nc2c(cc1C(=O)Nc1cccc(S(C)(=O)=O)c1)CCC2]

Step 1: Synthesis of 2-chloro-6,7-dihydro-5H-cyclopenta[b]pyridine-3-carboxylic acid

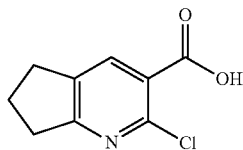 [SMILES: O=C(O)c1cc2c(nc1Cl)CCC2]

A solution of 2-chloro-6,7-dihydro-5H-cyclopenta[b]pyridine-3-carbonitrile (173 mg, 0.969 mmol) in 2 mL conc. sulfuric acid/water (1:1) was stirred at 100° C. for 9 h. After cooling, the contents were added portion wise to ice water with stirring. After stirring for 1 h, the precipitate was collected by filtration, washed with cold water and dried under vacuum to give 2-chloro-6,7-dihydro-5H-cyclopenta[b]pyridine-3-carboxylic acid (117 mg, 0.592 mmol, 61.1% yield) as a tan solid. MS, ES+ m/z 198.0 [M+H]+. $^1$H-NMR (400 MHz, DMSO-$d_6$) δ 13.53 (br. s., 1H), 8.02 (s, 1H), 2.93 (q, J=7.24 Hz, 4H), 2.10 (quin, J=7.24 Hz, 2H).

Step 2: Synthesis of 2-chloro-N-(3-methylsulfonylphenyl)-6,7-dihydro-5H-cyclopenta[b]pyridine-3-carboxamide

To a mixture of 2-chloro-6,7-dihydro-5H-cyclopenta[b]pyridine-3-carboxylic acid (114 mg, 0.577 mmol), 3-methylsulfonylaniline (104 mg, 0.607 mmol) and HBTU (241 mg, 0.637 mmol) in chloroform (4 mL) was added DIPEA (221 μL, 1.27 mmol). The resulting mixture was stirred at room temperature for 5 days (for convenience). The solvent was removed under a stream of N$_2$, and the residue treated with water/MeOH (3:1). This mixture was briefly sonicated then stirred at room temperature for 1 h. The resulting precipitate was collected by filtration, washed with water and dried under vacuum to give 2-chloro-N-(3-methylsulfonylphenyl)-6,7-dihydro-5H-cyclopenta[b]pyridine-3-carboxamide (147.6 mg, 0.421 mmol, 72.9% yield) as a brown solid which was used without further purification. MS, ES+ m/z 351.1 [M+H]+.

Step 3: Synthesis of 2-(4-fluoro-2-methoxy-phenoxy)-N-(3-methylsulfonylphenyl)-6,7-dihydro-5H-cyclopenta[b]pyridine-3-carboxamide

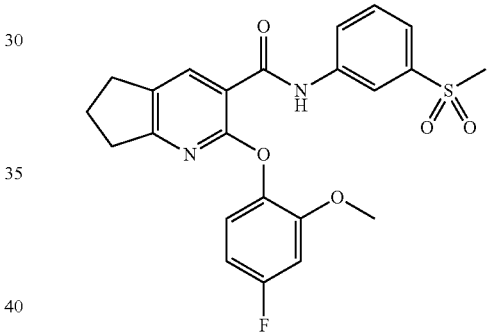

A mixture of 2-chloro-N-(3-methylsulfonylphenyl)-6,7-dihydro-5H-cyclopenta[b]pyridine-3-carboxamide (50.0 mg, 0.143 mmol), 4-fluoro-2-methoxyphenol (17.1 μL, 0.150 mmol) and cesium carbonate (102 mg, 0.313 mmol) in MeCN (3 mL) was stirred at 80° C. for 10 h. The solvent was removed under a stream of N$_2$, and the residue treated with water/MeOH (2:1). This mixture was briefly sonicated then stirred at room temperature for 24 h. The resulting precipitate was collected by filtration, washed with water and dried under vacuum to give 2-(4-fluoro-2-methoxyphenoxy)-N-(3-methylsulfonylphenyl)-6,7-dihydro-5H-cyclopenta[b]pyridine-3-carboxamide (24 mg, 0.053 mmol, 36.9% yield) as a brown solid. MS, ES+ m/z 457.1 [M+H]+. $^1$H-NMR (400 MHz, DMSO-$d_6$) δ 10.63 (s, 1H), 8.42 (br. s., 1H), 7.96 (s, 2H), 7.63-7.69 (m, 2H), 7.28-7.33 (m, 1H), 7.05-7.10 (m, 1H), 6.79-6.86 (m, 1H), 3.72 (s, 3H), 3.22 (s, 3H), 2.89 (t, J=7.20 Hz, 2H), 2.75 (t, J=7.71 Hz, 2H), 2.01-2.11 (m, 2H).

Example 121: N-(3-methylsulfinylphenyl)-2-[4-(trifluoromethoxy)phenoxy]-5-(trifluoromethyl)pyridine-3-carboxamide Method O

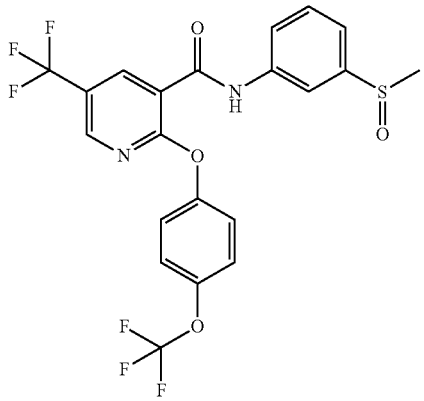 [SMILES: CS(=O)c1cccc(NC(=O)c2cc(C(F)(F)F)cnc2Oc2ccc(OC(F)(F)F)cc2)c1]

Step 1: Synthesis of 2-[4-(trifluoromethoxy)phenoxy]-5-(trifluoromethyl)pyridine-3-carboxylic acid

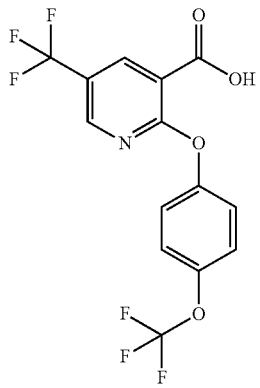 [SMILES: O=C(O)c1cc(C(F)(F)F)cnc1Oc1ccc(OC(F)(F)F)cc1]

A mixture of 2-chloro-5-(trifluoromethyl)pyridine-3-carboxylic acid (510 mg, 2.26 mmol), 4-(trifluoromethoxy)phenol (322 μL, 2.49 mmol) and cesium carbonate (1.84 g, 5.65 mmol) in MeCN (5 mL) was stirred at 80° C. for 5 h, then 4 days at room temperature (for convenience). The solvent was removed under a stream of $N_2$, and the residue treated with water/MeOH (5:1). This mixture was briefly sonicated then stirred at room temperature for 18 h. The resulting precipitate was collected by filtration, washed with water and dried under vacuum to give 2-[4-(trifluoromethoxy)phenoxy]-5-(trifluoromethyl)pyridine-3-carboxylic acid (604 mg, 1.65 mmol, 72.8% yield) as an off-white solid. MS, ES+ m/z 368.0 [M+H]+.

Step 2: Synthesis of N-(3-methylsulfinylphenyl)-2-[4-(trifluoromethoxy)phenoxy]-5-(trifluoromethyl)pyridine-3-carboxamide

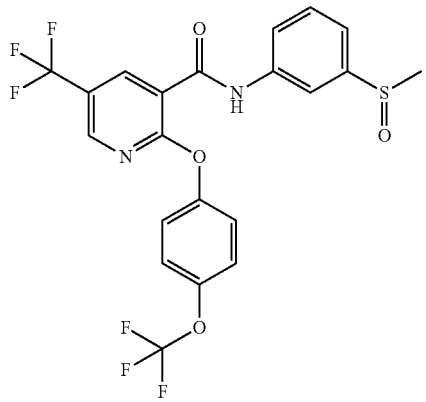 [SMILES: CS(=O)c1cccc(NC(=O)c2cc(C(F)(F)F)cnc2Oc2ccc(OC(F)(F)F)cc2)c1]

A mixture of 2-[4-(trifluoromethoxy)phenoxy]-5-(trifluoromethyl)pyridine-3-carboxylic acid (35.0 mg, 0.0953 mmol), 3-methylsulfinylaniline (16.3 mg, 0.105 mmol), HBTU (39.8 mg, 0.105 mmol) and DIPEA (41.5 μL, 0.238 mmol) in chloroform (2 mL) was stirred at room temperature for 3 days (for convenience). The solvent was removed under a stream of $N_2$, and the residue treated with water/MeOH (3:1). This mixture was briefly sonicated then stirred at room temperature for 24 h. The resulting precipitate was collected by filtration, washed with water and dried under vacuum to give N-(3-methylsulfinylphenyl)-2-[4-(trifluoromethoxy)phenoxy]-5-(trifluoromethyl)pyridine-3-carboxamide (39.0 mg, 0.0773 mmol, 81. yield) as a beige solid. MS, ES+ m/z 505.0 [M+H]+.

$^1$H-NMR (400 MHz, DMSO-$d_6$) δ 10.95 (s, 1H), 8.72 (d, J=1.52 Hz, 1H), 8.56 (d, J=2.53 Hz, 1H), 8.14 (s, 1H), 7.83 (d, J=7.58 Hz, 1H), 7.58 (t, J=7.83 Hz, 1H), 7.40-7.52 (m, 5H), 2.75 (s, 3H).

The following compounds have been synthesized according to Method O

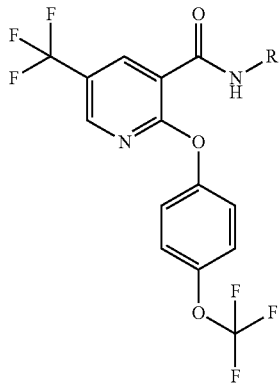

| Example | Name | R | Analytical data | Preparation details |
|---|---|---|---|---|
| 122 | N-(3-sulfamoyl-phenyl)-2-[4-(tri-fluoromethoxy)-phenoxy]-5-(tri-fluoromethyl)-pyridine-3-carbox-amide | 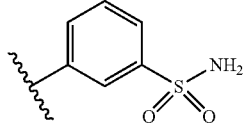 [SMILES: *c1cccc(S(N)(=O)=O)c1] | MS, ES+ m/z, 522.0 (M + H)+ $^1$H NMR (400 MHz, DMSO-d6) δ ppm 7.35-7.55 (m, 6 H) 7.55-7.63 (m, 2 H) 7.87 (d, J = 3.28 Hz, 1 H) 8.31 (s, 1 H) 8.57 (d, J = 2.53 Hz, 1 H) 8.70-8.75 (m, 1 H) 10.96 (s, 1 H) | Method O, using 3-aminobenzene-sulfonamide |
| 123 | N-[3-(methylsul-fonimidoyl)phenyl]-2-[4-(trifluorometh-oxy)phenoxy]-5-(trifluoromethyl)-pyridine-3-carbox-amide | 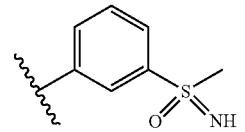 [SMILES: *c1cccc(S(C)(=N)=O)c1] | MS, ES+ m/z 520.8 (M + H)+ $^1$H NMR (400 MHz, DMSO-d6) δ ppm 3.07 (s, 3 H) 4.27 (s, 1 H) 7.39-7.54 (m, 4 H) 7.62 (t, J = 7.83 Hz, 1 H) 7.70 (dt, J = 7.96, 1.20 Hz, 1 H) 7.90-8.02 (m, 1 H) 8.38 (t, J = 1.89 Hz, 1 H) 8.57 (d, J = 2.53 Hz, 1 H) 8.72 (d, J = 1.52 Hz, 1 H) 11.01 (s, 1 H) | Method O, using (3-aminophenyl)-(imino)(methyl)-$\lambda^6$-sulfanone |
| 124 | N-3-(N,S-dimethyl-sulfonimidoyl)phen-yl]-2-[4-(trifluoro-methoxy)phenoxy]-5-(trifluoromethyl)-pyridine-3-carbox-amide | 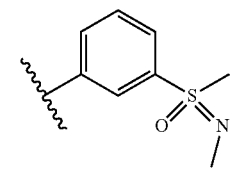 [SMILES: *c1cccc(S(C)(=O)=NC)c1] | MS, ES+ m/z 534.8 (M + H)+ $^1$H NMR (400 MHz, DMSO-d6) δ ppm 2.49 (s, 3 H) 3.12 (s, 3 H) 3.34 (s, 2 H) 7.39-7.53 (m, 4 H) 7.59 (dt, J = 7.77, 1.29 Hz, 1 H) 7.66 (t, J = 7.96 Hz, 1 H) 7.91-7.99 (m, 1 H) 8.30 (t, J = 1.89 Hz, 1 H) 8.58 (d, J = 2.53 Hz, 1 H) 8.69-8.76 (m, 1 H) 11.00 (s, 1 H) | Method O, using 3-aminophenyl)-(methyl)(methyl-imino)-$\lambda^6$-sul-fanone |
| 125 | N-(3-ethylsulfon-ylphenyl)-2-[4-(trifluoromethoxy)-phenoxy]-5-(tri-fluoromethyl)-pyridine-3-carbox-amide | 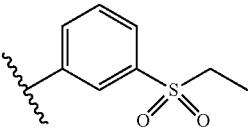 [SMILES: *c1cccc(S(=O)(=O)CC)c1] | MS, ES+ m/z, 535.0 (M + H)+ $^1$H NMR (400 MHz, DMSO-d6) δ ppm 1.13 (t, J = 7.33 Hz, 3 H) 3.26-3.34 (m, 2 H) 7.38-7.53 (m, 4 H) 7.62-7.74 (m, 2 H) 7.99 (d, J = 7.83 Hz, 1H) 8.37 (s, 1 H) 8.59 (d, J = 2.02 Hz, 1 H) 8.73 (s, 1 H) 11.06 (s, 1 H) | Method O, using 3-(ethylsulfonyl)-aniline |
| 126 | N-(3-pyridyl)-2-[4-(trifluoromethoxy)-phenoxy]-5-(tri-fluoromethyl)pyri-dine-3-carboxamide | 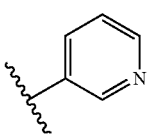 | MS, ES+ m/z, 444.0 (M + H)+ $^1$H NMR (400 MHz, DMSO-d6) δ ppm 7.40-7.53 (m, 5 H) 8.18 (ddd, J = 8.34, 2.53, 1.52 Hz, 1 H) 8.36 (dd, J = 4.55, 1.52 Hz, 1 H) 8.55-8.60 (m, 1H) 8.73 (dd, J = 2.53, 1.01 Hz, 1 H) 8.87 (d, J = 2.02 Hz, 1 H) 10.88 (s, 1 H) | Method O, using 3-aminopyridine |
| 127 | N-(4-pyridyl)-2-[4-(trifluoromethoxy)-phenoxy]-5-(tri-fluoromethyl)pyri-dine-3-carboxamide | 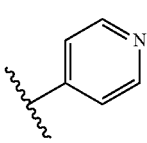 [SMILES: *c1ccncc1] | MS, ES+ m/z, 444.0 (M + H)+ $^1$H NMR (400 MHz, DMSO-d6) δ ppm 7.39-7.53 (m, 4 H) 7.64-7.73 (m, 2 H) 8.48-8.55 (m, 2 H) 8.58 (d, J = 2.53 Hz, 1 H) 8.73 (dd, J = 2.27, 1.01 Hz, 1 H) 11.05 (s, 1 H) | Method O, using 4-aminopyridine |

-continued

| Example | Name | R | Analytical data | Preparation details |
|---|---|---|---|---|
| 128 | N-pyridazin-4-yl-2-[4-(trifluoromethoxy)phenoxy]-5-(trifluoromethyl)-pyridine-3-carboxamide | (pyridazin-4-yl) | MS, ES+ m/z, 445.0 (M + H)+ $^1$H NMR (400 MHz, DMSO-d6) δ ppm 7.39-7.53 (m, 4 H) 8.07 (dd, J = 5.94. 2.65 Hz, 1 H) 8.62 (d, J = 2.53 Hz, 1 H) 8.76 (dt, J = 1.71, 0.79 Hz, 1 H) 9.14 (dd, J = 5.94, 0.88 Hz, 1 H) 9.40 (dd, J = 2.78, 0.76 Hz, 1 H) 11.32 (s, 1 H) | Method O, using 4-aminopyridazine |
| 129 | N-[3-[[dimethyl-(oxo)-λ$^6$-sulfanylidene]amino]phenyl]-2-[4-(trifluoromethoxy)phenoxy]-5-(trifluoromethyl)-pyridine-3-carboxamide | (3-(dimethylsulfoximino)phenyl) | MS, ES+ m/z, 534.0 (M + H)+ $^1$H NMR (400 MHz, DMSO-d6) δ ppm 3.22 (s, 6 H) 6.71 (ddd, J = 7.96, 2.15, 1.01 Hz, 1 H) 7.16 (t, J = 7.96 Hz, 1 H) 7.23-7.30 (m, 1 H) 7.36 (t, J = 2.02 Hz, 1 H) 7.40-7.46 (m, 2 H) 7.46-7.52 (m, 2 H) 8.51 (d, J = 2.53 Hz, 1 H) 8.65-8.72 (m, 1 H) 10.51 (s, 1 H) | Method O, using ((3-aminophenyl)-imino)dimethyl-λ$^6$-sulfanone |

Example 130: N-[3-(methylsulfonimidoyl)phenyl]-2-[4-(trifluoromethoxy)phenoxy]-5-(trifluoromethyl)pyridine-3-carboxamide, enantiomer A Example 131: N-[3-(methylsulfonimidoyl)phenyl]-2-[4-(trifluoromethoxy)phenoxy]-5-(trifluoromethyl)pyridine-3-carboxamide, enantiomer B

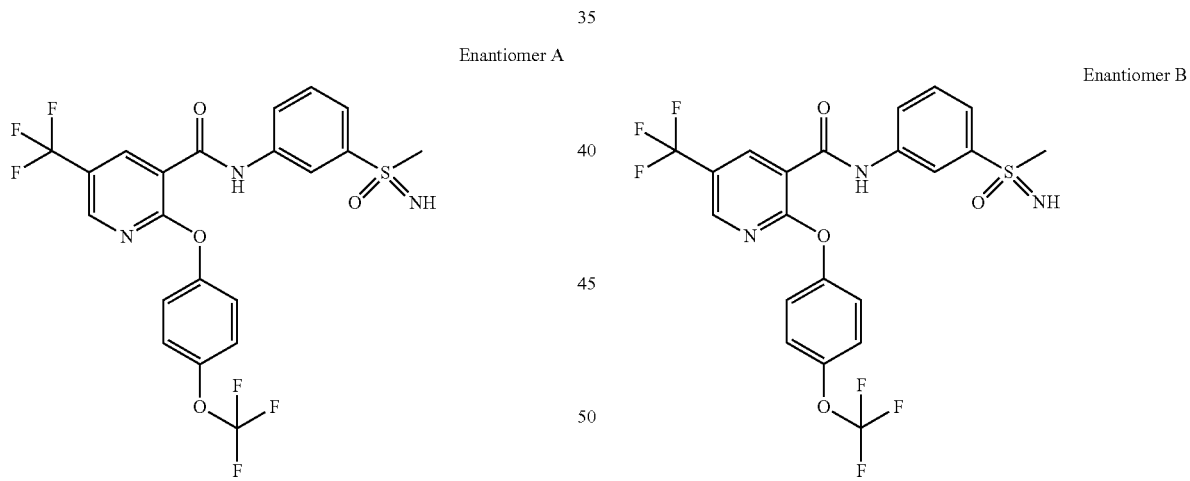

Enantiomer A / Enantiomer B

Racemic N-[3-(methylsulfonimidoyl)phenyl]-2-[4-(trifluoromethoxy)phenoxy]-5-(trifluoromethyl)pyridine-3-carboxamide (Example LI-1859) was resolved by chiral chromatography using a Chiralpak IG column, with a mobile phase consisting of a 5-40% gradient of methanol (modified with 0.05% DEA) in $CO_2$ affording the first eluting enantiomer, RT=1.46 min. MS, ES+ m/z, 520.8 (M+H)+. $^1$H NMR (400 MHz, DMSO-d$_6$) δ ppm 3.07 (s, 3H) 4.27 (s, 1H) 7.39-7.54 (m, 4H) 7.62 (t, J=7.83 Hz, 1H) 7.70 (dt, J=7.96, 1.20 Hz, 1H) 7.90-8.02 (m, 1H) 8.38 (t, J=1.89 Hz, 1H) 8.57 (d, J=2.53 Hz, 1H) 8.72 (d, J=1.52 Hz, 1H) 11.01 (s, 1H)

Racemic N-[3-(methylsulfonimidoyl)phenyl]-2-[4-(trifluoromethoxy)phenoxy]-5-(trifluoromethyl)pyridine-3-carboxamide (Example LI-1859) was resolved by chiral chromatography using a Chiralpak IG column, with a mobile phase consisting of a 5-40% gradient of methanol (modified with 0.05% DEA) in $CO_2$ affording the first eluting enantiomer, RT=1.98 min. MS, ES+ m/z, 520.8 (M+H)+. $^1$H NMR (400 MHz, DMSO-d$_6$) δ ppm 3.07 (s, 3H) 4.27 (s, 1H) 7.39-7.54 (m, 4H) 7.62 (t, J=7.83 Hz, 1H) 7.70 (dt, J=7.96, 1.20 Hz, 1H) 7.90-8.02 (m, 1H) 8.38 (t, J=1.89 Hz, 1H) 8.57 (d, J=2.53 Hz, 1H) 8.72 (d, J=1.52 Hz, 1H) 11.01 (s, 1H).

Example 132: N-(1-oxidopyridin-1-ium-3-yl)-2-[4-(trifluoromethoxy)phenoxy]-5-(trifluoromethyl)pyridine-3-carboxamide Method P

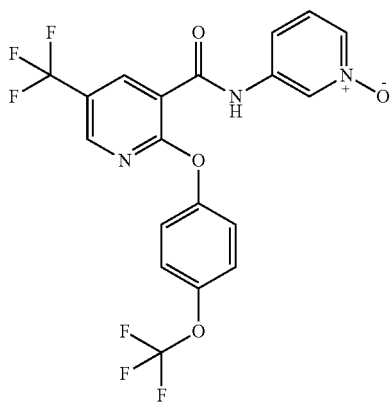

Step 1: Synthesis of 2-[4-(trifluoromethoxy)phenoxy]-5-(trifluoromethyl)pyridine-3-carboxylic acid (Intermediate ABC)

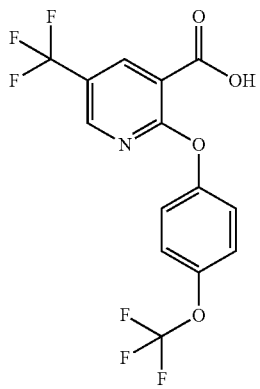 [SMILES: O=C(O)c1cc(C(F)(F)F)cnc1Oc1ccc(OC(F)(F)F)cc1]

A mixture of 2-chloro-5-(trifluoromethyl)pyridine-3-carboxylic acid (510 mg, 2.26 mmol), 4-(trifluoromethoxy)phenol (322 µL, 2.49 mmol) and cesium carbonate (1.84 g, 5.65 mmol) in MeCN (5 mL) was stirred at 80° C. for 5 h, then 4 days at room temperature (for convenience). The solvent was removed under a stream of $N_2$, and the residue treated with water/MeOH (5:1). This mixture was briefly sonicated then stirred at room temperature for 18 h. The resulting precipitate was collected by filtration, washed with water and dried under vacuum to give 2-[4-(trifluoromethoxy)phenoxy]-5-(trifluoromethyl)pyridine-3-carboxylic acid (604 mg, 1.65 mmol, 72.8% yield) as an off-white solid. MS, ES$^+$ m/z 368.0 [M+H]$^+$.

Step 2: Synthesis of N-(3-pyridyl)-2-[4-(trifluoromethoxy)phenoxy]-5-(trifluoromethyl)pyridine-3-carboxamide

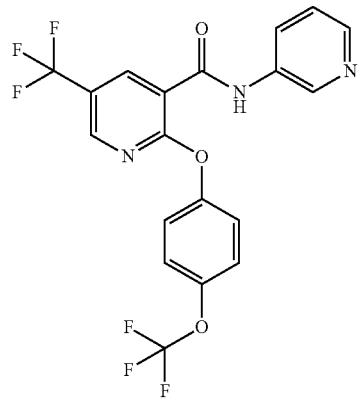 [SMILES: O=C(Nc1cccnc1)c1cc(C(F)(F)F)cnc1Oc1ccc(OC(F)(F)F)cc1]

2-[4-(trifluoromethoxy)phenoxy]-5-(trifluoromethyl)pyridine-3-carboxylic acid (250 mg, 0.68 mmol) was added to a screw-cap vial equipped with a magnetic stir bar and dissolved in dichloromethane (2.5 mL). Oxalyl chloride (72 µL, 0.82 mmol) was added followed by a drop of DMF, and the mixture was allowed to stir for 1 hour. 3-aminopyridine (96 mg, 1.0 mmol) and trimethylamine (190 µL, 1.36 mmol) were added dropwise as a solution in DCM (2.5 mL). Volatiles were evaporated under reduced pressure, and the residue was purified by preparative reversed-phase HPLC (high pH method) to give N-(3-pyridyl)-2-[4-(trifluoromethoxy)phenoxy]-5-(trifluoromethyl)pyridine-3-carboxamide as a colorless glass. (266 mg, 0.6 mmol, 88% yield) MS, ES$^+$ m/z 368.0 [M+H]$^+$. $^1$H NMR (400 MHz, DMSO-$d_6$) δ ppm 7.40-7.53 (m, 5H) 8.18 (ddd, J=8.34, 2.53, 1.52 Hz, 1H) 8.36 (dd, J=4.55, 1.52 Hz, 1H) 8.55-8.60 (m, 1H) 8.73 (dd, J=2.53, 1.01 Hz, 1H) 8.87 (d, J=2.02 Hz, 1H) 10.88 (s, 1H)

Step 3: Synthesis of N-(1-oxidopyridin-1-ium-3-yl)-2-[4-(trifluoromethoxy)phenoxy]-5-(trifluoromethyl)pyridine-3-carboxamide

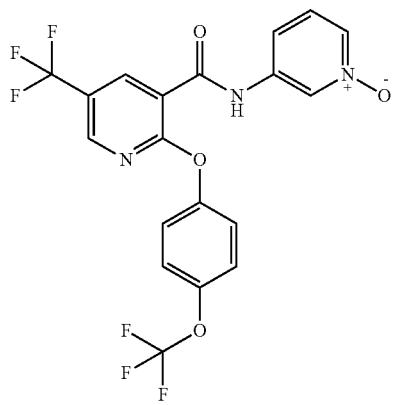

N-(3-pyridyl)-2-[4-(trifluoromethoxy)phenoxy]-5-(trifluoromethyl)pyridine-3-carboxamide (100 mg, 0.23 mmol) was added to a screw-cap vial equipped with a magnetic stir bar and dissolved in DCM (5 mL). mCPBA (61 mg, 0.27 mmol) was added, and the mixture was allowed to stir at room temperature for 15 minutes. Volatiles were evaporated under reduced pressure, and the resulting residue was purified by preparative reversed-phase HPLC (high pH method) to afford the title compound as a colorless glass (69 mg, 0.15 mmol, 67% yield). MS, ES$^+$ m/z 460.0 [M+H]$^+$. $^1$H NMR (400 MHz, DMSO-d$_6$) δ ppm 7.38-7.60 (m, 6H) 8.05 (ddd, J=6.32, 1.77, 1.01 Hz, 1H) 8.59 (d, J=2.53 Hz, 1H) 8.71-8.84 (m, 2H) 11.04 (s, 1H).

The following compounds have been synthesized according to Method P

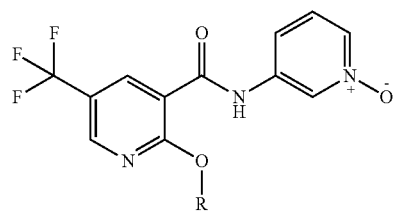

| Example | Name | R | Analytical data | Preparation details |
|---|---|---|---|---|
| 133 | 2-(4-fluoro-2-methyl-phenoxy)-N-(1-oxido-pyridin-1-ium-3-yl)-5-(trifluoromethyl)-pyridine-3-carboxamide | 4-fluoro-2-methylphenyl | MS, ES+ m/z, 408.0 (M + H)$^+$ $^1$H NMR (400 MHz, DMSO-d6) δ ppm 3.31-3.37 (m, 3 H) 7.12 (td, J = 8.59, 3.28 Hz, 1 H) 7.18-7.31 (m, 2 H) 7.44 (dd, J = 8.46, 6.44 Hz, 1 H) 7.52-7.60 (m, 1 H) 8.06 (dt, J = 6.32, 0.88 Hz, 1 H) 8.59 (d, J = 2.53 Hz, 1 H) 8.66-8.71 (m, 1 H) 8.74-8.79 (m, 1 H) 11.04 (s, 1 H) | Method P, using 4-fluoro-2-methyl phenol |
| 134 | 2-(4-fluoro-2-methoxy-phenoxy)-N-(1-oxidopyridin-1-ium-3-yl)-5-(trifluoromethyl)pyridine-3-carboxamide | 4-fluoro-2-methoxyphenyl | MS, ES+ m/z, 424.2 (M + H)$^+$ $^1$H NMR (400 MHz, DMSO-d6) δ ppm 3.71 (s, 3 H) 6.77-6.90 (m, 1 H) 7.11 (d, J = 10.86 Hz, 1 H) 7.25-7.37 (m, 1 H) 7.44 (t, J = 7.33 Hz, 1 H) 7.57 (d, J = 8.59 Hz, 1 H) 8.05 (d, J = 6.32 Hz, 1 H) 8.55 (s, 1 H) 8.68 (s, 1 H) 8.77 (s, 1 H) 11.00 (s, 1 H) | Method P, using 4-fluoro-2-methoxy-phenol |
| 135 | 2-(2,4-difluoro-phenoxy)-N-(1-oxidopyridin-1-ium-3-yl)-5-(trifluoromethyl)pyridine-3-carboxamide | 2,4-difluorophenyl | MS, ES+ m/z, 412.0 (M + H)$^+$ $^1$H NMR (400 MHz, DMSO-d6) δ ppm 7.15-7.25 (m, 1 H) 7.44 (dd, J = 8.46, 6.44 Hz, 1 H) 7.47-7.60 (m, 3 H) 8.06 (dt, J = 6.38, 0.85 Hz, 1 H) 8.63 (d, J = 2.27 Hz, 1H) 8.70-8.80 (m, 2 H) 11.07 (s, 1 H) | Method P, using 2,4-difluorophenol |
| 136 | 3-(2-(4-(difluoromethoxy)phenoxy)-5-(trifluoromethyl)-nicotinamido)pyridine 1-oxide | 4-(difluoromethoxy)phenyl | MS (ES+) m/z 442.0 [M + H]$^+$. $^1$H NMR (500 MHz, DMSO-d6) δ ppm 7.23-7.31 (m, 3 H) 7.32-7.39 (m, 2 H) 7.39-7.49 (m, 1 H) 7.56 (d, J = 8.17 Hz, 1 H) 8.06 (d, J = 6.29 Hz, 1H) 8.57 (d, J = 2.20 Hz, 1 H) 8.67-8.75 (m, 1 H) 8.78 (s, 1 H) 11.03 (s, 1H) | Method P, using 4-(difluoromethoxy)phenol |
| 137 | 3-(2-(2,4-dimethoxy-phenoxy)-5-(trifluoromethyl)nicotinamido)pyridine 1-oxide | 2,4-dimethoxyphenyl | MS (ES+) m/z 436.0 [M + H]$^+$. $^1$H NMR (500 MHz, DMSO-d6) δ ppm 3.69 (s, 3 H) 3.76-3.83 (m, 3 H) 6.57 (dd, J = 8.80, 2.83 Hz, 1H) 6.72 (d, J = 2.67 Hz, 1 H) 7.19 (d, J = 8.80 Hz, 1 H) 7.44 (dd, J = 8.41, 6.37 Hz, 1 H) 7.54-7.62 (m, 1 H) 8.06 (dd, J = 6.37, 0.86 Hz, 1 H) 8.51 (d, J = 2.20 Hz, 1 H) 8.66 (d, J = 1.57 Hz, 1 H) 8.78 (s, 1 H) 10.97 (s, 1 H) | Method P, using 2,4-dimethoxy-phenol |

| Example | Name | R | Analytical data | Preparation details |
|---|---|---|---|---|
| 138 | 3-(2-(2-chloro-4-methoxyphenoxy)-5-(trifluoromethyl)-nicotinamido)-pyridine 1-oxide | 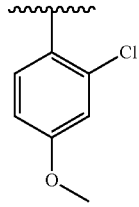 | MS (ES+) m/z 440.0 [M + H]$^+$. $^1$H NMR (500 MHz, DMSO-d6) δ ppm 3.77-3.85 (m, 3 H) 7.03 (dd, J = 9.04, 2.91 Hz, 1 H) 7.19 (d, J = 2.99 Hz, 1 H) 7.36-7.50 (m, 2 H) 7.52-7.63 (m, 1 H) 8.07 (dd, J = 6.45, 0.79 Hz, 1 H) 8.60 (d, J = 2.36 Hz, 1H) 8.71 (d, J = 1.41 Hz, 1 H) 8.78 (s, 1H) 11.04 (s, 1 H) | Method P, using 2-chloro-4-methoxy-phenol |
| 139 | 3-(2-(3,4-difluoro-phenoxy)-5-(tri-fluoromethyl)nico-tinamido)pyridine 1-oxide | 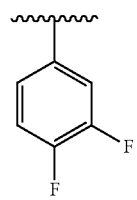 [SMILES: *c1ccc(F)c(F)c1] | MS (ES+) m/z 412.0 [M + H]$^+$. $^1$H NMR (500 MHz, DMSO-d6) δ ppm 7.16-7.24 (m, 1 H) 7.45 (dd, J = 8.41, 6.37 Hz, 1 H) 7.50-7.62 (m, 3 H) 8.03-8.11 (m, 1 H) 8.58 (d, J = 2.36 Hz, 1 H) 8.74 (d, J = 1.41 Hz, 1 H) 8.78 (s, 1 H) 11.01 (s, 1 H) | Method P, using 3,4-difluorophenol |
| 140 | 2-(2-chloro-4-fluoro-phenoxy)-N-(1-oxidopyridin-1-ium-3-yl)-5-(tri-fluoromethyl)-pyridine-3-carbox-amide | 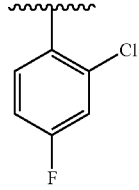 | MS (ES+) m/z 428.0 [M + H]$^+$. $^1$H NMR (500 MHz, DMSO-d6) δ ppm 7.37 (td, J = 8.57, 2.99 Hz, 1 H) 7.45 (dd, J = 8.33, 6.45 Hz, 1 H) 7.52-7.62 (m, 2 H) 7.65 (dd, J = 8.41, 3.07 Hz, 1 H) 8.07 (dd, J = 6.37, 0.86 Hz, 1 H) 8.63 (d, J = 2.36 Hz, 1 H) 8.73 (d, J = 1.41 Hz, 1 H) 8.78 (s, 1 H) 11.06 (s, 1 H) | Method P, |

Example 141: N-(1-oxidopyridin-1-ium-4-yl)-2-[4-(trifluoromethoxy)phenoxy]-5-(trifluoromethyl)pyridine-3-carboxamide

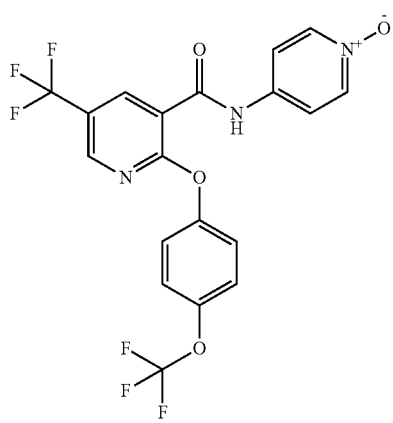

N-(4-pyridyl)-2-[4-(trifluoromethoxy)phenoxy]-5-(trifluoromethyl)pyridine-3-carboxamide (Example 129, 100 mg, 0.23 mmol) was added to a screw-top vial equipped with a magnetic stir bar and dissolved in DCM (5 mL). m-CPBA (61 mg, 0.27 mmol) was added, and the mixture was allowed to stir at room temperature for 15 minutes. Volatiles were evaporated under reduced pressure, and the resulting residue was purified by preparative reversed-phase HPLC (high pH method) to afford the desired product as a colorless glass. (55 mg, 0.12 mmol, 53% yield). MS, ES$^+$ m/z 460.0 [M+H]$^+$. $^1$H NMR (400 MHz, DMSO-d$_6$) δ ppm 7.38-7.55 (m, 4H) 7.69-7.80 (m, 2H) 8.15-8.26 (m, 2H) 8.58 (d, J=2.53 Hz, 1H) 8.73 (d, J=1.26 Hz, 1H) 11.16 (s, 1H).

Example 142: 2-[2-chloro-4-(trifluoromethoxy)phenoxy]-N-(3-methylsulfonylphenyl)-5-(trifluoromethyl)pyridine-3-carboxamide Method Q

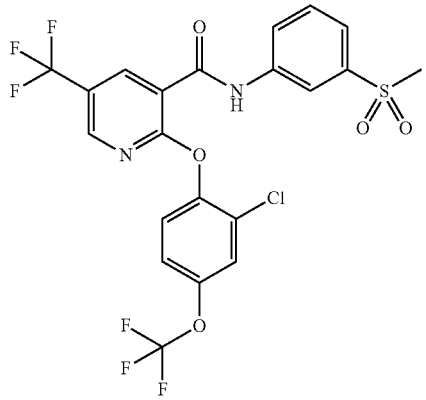 [SMILES: CS(=O)(=O)c1cccc(NC(=O)c2cc(C(F)(F)F)cnc2Oc2ccc(OC(F)(F)F)cc2Cl)c1]

Step 1: Synthesis of 2-[2-chloro-4-(trifluoromethoxy)phenoxy]-5-(trifluoromethyl)pyridine-3-carboxylic acid

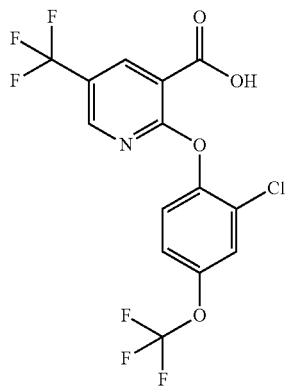 [SMILES: O=C(O)c1cc(C(F)(F)F)cnc1Oc1ccc(OC(F)(F)F)cc1Cl]

A mixture of 2-chloro-5-(trifluoromethyl)pyridine-3-carboxylic acid (150 mg, 0.665 mmol), 2-chloro-4-(trifluoromethoxy)phenol (141 mg, 0.665 mmol) and Cesium carbonate (433 mg, 1.33 mmol) in MeCN (2 mL) was stirred at 80° C. for 68 h. After cooling, the contents were diluted with 20 mL water and acidified to pH 6 via careful addition of 2 N HCL. The precipitate was collected by filtration, washed with water and dried under vacuum to give 2-[2-chloro-4-(trifluoromethoxy)phenoxy]-5-(trifluoromethyl)pyridine-3-carboxylic acid (149.5 mg, 0.372 mmol, 56.0% yield) as a beige solid. MS, ES$^+$ m/z 401.9 [M+H]$^+$.

Step 2: Synthesis of 2-[2-chloro-4-(trifluoromethoxy)phenoxy]-N-(3-methylsulfonylphenyl)-5-(trifluoromethyl)pyridine-3-carboxamide

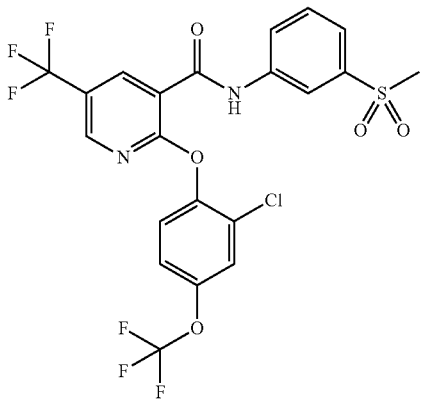 [SMILES: CS(=O)(=O)c1cccc(NC(=O)c2cc(C(F)(F)F)cnc2Oc2ccc(OC(F)(F)F)cc2Cl)c1]

A mixture of 2-[2-chloro-4-(trifluoromethoxy)phenoxy]-5-(trifluoromethyl)pyridine-3-carboxylic acid (33.4 mg, 0.0832 mmol), 3-methylsulfonylaniline (15.7 mg, 0.0915 mmol), HBTU (34.7 mg, 0.0915 mmol) and DIPEA (36.2 μL, 0.208 mmol) in chloroform (2 mL) was stirred at room temperature for 20 h. The solvent was removed under a stream of N$_2$, and the residue reacted with water/MeOH (4:1). This mixture was briefly sonicated then stirred at room temperature overnight. The resulting precipitate was collected by filtration, washed with water and dried under vacuum to give 2-[2-chloro-4-(trifluoromethoxy)phenoxy]-N-(3-methylsulfonylphenyl)-5-(trifluoromethyl)pyridine-3-carboxamide (34.8 mg, 0.0627 mmol, 75.4% yield) as a beige solid. MS, ES$^+$ m/z 554.9 [M+H]$^+$. $^1$H-NMR (400 MHz, DMSO-d$_6$) δ 11.07 (s, 1H), 8.74 (br. s., 1H), 8.64 (d, J=2.27 Hz, 1H), 8.40 (s, 1H), 7.99 (d, J=7.58 Hz, 1H), 7.81 (d, J=2.53 Hz, 1H), 7.65-7.74 (m, 3H), 7.52-7.57 (m, 1H), 3.23 (s, 3H).

The following compounds have been synthesized according to Method Q

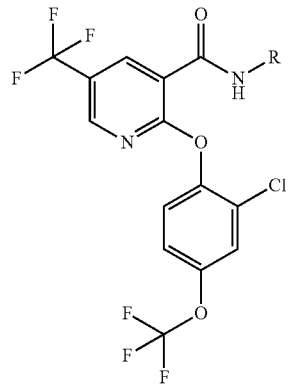

| Example | Name | R | Analytical data | Preparation details |
|---|---|---|---|---|
| 143 | 2-[2-chloro-4-(trifluoromethoxy)-phenoxy]-N-(3-ethylsulfonylphenyl)-5-(trifluoromethyl)pyridine-3-carboxamide | ![3-ethylsulfonylphenyl] | MS, ES$^+$ m/z, 569.8 (M + H)$^+$ $^1$H NMR (400 MHz, DMSO-d6) δ ppm 1.13 (t, J = 7.33 Hz, 3 H) 3.31 (q, J = 7.41 Hz, 2 H) 7.52-7.58 (m, 1 H) 7.63-7.74 (m, 3 H) 7.81 (d, J = 3.03 Hz, 1 H) 8.00 (dt, J = 7.52, 1.80 Hz, 1 H) 8.34-8.40 (m, 1 H) 8.66 (d, J = | Method Q, using 3-(ethylsulfonyl)-aniline |

-continued

| Example | Name | R | Analytical data | Preparation details |
|---|---|---|---|---|
| | | | 2.53 Hz, 1 H) 8.71-8.77 (m, 1 H) 11.08 (s, 1 H) | |
| 144 | 2-[2-chloro-4-(trifluoromethoxy)phenoxy]-N-[3-(N,S-dimethylsulfonimidoyl)phenyl]-5-(trifluoromethyl)pyridine-3-carboxamide | | MS, ES+ m/z, 568.8 (M + H)+ $^1$H NMR (400 MHz, DMSO-d6) δ ppm 2.49 (s, 3H) 3.13 (s, 3 H) 7.51-7.72 (m, 4 H) 7.81 (d, J = 2.78 Hz, 1 H) 7.93-8.03 (m, 1 H) 8.31 (s, 1 H) 8.64 (d, J = 2.53 Hz, 1 H) 8.71-8.80 (m, 1 H) 11.03 (s, 1 H) | Method Q, using (3-aminophenyl)(methyl)(methylimino)-$\lambda^6$-sulfanone |
| 145 | 4-pyridyl 2-[2-chloro-4-(trifluoromethoxy)phenoxy]-5-(trifluoromethyl)pyridine-3-carboxylate | | MS, ES+ m/z, 478.8 (M + H)+ $^1$H NMR (400 MHz, DMSO-d6) δ ppm 7.51-7.58 (m, 1 H) 7.63-7.74 (m, 3 H) 7.78-7.84 (m, 1 H) 8.49-8.56 (m, 2 H) 8.65 (dd, J = 2.53, 0.51 Hz, 1 H) 8.75 (dd, J = 2.40, 0.88 Hz, 1 H) 11.07 (s, 1 H) | Method Q, using 4-aminopyridine |
| 146 | 2-[2-chloro-4-(trifluoromethoxy)phenoxy]-N-(3-cyanophenyl)-5-(trifluoromethyl)pyridine-3-carboxamide | | MS, ES+ m/z, 502.0 (M + H)+ $^1$H NMR (400 MHz, DMSO-d6) δ ppm 7.50-7.58 (m, 1 H) 7.59-7.70 (m, 3 H) 7.78-7.84 (m, 1 H) 7.97 (dt, J = 6.69, 2.46 Hz, 1 H) 8.18-8.25 (m, 1 H) 8.64 (dd, J = 2.40, 0.63 Hz, 1 H) 8.75 (dd, J = 2.53, 1.01 Hz, 1H) 11.04 (br. s., 1 H) | Method Q, using 3-aminobenzonitrile |
| 147 | 2-[2-chloro-4-(trifluoromethoxy)phenoxy]-N-(1-methylpyrazol-4-yl)-5-(trifluoromethyl)pyridine-3-carboxamide | | MS, ES+ m/z, 481.0 (M + H)+ $^1$H NMR (400 MHz, DMSO-d6) δ ppm 3.84 (s, 3 H) 7.51-7.58 (m, 2 H) 7.63-7.69 (m, 1 H) 7.81 (dd, J = 2.78, 0.51 Hz, 1 H) 8.07 (s, 1 H) 8.53-8.59 (m, 1 H) 8.70 (dd, J = 2.53, 1.01 Hz, 1 H) 10.67 (s, 1 H) | Method Q, using 1-methyl-1H-pyrazol-4-amine |
| 148 | N-(3-carbamoylphenyl)-2-[2-chloro-4-(trifluoromethoxy)phenoxy]-5-(trifluoromethyl)pyridine-3-carboxamide | | MS, ES+ m/z, 520.8 (M + H)+ $^1$H NMR (400 MHz, DMSO-d6) δ ppm 7.46 (s, 1 H) 7.68 (d, J = 8.84 Hz, 1 H) 7.81 (d, J = 2.78 Hz, 1 H) 8.19 (s, 1 H) 8.59-8.63 (m, 1 H) 8.70-8.75 (m, 1 H) 10.79 (s, 1 H) | Method Q, using 3-aminobenzamide |
| 149 | N-(3-acetylphenyl)-2-[2-chloro-4-(trifluoromethoxy)phenoxy]-5-(trifluoromethyl)pyridine-3-carboxamide | | MS, ES+ m/z, 519.8 (M + H)+ $^1$H NMR (400 MHz, DMSO-d6) δ ppm 2.60 (s, 3 H) 7.50-7.60 (m, 2 H) 7.68 (d, J = 9.09 Hz, 1 H) 7.73-7.83 (m, 2 H) 7.99 (ddd, J = 8.08, 2.27, 1.01 Hz, 1 H) 8.33 (t, J = 1.77 Hz, 1 H) 8.63 (dd, J = 2.40, 0.63 Hz, 1 H) 8.74 (dd, J = 2.53, 1.01 Hz, 1 H) 10.89 (s, 1 H) | Method Q, using 1-(3-aminophenyl)ethan-1-one |
| 150 | 2-[2-chloro-4-(trifluoromethoxy)phenoxy]-N-(1-methyl-2-oxo-4-pyridyl)-5-(trifluoromethyl)pyridine-3-carboxamide | | MS, ES+ m/z, 508.8 (M + H)+ $^1$H NMR (400 MHz, DMSO-d6) δ ppm 3.38 (s, 3 H) 6.46 (dd, J = 7.45, 2.40 Hz, 1 H) 6.89 (d, J = 2.27 Hz, 1 H) 7.56 (s, 1 H) 7.67 (dd, J = 8.34, 3.54 Hz, 2 H) 7.81 (d, J = 2.78 Hz, 1 H) 8.62 (d, J = 2.53 Hz, 1 H) 8.74 (dd, J = 2.27, 101 Hz, 1 H) 10.79 (s, 1H) | Method Q, using 4-amino-1-methylpyridin-2(1H)-one |

| Example | Name | R | Analytical data | Preparation details |
|---|---|---|---|---|
| 151 | 2-[2-chloro-4-(trifluoromethoxy)phenoxy]-N-[3-(dimethylcarbamoyl)phenyl]-5-(trifluoromethyl)pyridine-3-carboxamide | | MS, ES+ m/z, 548.8 (M + H)+ $^1$H NMR (400 MHz, DMSO-d6) δ ppm 2.93 (br. s., 3 H) 3.00 (br. s., 3H) 7.17 (d, J = 7.58 Hz, 1 H) 7.45 (t, J = 7.83 Hz, 1 H) 7.54 (d, J = 9.09 Hz, 1 H) 7.68 (d, J = 9.10 Hz, 1 H) 7.74 (d, J = 9.09 Hz, 1 H) 7.78-7.85 (m, 2 H) 8.62 (s, 1 H) 8.73 (s, 1 H) 10.80 (s, 1 H) | Method Q, using 3-amino-N,N-dimethylbenzamide |
| 152 | 2-[2-chloro-4-(trifluoromethoxy)phenoxy]-N-(4-methylsulfonylphenyl)-5-(trifluoromethyl)pyridine-3-carboxamide | | MS, ES+ m/z, 555.8 (M + H)+ $^1$H NMR (400 MHz, DMSO-d6) δ ppm 3.20 (s, 3 H) 7.50-7.59 (m, 1 H) 7.68 (d, J = 9.09 Hz, 1 H) 7.81 (d, J = 2.78 Hz, 1 H) 7.90-8.04 (m, 4 H) 8.65 (d, J = 2.53 Hz, 1 H) 8.71-8.79 (m, 1 H) 11.13 (s, 1H) | Method Q, using 4-(methylsulfonyl)aniline |
| 153 | 2-[2-chloro-4-(trifluoromethoxy)phenoxy]-N-(4-methylsulfonylphenyl)-5-(trifluoromethyl)pyridine-3-carboxamide | | MS, ES+ m/z, 539.0 (M + H)+ $^1$H NMR (400 MHz, DMSO-d6) δ ppm 2.76 (s, 3 H) 7.42 (dt, J = 7.83, 1.26 Hz, 1 H) 7.51-7.62 (m, 2 H) 7.68 (d, J = 9.09 Hz, 1 H) 7.77-7.87 (m, 2 H) 8.16 (t, J = 1.77 Hz, 1 H) 8.63 (d, J = 2.27 Hz, 1 H) 8.73 (dd, J = 2.15, 0.88 Hz, 1 H) 10.97 (s, 1 H) | Method Q, using 3-(methylsulfinyl)aniline |
| 154 | 2-[2-chloro-4-(trifluoromethoxy)phenoxy]-N-[3-(dimethylsulfamoyl)phenyl]-5-(trifluoromethyl)pyridine-3-carboxamide | | MS, ES+ m/z, 584.0 (M + H)+ $^1$H NMR (400 MHz, DMSO-d6) δ ppm 2.65 (s, 6 H) 7.49-7.58 (m, 2 H) 7.63-7.72 (m, 2 H) 7.81 (d, J = 2.53 Hz, 1 H) 7.94-8.01 (m, 1 H) 8.25 (t, J = 1.89 Hz, 1 H) 8.66 (d, J = 2.53 Hz, 1 H) 8.72-8.77 (m, 1 H) 11.05 (s, 1 H) | Method Q, using 3-amino-N,N-dimethylbenzenesulfonamide |
| 155 | 2-[2-chloro-4-(trifluoromethoxy)phenoxy]-N-(3,4-difluorophenyl)-5-(trifluoromethyl)pyridine-3-carboxamide | | MS, ES+ m/z, 513.0 (M + H)+ $^1$H NMR (400 MHz, DMSO-d6) δ ppm 7.41-7.58 (m, 3 H) 7.66 (d, J = 9.09 Hz, 1 H) 7.81 (d, J = 2.78 Hz, 1 H) 7.86-7.97 (m, 1 H) 8.63 (d, J = 2.27 Hz, 1 H) 8.74 (dd, J = 2.40, 0.88 Hz, 1 H) 10.93 (s, 1H) | Method Q, using 3,4-difluoroaniline |
| 156 | 2-[2-chloro-4-(trifluoromethoxy)phenoxy]-N-(6-methoxy-3-pyridyl)-5-(trifluoromethyl)pyridine-3-carboxamide | | MS, ES+ m/z, 508.0 (M + H)+ $^1$H NMR (400 MHz, DMSO-d6) δ ppm 3.85 (s, 3 H) 6.89 (d, J = 8.84 Hz, 1 H) 7.55 (d, J = 7.83 Hz, 1 H) 7.59-7.71 (m, 1 H) 7.82 (br. s., 1 H) 8.04 (dd, J = 8.84, 2.78 Hz, 1 H) 8.51 (d, J = 2.53 Hz, 1 H) 8.63 (d, J = 2.27 Hz, 1 H) 8.73 (s, 1 H) 10.71 (s, 1 H) | Method Q, using 6-methoxypyridin-3-amine |
| 157 | 2-[2-chloro-4-(trifluoromethoxy)phenoxy]-N-pyrimidin-5-yl-5-(trifluoromethyl)pyridine-3-carboxamide | | MS, ES+ m/z, 479.0 (M + H)+ $^1$H NMR (400 MHz, DMSO-d6) δ ppm 7.55 (ddd, J = 9.09, 2.78, 1.01 Hz, 1 H) 7.67 (d, J = 8.84 Hz, 1 H) 7.82 (d, J = 2.78 Hz, 1 H) 8.69 (d, J = 2.27 Hz, 1 H) 8.77 (dd, J = 2.27, 1.01 Hz, 1 H) 9.00 (s, 1 H) 9.15 (s, 2 H) 11.13 (s, 1 H) | Method Q, using pyrimidin-5-amine |

-continued

| Example | Name | R | Analytical data | Preparation details |
|---|---|---|---|---|
| 158 | N-(2-chloro-4-pyridyl)-2-[2-chloro-4-(trifluoromethoxy)phenoxy]-5-(trifluoromethyl)pyridine-3-carboxamide | 2-chloropyridin-4-yl | MS, ES+ m/z, 513.0 (M + H)+ $^1$H NMR (400 MHz, DMSO-d6) δ ppm 7.55 (dt, J = 8.97, 1.33 Hz, 1 H) 7.59-7.72 (m, 2 H) 7.82 (d, J = 2.78 Hz, 1 H) 7.88 (d, J = 1.77 Hz, 1 H) 8.37 (d, J = 5.56 Hz, 1 H) 8.67 (d, J = 2.53 Hz, 1 H) 8.73 8.80 (m, 1 H) 11.31 (s, 1H) | Method Q, using 2-chloropyridin-4-amine |
| 159 | 2-[2-chloro-4-(trifluoromethoxy)phenoxy]-N-(6-fluoro-3-pyridyl)-5-(trifluoromethyl)pyridine-3-carboxamide | 6-fluoropyridin-3-yl | MS, ES+ m/z, 496.0 (M + H)+ $^1$H NMR (400 MHz, DMSO-d6) δ ppm 7.26 (dd, J = 8.97, 3.16 Hz, 1 H) 7.55 (ddd, J = 9.03, 2.72, 0.88 Hz, 1 H) 7.67 (d, J = 9.09 Hz, 1 H) 7.82 (d, J = 2.53 Hz, 1H) 8.30 (ddd, J = 8.84, 7.33, 2.78 Hz, 1 H) 8.56 (s, 1 H) 8.66 (d, J = 2.53 Hz, 1 H) 8.75 (dd, J = 2.40, 0.88 Hz, 1 H) 11.00 (s, 1 H) | Method Q, using 6-fluoropyridin-3-amine |
| 160 | 2-[2-chloro-4-(trifluoromethoxy)phenoxy]-N-[3-(hydroxymethyl)phenyl]-5-(trifluoromethyl)pyridine-3-carboxamide | 3-(hydroxymethyl)phenyl | MS, ES+ m/z, 507.0 (M + H)+ $^1$H NMR (400 MHz, DMSO-d6) δ ppm 4.51 (d, J = 5.56 Hz, 2 H) 5.27 (t, J = 5.81 Hz, 1 H) 7.08 (d, J = 8.08 Hz, 1 H) 7.33 (t, J = 7.96 Hz, 1 H) 7.55 (d, J = 9.09 Hz, 1 H) 7.62 (d, J = 8.08 Hz, 1 H) 7.65-7.75 (m, 2 H) 7.82 (d, J = 2.53 Hz, 1 H) 8.59 (d, J = 2.53 Hz, 1 H) 8.71 (s, 1 H) 10.65 (s, 1 H) | Method Q, using (3-aminophenyl)methanol |
| 161 | 2-[2-chloro-4-(trifluoromethoxy)phenoxy]-N-pyridazin-4-yl-5-(trifluoromethyl)pyridine-3-carboxamide | pyridazin-4-yl | MS, ES+ m/z, 479.0 (M + H)+ $^1$H NMR (400 MHz, DMSO-d6) δ ppm 7.50-7.60 (m, 1 H) 7.67 (d, J = 8.84 Hz, 1 H) 7.82 (d, J = 2.78 Hz, 1 H) 8.09 (dd, J =5.81, 2.78 Hz, 1 H) 8.70 (d, J = 2.53 Hz, 1 H) 8.78 (dd, J = 2.27, 0.76 Hz, 1 H) 9.15 (dd, J = 5.94, 0.88 Hz, 1 H) 9.40 (dd, J = 2.78, 0.76 Hz, 1 H) 11.36 (s, 1 H) | Method Q, using pyridazin-4-amine |
| 162 | 2-[2-chloro-4-(trifluoromethoxy)phenoxy]-N-(2-fluoro-5-methylsulfonylphenyl)-5-(trifluoromethyl)-pyridine-3-carbox- | 2-fluoro-5-methylsulfonylphenyl | MS, ES+ m/z, 573.0 (M + H)+ $^1$H NMR (400 MHz, DMSO-d6) δ ppm 3.27 (s, 3 H) 7.50-7.60 (m, 1 H) 7.61-7.75 (m, 2 H) 7.78-7.93 (m, 2 H) 8.65 (d, J = 2.27 Hz, 1 H) 8.68-8.82 (m, 2 H) 10.82 (s, 1H) | Method Q, using 2-fluoro-5-(methylsulfonyl)aniline |
| 163 | 2-[2-chloro-4-(trifluoromethoxy)phenoxy]-N-(3-fluorophenyl)-5-(trifluoromethyl)-pyridine-3-carbox- | 3-fluorophenyl | MS, ES+ m/z, 495.0 (M + H)+ $^1$H NMR (400 MHz, DMSO-d6) δ ppm 6.92-7.06 (m, 1 H) 7.36-7.49 (m, 2 H) 7.55 (dd, J = 8.59, 2.27 Hz, 1 H) 7.63-7.77 (m, 2 H) 7.82 (d, J = 2.78 Hz, 1 H) 8.62 (d, J = 2.53 Hz, 1 H) 8.69-8.78 (m, 1 H) 10.91 (s, 1 H) | Method Q, using 3-fluoroaniline |
| 164 | 2-[2-chloro-4-(trifluoromethoxy)phenoxy]-N-(2-methyl-4-pyridyl)-5-(trifluoromethyl)pyridine-3-carboxamide | 2-methylpyridin-4-yl | MS, ES+ m/z, 492.1 (M + H)+ $^1$H NMR (400 MHz, DMSO-d6) δ ppm 2.46 (s, 3 H) 7.39-7.61 (m, 3H) 7.68 (d, J = 8.84 Hz, 1 H) 7.81 (d, J = 2.78 Hz, 1 H) 8.38 (d, J = 5.56 Hz, 1 H) 8.63 (d, J = 2.27 Hz, 1 H) 8.74 (dd, J = 2.40, 0.88 Hz, 1 H) 10.99 (s, 1 H) | Method Q, using 2-methylpyridin-4-amine |

-continued

| Example | Name | R | Analytical data | Preparation details |
|---|---|---|---|---|
| 165 | 2-[2-chloro-4-(tri-fluoromethoxy)-phenoxy]-N-(2-fluoro-4-pyridyl)-5-(trifluoromethyl)pyridine-3-carboxamide | | MS, ES+ m/z, 496.0 (M + H)+ $^1$H NMR (400 MHz, DMSO-d6) δ ppm 7.48-7.58 (m, 3 H) 7.68 (d, J = 9.09 Hz, 1 H) 7.81 (d, J = 3.03 Hz, 1 H) 8.20 (d, J = 5.31 Hz, 1 H) 8.68 (d, J = 2.53 Hz, 1 H) 8.77 (dd, J = 2.40, 0.88 Hz, 1 H) 11.39 (s, 1 H) | Method Q, using 2-fluoropyridin-4-amine |
| 166 | 2-[2-chloro-4-(tri-fluoromethoxy)-phenoxy]-N-(thia-diazol-5-yl)-5-(trifluoromethyl)pyridine-3-carboxamide | | MS, ES+ m/z, 485.0 (M + H)+ $^1$H NMR (400 MHz, DMSO-d6) δ ppm 7.52-7.60 (m, 1 H) 7.68 (d, J = 8.84 Hz, 1 H) 7.83 (d, J = 2.78 Hz, 1 H) 8.78 (d, J = 2.53 Hz, 1 H) 8.82 (dd, J = 2.27, 0.76 Hz, 1 H) 8.91 (s, 1 H) 13.08 (s, 1 H) | Method Q, using 1,2,3-thiadiazol-5-amine |
| 167 | 2-[2-chloro-4-(tri-fluoromethoxy)-phenoxy]-N-(2-methylpyrazol-3-yl)-5-(trifluoromethyl)pyridine-3-carboxamide | | MS, ES+ m/z, 481.0 (M + H)+ $^1$H NMR (400 MHz, DMSO-d6) δ ppm 3.76 (s, 3 H) 6.38 (d, J = 2.02 Hz, 1H) 7.42 (d, J = 1.77 Hz, 1 H) 7.52-7.60 (m, 1 H) 7.68 (d, J = 8.84 Hz, 1H) 7.83 (d, J = 2.78 Hz, 1 H) 8.67 (d, J = 2.53 Hz, 1 H) 8.75 (d, J = 1.52 Hz, 1 H) 10.76 (s, 1 H) | Method Q, using 1-methyl-1H-pyrazol-5-amine |
| 168 | 2-[2-chloro-4-(tri-fluoromethoxy)-phenoxy]-N-(2-methyl-5-methyl-sulfonylphenyl)-5-(trifluoromethyl)pyridine-3-carbox- | | MS, ES+ m/z, 569.0 (M + H)+ $^1$H NMR (400 MHz, DMSO-d6) δ ppm 2.39 (s, 3 H) 3.23 (s, 3 H) 7.57 (d, J = 7.83 Hz, 2 H) 7.66-7.76 (m, 2 H) 7.85 (d, J = 2.78 Hz, 1 H) 8.30 (d, J = 2.02 Hz, 1 H) 8.70 (d, J = 2.53 Hz, 1 H) 8.73-8.80 (m, 1 H) 10.35 (s, 1 H) | Method Q, using 2-methyl-5-(methylsulfonyl)aniline |
| 169 | 2-[2-chloro-4-(tri-fluoromethoxy)-phenoxy]-N-(2-methyl-1,2,4-tri-azol-3-yl)-5-(tri-fluoromethyl)pyridine-3-carboxamide | | MS, ES+ m/z, 482.0 (M + H)+ | Method Q, using 1-methyl-1H-1,2,4-triazol-5-amine |
| 170 | 2-[2-chloro-4-(tri-fluoromethoxy)-phenoxy]-N-(1-methyl-1,2,4-tri-azol-3-yl)-5-(tri-fluoromethoxy)pyridine-3-carboxamide | | MS, ES+ m/z, 482.0 (M + H)+ | Method Q, using 1-methyl-1H-1,2,4-triazol-3-amine |

Example 171: 2-(2,4-dimethoxyphenoxy)-N-[3-(N,S-dimethylsulfonimidoyl)phenyl]-5-(trifluoromethyl)pyridine-3-carboxamide Method R

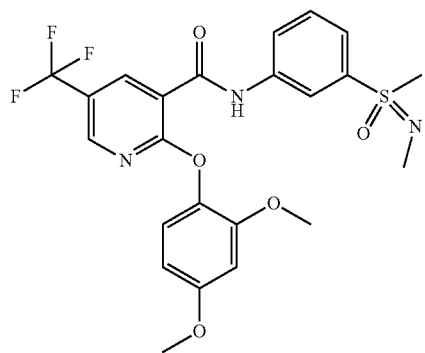 [SMILES: CN=S(C)(=O)c1cccc(NC(=O)c2cc(C(F)(F)F)cnc2Oc2ccc(OC)cc2OC)c1]

Step 1: Synthesis of 2-(2,4-dimethoxyphenoxy)-5-(trifluoromethyl)pyridine-3-carboxylic acid

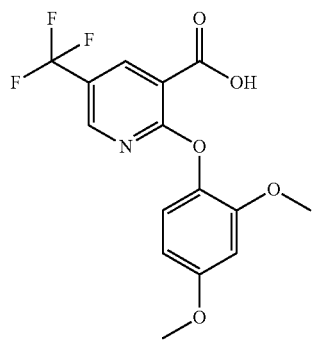 [SMILES: COc1ccc(Oc2ncc(C(F)(F)F)cc2C(=O)O)c(OC)c1]

2-chloro-5-(trifluoromethyl)pyridine-3-carboxylic acid (1.5 g, 6.7 mmol) was charged to a round-bottom flask equipped with a magnetic stir bar, and acetonitrile (15 mL) was added. Cesium carbonate (4.3 g, 13.3 mmol) and 2,4-dimethoxyphenol (1.1 g, 7.3 mmol) were added, and the mixture was heated to reflux for 12 hours. Volatiles were evaporated under reduced pressure, and the residue was dissolved in water. The pH was adjusted to about 3 by careful addition of 2N HCL, and the resulting precipitate was collected by filtration, rinsed with water, and sucked to dryness to afford the desired product as a solid. (1.75 g, 5.1 mmol, 76% yield). MS, ES$^+$ m/z 344.0 [M+H]$^+$.

Step 2: Synthesis of 2-(2,4-dimethoxyphenoxy)-N-[3-(N,S-dimethylsulfonimidoyl)phenyl]-5-(trifluoromethyl)pyridine-3-carboxamide

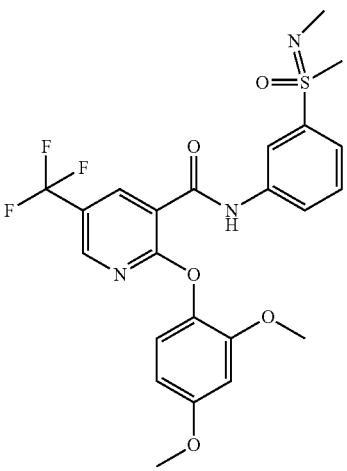 [SMILES: CN=S(C)(=O)c1cccc(NC(=O)c2cc(C(F)(F)F)cnc2Oc2ccc(OC)cc2OC)c1]

2-(2,4-dimethoxyphenoxy)-5-(trifluoromethyl)pyridine-3-carboxylic acid (150 mg, 0.44 mmol) was added to a screw-cap vial and dissolved in DMF (3 mL). Triethylamine (122 µL, 0.87 mmol) and HBTU (200 mg, 0.52 mmol) were added, and the mixture was stirred at room temperature for 10 minutes. 3-(N,S-dimethylsulfonimidoyl)aniline (81 mg, 0.44 mmol) was added, and stirring was continued for an additional 12 hours. Purification by preparative reversed phase HPLC (high pH method) afforded the title compound as a beige solid. (111 mg, 0.22 mmol, 50% yield). MS, ES$^+$ m/z 510.4 [M+H]$^+$. $^1$H NMR (400 MHz, DMSO-d$_6$) δ ppm 2.49 (s, 3H) 3.12 (s, 3H) 3.66-3.71 (m, 3H) 3.79 (s, 3H) 6.57 (dd, J=8.84, 2.78 Hz, 1H) 6.72 (d, J=2.78 Hz, 1H) 7.20 (d, J=8.84 Hz, 1H) 7.56-7.61 (m, 1H) 7.62-7.69 (m, 1H) 7.96 (d, J=8.08 Hz, 1H) 8.32 (s, 1H) 8.50 (d, J=2.27 Hz, 1H) 8.65 (d, J=1.52 Hz, 1H) 10.93 (s, 1H).

The following compounds have been synthesized according to Method R

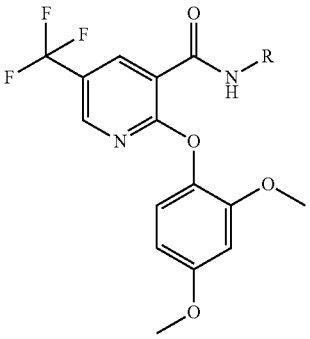

| Example | Name | R | Analytical data | Prep details |
|---|---|---|---|---|
| 172 | 2-(2,4-dimethoxy-phenoxy)-N-3(methylsulfonimidoyl)-phenyl]-5-(trifluoromethyl)pyridine-3-carboxamide | 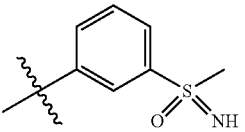 [SMILES: *c1cccc(S(C)(=N)=O)c1] | MS, ES+ m/z, 496.2 (M + H)+ $^1$H NMR (400 MHz, DMSO-d6) δ ppm 3,07 (s, 3 H) 3.69 (s, 3 H) 3.79 (s, 3 H) 6.57 (d, J = 8.84 Hz, 1 H) 6.72 (br. s., 1 H) 7.20 (d, J = 7.83 Hz, 1 H) 7.54-7.73 (m, 2 H) 7.95 (d, J = 7.58 Hz, 1 H) 8.40 (br. s., 1 H) 8.49 (br. s., 1 H) 8.65 (br. s., 1 H) 10.91 (br. s., 1 H) | Method R, using (3-aminophenyl)(imino)(methyl)-$\lambda^6$-sulfanone |
| 173 | 2-(2,4-dimethoxy-phenoxy)-N-pyridazin-4-yl-5-(trifluoromethyl)pyridine-3-carboxamide | 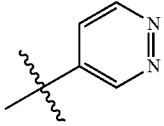 [SMILES: *c1ccnnc1] | MS, ES+ m/z, 421.0 (M + H)+ $^1$H NMR (400 MHz, DMSO-d6) δ ppm 3.69 (s, 3 H) 3.79 (s, 3 H) 6.57 (dd, J = 8.59, 2.78 Hz, 1 H) 6.72 (d, J = 2.78 Hz, 1 H) 7.19 (d, J = 8.84 Hz, 1 H) 8.01-8.12 (m, 1 H) 8.56 (d, J = 2.53 Hz, 1 H) 8.69 (s, 1 H) 9.06-9.19 (m, 1 H) 9.41 (d, J = 2.53 Hz, 1 H) 11.26 (s, 1 H) | Method R, using pyridazin-4-amine |

Example 174: 2-(2,4-difluorophenoxy)-N-[3-(methylsulfonimidoyl)phenyl]-5-(trifluoromethyl)pyridine-3-carboxamide Method S

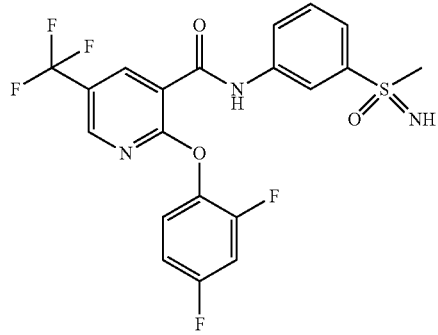 [SMILES: CS(=N)(=O)c1cccc(NC(=O)c2cc(C(F)(F)F)cnc2Oc2ccc(F)cc2F)c1]

Step 1: 2-(2,4-difluorophenoxy)-5-(trifluoromethyl)pyridine-3-carboxylic acid

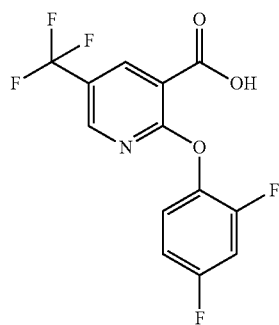 [SMILES: O=C(O)c1cc(C(F)(F)F)cnc1Oc1ccc(F)cc1F]

2-chloro-5-(trifluoromethyl)pyridine-3-carboxylic acid (1.5 g, 6.7 mmol) was added to a round-bottom flask equipped with a magnetic stir bar, and acetonitrile (15 mL) was added. Cesium carbonate (4.3 g, 13.3 mmol) and 2,4-difluorophenol (952 mg, 7.3 mmol) were added, and the mixture was heated to reflux for 12 hours. The solvent was removed under reduced pressure, and the resulting residue was dissolved in water. pH was adjusted to about 3 by addition of 2N HCl, and the resulting precipitate was collected by filtration, rinsed with water, and sucked to dryness to afford the desired product as a white solid (1.9 g, 2.1 mmol, 91% yield). MS, ES+ m/z 320 [M+H]+.

Step 2: Synthesis of 2-(2,4-difluorophenoxy)-N-[3-(methylsulfonimidoyl)phenyl]-5-(trifluoromethyl)pyridine-3-carboxamide

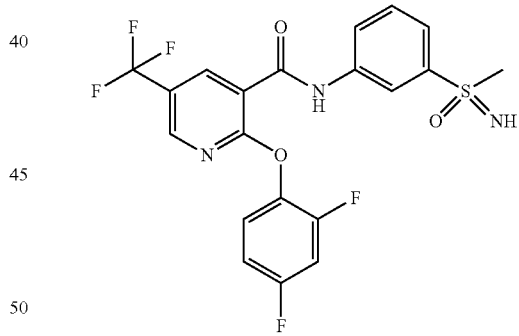

2-(2,4-difluorophenoxy)-5-(trifluoromethyl)pyridine-3-carboxylic acid (150 mg, 0.44 mmol) was added to a screw-cap vial and dissolved in DMF (3 mL). Triethylamine (122 μL, 0.87 mmol) and HBTU (200 mg, 0.52 mmol) were added, and the mixture was stirred at room temperature for 10 minutes. 3-(N,S-dimethylsulfonimidoyl)aniline (75 mg, 0.44 mmol) was added, and stirring was continued for an additional 12 hours. Purification by preparative reversed phase HPLC (high pH method) afforded the title compound as a beige solid. (97 mg, 0.21 mmol, 47% yield). MS, ES+ m/z 472.0 [M+H]+. $^1$H NMR (400 MHz, DMSO-d$_6$) δ ppm 3.07 (s, 3H) 7.46-7.59 (min, 2H) 7.59-7.66 (i, 1H) 7.67-7.74 (m, 1H) 7.96 (d, J=8.08 Hz, 1H) 8.39 (t, J=1.77 Hz, 1H) 8.61 (d, J=2.53 Hz, 1H) 8.72 (d, J=1.52 Hz, 1H) 11.03 (s, 1H).-

The following compounds have been synthesized according to Method S:

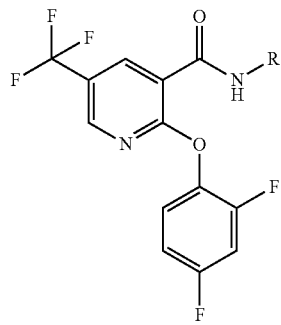

| Example | Name | R | Analytical data | Prep details |
|---|---|---|---|---|
| 175 | 2-(2,4-difluorophenoxy)-N-[3-(N,S-dimethylsulfonimidoyl)phenyl]-5-(trifluoromethyl)pyridine-3-carboxamide | *(3-substituted phenyl with S(=O)(=N-CH₃)-CH₃ group)* | MS, ES+ m/z, 486.0 (M + H)+ $^1$H NMR (400 MHz, DMSO-d6) δ ppm 2.49 (s, 3 H) 3.13 (s, 3 H) 7.16-7.25 (m, 1 H) 7.46-7.62 (m, 3 H) 7.62-7.70 (m, 1 H) 7.97 (d, J = 8.08 Hz, 1 H) 8.31 (t, J = 1.77 Hz, 1 H) 8.62 (d, J = 2.53 Hz, 1 H) 8.69-8.76 (m, 1 H) 11.04 (s, 1 H) | Method S, using (3-aminophenyl)(methyl)(methylimino)-λ$^6$-sulfanone |
| 176 | 2-(2,4-difluorophenoxy)-N-pyridazin-4-yl-5-(trifluoromethyl)pyridine-3-carboxamide | *(pyridazin-4-yl)* | MS, ES+ m/z, 397.0 (M + H)+ $^1$H NMR (400 MHz, DMSO-d6) δ ppm 7.14-7.26 (m, 1 H) 7.45-7.62 (m, 2 H) 8.08 (dd, J = 5.81, 2.78 Hz, 1 H) 8.67 (d, J = 2.53 Hz, 1 H) 8.74-8.79 (m, 1 H) 9.12-9.17 (m, 1 H) 9.41 (dd, J = 2.65, 0.88 Hz, 1 H) 11.35 (s, 1 H) | Method S, using pyridazin-4-amine |

Example 177: 5-cyano-2-(4-fluoro-2-methoxy-phenoxy)-6-methyl-N-(3-methylsulfonylphenyl)pyridine-3-carboxamide

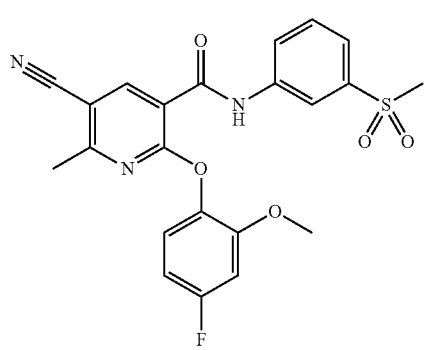 [SMILES: COc1cc(F)ccc1Oc1nc(C)c(C#N)cc1C(=O)Nc1cccc(S(C)(=O)=O)c1]

Step 1: Synthesis of ethyl 5-cyano-2-(4-fluoro-2-methoxy-phenoxy)-6-methyl-pyridine-3-carboxylate

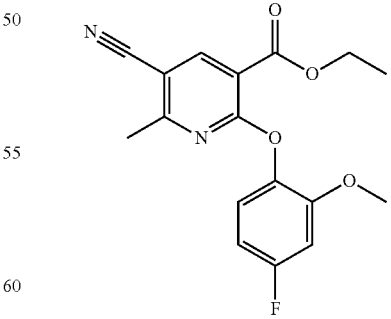

A mixture of ethyl 2-chloro-5-cyano-6-methyl-pyridine-3-carboxylate (150 mg, 0.668 mmol), 4-fluoro-2-methoxy-phenol (95.1 μL, 0.835 mmol) and cesium carbonate (653 mg, 2.00 mmol) in MeCN (5 mL) was stirred at 60° C. for 1 h. After cooling, the contents were treated with water and stirred overnight at room temperature. A precipitate was collected by filtration, washed with water and dried under vacuum to give ethyl 5-cyano-2-(4-fluoro-2-methoxy-phenoxy)-6-methyl-pyridine-3-carboxylate (135 mg, 0.409 mmol, 61.2% yield) as a greenish-gray solid. MS, ES+ m/z 331.0 [M+H]+. ¹H-NMR (400 MHz, DMSO-d₆) δ 8.64 (s, 1H), 7.20 (dd, J=8.97, 5.94 Hz, 1H), 7.11 (dd, J=10.48, 2.65 Hz, 1H), 6.82 (td, J=8.46, 2.78 Hz, 1H), 4.33 (q, J=7.07 Hz, 2H), 3.70 (s, 3H), 2.46 (s, 3H), 1.32 (t, J=7.07 Hz, 3H).

Step 2: Synthesis of 5-cyano-2-(4-fluoro-2-methoxy-phenoxy)-6-methyl-pyridine-3-carboxylic acid

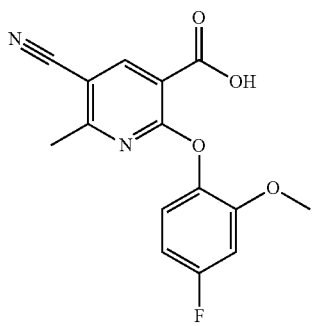 [SMILES: COc1cc(F)ccc1Oc1nc(C)c(C#N)cc1C(=O)O]

A mixture of ethyl 5-cyano-2-(4-fluoro-2-methoxy-phenoxy)-6-methyl-pyridine-3-carboxylate (135 mg, 0.409 mmol) and lithium hydroxide monohydrate (18.9 mg, 0.450 mmol) in THF (2 mL) and Water (0.1 mL) was stirred at room temperature for 2 h. The solvent was removed under a stream of N₂ and the residue dissolved in water. The pH was lowered to pH 5 by careful addition of 6N HCl, and the product was extracted with CHCl3 (4×) and the solvent removed in vacuo to give a residue which was purified by automated normal-phase chromatography (0-100% EtOAc/heptane, 4 g silica gel cartridge) to give 5-cyano-2-(4-fluoro-2-methoxy-phenoxy)-6-methyl-pyridine-3-carboxylic acid (77.2 mg, 0.255 mmol, 62.5% yield) as a yellow solid. MS, ES+ m/z 303.0 [M+H]+. ¹H-NMR (400 MHz, DMSO-d₆) δ 13.55 (br. s., 1H), 8.57 (s, 1H), 7.19 (dd, J=8.84, 6.06 Hz, 1H), 7.11 (dd, J=10.74, 2.91 Hz, 1H), 6.82 (td, J=8.53, 2.91 Hz, 1H), 3.70 (s, 3H), 2.44 (s, 3H).

Step 3: Synthesis of 5-cyano-2-(4-fluoro-2-methoxy-phenoxy)-6-methyl-N-(3-methylsulfonylphenyl)pyridine-3-carboxamide

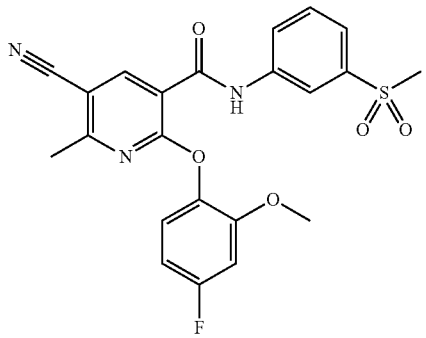 [SMILES: COc1cc(F)ccc1Oc1nc(C)c(C#N)cc1C(=O)Nc1cccc(S(C)(=O)=O)c1]

A mixture of 5-cyano-2-(4-fluoro-2-methoxy-phenoxy)-6-methyl-pyridine-3-carboxylic acid (75.0 mg, 0.248 mmol), 3-methylsulfonylaniline (46.7 mg, 0.273 mmol), HBTU (113 mg, 0.298 mmol) and DIPEA (130 µL, 0.744 mmol) in Chloroform (3 mL) was stirred at room temperature for 19 h. The contents were diluted with EtOAc, washed with water (3×), brine (1×), dried over MgSO4, filtered and the solvent removed in vacuo to give a residue which was purified by automated normal-phase chromatography (0-100% EtOAc/heptane, 4 g silica gel cartridge) to give 5-cyano-2-(4-fluoro-2-methoxy-phenoxy)-6-methyl-N-(3-methylsulfonylphenyl)pyridine-3-carboxamide (49.0 mg, 0.108 mmol, 43.4% yield) as a pale yellow solid. MS, ES+ m/z 456.0 [M+H]+. ¹H-NMR (400 MHz, DMSO-d₆) δ 10.89 (s, 1H), 8.57 (s, 1H), 8.39 (s, 1H), 7.94-7.99 (m, 1H), 7.64-7.72 (m, 2H), 7.31 (dd, J=8.84, 5.81 Hz, 1H), 7.11 (dd, J=10.74, 2.91 Hz, 1H), 6.84 (td, J=8.53, 2.91 Hz, 1H), 3.71 (s, 3H), 3.22 (s, 3H).

Example 178: 5-fluoro-2-(4-fluoro-2-methoxy-phenoxy)-6-methoxy-N-(3-methylsulfonylphenyl)pyridine-3-carboxamide

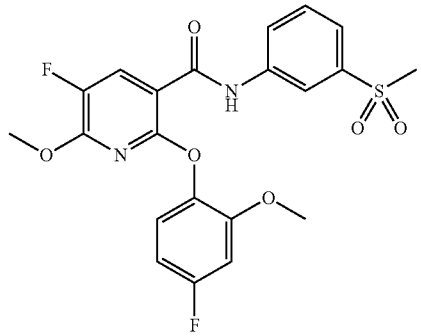

Step 1: Synthesis of methyl 5-fluoro-2-(4-fluoro-2-methoxy-phenoxy)-6-methoxy-pyridine-3-carboxylate

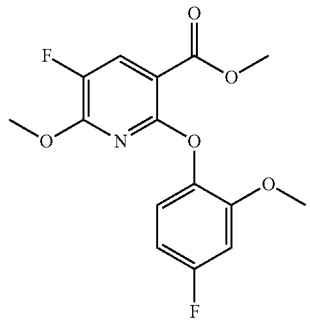

A mixture of methyl 2-chloro-5-fluoro-6-methoxy-pyridine-3-carboxylate (200 mg, 0.911 mmol), 4-fluoro-2-methoxyphenol (114 µL, 1.00 mmol) and cesium carbonate (742 mg, 2.28 mmol) in MeCN (8 mL) was stirred at 80° C. for 3 h, then allowed to cool to room temperature with stirring. Water (30 mL) and methanol (5 mL) were added and the resulting mixture was sonicated briefly then stirred for 4 h. The precipitate was collected by filtration, washed with water and dried under vacuum to give methyl 5-fluoro-2-(4-fluoro-2-methoxy-phenoxy)-6-methoxy-pyridine-3-carboxylate (237 mg, 0.727 mmol, 79.9% yield) as a beige solid. MS, ES+ m/z 326.0 [M+H]+. 1H-NMR (400 MHz, DMSO-d6) δ 8.12 (d, J=10.11 Hz, 1H), 7.18 (dd, J=8.72, 5.94 Hz, 1H), 7.09 (dd, J=10.74, 2.91 Hz, 1H), 6.81 (td, J=8.46, 2.78 Hz, 1H), 3.83 (s, 3H), 3.72 (s, 3H), 3.57 (s, 3H).

Step 2: Synthesis of 5-fluoro-2-(4-fluoro-2-methoxy-phenoxy)-6-methoxy-pyridine-3-carboxylic acid

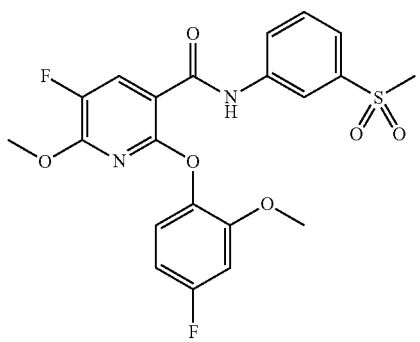

A mixture of methyl 5-fluoro-2-(4-fluoro-2-methoxy-phenoxy)-6-methoxy-pyridine-3-carboxylate (231 mg, 0.710 mmol) and lithium hydroxide monohydrate (32.8 mg, 0.781 mmol) in THF (3 mL) and water (0.1 mL) was stirred at room temperature for 48 h. The solvent was removed with a stream of N2 and the contents diluted with water (15 mL). The contents were filtered and the pH of the filtrate was lowered to pH 4 by careful addition of 2 N HCl. After stirring for 1 h, the precipitate was collected by filtration, washed with water and dried under vacuum to give 5-fluoro-2-(4-fluoro-2-methoxy-phenoxy)-6-methoxy-pyridine-3-carboxylic acid (201 mg, 0.646 mmol, 90.9% yield) as a white solid. MS, ES+ m/z 312.0 [M+H]+.

1H-NMR (400 MHz, DMSO-d6) δ 13.05 (br. s., 1H), 8.08 (d, J=10.11 Hz, 1H), 7.17 (dd, J=8.84, 6.06 Hz, 1H), 7.08 (dd, J=10.74, 2.91 Hz, 1H), 6.80 (td, J=8.53, 2.91 Hz, 1H), 3.72 (s, 3H), 3.56 (s, 3H).

Step 3: Synthesis of 5-fluoro-2-(4-fluoro-2-methoxy-phenoxy)-6-methoxy-N-(3-methylsulfonylphenyl)pyridine-3-carboxamide

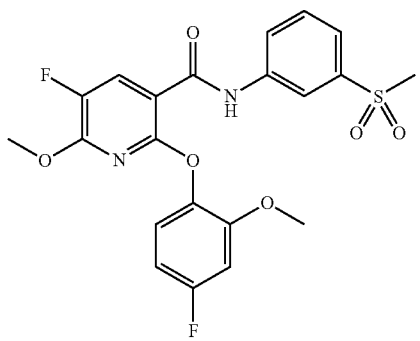

A mixture of 5-fluoro-2-(4-fluoro-2-methoxy-phenoxy)-6-methoxy-pyridine-3-carboxylic acid (40 mg, 0.129 mmol), 3-methylsulfonylaniline (24.2 mg, 0.141 mmol), HBTU (53.6 mg, 0.141 mmol) and DIPEA (56.0 μL, 0.321 mmol) in chloroform (2 mL) was stirred at room temperature for 22 h. Reaction only ~25% complete by LCMS. Stirred at 50° C. for 54 h. The solvent was removed under a stream of N2, and the residue treated with water/MeOH (3:1). This mixture was briefly sonicated then stirred at room temperature for 24 h. The resulting precipitate was collected by filtration, washed with water and dried under vacuum to give 5-fluoro-2-(4-fluoro-2-methoxy-phenoxy)-6-methoxy-N-(3-methylsulfonylphenyl)pyridine-3-carboxamide (45.8 mg, 0.0986 mmol, 76.7% yield) as a white solid. MS, ES+ m/z 465.1 [M+H]+. 1H-NMR (400 MHz, DMSO-d6) δ 10.52 (s, 1H), 8.38 (s, 1H), 8.14 (d, J=9.85 Hz, 1H), 7.99 (d, J=7.07 Hz, 1H), 7.63-7.70 (m, 2H), 7.39-7.44 (m, 1H), 7.11 (dd, J=10.74, 2.65 Hz, 1H), 6.85 (td, J=8.59, 2.78 Hz, 1H), 3.75 (s, 3H), 3.64 (s, 3H), 3.22 (s, 3H).

Example 179: 5-(difluoromethoxy)-2-(4-fluoro-2-methoxy-phenoxy)-N-(3-methylsulfonylphenyl)pyridine-3-carboxamide

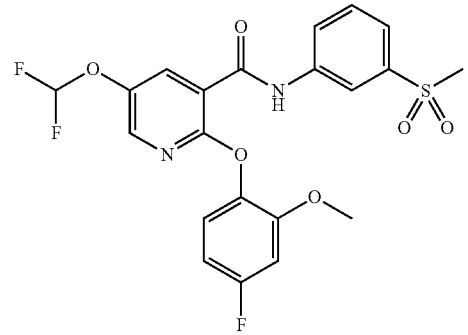 [SMILES: COc1cc(F)ccc1Oc1ncc(OC(F)F)cc1C(=O)Nc1cccc(S(C)(=O)=O)c1]

Step 1: Synthesis of 3-bromo-2-chloro-5-(difluoromethoxy)pyridine

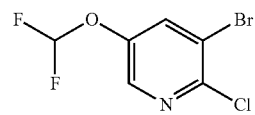

A round-bottom flask equipped with a magnetic stir bar was charged with 5-bromo-6-chloro-pyridin-3-ol (1.0 g, 4.8 mmol), and then acetonitrile (20 mL) and water (20 mL) were added. Solid potassium hydroxide (5.4 g, 96 mmol) was added, and the mixture was cooled in a dry ice/acetone bath. When the mixture began to freeze, 1-[[bromo(difluoro)methyl]-ethoxy-phosphoryl]oxyethane (2.6 g, 9.6 mmol) was added, and the mixture was allowed to warm to room temperature. The crude mixture was partitioned between water and diethyl ether, and the ether layer was collected, dried, and concentrated to give a colorless oil containing the desired product, which was used without further purification.

Step 2: Synthesis of 3-bromo-2-chloro-5-(difluoromethoxy)pyridine

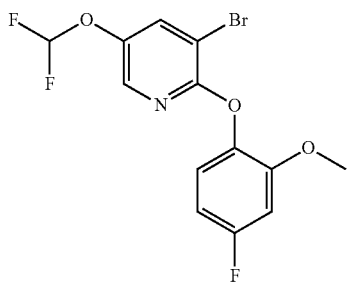 [SMILES: COc1cc(F)ccc1Oc1ncc(OC(F)F)cc1Br]

The crude product from step 1 (1.2 g, 4.6 mmol) was added to a round-bottom flask equipped with a magnetic stir bar and dissolved in acetonitrile (20 mL). 4-fluoro-2-methoxy-phenol (726 mg, 5.11 mmol) and cesium carbonate (1.7 g, 5.1 mmol) were added, and the mixture was heated to 60° C. for 24 hours. After cooling to room temperature, the crude mixture was diluted with water and extracted with dichloromethane. The combined organic layers were dried, concentrated and purified by silica gel chromatography (0-35% EtOAc in heptane) to afford the desired product as a colorless oil which solidified on standing (1.1 g, 3.1 mmol). MS, ES$^+$ m/z 364.0/365.0 [M+H]$^+$.

Step 3: Synthesis of 5-(difluoromethoxy)-2-(4-fluoro-2-methoxy-phenoxy)-N-(3-methylsulfonylphenyl)pyridine-3-carboxamide

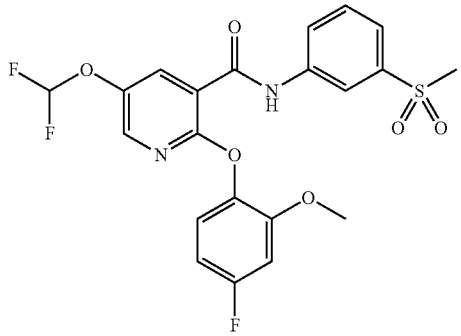 [SMILES: COc1cc(F)ccc1Oc1ncc(OC(F)F)cc1C(=O)Nc1cccc(S(C)(=O)=O)c1]

To a microwave vial equipped with a magnetic stir bar were added 3-bromo-5-(difluoromethoxy)-2-(4-fluoro-2-methoxy-phenoxy)pyridine (250 mg, 0.69 mmol), DPEPhos (27.7) mg, 0.05 mmol), palladium (II) acetate (3.85 mg, 0.02 mmol), 3-methylsulfonylaniline (235 mg, 1.37 mmol), and cesium hydroxide (1.2 g, 6.9 mmol). The vial was sealed, evacuated and backfilled with nitrogen three times, and then toluene (4 mL) and chloroform (0.17 mL) were added. The resulting mixture was heated to 80° C. for 18 hours, and after cooling to room temperature, was diluted with dichloromethane and filtered through a plug of celite. The clear filtrate was concentrated and purified by preparative reversed phase HPLC (high pH method) to afford the desired product as a colorless solid (166 mg, 50.1% yield). MS, ES$^+$ m/z 483.0 [M+H]$^+$. $^1$H NMR (400 MHz, DMSO-d$_6$) δ ppm 3.18-3.26 (m, 3H) 3.68-3.72 (m, 3H) 6.83 (td, J=8.53, 2.91 Hz, 1H) 7.06-7.11 (m, 1H) 7.32 (dd, J=8.72, 5.94 Hz, 1H) 7.64-7.73 (m, 2H) 7.93-8.02 (m, 1H) 8.07 (d, J=3.03 Hz, 1H) 8.16 (d, J=2.78 Hz, 1H) 8.41 (s, 1H) 10.90 (s, 1H)

Example 180: N-(3-methylsulfonylphenyl)-5-nitro-2-[4-(trifluoromethoxy)phenoxy]pyridine-3-carboxamide

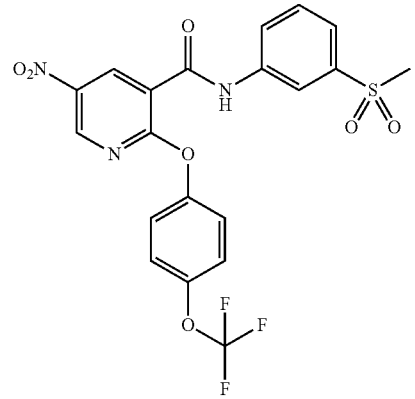 [SMILES: CS(=O)(=O)c1cccc(NC(=O)c2cc(N)cnc2Oc2ccc(OC(F)(F)F)cc2)c1]

Step 1: Synthesis of 2-chloro-N-(3-methylsulfonylphenyl)-5-nitro-pyridine-3-carboxamide

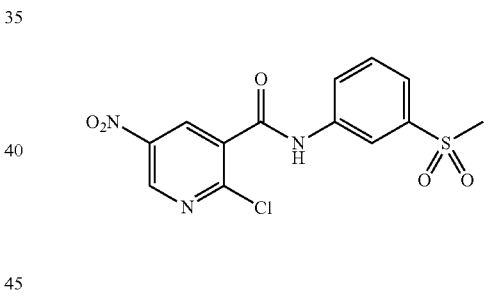

To a stirring solution of 2-chloro-5-nitro-pyridine-3-carboxylic acid (10 g, 49.37 mmol) in dichloromethane (200 mL), oxalyl chloride (6.35 mL, 74.06 mmol) was added. DMF (g, 2.47 mmol)(three drops) was added. The solution was stirred at room temperature for five hours until no bubble from solution was seen. 3-methylsulfonylaniline (10.14 g, 59.24 mmol) was added. N,N-diisopropylethylamine (17.72 mL, 98.74 mmol) was added to the solution dropwise. The solution was stirred at room temperature for one hour. DCM (200 mL) was added, and the solution was extracted with hydrochloric acid solution (1N, 2×100 mL), brine (100 mL), and then dried over sodium sulfate. The solution was filtered and concentrated. The residue was purified by silica gel chromatography, eluting with ethyl acetate/heptane (30-100% gradient) to give 2-chloro-N-(3-methylsulfonylphenyl)-5-nitro-pyridine-3-carboxamide (11.28 g, 22.195 mmol, 44.957% yield) as purple solid. MS, ES$^+$ m/z 356.0 [M+H]$^+$. $^1$H NMR (400 MHz, CHLOROFORM-d) δ ppm 3.02-3.11 (m, 3H) 7.60-7.82 (m, 3H) 7.94-8.05 (m, 1H) 8.61 (d, J=2.78 Hz, 1H) 9.22-9.31 (m, 1H).

Step 2: Synthesis of N-(3-methylsulfonylphenyl)-5-nitro-2-[4-(trifluoromethoxy)phenoxy]pyridine-3-carboxamide

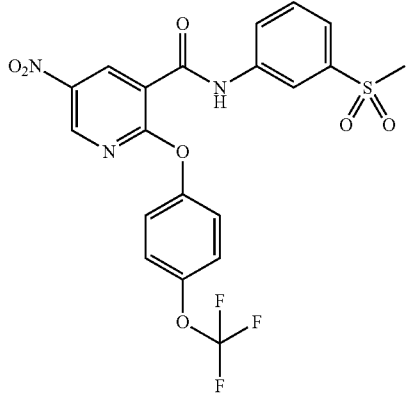

To a stirring solution of 2-chloro-N-(3-methylsulfonylphenyl)-5-nitro-pyridine-3-carboxamide (11.18 g, 22 mmol) in acetonitrile (100 mL), 4-(trifluoromethoxy)phenol (5.88 g, 33 mmol) and potassium carbonate (6.08 g, 44 mmol) were added. The solution was stirred at 60° C. overnight. The solution was cooled to room temperature and filtered to remove the solid. Water (300 mL) was added. The slightly colored solid was isolated by filtration and dried to give N-(3-methylsulfonylphenyl)-5-nitro-2-[4-(trifluoromethoxy)phenoxy]pyridine-3-carboxamide (10.43 g, 20.969 mmol, 95.32% yield) as slightly colored solid. A small sample of 100 mg) was purified over ISCO eluted with ethyl acetate/heptane (0-60%) to give N-(3-methylsulfonylphenyl)-5-nitro-2-[4-(trifluoromethoxy)phenoxy]pyridine-3-carboxamide (10.43 g, 20.97 mmol, 95.32% yield) as white solid. MS, ES$^+$ m/z 498.0 [M+H]$^+$. 1H NMR (400 MHz, CHLOROFORM-d) δ ppm 3.12 (s, 3H) 7.26-7.38 (m, 3H) 7.43 (d, J=8.84 Hz, 2H) 7.61-7.70 (m, 1H) 7.79 (dd, J=7.83, 1.26 Hz, 1H) 8.10-8.21 (m, 2H) 9.12 (d, J=2.78 Hz, 1H) 9.48 (d, J=2.78 Hz, 1H) 9.68 (s, 1H).

Example 181: 5-chloro-N-(3-methylsulfonylphenyl)-2-[4-(trifluoromethoxy)phenoxy]pyridine-3-carboxamide

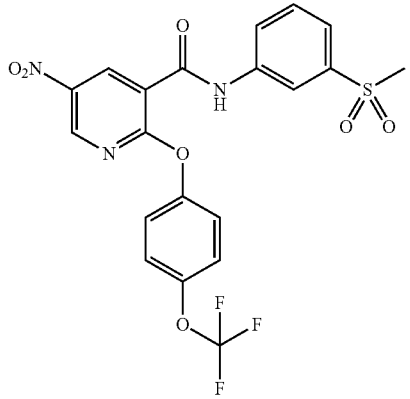

Step 1: Synthesis of 5-amino-N-(3-methylsulfonylphenyl)-2-[4-(trifluoromethoxy)phenoxy]pyridine-3-carboxamide

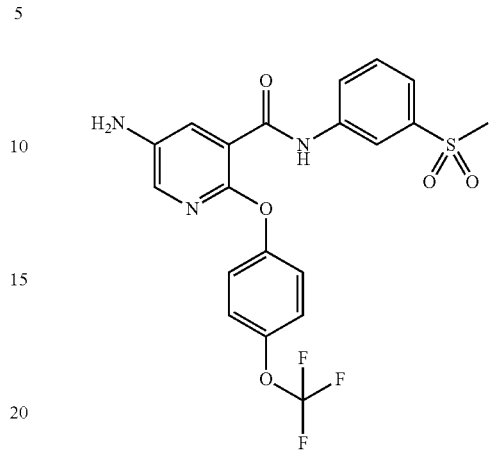

To a stirring solution of N-(3-methylsulfonylphenyl)-5-nitro-2-[4-(trifluoromethoxy)phenoxy]pyridine-3-carboxamide (10.33 g, 20.77 mmol) in THF (50 mL) and ethanol (100 mL), palladium on carbon 10% (g, 20.77 mmol) was added. The solution was bubbled nitrogen for 5 minutes. The solution was charged with hydrogen balloon and stirred for two days. The solution was filtered and concentrated. The residue was purified over ISCO eluted with methanol/DCM (0-8%) to give 5-amino-N-(3-methylsulfonylphenyl)-2-[4-(trifluoromethoxy)phenoxy]pyridine-3-carboxamide (4.64 g, 9.9268 mmol, 47.799% yield) as white solid. MS, ES$^+$ m/z 468.0 [M+H]$^+$. 1H NMR (400 MHz, DMSO-d6) δ ppm 3.15-3.26 (m, 3H) 5.44 (s, 2H) 7.12-7.21 (m, 2H) 7.30-7.41 (m, 3H) 7.60-7.71 (m, 3H) 7.92 (d, J=7.58 Hz, 1H) 8.38 (s, 1H) 10.76 (s, 1H).

Step 2: Synthesis of 5-chloro-N-(3-methylsulfonylphenyl)-2-[4-(trifluoromethoxy)phenoxy]pyridine-3-carboxamide

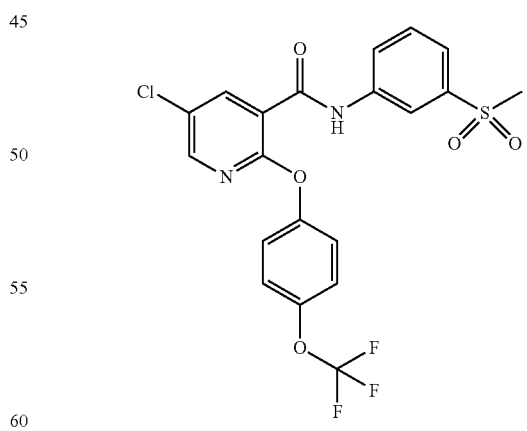

To a stirring solution of 5-amino-N-(3-methylsulfonylphenyl)-2-[4-(trifluoromethoxy)phenoxy]pyridine-3-carboxamide (200 mg, 0.4300 mmol) in water (3 mL), hydrochloric acid (2 mL) was added. The solution was cooled to ice-water bath. sodium nitrite (32.48 mg, 0.4700 mmol) dissolved in water (0.2 mL) was added. After stirring 15 min. at 0° C., copper(II) chloride (172.59 mg, 1.28 mmol) dissolved in water (1 mL) was added. The solution was stirred at room temperature overnight. The solution was extracted with ethyl acetate (2×3 mL). The combined organic solution was washed with water (2 mL), brine (2 mL), dried over sodium sulfate. The solution was filtered and concentrated. The residue was purified over ISCO eluted with ethyl acetate/heptane (0-50%) to give 5-chloro-N-(3-methylsulfonylphenyl)-2-[4-(trifluoromethoxy)phenoxy]pyridine-3-carboxamide (43 mg, 0.0883 mmol, 20.642% yield) as white solid. MS, ES+ m/z 487.0 [M+H]+. 1H NMR (400 MHz, CHLOROFORM-d) δ ppm 3.11 (s, 3H) 7.24-7.32 (m, 2H) 7.39 (d, J=8.34 Hz, 2H) 7.58-7.68 (m, 1H) 7.74-7.83 (m, 1H) 8.10 (d, J=8.08 Hz, 1H) 8.17 (t, J=1.89 Hz, 1H) 8.23 (d, J=2.53 Hz, 1H) 8.70 (d, J=2.53 Hz, 1H) 9.79 (s, 1H).

Assay Methods

The ability of pyridine carboxamide derivatives exemplified above to inhibit the Nav1.8 channel was determined using one or more of the methods described below.

HEK Nav1.8 β1/β2 Stably Expressing Cell Line

A HEK293 cell line stably expressing the human Nav1.8 (hNav1.8) ion channel with β1/β2 subunits was constructed. The cell line is suitable for $IC_{50}$ determination in fluorescence and electrophysiological based assays. It is also suitable to form mechanism of action pharmacology studies in electrophysiological assays. HEK293 Nav 1.8 cells are grown as adherent monolayers in DMEM/high glucose media, 10% fetal bovine serum, Na pyruvate (2 mM), Hepes (10 mM) with selection agents G418 (400 mg/L) and puromycin (0.5 mg/L) at 37 degrees C., 10% $CO_2$.

$Na_v$ 1.8 Fluorescence Inhibition Assay

Compounds were made up to or supplied as a 10-mM stock solution using DMSO as the vehicle. Concentration-response curves were generated using a Matrix multichannel pipettor. Compound source plates were made by diluting 10 mM compound stocks to create 500 µM (100×) solutions in DMSO in 96-well v-bottom plates. Compounds were then serially diluted in 100% DMSO to generate a 5 point, 4-fold dilution scheme dose response curve. 2 µL of the 100× dose response curves was then added to preincubation and stimulation assay plates. 100 µL of pre-incubation buffer and 200 µL of stimulation buffer were then added to the plates resulting in a final assay test concentration range of 5 µM to 0.02 µM with a final DMSO concentration of 1%.

On the day of assay, plates were washed to remove cell culture media using 2K EBSS buffer (135 mM NaCl, 2 mM KCl, 5 mM Glucose, 2 mM $CaCl_2$), 1 mM $MgCl_2$, 10 mM HEPES, pH 7.4). The Na-sensitive fluorescent dye, Asante Natrium Green-2 (ANG-2) is incubated for 60 min to allow equilibration and then washed with 2K EBSS. Plates are the transferred to a fluorescence plate reader (FLIPR™, Molecular Devices) for fluorescence measurement using an excitation wavelength of 490 nm and an emission wavelength of 565 nm. Compounds are pre-incubated at for 5 min at final test concentration in the presence of ouabain (30 µM) to inhibit Na+ efflux through Na+/K+ exchanger. Following the pre-incubation phase, hNav1.8 channels are stimulated with 10 µM of the pyrethroid deltamethrin to prevent channel inactivation. The assay was run for 15 min with vehicle and 30 µM tetracaine serving as negative and positive controls, respectively. The peak change in fluorescence relative to negative and positive control wells was calculated and fit with a logistic equation to determine $IC_{50}$.

PatchXpress $Na_v$ 1.8 Inhibition Assay

HEK-Nav1.8 β1/β2 cells were recorded in whole cell patch-clamp using the PatchXpress automated patch clamp platforms (Molecular Devices). Cells suspensions were obtained by trypsinization of adherent monolayers, followed by gentle rocking for minimally 30 min. Compounds were prepared from 10 mM DMSO stocks.

Nav1.8 channel variants were evaluated using Protocol 1 (FIG. 2) in which cells were initially voltage clamped at a holding potential of −100 mV to maintain Nav1.8 in a closed resting state. After current amplitude becomes stable, the mid-point voltage of steady state inactivation was determined for each cell using a series of 5 sec conditioning steps to increasingly depolarized voltages (−100 to 0 mV) The holding potential was then reset to a voltage that produces ~50% inactivation ($V_{half}$-set automatically via PatchXpress scripts) so that closed and inactivated channel inhibition can be assessed. Protocol 1 was run at a frequency of 0.1 Hz until current amplitude is steady (automatically determined by PatchXpress scripts). The effect of test reagent on Nav current amplitude was monitored using custom PatchXpress stability scripts which determines the timing of compound addition and washout. Data were processed and analyzed using DataXpress 2.0 (Molecular Devices). Percent inhibition is calculated using Microsoft Excel such that compound block is normalized to the average of control and washout currents according to the formula, % Inhibition=(((Ctrl+Wash)/2)−Drug)/((Ctrl+Wash)/2)*100 (see schematic hereinabove). Normalized concentration-response relationships were fit using XLfit software (IDBS) 4 Parameter Logistic Model or Sigmoidal Dose-Response Model.

hNa$_V$1.8 Automated Patch Clamp-IonFlux$^{HT}$ Assay

The IonFlux HT automated whole-cell patch-clamp instrument (Fluxion Biosciences, Inc., Almeda, CA USA) was used to record the inward sodium currents.

Cells: HEK-293 cells were stably transfected with human Nav1.8 cDNA (type X voltage-gated sodium channel alpha subunit, accession #NM_006514) and the human beta subunit 1 (accession #NM_001037). The cells were harvested with trypsin and maintained in serum free medium at room temperature before recording. The cells were washed and re-suspended in the Extracellular Solution before being applied to the instrument.

Test concentrations: Stock solution was prepared in DMSO at 300× the final assay concentrations, and stored at −80° C. until the day of assay. On the day of the assay, an aliquot of the stock solution was thawed and diluted into external solution to make final test concentrations. A final concentration of 0.33% DMSO was maintained for each concentration of the assay compounds and controls.

Recording conditions: Intracellular Solution (mM): 100 CsF, 45 CsCl, 5 NaCl, 10 HEPES, 5 EGTA (pH 7.3, titrated with 1M CsOH).

Extracellular Solution (mM): 150 NaCl, 4 BaCl, 1 $MgCl_2$, 1.8 $CaCl_2$), 10 HEPES, 5 Glucose, (pH 7.4, titrated with 10M NaOH).

When sodium channels are held at a depolarized membrane potential, the channels open and inactivate and remain inactivated until the membrane potential is stepped back to a hyperpolarized membrane potential, when the inactivated channels recover into the closed state. Compounds that show more inhibition at pulse 2 compared to pulse 1 are state-dependent inhibitors. An example is Tetracaine, which is a much more potent inhibitor in the inactivated state than in the tonic or open state.

Cells were held at −120 mV for 50 ms before stepping to −10 mV for 2 s to completely inactivate the sodium channels (pulse 1), and stepped back to −120 mV for 10 ms (to completely recover from inactivation, however, channels that have inhibitors bound to them may not recover from inactivation) before stepping to −10 mV for 50 ms (pulse 2). The sweep interval is 20 s (0.05 Hz). Each concentration of compound was applied for two minutes. The assay was performed at room temperature.

Reference compounds: Tetracaine was used as the positive control and was tested concurrently with the test compound.

Data analysis: Only current amplitudes in excess of 3 nA at the control stage were analyzed. The amplitude of the sodium current was calculated by measuring the difference between the peak inward current on stepping to −10 mV (i.e., peak of the current) and remaining current at the end of the step. The sodium current was assessed in vehicle control conditions and then at the end of each two (2) minute compound application. Individual cell trap results were normalized to the vehicle control amplitude and the mean±SEM calculated for each compound concentration. These values were then plotted and estimated IC50 curve fits calculated.

Estimated $IC_{50}$ values for pyridine carboxamide compounds exemplified above are listed in Table 1.

TABLE 1

| Example | Activity range |
|---|---|
| 1 | + |
| 2 | + |
| 3 | +++ |
| 4 | + |
| 5 | + |
| 6 | ++ |
| 7 | + |
| 8 | +++ |
| 9 | + |
| 10 | +++ |
| 11 | + |
| 12 | +++ |
| 13 | + |
| 14 | +++ |
| 15 | + |
| 16 | +++ |
| 17 | + |
| 18 | + |
| 19 | ++ |
| 20 | + |
| 21 | +++ |
| 22 | + |
| 23 | +++ |
| 24 | + |
| 25 | + |
| 26 | +++ |
| 27 | + |
| 28 | |
| 29 | |
| 30 | |
| 31 | |
| 32 | |
| 33 | + |
| 34 | + |
| 35 | +++ |
| 36 | +++ |
| 37 | +++ |
| 38 | +++ |
| 39 | +++ |
| 40 | +++ |
| 41 | + |
| 42 | ++ |
| 43 | ++ |
| 44 | + |
| 45 | + |
| 46 | +++ |
| 47 | +++ |
| 48 | +++ |
| 49 | + |

TABLE 1-continued

| Example | Activity range |
|---|---|
| 50 | +++ |
| 51 | +++ |
| 52 | ++ |
| 53 | +++ |
| 54 | +++ |
| 55 | ++ |
| 56 | + |
| 57 | + |
| 58 | + |
| 59 | +++ |
| 60 | +++ |
| 61 | +++ |
| 62 | +++ |
| 63 | ++ |
| 64 | + |
| 65 | + |
| 66 | +++ |
| 67 | +++ |
| 68 | +++ |
| 69 | +++ |
| 70 | +++ |
| 71 | +++ |
| 72 | +++ |
| 73 | + |
| 74 | +++ |
| 75 | +++ |
| 76 | ++ |
| 77 | +++ |
| 78 | +++ |
| 79 | +++ |
| 80 | +++ |
| 81 | +++ |
| 82 | +++ |
| 83 | +++ |
| 84 | ++ |
| 85 | ++ |
| 86 | ++ |
| 87 | +++ |
| 88 | +++ |
| 89 | + |
| 90 | +++ |
| 91 | +++ |
| 92 | +++ |
| 93 | + |
| 94 | +++ |
| 95 | +++ |
| 96 | ++ |
| 97 | + |
| 98 | +++ |
| 99 | +++ |
| 100 | + |
| 101 | + |
| 102 | + |
| 103 | + |
| 104 | |
| 105 | |
| 106 | |
| 107 | |
| 108 | |
| 109 | + |
| 110 | + |
| 111 | + |
| 112 | + |
| 113 | ++ |
| 114 | +++ |
| 115 | +++ |
| 116 | + |
| 117 | + |
| 118 | +++ |
| 119 | ++ |
| 120 | +++ |
| 121 | +++ |
| 122 | +++ |
| 123 | +++ |
| 124 | +++ |
| 125 | +++ |
| 126 | ++ |

TABLE 1-continued

| Example | Activity range |
|---|---|
| 127 | +++ |
| 128 | +++ |
| 129 | + |
| 130 | +++ |
| 131 | +++ |
| 132 | +++ |
| 133 | + |
| 134 | + |
| 135 | + |
| 136 | +++ |
| 137 | +++ |
| 138 | +++ |
| 141 | +++ |
| 142 | +++ |
| 143 | ++ |
| 144 | +++ |
| 145 | +++ |
| 146 | +++ |
| 147 | +++ |
| 148 | ++ |
| 149 | + |
| 150 | +++ |
| 151 | +++ |
| 152 | +++ |
| 153 | ++ |
| 154 | + |
| 155 | +++ |
| 156 | ++ |
| 157 | ++ |
| 158 | + |
| 159 | ++ |
| 158 | ++ |
| 159 | +++ |
| 160 | +++ |
| 161 | +++ |
| 162 | +++ |
| 163 | + |
| 164 | +++ |
| 165 | +++ |
| 166 | ++ |
| 167 | ++ |
| 168 | ++ |
| 169 | + |
| 170 | + |
| 171 | +++ |
| 172 | +++ |
| 173 | + |
| 174 | +++ |
| 175 | +++ |
| 176 | + |
| 177 | ++ |
| 178 | +++ |
| 179 | +++ |
| 180 | +++ |
| 181 | +++ |

+ $IC_{50} > 1$ uM
++ $IC_{50}$ 500 nM-1 uM
+++ $IC_{50} < 500$ nM

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Pain Medicine: An Essential Review, Young, RJ, Nguyen, M, Nelson, E, Urman, Eds. Springer, Chain, Switzerland. 2017, ISBN 978-3-319-43131-4.

Yekkirala, A. S.; Roberson, D. P.; Bean, B. P.; Woolf, C. J., Breaking barriers to novel analgesic drug development. Nat Rev Drug Discov 2017, 16 (8), 544-563.

Skolnick, P., The Opioid Epidemic: Crisis and Solutions. Annual Review of Pharmacology and Toxicology, Vol 58 2018, 58, 143-159.

Catterall, W. A., Voltage-gated sodium channels at 60: structure, function and pathophysiology. J Physiol-London 2012, 590 (11), 2577-2589.

Ruiz, M. D.; Kraus, R. L., Voltage-Gated Sodium Channels: Structure, Function, Pharmacology, and Clinical Indications. J Med Chem 2015, 58 (18), 7093-7118.

Yu, F. H.; Catterall, W. A., Overview of the voltage-gated sodium channel family. Genome Biol 2003, 4 (3).

Eijkelkamp, N.; Linley, J. E.; Baker, M. D.; Minett, M. S.; Cregg, R.; Werdehausen, R.; Rugiero, F.; Wood, J. N., Neurological perspectives on voltage-gated sodium channels. Brain 2012, 135, 2585-2612.

Bagal, S. K.; Chapman, M. L.; Marron, B. E.; Prime, R.; Storer, R. I.; Swain, N. A., Recent progress in sodium channel modulators for pain. Bioorganic & medicinal chemistry letters 2014, 24 (16), 3690-3699.

Jukic, M.; Kikelj, D.; Anderluh, M., Isoform Selective Voltage-Gated Sodium Channel Modulators and the Therapy of Pain. Curr Med Chem 2014, 21 (2), 164-186.

Deuis, J. R.; Mueller, A.; Israel, M. R.; Vetter, I., The pharmacology of voltage-gated sodium channel activators. Neuropharmacology 2017, 127, 87-108.

Vetter, I.; Deuis, J. R.; Mueller, A.; Israel, M. R.; Starobova, H.; Zhang, A.; Rash, L. D.; Mobli, M., Na(V)1.7 as a pain target—From gene to pharmacology. Pharmacology & Therapeutics 2017, 172, 73-100.

Bennett, D. L. H.; Woods, C. G., Painful and painless channelopathies. Lancet Neurol 2014, 13 (6), 587-599.

McCormack, K.; Santos, S.; Chapman, M. L.; Krafte, D. S.; Marron, B. E.; West, C. W.; Krambis, M. J.; Antonio, B. M.; Zellmer, S. G.; Printzenhoff, D.; Padilla, K. M.; Lin, Z. X.; Wagoner, P. K.; Swain, N. A.; Stupple, P. A.; de Groot, M.; Butt, R. P.; Castle, N. A., Voltage sensor interaction site for selective small molecule inhibitors of voltage-gated sodium channels. P Natl Acad Sci USA 2013, 110 (29), E2724-E2732.

Donnell, A.; Collins, S.; Ali, Z.; Iavarone, L.; Surujbally, R.; Kirby, S.; Butt, R. P., Efficacy of the Nayl. 7 Blocker Pf-05089771 in A Randomised, Placebo-Controlled, Double-Blind Clinical Study in Subjects with Painful Diabetic Peripheral Neuropathy. Pain 2018.

Zakrzewska, J. M.; Palmer, J.; Morisset, V.; Giblin, G. M. P.; Obermann, M.; Ettlin, D. A.; Cruccu, G.; Bendtsen, L.; Estacion, M.; Derjean, D.; Waxman, S. G.; Layton, G.; Gunn, K.; Tate, S., Safety and efficacy of a Nayl.7 selective sodium channel blocker in patients with trigeminal neuralgia: a double-blind, placebo-controlled, randomised withdrawal phase 2a trial. The Lancet Neurology 2017, 16 (4), 291-300.

Han, C. Y.; Huang, J. Y.; Waxman, S. G., Sodium channel Na(v)1.8 Emerging links to human disease. Neurology 2016, 86 (5), 473-483.

Akopian, A. N.; Sivilotti, L.; Wood, J. N., A tetrodotoxin-resistant voltage-gated sodium channel expressed by sensory neurons. Nature 1996, 379 (6562), 257.

Shields, S. D.; Ahn, H.-S.; Yang, Y.; Han, C.; Seal, R. P.; Wood, J. N.; Waxman, S. G.; Dib-Hajj, S. D., Nav1.8 expression is not restricted to nociceptors in mouse peripheral nervous system. *PAIN®* 2012, 153 (10), 2017-2030.

Akopian, A. N.; Souslova, V.; England, S.; Okuse, K.; Ogata, N.; Ure, J.; Smith, A.; Kerr, B. J.; McMahon, S. B.; Boyce, S.; Hill, R.; Stanfa, L. C.; Dickenson, A. H.; Wood, J. N., The tetrodotoxin-resistant sodium channel SNS has a specialized function in pain pathways. *Nat Neurosci* 1999, 2, 541.

Dong, X.-W.; Goregoaker, S.; Engler, H.; Zhou, X.; Mark, L.; Crona, J.; Terry, R.; Hunter, J.; Priestley, T., Small interfering RNA-mediated selective knockdown of NaV1.8 tetrodotoxin-resistant sodium channel reverses mechanical allodynia in neuropathic rats. *Neuroscience* 2007, 146 (2), 812-821.

Faber, C. G.; Lauria, G.; Merkies, I. S. J.; Cheng, X.; Han, C.; Ahn, H.-S.; Persson, A.-K.; Hoeijmakers, J. G. J.; Gerrits, M. M.; Pierro, T.; Lombardi, R.; Kapetis, D.; Dib-Hajj, S. D.; Waxman, S. G., Gain-of-function Na$_v$1.8 mutations in painful neuropathy. *Proceedings of the National Academy of Sciences* 2012, 109 (47), 19444-19449.

Lu, V. B.; Ikeda, S. R.; Puhl, H. L., A 3.7 kb Fragment of the Mouse Scn10a Gene Promoter Directs Neural Crest But Not Placodal Lineage EGFP Expression in a Transgenic Animal. *J Neurosci* 2015, 35 (20), 8021-8034.

Black, J. A.; Dib-Hajj, S.; Baker, D.; Newcombe, J.; Cuzner, M. L.; Waxman, S. G., Sensory neuron-specific sodium channel SNS is abnormally expressed in the brains of mice with experimental allergic encephalomyelitis and humans with multiple sclerosis. *P Natl Acad Sci USA* 2000, 97 (21), 11598-11602.

Damarjian, T. G.; Craner, M. J.; Black, J. A.; Waxman, S. G., Upregulation and colocalization of p75 and Na(v)1.8 in Purkinje neurons in experimental autoimmune encephalomyelitis. *Neurosci Lett* 2004, 369 (3), 186-190.

Shields, S. D.; Cheng, X. Y.; Gasser, A.; Saab, C. Y.; Tyrrell, L.; Eastman, E. M.; Iwata, M.; Zwinger, P. J.; Black, J. A.; Dib-Hajj, S. D.; Waxman, S. G., A channelopathy contributes to cerebellar dysfunction in a model of multiple sclerosis. *Ann Neurol* 2012, 71 (2), 186-194.

Shields, S. D.; Butt, R. P.; Dib-Hajj, S. D.; Waxman, S. G., Oral Administration of PF-01247324, a Subtype-Selective Nav1.8 Blocker, Reverses Cerebellar Deficits in a Mouse Model of Multiple Sclerosis. *Plos One* 2015, 10 (3).

Sweatt, J. D., Pitt-Hopkins Syndrome: intellectual disability due to loss of TCF4-regulated gene transcription. *Exp Mol Med* 2013, 45.

Rannals, M. D.; Hamersky, G. R.; Page, S. C.; Campbell, M. N.; Briley, A.; Gallo, R. A.; Phan, B. N.; Hyde, T. M.; Kleinman, J. E.; Shin, J. H.; Jaffe, A. E.; Weinberger, D. R.; Maher, B. J., Psychiatric R$_{18}$ k Gene Transcription Factor 4 Regulates Intrinsic Excitability of Prefrontal Neurons via Repression of SCN10a and KCNQ1. *Neuron* 2016, 90 (1), 43-55.

Bucknill, A. T.; Coward, K.; Plumpton, C.; Tate, S.; Bountra, C.; Birch, R.; Sandison, A.; Hughes, S. P.; Anand, P., Nerve fibers in lumbar spine structures and injured spinal roots express the sensory neuron-specific sodium channels SNS/PN3 and NaN/SNS2. *Spine* 2002, 27 (2), 135-140.

Renton, T.; Yiangou, Y.; Plumpton, C.; Tate, S.; Bountra, C.; Anand, P., Sodium channel Na v 1.8 immunoreactivity in painful human dental pulp. *BMC oral health* 2005, 5 (1), 5.

Shembalkar, P. K.; Till, S.; Boettger, M. K.; Terenghi, G.; Tate, S.; Bountra, C.; Anand, P., Increased sodium channel SNS/PN3 immunoreactivity in a causalgic finger. *Eur J Pain* 2001, 5 (3), 319-323.

Beyak, M.; Vanner, S., Inflammation-induced hyperexcitability of nociceptive gastrointestinal DRG neurones: the role of voltage-gated ion channels. *Neurogastroenterology & Motility* 2005, 17 (2), 175-186.

Cestele, S.; Catterall, W. A., Molecular mechanisms of neurotoxin action on voltage-gated sodium channels. *Biochimie* 2000, 82 (9-10), 883-892.

Bagal, S. K.; Bungay, P. J.; Denton, S. M.; Gibson, K. R.; Glossop, M. S.; Hay, T. L.; Kemp, M. I.; Lane, C. A. L.; Lewis, M. L.; Maw, G. N.; Million, W. A.; Payne, C. E.; Poinsard, C.; Rawson, D. J.; Stammen, B. L.; Stevens, E. B.; Thompson, L. R., Discovery and Optimization of Selective Na(v)1.8 Modulator Series That Demonstrate Efficacy in Preclinical Models of Pain. *Acs Med Chem Lett* 2015, 6 (6), 650-654.

Kort, M. E.; Drizin, I.; Gregg, R. J.; Scanio, M. J. C.; Shi, L.; Gross, M. F.; Atkinson, R. N.; Johnson, M. S.; Pacofsky, G. J.; Thomas, J. B.; Carroll, W. A.; Krambis, M. J.; Liu, D.; Shieh, C. C.; Zhang, X. F.; Hernandez, G.; Mikusa, J. P.; Zhong, C. M.; Joshi, S.; Honore, P.; Roeloffs, R.; Marsh, K. C.; Murray, B. P.; Liu, J. R.; Werness, S.; Faltynek, C. R.; Krafte, D. S.; Jarvis, M. F.; Chapman, M. L.; Marron, B. E., Discovery and biological evaluation of 5-aryl-2-furfuramides, potent and selective blockers of the Na(v)1.8 sodium channel with efficacy in models of neuropathic and inflammatory pain. *J Med Chem* 2008, 51 (3), 407-416.

Zhang, X. F.; Shieh, C. C.; Chapman, M. L.; Matulenko, M. A.; Hakeem, A. H.; Atkinson, R. N.; Kort, M. E.; Marron, B. E.; Joshi, S.; Honore, P.; Faltynek, C. R.; Krafte, D. S.; Jarvis, M. F., A-887826 is a structurally novel, potent and voltage-dependent Na(v)1.8 sodium channel blocker that attenuates neuropathic tactile allodynia in rats. *Neuropharmacology* 2010, 59 (3), 201-207.

Jarvis, M. F.; Honore, P.; Shieh, C. C.; Chapman, M.; Joshi, S.; Zhang, X. F.; Kort, M.; Carroll, W.; Marron, B.; Atkinson, R.; Thomas, J.; Liu, D.; Krambis, M.; Liu, Y.; McGaraughty, S.; Chu, K.; Roeloffs, R.; Zhong, C. M.; Mikusa, J. P.; Hernandez, G.; Gauvin, D.; Wade, C.; Zhu, C.; Pai, M.; Scanio, M.; Shi, L.; Drizin, I.; Gregg, R.; Matulenko, M.; Hakeem, A.; Grosst, M.; Johnson, M.; Marsh, K.; Wagoner, P. K.; Sullivan, J. P.; Faltynek, C. R.; Krafte, D. S., A-803467, a potent and selective Na(v)1.8 sodium channel blocker, attenuates neuropathic and inflammatory pain in the rat. *P Natl Acad Sci USA* 2007, 104 (20), 8520-8525.

Payne, C. E.; Brown, A. R.; Theile, J. W.; Loucif, A. J. C.; Alexandrou, A. J.; Fuller, M. D.; Mahoney, J. H.; Antonio, B. M.; Gerlach, A. C.; Printzenhoff, D. M.; Prime, R. L.; Stockbridge, G.; Kirkup, A. J.; Bannon, A. W.; England, S.; Chapman, M. L.; Bagal, S.; Roeloffs, R.; Anand, U.; Anand, P.; Bungay, P. J.; Kemp, M.; Butt, R. P.; Stevens, E. B., A novel selective and orally bioavailable Na(v)1.8 channel blocker, PF-01247324, attenuates nociception and sensory neuron excitability. *Brit J Pharmacol* 2015, 172 (10), 2654-2670.

U.S. Pat. No. 10,005,768 to Yao et al., for Carboxamide Derivatives and Use Thereof, issued Jun. 26, 2018;

U.S. Pat. No. 10,005,724 to Andrez et al., for Therapeutic Compounds and Methods of Use Thereof, issued Jun. 26, 2018;

U.S. Pat. No. 10,000,475 to Tadesse et al., for Triazine Carboxamides as Sodium Channel Blockers, issued Jun. 19, 2018;

U.S. Pat. No. 9,969,693 to Bogdan et al., for 6-heteroaryloxy- or 6-aryloxy-quinoline-2-Carboxamides and Method of Use, issued May 15, 2018;

U.S. Pat. No. 9,828,397 to Anderson et al., for Prodrugs of Pyridone Amides Useful as Modulators of Sodium Channels, issued Nov. 28, 2017;

U.S. Pat. No. 9,783,501 to Hadida-Ruah et al., for Substituted Quinolines as Modulators of Sodium Channels, issued Oct. 10, 2017;

U.S. Pat. No. 8,536,195 to Termin et al., for Bicylic Derivatives as Modulators of Voltage Gated Ion Channels, issued Sep. 17, 2013;

U.S. Pat. No. 8,492,403 to Kawatkar et al., for Bicylic Derivatives as Modulators of Voltage Gated Ion Channels, issued Jul. 23, 2013;

U.S. Pat. No. 8,314,125 to Termin et al., for Bicyclic Derivatives as Modulators of Ion Channels, issued Nov. 20, 2012;

U.S. Pat. No. 8,309,543 to Gonzalez et al., for Compositions Useful as Inhibitors of Voltage-Gated Sodium Channels, issued Nov. 13, 2012;

U.S. Pat. No. 8,236,833 to Martinborough et al., for Biphenyl Derivatives as Modulators of Voltage Gated Ion Channels, issued Aug. 7, 2012;

U.S. Pat. No. 8,236,829 to Neubert et al., for Bicyclic Derivatives as Modulators of Voltage Gated ION Channels, issued Aug. 7, 2012;

U.S. Pat. No. 7,989,481 to Neubert et al., for Indane Derivatives as Modulators of Sodium Channels, issued Aug. 2, 2011;

U.S. Pat. No. 7,705,031 to Wilson et al., for Benzimidazoles Useful as Modulators of Ion Channels, issued Apr. 28, 2010.

U.S. Patent Application Publication No. US 2019/0016671 A1, to Ahmad et al., for Carboxamides as Modulators of Sodium Channels, published Jan. 17, 2019.

Although the foregoing subject matter has been described in some detail by way of illustration and example for purposes of clarity of understanding, it will be understood by those skilled in the art that certain changes and modifications can be practiced within the scope of the appended claims.

That which is claimed is:

1. A compound of formula (I-H-i):

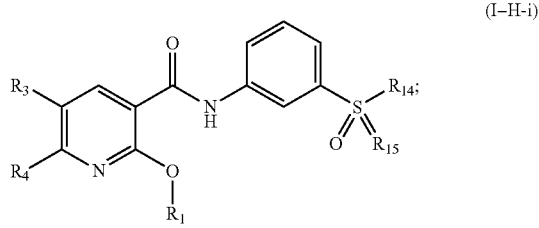

(I-H-i)

wherein:

$R_1$ is selected from the group consisting of phenyl, pyridyl, and 1,3-benzothiazol-4yl, wherein the phenyl and pyridyl can be unsubstituted or substituted with one or more of halogen, $C_1$-$C_8$ alkyl, —O—$R_5$, wherein $R_5$ is selected from the group consisting of $C_1$-$C_8$ alkyl, —$CF_3$, —$CHF_2$, and —$(CH_2)_p$—$CF_3$, wherein p is an integer selected from the group consisting of 1, 2, 3, 4, 5, 6, 7, and 8, —S—$CF_3$, —$NR_6R_7$, wherein $R_6$ and $R_7$ are selected from the group consisting of H and $C_1$-$C_4$ alkyl;

$R_3$ and $R_4$ are H or —$CF_3$, provided that if $R_3$ is H, then $R_4$ is —$CF_3$ and if $R_4$ is H, then $R_3$ is —$CF_3$;

$R_{14}$ is $C_1$-$C_4$ alkyl; and $R_{15}$ is O or $NR_{10}$, wherein $R_{10}$ is H or $C_1$-$C_4$ alkyl.

2. The compound of claim 1, wherein $R_1$ is selected from the group consisting of phenyl, 4-fluorophenyl, 4-fluoro-2-methylphenyl, 4-fluoro-2-methoxyphenyl, 2-chloro-4-fluorophenyl, 2-methyl-4-trifluromethoxyphenyl, 4-trifluoromethoxyphenyl, difluoromethoxyphenyl, 3-fluoro-4-trifluoromethoxyphenyl, 3-fluorophenyl, 2,5-difluorophenyl, 4-methylphenyl, 3-chloro-5-flurophenyl, 2-isopropylphenyl, 3,4-difluorophenyl, 2,4-difluorophenyl, 3,5-difluorophenyl, 4-(2,2,2-trifluoroethoxy)phenyl, 4-(trifluoromethylsulfanyl)phenyl, 2-dimethylaminophenyl, 2-trifluromethylphenyl, 2,4-dimethoxyphenyl, 3,4,5-trifluorophenyl, 3,5-dichlorophenyl, 6-trifluoromethyl-3-pyridyl, 1,3-benzothiazol-4-yl, 4-difluoromethoxyphenyl, 2-chloro-4-fluorophenyl, 2-chloro-4-methoxyphenyl, and 2-chlorophenyl.

3. The compound of claim 1, wherein the compound of formula (I) is selected from the group consisting of:

2-(4-fluorophenoxy)-N-(3-methylsulfonylphenyl)-5-(trifluoromethyl)pyridine-3-carboxamide (34);

2-(4-fluoro-2-methoxy-phenoxy)-N-(3-methylsulfonylphenyl)-5-(trifluoromethyl)pyridine-3-carboxamide (35);

2-(2-chloro-4-fluoro-phenoxy)-N-(3-methylsulfonylphenyl)-5-(trifluoromethyl)pyridine-3-carboxamide (36);

N-(3-methylsulfonylphenyl)-2-[2-methyl-4-(trifluoromethoxy)phenoxy]-5-(trifluoromethyl)pyridine-3-carboxamide (37);

N-(3-methylsulfonylphenyl)-2-[4-(trifluoromethoxy)phenoxy]-5-(trifluoromethyl)pyridine-3-carboxamide (38);

2-[4-(difluoromethoxy)phenoxy]-N-(3-methylsulfonylphenyl)-5-(trifluoromethyl)pyridine-3-carboxamide (39);

2-[3-fluoro-4-(trifluoromethoxy)phenoxy]-N-(3-methylsulfonylphenyl)-5-(trifluoromethyl)pyridine-3-carboxamide (40);

N-(3-methylsulfonylphenyl)-2-phenoxy-5-(trifluoromethyl)pyridine-3-carboxamide (41);

2-(3-fluorophenoxy)-N-(3-methylsulfonylphenyl)-5-(trifluoromethyl)pyridine-3-carboxamide (42);

2-(2,5-difluorophenoxy)-N-(3-methylsulfonylphenyl)-5-(trifluoromethyl)pyridine-3-carboxamide (43);

2-(4-methylphenoxy)-N-(3-methylsulfonylphenyl)-5-(trifluoromethyl)pyridine-3-carboxamide (44);

2-(3-chloro-5-fluoro-phenoxy)-N-(3-methylsulfonylphenyl)-5-(trifluoromethyl)pyridine-3-carboxamide (45);

2-(2-isopropylphenoxy)-N-(3-methylsulfonylphenyl)-5-(trifluoromethyl)pyridine-3-carboxamide (46);

2-(3,4-difluorophenoxy)-N-(3-methylsulfonylphenyl)-5-(trifluoromethyl)pyridine-3-carboxamide (47);

2-(2,4-difluorophenoxy)-N-(3-methylsulfonylphenyl)-5-(trifluoromethyl)pyridine-3-carboxamide (48);

2-(3,5-difluorophenoxy)-N-(3-methylsulfonylphenyl)-5-(trifluoromethyl)pyridine-3-carboxamide (49);

N-(3-methylsulfonylphenyl)-2-[4-(2,2,2-trifluoroethoxy)phenoxy]-5-(trifluoromethyl)pyridine-3-carboxamide (50);

N-(3-methylsulfonylphenyl)-5-(trifluoromethyl)-2-[4-(trifluoromethylsulfanyl)phenoxy]pyridine-3-carboxamide (51);
2-[2-(dimethylamino)phenoxy]-N-(3-methylsulfonylphenyl)-5-(trifluoromethyl)pyridine-3-carboxamide (52);
N-(3-methylsulfonylphenyl)-5-(trifluoromethyl)-2-[2-(trifluoromethyl)phenoxy]pyridine-3-carboxamide (53);
2-(2,4-dimethoxyphenoxy)-N-(3-methylsulfonylphenyl)-5-(trifluoromethyl)pyridine-3-carboxamide (54);
N-(3-methylsulfonylphenyl)-5-(trifluoromethyl)-2-(3,4,5-trifluorophenoxy)pyridine-3-carboxamide (55);
2-(3,5-dichlorophenoxy)-N-(3-methylsulfonylphenyl)-5-(trifluoromethyl)pyridine-3-carboxamide (56);
N-(3-methylsulfonylphenyl)-5-(trifluoromethyl)-2-[[6-(trifluoromethyl)-3-pyridyl]oxy]pyridine-3-carboxamide (57);
2-(1,3-benzothiazol-4-yloxy)-N-(3-methylsulfonylphenyl)-5-(trifluoromethyl)pyridine-3-carboxamide (58);
2-[4-(difluoromethoxy)phenoxy]-N-[3-(methylsulfonimidoyl)phenyl]-5-(trifluoromethyl)pyridine-3-carboxamide (59);
2-(2-chloro-4-fluoro-phenoxy)-N-[3-(methylsulfonimidoyl)phenyl]-5-(trifluoromethyl)pyridine-3-carboxamide (60);
2-(2-chloro-4-methoxy-phenoxy)-N-[3-(methylsulfonimidoyl)phenyl]-5-(trifluoromethyl)pyridine-3-carboxamide (61); and
2-(2-chlorophenoxy)-N-[3-(methylsulfonimidoyl)phenyl]-5-(trifluoromethyl)pyridine-3-carboxamide (62).

4. A method for modulating a $Na_v$ 1.8 sodium ion channel, the method comprising administering to a subject in need thereof, a modulating-effective amount of a compound of claim 1 to the subject.

5. A method for inhibiting $Na_v$ 1.8, the method comprising administering to a subject in need thereof, an inhibiting-effective amount of a compound of claim 1 to the subject.

6. A method for treating a condition, disease, or disorder associated with an increased $Na_v$ 1.8 activity or expression, the method comprising administering to a subject in need of treatment thereof a therapeutically effective amount of a compound of claim 1 to the subject to treat the condition, disease, or disorder, wherein the condition, disease, or disorder associated with an increased $Na_v$ 1.8 activity or expression is selected from the group consisting of pain, respiratory diseases, neurological disorders, and psychiatric diseases, and combinations thereof.

7. The method of claim 6, wherein the pain is selected from the group consisting of neuropathic pain, inflammatory pain, visceral pain, cancer pain, chemotherapy pain, trauma pain, surgical pain, post-surgical pain, childbirth pain, labor pain, neurogenic bladder, ulcerative colitis, chronic pain, persistent pain, peripherally mediated pain, centrally mediated pain, chronic headache, migraine headache, sinus headache, tension headache, phantom limb pain, dental pain, peripheral nerve injury, and combinations thereof.

8. The method of claim 6, wherein the disease or condition is selected from the group consisting of HIV-treatment induced neuropathy, trigeminal neuralgia, post-herpetic neuralgia, eudynia, heat sensitivity, tosarcoidosis, irritable bowel syndrome, Crohn's disease, multiple sclerosis (MS), amyotrophic lateral sclerosis (ALS), diabetic neuropathy, peripheral neuropathy, arthritis, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxi related illnesses, familial erythromelalgia, primary erythromelalgia, familial rectal pain, cancer, epilepsy, partial and general tonic seizures, restless leg syndrome, arrhythmias, fibromyalgia, neuroprotection under ischaemic conditions cause by stroke or neural trauma, tach-arrhythmias, atrial fibrillation, ventricular fibrillation, and Pitt Hopkins Syndrome (PTHS).

9. The method of claim 6, further comprising administering to the subject one or more additional therapeutic agents.

10. The method of claim 9, wherein the one or more additional therapeutic agents is selected from the group consisting of acetaminophen, one or more NSAIDs, opioid analgesics, and combinations thereof.

11. The compound of claim 1, wherein:
$R_3$ is selected from the group consisting of cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, $C_3$-$C_8$ cycloalkyl, —$NO_2$, and is absent when Y is nitrogen; and
$R_4$ is selected from the group consisting of hydrogen, cyano, halogen, $C_1$-$C_8$ alkoxyl, mono-, di-, and trihalo-$C_1$-$C_4$ alkyl, mono-, di-, and trihalo-$C_1$-$C_4$ alkoxyl, substituted or unsubstituted $C_1$-$C_8$ alkyl, and morpholinyl.

12. The compound of claim 1, wherein $R_3$ is $CF_3$.

* * * * *